US012655157B2

(12) United States Patent
Bagley et al.

(10) Patent No.: US 12,655,157 B2
(45) Date of Patent: Jun. 16, 2026

(54) SPIRO[BENZO[D]THIAZOLE-6,4'-PIPERIDINE AS ACC INHIBITORS

(71) Applicant: Pfizer Inc., New York, NY (US)

(72) Inventors: Scott William Bagley, Voluntown, CT (US); Andrea Nicole Bootsma, Arlington, MA (US); Chulho Choi, Mystic, CT (US); Robert Lee Dow, Groton, CT (US); David James Edmonds, Inzlingerstrasse (CH); Carmen Noemi Garcia-Irizarry, Gales Ferry, CT (US); Brian Stephen Gerstenberger, Cambridge, MA (US); Gajendra Ingle, Cambridge, MA (US); Jessica Gloria Katherine O'Brien, Cambridge, MA (US); Mihir Dineshkumar Parikh, East Greenwich, RI (US); Gwenaella Christine Rescourio, San Diego, CA (US); Daniel Copley Schmitt, Zionsville, IN (US)

(73) Assignee: Pfizer Inc., New York, NY (US)

( * ) Notice: Subject to any disclaimer, the term of this patent is extended or adjusted under 35 U.S.C. 154(b) by 405 days.

(21) Appl. No.: 18/359,709

(22) Filed: Jul. 26, 2023

(65) Prior Publication Data

US 2024/0109915 A1 Apr. 4, 2024

Related U.S. Application Data

(60) Provisional application No. 63/393,712, filed on Jul. 29, 2022.

(51) Int. Cl.
*C07D 513/10* (2006.01)
*A61P 17/10* (2006.01)

(52) U.S. Cl.
CPC ............ *C07D 513/10* (2013.01); *A61P 17/10* (2018.01)

(58) Field of Classification Search
CPC .................................................... C07D 513/10
See application file for complete search history.

(56) References Cited

U.S. PATENT DOCUMENTS

2010/0113418 A1 5/2010 Fukatsu et al.
2016/0220557 A1 8/2016 Esler et al.

FOREIGN PATENT DOCUMENTS

CN 110143949 8/2019
WO 2009144554 12/2009

OTHER PUBLICATIONS

Batchuluun, Battsetseg, et al., "Lipogenesis inhibitors: therapeutic opportunities and challenges", Nature Reviews Drug Discovery, Jan. 14, 2022, pp. 283-305, 21(4).
Esler, William P., et al., "Human sebum requires de novo lipogenesis, which is increased in acne vulgaris and suppressed by acetyl-CoA carboxylase inhibition", Science Translational Medicine, May 15, 2019, 11(492), pp. 1-13.
International Patent Application No. PCT/IB2023/057576, filed Jul. 26, 2023, International Search Report and Written Opinion, mailed Oct. 16, 2023, 16 pages.
Orozco, Christine C., et al., "Structural attributes influencing unbound tissue distribution", European Journal of Medicinal Chemistry, Jan. 1, 2020, Article 111813, pp. 1-18, vol. 185.

*Primary Examiner* — Susanna Moore
(74) *Attorney, Agent, or Firm* — Zhigang Rao

(57) ABSTRACT

The invention relates to compounds of Formula (I), or a pharmaceutically acceptable salt thereof, or a pharmaceutically acceptable solvate of said compound or pharmaceutically acceptable salt; to compositions containing such compounds; and to the uses of such compounds in the treatment of various diseases, particularly acne.

14 Claims, No Drawings

SPIRO[BENZO[D]THIAZOLE-6 ,4'-PIPERIDINE AS ACC INHIBITORS

This application is a U.S. Non-Provisional Patent application under 35 U.S.C. 119(e) which claims the benefit of U.S. Provisional Patent Application No. 63/393,712, filed on Jul. 29, 2022, under 35 USC 119 (e), the disclosures of which are hereby incorporated by reference in their entirety.

FIELD OF THE INVENTION

The present invention relates to novel Acetyl CoA-Carboxylase (ACC) inhibitors, pharmaceutical compositions comprising such compounds and their use as medicaments. More particularly, the present invention provides novel ACC inhibitors which are useful for the treatment of and prevention of acne.

BACKGROUND

Acne vulgaris consists of a spectrum of skin lesions including comedones, inflammatory papules, pustules, nodules and cysts. The disease is classified as mild, moderate or severe depending on lesion severity and anatomical lesion distribution. Disease onset typically occurs at puberty because of elevated sebum production triggered by increased androgen levels. Approximately 90% of adolescents are affected by acne with 15% seeking medical treatment; moreover, the disease continues to be prevalent in 23-35% of young adults (18-28 years). Biologically, acne is considered an inflammatory disease of the pilosebaceous duct with several distinguishing characteristics, including: (a) excess sebum production; (b) abnormal keratinocyte proliferation and desquamation leading to ductal obstruction; (c) proliferation of *Cutibacterium acnes* (*C. acnes*; formerly known as *Propionibacterium acnes*); and (d) inflammation. These factors are often interdependent. For example, elevated androgen levels lead to epithelial desquamation and follicular obstruction as well as excess sebum production causing the obstructed follicles to fill with lipid forming comedones. This excess sebum then serves as a substrate for *C. acnes* bacteria which metabolizes the sebum to release free fatty acids that promotes further bacterial replication and inflammation. While multiple factors contribute to the etiology of the disorder, acne cannot occur without sebum as sebum serves as the nutrient source for *C. acnes* (Smith and Thiboutot, J Lipid Research, 49, 271-281 (2008)).

Current standard of care for acne includes topical therapies for mild to moderate disease, and systemic therapy for moderate to severe disease. These current therapies are either marginally effective or lack suitable safety profiles for widespread use. Topical acne treatments include retinoids, topical antibiotics, benzoyl peroxides and combinations thereof. Systemic treatments include hormonal therapies, oral antibiotics and isotretinoin (Dawson et al., BMJ 2013; 346:12634). Hormonal therapies, including oral contraceptives and androgen receptor blockers, are used in female patients for the treatment of moderate to severe acne with modest efficacy. Oral antibiotics including doxycycline, minocycline, tetracycline and erythromycin are also modestly effective in treating acne, particularly when matched against patterns of *C. acnes* resistance; although, photosensitivity and gastrointestinal disturbance limit their use (Gannon et al., Family Pract. 2011; 60:290-92). Isotretinoin, although highly efficacious, presents a number of serious adverse effects. The agent is highly teratogenic and requires special prescribing precautions and routine pregnancy testing. Additionally, isotretinoin causes severe mucocutaneous toleration issues (dry skin, eyes, nasal passages, lips, etc.) which can be dose limiting if not adequately managed with palliative care. Isotretinoin treatment is associated with adverse plasma lipid changes (increased TG, LDL) and hepatic toxicity (ALT/AST elevation requiring liver function testing prior to treatment. Additionally, isotretinoin therapy has also been associated with myalgia (50% of patients have elevated CK levels), calcification of ligaments and detrimental ocular effects (loss of night vision, loss of color vision and eye dryness). In isolated cases, isotretinoin has been associated with neurological/psychological adverse effects including depression, psychosis and potentially suicide.

ACC, which catalyzes the conversion of acetyl-CoA to malonyl-CoA, plays a key role in regulating lipid metabolism. ACC is an essential and rate-limiting step in the de novo synthesis of fatty acids and regulates the oxidation of long chain fatty acids. The terms “de novo lipogenesis”, “DNL”, and “de novo fatty acid synthesis” are used to address the synthesis of fatty acids from non-lipid based sources. There are two closely related isoforms, ACC1 and ACC2. ACC inhibition has been of interest as a potential mechanism to treat type 2 diabetes mellitus and obesity (WO2009144554).

In the course of preclinical in vivo studies in rats and dogs, it was discovered that multiple ACC inhibitors induced microscope morphologic changes in sebocytes consistent with reduced lipid/sebum content of sebaceous glands. Based on these observations, it was hypothesized that the ACC inhibitors may be reducing sebum lipid production in rats and dogs by inhibiting the de novo synthesis of fatty acids. Sebum is a complex mixture of lipids, comprised of triglycerides (30 to 50%), wax esters (26% to 30%), free fatty acids (15 to 30%), squalene (12 to 20%), cholesterol esters (3% to 6%) and free cholesterol (1.5 to 2.5%) (Ottaviani et al., *Lipid mediators in acne. Mediators of Inflammation,* 2010. doi: 10.1155/2010/858176)

Of these lipid classes, triglycerides, wax esters, free fatty acids and cholesterol esters all contain or are comprised of fatty acids. Elevated rates of sebum production are linked to both the onset and severity of acne (Janiczek-Dolphin et al., *Br J. Dermatol.* 2010; 163:683-688.). While it is known that human sebaceous glands are capable of de novo fatty acid synthesis (Downie and Kealey, J Invest. Dermatol. 1998; 111:199-205), the relative importance of this pathway within the sebocyte versus the use of exogenous circulating fatty acids for sebum biosynthesis was unknown.

Therefore, a need exists for a novel approach to treating acne with a favorable efficacy/safety profile. The present invention provides a new therapeutic approach for treating acne comprising the use of ACC inhibitors. There is thus a need to provide new compounds that are potent, selective inhibitors of sebum secretion with suitable pharmacokinetic properties, particularly compounds which can be administered by topical administration and are efficacious in the treatment of acne.

SUMMARY OF THE INVENTION

The present invention relates to a compound of formulas (Ia and Ib) having the structure:

(Ia)

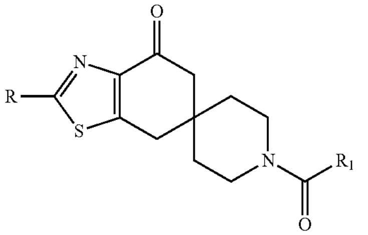

or (Ib)

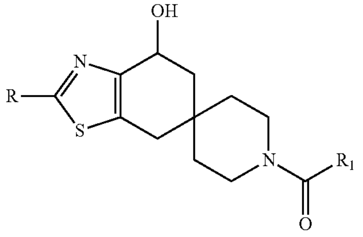

or a pharmaceutically acceptable salt thereof, or a pharmaceutically acceptable solvate of said compound or pharmaceutically acceptable salt, wherein:

R is selected from the group consisting of H, $C_1$-$C_6$ alkoxy, $C_1$-$C_6$ alkyl and $—(CH_2)_m$-W, where W is $C_3$-$C_8$ cycloalkyl, bicyclo alkyl, bridged bicycloalkyl, phenyl, 5- or 6-membered heteroaryl or heterocyclic containing one, two or three heteroatoms selected from the group consisting of N, S and O atoms; wherein each of said alkyl, cycloalkyl, heterocyclic, phenyl, naphthyl or heteroaryl may be unsubstituted or substituted by phenyl, halo, cyano, deuterium, hydroxy, $C_1$-$C_6$ alkyl, $C_1$-$C_6$ alkoxy, $—SO_2—R'$, —CONR'R", NR'COR", —NR'CONR'R", $—NR'CO_2R"$, $—(CH_2)_n—SO_2—R'$, $—NHSO_2—R'$, $—NR"SO_2—R'$, $—SO_2NR'R"$, NR'R" or SR' where R' and R" are independently H, $C_1$-$C_6$ alkyl or $C_3$-$C_8$ cycloalkyl;

$R_1$ is selected from the group consisting of phenyl, naphthyl, 5- or 6-membered heteroaryl or heterocyclic containing one, two, three or four heteroatoms selected from the group consisting of N, S and O atoms; and, a 9- or 10-membered bicyclic aryl, heteroaryl or heterocyclic containing one, two or three heteroatoms selected from the group consisting of N, S and O atoms; wherein each of said phenyl, naphthyl, aryl, heterocyclic, or heteroaryl may be unsubstituted or substituted by halo, cyano, deuterium, hydroxy, $C_1$-$C_6$ alkyl, $C_1$-$C_6$ alkoxy, phenyl, $—SO_2—R'$, —CONR'R", NR'COR", —NR'CONR'R", $—NR'CO_2R"$, $—(CH_2)_n—SO_2—R'$, $—NHSO_2—R'$, $—NR"SO_2—R'$, $—SO_2NR'R"$, NR'R", —P(O)R'R",

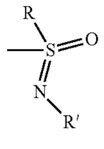

or SR' where R' and R" are independently H, $C_1$-$C_6$ alkyl or $C_3$-$C_8$ cycloalkyl; and, m and n are independently 0, 1, 2 or 3.

In other aspects, the present invention also provides:

pharmaceutical compositions which comprise a pharmaceutically acceptable carrier and a compound of formula I, or a pharmaceutically acceptable salt thereof; and, methods for treating conditions or disorders including:

Arthritis, including rheumatoid arthritis, juvenile arthritis, and psoriatic arthritis;

Autoimmune or inflammatory diseases or disorders, including Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, autoimmune hepatitis, primary sclerosing cholangitis, chronic aggressive hepatitis, non-alcoholic fatty liver disease, non-alcoholic steatohepatitis ulcerative colitis and membranous glomerulopathy, systemic lupus erythematosis, rheumatoid arthritis, psoriatic arthritis, Sjogren's syndrome, Reiter's syndrome, polymyositis, dermatomyositis, type I interferonopathies including Aicardi-Goutieres syndrome and other mendelian diseases of overexpression of type I interferon systemic sclerosis, polyarteritis nodosa, multiple sclerosis, relapsing remitting multiple sclerosis, primary progressive multiple sclerosis, secondary progressive multiple sclerosis, and bullous pemphigoid, and additional autoimmune diseases, which can be O-cell (humoral) based or T-cell based, including Cogan's syndrome, ankylosing spondylitis, Wegener's granulomatosis, autoimmune alopecia, Type I or juvenile onset diabetes, or thyroiditis;

Cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, or angiogenic-associated disorders including solid tumors;

Diabetes, including Type I diabetes or complications from diabetes;

Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, or ocular neovascularization;

Intestinal inflammations, including Crohn's disease, ulcerative colitis, inflammatory bowel disease, celiac diseases, proctitis, eosinophilic gastroenteritis, or mastocytosis;

Neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemia, renal ischemia, heart attacks, cardiac hypertrophy, atherosclerosis and arteriosclerosis, organ hypoxia, or platelet aggregation;

Skin diseases, conditions or disorders including atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummular dermatitis, seborrheic dermatitis, seborrhea, oily skin, eyelid dermatitis, diaper dermatitis, dermatomyositis, scleroderma, keloid, hypertrophic scar, morphea, frontal fibrosing alopecia, cicatricial alopecia, lichen planus, lichen sclerosis, alopecia areata, vitiligo, rosacea, rosacea-like dermatitis, steroid-induced dermatitis, drug eruptions (including papulopustular drug eruption), epidermolysis bullosa, keratosis pilaris, pityriasis alba, pemphigus, vulvovaginitis, acne (including but not limited to acne vulgaris, nodular acne, nodulocystic acne, cystic acne, conglobate acne, steroid acne, and autoinflammatory syndromes [including but not limited to PAPA, PAPASH, PASS, PASH, SAPHO, PCO, and SH], and acne scar), chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, inverse psoriasis, intractable wounds, sebaceous hyperplasia, Fordyce's condition (Fordyce's granules; Fordyce's spots), Fox-Fordyce's disease, osmidrosis (bromhidrosis), hirsutism, or skin tumors (nevus sebaceous, sebaceous adenoma, sebaceoma, sebaceous epithelioma, steatocytoma simplex, steatocytoma multiplex, Muir-Torre syndrome, sebaceous carcinoma);

The present invention will be further understood from the following description given by way of example only. The present invention is directed to a class of tricyclic spiropiperidine compounds. In particular, the present invention is directed to certain tricyclic spiropiperidine compounds useful as inhibitors of ACC useful in the treatment of acne. While the present invention is not so limited, an appreciation of various aspects of the invention will be gained through the following discussion and the examples.

DETAILED DESCRIPTION OF THE INVENTION

Unless otherwise defined herein, scientific and technical terms used in connection with the present invention have the meanings that are commonly understood by those of ordinary skill in the art.

The phrase "therapeutically effective" is intended to qualify the amount of compound or pharmaceutical composition, or the combined amount of active ingredients in the case of combination therapy. This amount or combined amount will achieve the goal of treating the relevant condition.

The term "treatment," as used herein to describe the present invention and unless otherwise qualified, means administration of the compound, pharmaceutical composition or combination to effect preventative, palliative, supportive, restorative, or curative treatment. The term treatment encompasses any objective or subjective improvement in a subject with respect to a relevant condition or disease.

The term "preventive treatment," as used herein to describe the present invention, means that the compound, pharmaceutical composition or combination is administered to a subject to inhibit or stop the relevant condition from occurring in a subject, particularly in a subject or member of a population that is significantly predisposed to the relevant condition.

The term "ACC inhibitor" as used herein means a compound that inhibits ACC1 and potentially ACC2. The ACC1 assay disclosed herein may be used to establish inhibition activity ($IC_{50}$) for compounds against ACC1. A compound with an $IC_{50}$ below about 10 μM in the ACC1 assay is considered an ACC inhibitor. A preferred $IC_{50}$ is less than about 1 μM in the assay, and an especially preferred IC50 is less than about 0.1 μM in the assay. In addition, ACC inhibitors of the present invention selectively inhibit ACC1 and potentially ACC2 as compared to other enzymes, g-protein coupled receptors or ion channels. The compounds contemplated by the present invention inhibit other enzymes or bind ($K_i$) to receptors or ion channels at concentrations greater than the concentration required to inhibit ACC1. Preferred ACC inhibitory activity is about 2 to 10-fold greater than the IC50 or $K_i$ for other enzymes, receptors or ion channels, 10-100-fold is more preferred, and greater than 100 fold is especially preferred.

The term "selective", when used to describe a functionally defined receptor ligand or enzyme inhibitor means selective for the defined receptor or enzyme subtype as compared with other receptor or enzyme subtypes in the same family. For instance, a selective ACC inhibitor is a compound which inhibits an ACC enzyme subtype more potently than any other enzyme subtype. Such selectivity is preferably at least 2-fold (as measured using conventional binding assays), more preferably at least 10-fold, most preferably at least 100 fold.

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms.

The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to an alkyl of one to six carbon atoms, inclusive.

The term "hydroxy," as used herein, means an OH radical.

The term "heterocyclic" refers to a saturated or partially saturated (i.e., non-aromatic) ring system which may be attached via a ring nitrogen atom (when the heterocycle is attached to a carbon atom) or a ring carbon atom (in all cases). Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

The term "heteroaryl" is an aromatic heterocycle which may be attached via a ring carbon atom or a ring nitrogen atom with an appropriate valency (when the heterocycle is attached to a carbon atom). Equally, when substituted, the substituent may be located on a ring carbon atom (in all cases) or a ring nitrogen atom with an appropriate valency (if the substituent is joined through a carbon atom). Specific examples include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl.

The term "fused bicycle" refers to a ring system comprising two rings fused together. Specific examples include naphthyl, imidazo[2,1-b][1,3]thiazolyl, benzofuranyl, benzothienyl, indolyl, benzimidazolyl, indazolyl, benzotriazolyl, pyrrolo[2,3-b]pyridyl, pyrrolo[2,3-c]pyridyl, pyrrolo [3,2-c]pyridyl, pyrrolo[3,2-b]pyridyl, imidazo[4,5-b] pyridyl, imidazo[4,5-c]pyridyl, pyrazolo[4,3-d]pyridyl, pyrazolo[4,3-c]pyridyl, pyrazolo[3,4-c]pyridyl, pyrazolo[3, 4-b]pyridyl, isoindolyl, indazolyl, purinyl, indolizinyl, imidazo[1,2-a]pyridyl, imidazo[1,5-a]pyridyl, pyrazolo[1,5-a] pyridyl, pyrrolo[1,2-b]pyridazinyl, imidazo[1,2-c] pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d] pyrimidinyl, pyrido[2,3-d]pyrimidinyl, pyrido[2,3-d] pyrazinyl, pyrido[3,4-b]pyrazinyl, pyrimido[5,4-d] pyrimidinyl, pyrazino[2,3-b]pyrazinyl and pyrimido[4,5-d] pyrimidine.

The term "cycloalkyl" means monocyclic or bicyclic, saturated hydrocarbon group of the formula $C_nH_{2n-1}$. Examples include cyclopropyl, cyclobutyl, cyclopentyl, cyclohexyl, and cycloheptyl. Bicyclic compounds include bridged ring compounds such as bicyclo[1.1.1]pentanyl. Unless otherwise specified, a cycloalkyl group comprises from 3 to 8 carbon atoms.

The term "alkoxy" means a radical comprising an alkyl radical that is bonded to an oxygen atom, such as a methoxy radical. Examples of such radicals include methoxy, ethoxy, propoxy, isopropoxy, butoxy and tert-butoxy. The term "halo" means, fluoro, chloro, bromo or iodo.

As used herein, the terms "co-administration", "co-administered" and "in combination with", referring to a combination of a compound of formula I and one or more other therapeutic agents, includes the following:

- simultaneous administration of such a combination of a compound of formula I and a further therapeutic agent to a patient in need of treatment, when such components are formulated together into a single dosage form which releases said components at substantially the same time to said patient,
- substantially simultaneous administration of such a combination of a compound of formula I and a further therapeutic agent to a patient in need of treatment, when such components are formulated apart from each other into separate dosage forms which are taken at substantially the same time by said patient, whereupon said components are released at substantially the same time to said patient,
- sequential administration of such a combination of a compound of formula I and a further therapeutic agent to a patient in need of treatment, when such components are formulated apart from each other into separate dosage forms which are taken at consecutive times by said patient with a significant time interval between each administration, whereupon said components are released at substantially different times to said patient; and
- sequential administration of such a combination of a compound of formula I and a further therapeutic agent to a patient in need of treatment, when such components are formulated together into a single dosage form which releases said components in a controlled manner.

The term 'excipient' is used herein to describe any ingredient other than a compound of formula I. The choice of excipient will to a large extent depend on factors such as the particular mode of administration, the effect of the excipient on solubility and stability, and the nature of the dosage form. The term "excipient" encompasses diluent, carrier or adjuvant.

The present invention is related to novel compounds which are ACC modulators useful for the treatment of diseases and conditions associated with dysregulation of ACC. The present invention further provides pharmaceutical compositions comprising such ACC enzyme modulators as well as methods of treating and/or preventing such diseases and conditions. Accordingly, the present invention provides a compound of formula I, as represented above, or a pharmaceutically acceptable salt thereof.

Described below are a number of embodiments (E) of this first aspect of the invention, where for convenience E1 is identical thereto.

E1 A compound of formula I as defined above, or a pharmaceutically acceptable salt thereof.

E2. A compound according to E1 wherein R is selected from the group consisting of H, $C_1$-$C_6$ alkyl and —$(CH_2)_m$-W, where W is $C_3$-$C_8$ cycloalkyl, wherein each of said alkyl, cycloalkyl, bicycloalkyl, and bridged bicycloalkyl may be unsubstituted or substituted by halo, cyano, deuterium, hydroxy, $C_1$-$C_6$ alkyl and $C_1$-$C_6$ alkoxy; and, m and n are independently 0, 1, 2 or 3.

E3. A compound according to E1 wherein R is t-butyl.

E4 A compound according to E1 wherein $R_1$ is phenyl, pyridyl, indolyl, indazolyl, pyrrolopyridinyl, quinolinyl, isoquinolinyl or naphthyl; wherein each of said phenyl, pyridyl, indolyl, indazolyl, pyrrolopyridinyl, quinolinyl, isoquinolinyl or naphthyl may be unsubstituted or substituted by halo, cyano, hydroxy, $C_1$-$C_6$ alkyl, $C_1$-$C_6$ alkoxy, phenyl, —CONR'R", NR'R" or SR' where R' and R" are independently H, $C_1$-$C_6$ alkyl or $C_3$-$C_8$ cycloalkyl; and, m and n are independently 0, 1, 2 or 3.

E5. A compound according to E1 selected from the group consisting of:

2-(tert-butyl)-1'-(7-methoxy-1,3-dimethyl-1H-indazole-5-carbonyl)-5H-spiro[benzo[d]thiazole-6,4'-piperidin]-4(7H)-one;

2-(tert-butyl)-1'-(7-methyl-1H-indole-5-carbonyl)-5H-spiro[benzo[d]thiazole-6,4'-piperidin]-4(7H)-one;

2-(tert-butyl)-1'-(8-methyl-3-(methylamino)quinoline-6-carbonyl)-5H-spiro[benzo[d]thiazole-6,4'-piperidin]-4(7H)-one;

2-(tert-butyl)-1'-(7-ethoxy-1,3-dimethyl-1H-indazole-5-carbonyl)-5H-spiro[benzo[d]thiazole-6,4'-piperidin]-4(7H)-one;

2-(tert-butyl)-1'-(4-methyl-2-naphthoyl)-5H-spiro[benzo[d]thiazole-6,4'-piperidin]-4(7H)-one;

or, a pharmaceutically acceptable salt thereof, or a pharmaceutically acceptable solvate of said compound or pharmaceutically acceptable salt.

E6. The compound according to E1 wherein the compound is 2-(tert-butyl)-1'-(7-methoxy-1,3-dimethyl-1H-indazole-5-carbonyl)-5H-spiro[benzo[d]thiazole-6,4'-piperidin]-4(7H)-one; or, a pharmaceutically acceptable salt thereof, or a pharmaceutically acceptable solvate of said compound or pharmaceutically acceptable salt.

E7. The compound according to E1 wherein the compound is 2-(tert-butyl)-1'-(7-methyl-1H-indole-5-carbonyl)-5H-spiro[benzo[d]thiazole-6,4'-piperidin]-4 (7H)-one; or, a pharmaceutically acceptable salt thereof, or a pharmaceutically acceptable solvate of said compound or pharmaceutically acceptable salt.

E8. The compound according to E1 wherein the compound is 2-(tert-butyl)-1'-(8-methyl-3-(methylamino) quinoline-6-carbonyl)-5H-spiro[benzo[d]thiazole-6,4'-piperidin]-4(7H)-one; or, a pharmaceutically acceptable salt thereof, or a pharmaceutically acceptable solvate of said compound or pharmaceutically acceptable salt.

E9. The compound according to E1 wherein the compound is 2-(tert-butyl)-1'-(7-ethoxy-1,3-dimethyl-1H-indazole-5-carbonyl)-5H-spiro[benzo[d]thiazole-6,4'-piperidin]-4(7H)-one; or, a pharmaceutically acceptable salt thereof, or a pharmaceutically acceptable solvate of said compound or pharmaceutically acceptable salt.

E10. The compound according to E1 wherein the compound is 2-(tert-butyl)-1'-(4-methyl-2-naphthoyl)-5H-spiro[benzo[d]thiazole-6,4'-piperidin]-4(7H)-one; or, a pharmaceutically acceptable salt thereof, or a pharmaceutically acceptable solvate of said compound or pharmaceutically acceptable salt.

E11. A pharmaceutical composition comprising a compound according to any one of E1 to E10, or a pharmaceutically acceptable salt thereof, or a pharmaceutically acceptable solvate of said compound or salt, and a pharmaceutically acceptable excipient.

E12. A method of treating a disease or condition selected from inflammation, autoimmune disease, neuroinflammation, arthritis, rheumatoid arthritis, spondyloarthropathies, systemic lupus erythematous, lupus nephritis, osteoarthritis, gouty arthritis, pain, fever, pulmonary sarcoidosis, silicosis, cardiovascular disease, atherosclerosis, myocardial infarction, thrombosis, congestive heart failure and cardiac reperfusion injury, cardiomyopathy, stroke, ischemia, reperfusion injury, brain edema, brain trauma, neurodegeneration, liver disease, inflammatory bowel disease, Crohn's disease, ulcerative colitis, nephritis, retinitis, retinopathy, macular degeneration, glaucoma, diabetes (type 1 and type 2), diabetic neuropathy, viral and bacterial infection, myalgia, endotoxic shock, toxic shock syndrome, osteoporosis, multiple sclerosis, endometriosis, menstrual cramps, vaginitis, candidiasis, cancer, fibrosis, obesity, muscular dystrophy, polymyositis, dermatomyositis, autoimmune hepatitis, primary biliary cirrhosis, primary sclerosing cholangitis, vitiligo, Alzheimer's disease, skin flushing, eczema, psoriasis, atopic dermatitis, sunburn, keloid, hypertrophic scar, rheumatic diseases, urticaria, discoid lupus, cutaneous lupus, central nervous system lupus, psoriatic arthritis, asthma, allergic asthma, type I interferonopathies including Aicardi-Goutieres syndrome and other mendelian diseases of overexpression of type I interferon, primary progressive multiple sclerosis, relapsing remitting multiple sclerosis, non-alcoholic fatty liver disease, non-alcoholic steatohepatitis, scleroderma, alopecia areata, scarring alopecia, prurigo, prurigo nodularis, CPUO, lichen diseases, lichen planus, Steven's Johnson's syndrome, spondylopathy, myositis, vasculitis, pemphigus, lupus, major depression disorder, allergy, dry eye syndrome, transplant rejection, cancer, septic shock, cardiopulmonary dysfunction, acute respiratory disease, ankylosing spondylitis, cachexia, chronic graft-versus-host disease, acute graft-versus-host disease, Celiac Sprue, idiopathic thrombocytopenic thrombotic purpura, thrombotic thrombocytopenic purpura, myasthenia gravis, Sjogren's syndrome, epidermal hyperplasia, cartilage inflammation, bone degradation, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, reactive arthritis, Reter's Syndrome, myolitis, polymyolitis, dermatomyolitis, polyarteritis nodosa, Wegener's granulomatosis, arteritis, polymyalgia rheumatica, sarcoidosis, sclerosis, primary biliary sclerosis, sclerosing cholangitis, dermatitis, Still's disease, chronic obstructive pulmonary disease, Guillain-Barre disease, Graves' disease, Addison's disease, Raynaud's phenomenon, psoriatic epidermal hyperplasia, plaque psoriasis, guttate psoriasis, inverse psoriasis, pustular psoriasis, erythrodermic psoriasis, an immune disorder associated with or arising from activity of pathogenic lymphocytes, noninfectious uveitis, Behcet's disease and Vogt-Koyanagi-Harada syndrome, comprising administering to a subject in need thereof a therapeutically effective amount of a compound according to E1 to E10, or a pharmaceutically acceptable salt thereof, or a pharmaceutically acceptable solvate of said compound or salt.

E13. A method according to E12 wherein the compound is administered topically.

E14. A method according to E12 or E13, wherein the compound is administered as a cream, ointment, lotion, gel, solution, suspension, foam, aerosol, spray, shampoo, patch or tape.

E15. A method of treating acne, comprising administering to the subject a therapeutically effective amount of a compound according to E1 to E10, or a pharmaceutically acceptable salt thereof, or a pharmaceutically acceptable solvate of said compound or salt.

E16. A method according to E15 wherein the compound is administered topically.

E17. A method according to E15 or E16, wherein the compound is administered as a cream, ointment, lotion gel, solution, suspension, foam, aerosol, spray, shampoo, patch or tape.

E18. Use of a compound according to any of E1 to E10 for the manufacture of a medicament for the treatment of a disorder for which an ACC inhibitor is indicated.

E19. Use of a compound according to any of E1 to E10 for the manufacture of a medicament for the treatment of acne.

E20. A compound according to any of E1 to E10 for use in the treatment of a disorder for which an ACC inhibitor is indicated.

Compounds of the invention that have the same molecular formula but differ in the nature or sequence of bonding of their atoms or the arrangement of their atoms in space are termed "isomers". Isomers that differ in the arrangement of their atoms in space are termed "stereoisomers". These stereoisomers are "R" or "S" depending on the configuration of substituents around the chiral carbon atom. The terms "R"

and "S" used herein are configurations as defined in IUPAC 1974 Recommendations for Section E, Fundamental Stereochemistry, Pure Appl. Chem., 1976, 45: 13-30. The enantiomers of the present invention indicated by (R), (S), or * are substantially free of the other enantiomer. "Substantially free" means that the enantiomeric excess is greater than about 90%, preferably greater than about 95%, and more preferably greater than about 99%. Within the context of enantiomeric excess, the term "about" means±1.0%. The symbol * designates a chiral carbon atom as either (R) or (S) stereochemistry depending on the configuration of substituents around the chiral carbon atom. The present invention contemplates various stereoisomers and mixtures thereof that are specifically included within the scope of this invention. Stereoisomers include enantiomers and mixtures of enantiomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution include, but are not limited to, (1) attachment of a chiral auxiliary to a mixture of enantiomers, separation of the resulting mixture of diastereomers by recrystallization or chromatography and liberation of the optically pure product from the auxiliary or (2) direct separation of the mixture of optical enantiomers on chiral chromatographic columns. Compounds of the present invention not designated (R), (S), or * may exist as racemates (i.e., 50% (R) and 50% (S)) or as a mixture of two enantiomers wherein one enantiomer is in excess. For example, enantiomeric mixtures may include the (R) enantiomer in 51% and the (S) enantiomer in 49% or vice versa or any combination of (R) and (S) other than the racemic mixture of 50% (R) and 50% (S).

Included within the scope of the described compounds are all isomers (e.g., cis-, trans-, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds. Stereoisomeric mixtures, e.g., mixtures of diastereomers, can be separated into their corresponding isomers in a known manner by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands. The present invention includes all pharmaceutically acceptable isotopically labelled compounds of formula I or a pharmaceutically acceptable salt thereof, wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically labelled compounds of formula I or a pharmaceutically acceptable salt thereof, for example, those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically labeled compounds of formula I can generally be prepared by conventional techniques known to those skilled in the art or by processes analogous to those described in the accompanying Examples and Preparations using an appropriate isotopically labeled reagent in place of the non-labeled reagent previously employed.

In some embodiments, the disclosure provides deuterium-labeled (or deuterated) compounds and salts, where the formula and variables of such compounds and salts are each and independently as described herein. "Deuterated" means that at least one of the atoms in the compound is deuterium in an abundance that is greater than the natural abundance of deuterium (typically approximately 0.015%). A skilled artisan recognized that in chemical compounds with a hydrogen atom, the hydrogen atom actually represents a mixture of H and D, with about 0.015% being D. The concentration of the deuterium incorporated into the deuterium-labeled compounds and salt of the invention may be defined by the deuterium enrichment factor.

"Deuterium enrichment factor" as used herein means the ratio between the deuterium abundance and the natural abundance of deuterium, each relative to hydrogen abundance. An atomic position designated as having deuterium typically has a deuterium enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

It is understood that one or more deuteriums may exchange with hydrogen under physiological conditions.

In some embodiments, the disclosure provides a deuterium compound of Formula I in place of the non-labeled reagent previously employed, or a pharmaceutically acceptable salt thereof.

In some embodiments, $R^1$ is selected from $CH_3$, $CH_2D$, $CHD_2$ and CDs.

In some embodiments, the deuterium compound of Formula I is selected from any one of the compounds set forth in the Examples section.

In some embodiments, metabolically labile sites in the compounds of the invention are deuterated.

Isotopically-labeled compounds of the invention may generally be prepared by conventional techniques known to those skilled in the art or by processes analogous to those described in the accompanying Examples and Preparations using an appropriate isotopically-labeled reagent in place of the non-labeled reagent previously employed. It is also well recognized in the art that some variation of natural isotopic abundance can occur in synthesized compounds, which can depend on the origin of the synthetic materials used in the syntheses of the compounds.

The deuterium enrichment of the compounds provided herein can be determined using conventional analytical methods known to one of ordinary skill in the art, including mass spectrometry, nuclear magnetic resonance spectroscopy, and crystallography.

Pharmaceutically acceptable solvates in accordance with the invention include those wherein the solvent of crystallization may be isotopically substituted, e.g., $D_2O$, $d_6$-acetone, $d_6$-DMSO.

In therapeutic use for treating disorders in a mammal, a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Pharmaceutically acceptable salts of the compound of formula I or a pharmaceutically acceptable salt thereof, include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of a compound of formula I or a pharmaceutically acceptable salt thereof, may be prepared, respectively, by one or more of three methods: (i) by reacting the compound of formula I with the desired acid or base; (ii) by removing an acid- or base-labile protecting group from a suitable precursor of a compound of formula I or by ring-opening a suitable cyclic precursor, for example, a lactone or lactam, using the desired acid or base; or (iii) by converting one salt of a compound of formula I to another by reaction with an appropriate acid or base or by means of a suitable ion exchange column. All three reactions are typically carried out in solution. The resulting salt may precipitate out and be collected by filtration or may be recovered by evaporation of the solvent. The degree of ionization in the resulting salt may vary from completely ionized to almost non-ionized.

Pharmaceutical compositions of the present invention may be manufactured by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in Remington's Pharmaceutical Sciences, Mack Pub. Co., New Jersey (1991). The formulations of the invention can be designed to be short-acting, fast-releasing, long-acting, and sustained-releasing. Thus, the pharmaceutical formulations can also be formulated for controlled release or for slow release.

Pharmaceutical compositions suitable for use in the present invention include compositions wherein the active ingredients are contained in an amount sufficient to achieve the intended purpose, i.e., control or the treatment of disorders or diseases. More specifically, a therapeutically effective amount means an amount of compound effective to prevent, alleviate or ameliorate symptoms/signs of disease or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 to about 100 mg/kg of body weight/day, preferably about 0.1 to about 10 mg/kg of body weight/day, more preferably about 0.3 to 3 mg/kg of body weight/day, even more preferably about 0.3 to 1.5 mg/kg of body weight/day It is to be understood that the dosages may vary depending upon the requirements of each subject and the severity of the disorders or diseases being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired concentration at the site of action. On the other hand, the initial dosage may be smaller than the optimum and the daily dosage may be progressively increased during the course of treatment depending on the particular situation. If desired, the daily dose may also be divided into multiple doses for administration, e.g., two to four times per day.

The invention also includes the following embodiments:

a compound of I or a pharmaceutically acceptable salt thereof, or pharmaceutically acceptable solvate of said compound or salt, as defined in any of the embodiments described herein, for use as a medicament;

a compound of I or a pharmaceutically acceptable salt thereof, or pharmaceutically acceptable solvate of said compound or salt as defined in any of the embodiments described herein, for use in the treatment of selected from inflammation, autoimmune disease, neuroinflammation, arthritis, rheumatoid arthritis, spondyloarthropathies, systemic lupus erythematous, lupus nephritis, osteoarthritis, gouty arthritis, pain, fever, pulmonary sarcoidosis, silicosis, cardiovascular disease, atherosclerosis, myocardial infarction, thrombosis, congestive heart failure and cardiac reperfusion injury, cardiomyopathy, stroke, ischemia, reperfusion injury, brain edema, brain trauma, neurodegeneration, liver disease, inflammatory bowel disease, Crohn's disease, ulcerative colitis, nephritis, retinitis, retinopathy, macular degeneration, glaucoma, diabetes (type 1 and type 2), diabetic neuropathy, viral and bacterial infection, myalgia, endotoxic shock, toxic shock syndrome, osteoporosis, multiple sclerosis, endometriosis, menstrual cramps, vaginitis, candidiasis, cancer, fibrosis, obesity, muscular dystrophy, polymyositis, autoimmune hepatitis, primary biliary cirrhosis, primary sclerosing cholangitis, vitiligo, Alzheimer's disease, skin flushing, eczema, psoriasis, atopic dermatitis, sunburn, keloid, hand dermatitis, contact dermatitis, allergic contact dermatitis, irritant contact dermatitis, neurodermatitis, perioral dermatitis, stasis dermatitis, dyshidrotic eczema, xerotic dermatitis, nummular dermatitis, seborrheic dermatitis, seborrhea, oily skin, eyelid dermatitis, diaper dermatitis, dermatomyositis, scleroderma, hypertrophic scar, morphea, frontal fibrosing alopecia, cicatricial alopecia, lichen planus, lichen sclerosis, alopecia areata, vitiligo, rosacea, rosacea-like dermatitis, steroid-induced dermatitis, drug eruptions (including papulopustular drug eruption), epidermolysis bullosa, keratosis pilaris, *pityriasis* alba, pemphigus, vulvovaginitis, acne (including but not limited to acne vulgaris, nodular acne, nodulocystic acne, cystic acne, conglobate acne, steroid acne), and autoinflammatory syndromes (including but not limited to PAPA, PAPASH, PASS, PASH, SAPHO, PCO, and SH], and acne scar), chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, palmoplantar pustulosis, pemphigoid, sweet's syndrome, hidradenitis suppurativa, nail psoriasis, flexural psoriasis, intractable wounds, sebaceous hyperplasia, Fordyce's condition (Fordyce's granules; Fordyce's spots), Fox-Fordyce's disease, osmidrosis (bromhidrosis), hirsutism, or skin tumors (nevus sebaceous, sebaceous adenoma, sebaceoma, sebaceous epithelioma, steatocytoma simplex, steatocytoma multiplex, Muir-Torre syndrome, sebaceous carcinoma, hypertrophic scar, rheumatic diseases, urticaria, discoid lupus, central nervous system lupus, psoriatic arthritis, asthma, allergic asthma, type I interferonopathies including Aicardi-Goutieres syndrome and other mendelian diseases of overexpression of type I interferon, primary progressive multiple sclerosis, relapsing remitting multiple sclerosis, non-alcoholic fatty liver disease, non-alcoholic steatohepatitis, scleroderma, alopecia areata, spondylopathy, myositis, vasculitis, pemphigus, lupus, major depression disorder, allergy, dry eye syndrome, transplant rejection, cancer, septic shock, cardiopulmonary dysfunction, acute respiratory disease, ankylosing spondylitis, cachexia, chronic graft-versus-host disease, acute graft-versus-host disease, Celiac Sprue, idiopathic thrombocytopenic thrombotic purpura, myasthenia gravis, Sjogren's syndrome, epidermal hyperplasia, cartilage inflammation, bone degradation, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, reactive arthritis, Reter's Syndrome, myolitis, polymyolitis, dermatomyolitis, polyarteritis nodosa, Wegener's granulomatosis, arteritis, polymyalgia rheumatica, sarcoidosis, sclerosis, primary biliary sclerosis, sclerosing cholangitis, dermatitis, Still's disease, chronic obstructive pulmonary disease, Guillain-Barre disease, Graves' disease, Addison's disease, Raynaud's phenomenon, psoriatic epidermal hyperplasia, plaque psoriasis, guttate psoriasis, inverse psoriasis, pustular psoriasis, erythrodermic psoriasis, an immune disorder associated with or arising from activity of pathogenic lymphocytes, noninfectious uveitis, Behcet's disease or Vogt-Koyanagi-Harada syndrome;

a method of treating a disease for which an inhibitor of ACC is indicated, in a subject in need of such treatment, comprising administering to the subject a therapeutically effective amount of a compound of formula I or a pharmaceutically acceptable salt thereof, or pharmaceutically acceptable solvate of said compound or salt as defined in any of the embodiments described herein;

the use of a compound of formula I or a pharmaceutically acceptable salt thereof, or pharmaceutically acceptable solvate of said compound or salt as defined in any of the embodiments described herein, for the manufacture of a medicament for treating a disease or condition for which an inhibitor of ACC is indicated; and, a pharmaceutical composition for the treatment of a disease or condition for which an inhibitor of ACC is indicated, comprising a compound of formula I or a pharmaceutically acceptable salt thereof, or pharmaceutically acceptable solvate of said compound or salt as defined in any of the embodiments described herein.

The present invention also provides any of the uses, methods or compositions as defined above wherein the compound of formula I or a pharmaceutically acceptable salt thereof, or pharmaceutically acceptable solvate of said compound or salt, is used in combination with another pharmacologically active compound, particularly one of the functionally defined classes or specific compounds listed below. These agents may be administered as part of the same or separate dosage forms, via the same or different routes of administration, and on the same or different administration schedules according to standard pharmaceutical practice known to one skilled in the art.

Suitable agents for use in combination therapy with a compound of formula I or a pharmaceutically acceptable salt thereof, or pharmaceutically acceptable solvate of said compound or salt, sulfasalazine, mesalazine, prednisone, azathioprine, infliximab, adalimumab, belimumab, becertolizumab, natalizumab, vedolizumab, hydrocortisone, budesonide, cyclosporin, tacrolimus, fexofenadine, 6-mercaptopurine, methotrexate, ursodeoxycholic acid, obeticholic acid, anti-histamines, rifampin, prednisone, methotrexate, azathioprine, cyclophosphamide, hydroxychloroquine, mofetil, sodium mycophenolate, tacrolimus, leflunomide, chloroquine and quinacrine, thalidomide, rituxan, NSAIDs, solumedrol, depomedrol and dexamethasone.

Other suitable agents for use in combination therapy with a compound of formula I, or a pharmaceutically acceptable salt thereof, or pharmaceutically acceptable solvate of said compound or salt, include: a retinoid, antibiotics, benzoyl peroxide, an ITK or TRK inhibitor, a 5-lipoxygenase activating protein (FLAP) antagonist; a leukotriene antagonist (LTRA) such as an antagonist of LTB4, LTC4, LTD4, LTE4, CysLT1 or CysLT2, e.g., montelukast or zafirlukast; a histamine receptor antagonist, such as a histamine type 1 receptor antagonist or a histamine type 2 receptor antagonist, e.g., loratidine, fexofenadine, desloratidine, levocetirizine, methapyrilene or cetirizine; an α1-adrenoceptor agonist or an α2-adrenoceptor agonist, e.g., phenylephrine, methoxamine, oxymetazoline or methylnorephrine; a muscarinic M3 receptor antagonist, e.g. tiotropium or ipratropium; a dual muscarinic M3 receptor antagononist/β2 agonist; a PDE inhibitor, such as a PDE3 inhibitor, a PDE4 inhibitor or a PDE5 inhibitor, e.g., theophylline, sildenafil, vardenafil, tadalafil, ibudilast, cilomilast or roflumilast; sodium cromoglycate or sodium nedocromil; a cyclooxygenase (COX) inhibitor, such as a non-selective inhibitor (e.g., aspirin or ibuprofen) or a selective inhibitor (e.g. celecoxib or valdecoxib); a glucocorticosteroid, e.g., fluticasone, mometasone, dexamethasone, prednisolone, budesonide, ciclesonide or beclamethasone; an anti-inflammatory monoclonal antibody, e.g., infliximab, adalimumab, tanezumab, ranibizumab, bevacizumab or mepolizumab; a β2 agonist, e.g., salmeterol, albuterol, salbutamol, fenoterol or formoterol, particularly a long-acting β2 agonist; an integrin antagonist, e.g., natalizumab; an adhesion molecule inhibitor, such as a VLA-4 antagonist; a kinin B1 or B2 receptor antagonist; an immunosuppressive agent, such as an inhibitor of the IgE pathway (e.g., omalizumab) or cyclosporine; a matrix metalloprotease (MMP) inhibitor, such as an inhibitor of MMP-9 or MMP-12; a tachykinin NK1, NK2 or NK3 receptor antagonist; a protease inhibitor, such as an inhibitor of elastase, chymase or catheopsin G; an adenosine A2a receptor agonist; an adenosine A2b receptor antagonist; a urokinase inhibitor; a dopamine receptor agonist (e.g., ropinirole), particularly a dopamine D2 receptor agonist (e.g., bromocriptine); a modulator of the NFκB pathway, such as an IKK inhibitor; a further modulator of a cytokine signaling pathway such as an inhibitor of JAK kinase, syk kinase, p38 kinase, SPHK-1 kinase, Rho kinase, EGF-R or MK-2; a mucolytic, mucokinetic or anti-tussive agent; an antibiotic; an antiviral agent; a vaccine; a chemokine; an epithelial sodium channel (ENaC) blocker or Epithelial sodium channel (ENaC) inhibitor; a nucleotide receptor agonist, such as a P2Y2 agonist; a thromboxane inhibitor; niacin; a 5-lipoxygenase (5-LO) inhibitor, e.g., Zileuton; an adhesion factor, such as VLAM, ICAM or ELAM; a CRTH2 receptor (DP2) antagonist; a prostaglandin D2 receptor (DP1) antagonist; a haematopoietic prostaglandin D2 synthase (HPGDS) inhibitor; interferon-β; a soluble human TNF receptor, e.g., Etanercept; a HDAC inhibitor; a phosphoinositotide 3-kinase gamma (PI3Kγ) inhibitor; a phosphoinositide 3-kinase delta (PI3Kδ) inhibitor; a CXCR-1 or a CXCR-2 receptor antagonist; an IRAK-4 inhibitor; diacylglycerol acyltransferase-1 (DGAT1) or a diacylglycerol acyltransferase-2 (DGAT2) inhibitor and, a TLR-4 or TLR-9 inhibitor, including the pharmaceutically acceptable salts of the specifically named compounds and the pharmaceutically acceptable solvates of said specifically named compounds and salts. The agents may be administered with another active agent, wherein the second active agent may be administered either orally or topically.

Accordingly, the invention provides methods of treating or preventing a disease, condition or disorder associated with ACC in a subject, such as a human or non-human mammal, comprising administering an effective amount of one or more compounds described herein to the subject in need thereof.

One way of carrying out the invention is to administer a compound of formula I in the form of a prodrug. Thus, certain derivatives of a compound of formula I which may have little or no pharmacological activity themselves can, when administered into or onto the body, be converted into a compound of formula I having the desired activity, for example by hydrolytic cleavage, particularly hydrolytic cleavage promoted by an esterase or peptidase enzyme. Such derivatives are referred to as "prodrugs." Further information on the use of prodrugs may be found in "Prodrugs as Novel Delivery Systems," Vol. 14, ACS Symposium Series (T. Higuchi and W. Stella) and "Bioreversible Carriers in Drug Design," Pergamon Press, 1987 (Ed. E. B. Roche, American Pharmaceutical Association). Reference can also be made to Nature Reviews/Drug Discovery, 2008, 7, 355 and Current Opinion in Drug Discovery and Development, 2007, 10, 550.

Prodrugs in accordance with the invention can, for example, be produced by replacing appropriate functionalities present in the compounds of formula I with certain moieties known to those skilled in the art as 'pro-moieties' as described, for example, in 'Design of Prodrugs' by H. Bundgaard (Elsevier, 1985).

Thus, a prodrug in accordance with the invention is (a) an ester or amide derivative of a carboxylic acid in a compound of formula I; (b) an ester, carbonate, carbamate, phosphate or ether derivative of a hydroxyl group in a compound of formula I; (c) an amide, imine, carbamate or amine derivative of an amino group in a compound form formula I; (d) a thioester, thiocarbonate, thiocarbamate or sulfide derivatives of a thiol group in a compound of formula I; or, (e) an oxime, enol ester or imine derivative of a carbonyl group in a compound of formula I.

Some specific examples of prodrugs in accordance with the invention include:

(i) where the compound of formula I contains a carboxylic acid functionality (—COOH), an ester thereof, such as a compound wherein the hydrogen of the carboxylic acid functionality of the compound of formula I is replaced by $C_1$-$C_8$ alkyl (e.g., ethyl) or ($C_1$-$C_8$ alkyl)C(═O)$OCH_2$— (e.g., t-BuC(═O)$OCH_2$—);

(ii) where the compound of formula I contains an alcohol functionality (—OH), an ester thereof, such as a compound wherein the hydrogen of the alcohol functionality of the compound of formula I is replaced by —CO($C_1$-$C_8$ alkyl) (e.g., methylcarbonyl) or the alcohol is esterified with an amino acid;

(iii) where the compound of formula I contains an alcohol functionality (—OH), an ether thereof, such as a compound wherein the hydrogen of the alcohol functionality of the compound of formula I is replaced by ($C_1$-$C_8$ alkyl)C(═O)OCH$_2$— or —CH$_2$OP(═O)(OH)$_2$;

(iv) where the compound of formula I contains an alcohol functionality (—OH), a phosphate thereof, such as a compound wherein the hydrogen of the alcohol functionality of the compound of formula I is replaced by —P(═O)(OH)$_2$ or —P(═O)(ONa)$_2$ or —P(═O)(O—)$_2$Ca$^{2+}$;

(v) where the compound of formula I contains a primary or secondary amino functionality (—NH2 or —NHR where R≠H), an amide thereof, for example, a compound wherein, as the case may be, one or both hydrogens of the amino functionality of the compound of formula I is/are replaced by ($C_1$-$C_{10}$)alkanoyl, —COCH2NH2 or the amino group is derivatized with an amino acid;

(vi) where the compound of formula I contains a primary or secondary amino functionality (—NH$_2$ or —NHR where R≠H), an amine thereof, for example, a compound wherein, as the case may be, one or both hydrogens of the amino functionality of the compound of formula I is/are replaced by —CH$_2$OP(═O)(OH)$_2$.

(vii) where the ketone functionality of compound of formula I is replaced by an oxime, an imine or an enol ester.

Certain compounds of formula I may themselves act as prodrugs of other compounds of formula I. It is also possible for two compounds of formula I to be joined together in the form of a prodrug. In certain circumstances, a prodrug of a compound of formula I may be created by internally linking two functional groups in a compound of formula I, for instance by forming a lactone.

References to compounds of formula I are taken to include the compounds themselves and prodrugs thereof. The invention includes such compounds of formula I as well as pharmaceutically acceptable salts of such compounds and pharmaceutically acceptable solvates of said compounds and salts.

Also included within the scope of the invention are active metabolites of compounds of formula I, that is, compounds formed in vivo upon administration of the drug, often by oxidation, reduction or dealkylation. Some examples of metabolites in accordance with the invention include (i) where the compound of formula I contains a methyl group, an hydroxymethyl derivative thereof (—CH$_3$→—CH$_2$OH or —CH$_3$→—COOH):

(ii) where the compound of formula I contains an alkoxy group, a hydroxy derivative thereof (—OR→—OH);

(iii) where the compound of formula I contains a tertiary amino group, a secondary amino derivative thereof (—NRR'→—NHR or —NHR');

(iv) where the compound of formula I contains a secondary amino group, a primary derivative thereof (—NHR→—NH$_2$);

(v) where the compound of formula I contains a phenyl moiety, a phenol derivative thereof (-Ph→-PhOH); and (vi) where the compound of formula I contains an amide group, a carboxylic acid derivative thereof (—CONH$_2$→COOH).

(vii) where the compound of formula I contains a carbonyl group thereof (—C═O(R))→—CHOH(R))

A compound of formula I can be administered per se, or in the form of a pharmaceutical composition, which, as active constituent contains an efficacious dose of at least one compound of the invention, in addition to customary pharmaceutically innocuous excipients and/or additives.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

Compounds of formula I may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of formula I may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %. In one embodiment of the present invention, lubricants comprise from 0.5 weight % to 3 weight % of the tablet. Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated. Formulations of tablets are discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula I, a film-forming polymer, a binder, a solvent, a humectant, a plasticizer, a stabilizer or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO-A-00/35298.

Compounds of formula I may also be administered directly into the blood stream, into muscle, or into an internal organ. Such parenteral administration includes intravenous, intraarterial, intraperitoneal, intrathecal, intraventricular, intraurethral, intrasternal, intracranial, intramuscular, intra-articular and subcutaneous administration. Suitable devices for parenteral administration include needle (including microneedle) injectors, needle-free injectors and infusion techniques.

Compounds of formula I may also be administered topically to the skin or mucosa, that is, dermally or transdermally.

Parenteral formulations of compounds of the invention are typically aqueous solutions which may contain excipients such as salts, carbohydrates and buffers (preferably buffering to a pH of from 3 to 9). Formulations for parenteral administration may also be sterile non-aqueous solutions, or dried (e.g. lyophilized) forms to be administered on reconstitution with a suitable vehicle such as sterile, pyrogen-free water.

Pharmaceutical compositions for topical or transdermal administration of a compound of the invention include ointments, pastes, creams, lotions, gels, suppositories, powders, solutions, sprays, drops, inhalants and patches. The compound of the invention is admixed under sterile conditions with a pharmaceutically acceptable topical carrier and any preservatives or buffers as may be required. Compounds that are volatile may require admixture with formulating agents or with packaging materials to assure proper dosage delivery. Compounds of the invention that have poor skin permeability may require one or more permeation enhancers, whereas compounds rapidly absorbed through the skin may require formulation with absorption-retarding agents or barriers.

The term “pharmaceutically acceptable topical carrier” refers to a carrier medium, suitable for topical application, that provides appropriate delivery of an effective amount of a compound of the invention, such as an inactive liquid or cream vehicle capable of suspending or dissolving the compound. The skilled person will appreciate that this term encompasses carrier materials approved for use in topical cosmetics as well.

The terms “permeation enhancer” relates to an increase in the permeability of the skin, nail, hair, claw or hoof to the compound of the invention, so as to increase the rate and extent of permeation of the compound. The enhanced permeation can be observed, for example, by measuring the rate of diffusion of the drug through animal or human skin, nail, hair, claw or hoof using a diffusion cell apparatus. A diffusion cell is described by Merritt et al. Diffusion Apparatus for Skin Penetration, J of Controlled Release, 1 (1984) pp. 161-162.

The ointments, pastes, creams, lotions, gels, suppositories, powders, solutions, sprays, drops, inhalants and patches for topical administration may contain, in addition to a compound of the invention, one or more pharmaceutically acceptable excipients, such animal or vegetable fats, oils, waxes, paraffins, starch, tragacanth, cellulose derivatives, polyethylene glycols, silicones, bentonites, silicic acid, talc, zinc oxide, preservatives, antioxidants, fragrances, emulsifiers, dyes, inert fillers, anti-irritants, tackifiers, fragrances, opacifiers, antioxidants, gelling agents, stabilizers, surfactants, emollients, coloring agents, preservatives, buffering agents, permeation enhancers. Such excipients should not interfere with the effectiveness of the biological activity of the active agent and not be deleterious to the epithelial cells or their function.

Transdermal administration may be achieved by means of a transdermal patch. The transdermal patch may be of the ‘reservoir and porous membrane’ type or employ a ‘matrix system’.

The solubility of compounds of compounds of the invention used in the preparation of pharmaceutical compositions may be increased by the use of appropriate formulation techniques, such as the incorporation of solubility-enhancing agents.

The compounds of formula I can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin. Delivery by inhalation is the preferred route of administration for the compounds of the present invention.

The pressurized container, pump, spray, atomizer, or nebulizer contains a solution or suspension of the compound of formula I comprising, for example, ethanol, aqueous ethanol, or a suitable alternative agent for dispersing, solubilizing, or extending release of the compound, a propellant as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μl to 100 μl. A typical formulation may comprise a compound of formula I propylene glycol, sterile water, ethanol and sodium chloride. Alternative solvents which may be used instead of propylene glycol include glycerol and polyethylene glycol.

Suitable scents, such as a fruit or floral aroma may be added to those formulations of the invention intended for intranasal administration. Formulations for intranasal administration may be formulated to be immediate and/or modified release using, for example, PGLA. Modified release includes delayed, sustained, pulsed, controlled, targeted and programmed release.

Compounds of formula I may also be administered directly to the eye or ear, typically in the form of drops of a micronized suspension or solution in isotonic, pH-adjusted, sterile saline.

Compounds of formula I may be combined with soluble macromolecular entities, such as cyclodextrin and suitable derivatives thereof or polyethylene glycol-containing polymers, in order to improve their solubility, dissolution rate, taste, bioavailability and/or stability when using any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in international patent publications WO91/11172, WO94/02518 and WO98/55148.

In as much as it may be desirable to administer a combination of active compounds, for example, for the purpose of treating a particular disease or condition, it is within the scope of the present invention that two or more pharmaceutical compositions, at least one of which contains a compound of formula I may conveniently be combined in the form of a kit suitable for coadministration of the compositions. Thus, a kit of the invention comprises two or more separate pharmaceutical compositions, at least one of which contains a compound of formula I and means for separately retaining said compositions, such as a container, divided bottle, or divided foil packet. An example of such a kit is the familiar blister pack used for the packaging of tablets, capsules and the like. Such a kit is particularly suitable for administering different dosage forms, for example, oral and parenteral, for administering separate compositions at different dosage intervals, or for titrating the separate compositions against one another. To assist compliance, the kit typically comprises directions for administration and may be provided with a so-called memory aid.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by processes similar to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula I. It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in *Protective Groups in Organic Synthesis* by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

Compounds of formula I (shown generically as compound G) may be prepared from compounds A-G, as illustrated by Scheme 1 or Scheme 2. Compounds of formula A-G are commercially available or may be synthesized by those skilled in the art according to the literature or preparations described herein.

Scheme 1

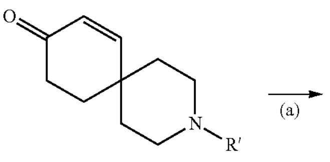

A

-continued

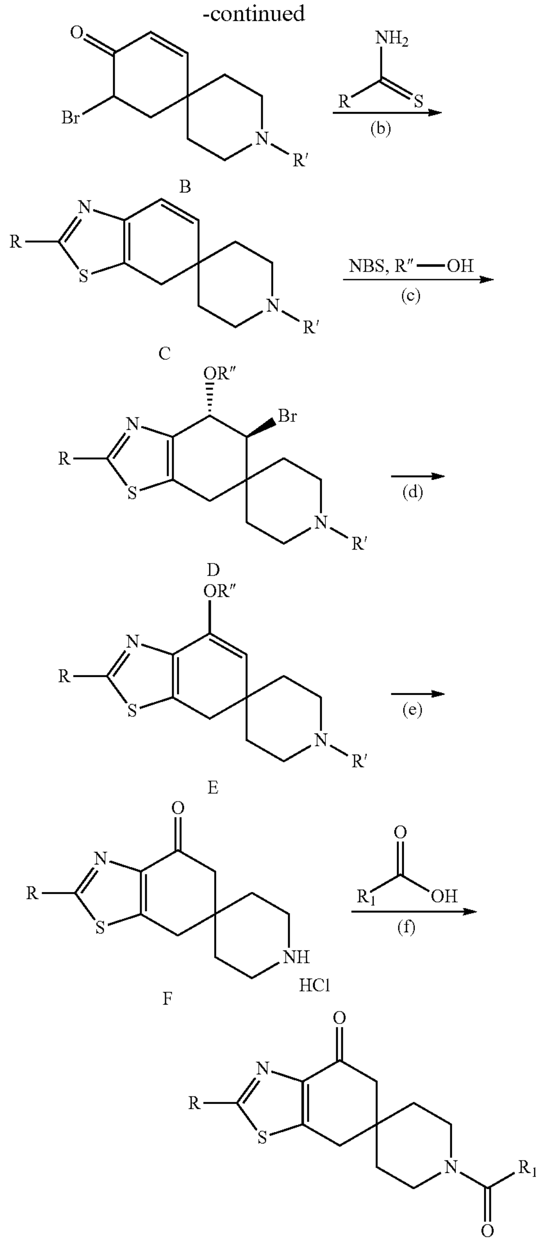

Compounds Prepared Via Scheme 1

Compounds of formula B may be prepared from compounds of formula A according to process step (a), a bromination under suitable conditions including treatment with TMS triflate in the presence of an organic base such as triethyl amine, followed by reaction with a brominating agent such as N-bromosuccinimide. Alternative conditions for step (b) include use of trimethyl-phenylammonium tribromide in THF at 25° C.

Compounds of formula C may be prepared from compounds of formula B according to process step (b), an annellation with 2,2-dimethylpropanethioamide under suitable basic conditions. Preferred conditions comprise pyridine in ethanol at about 80° C. Compounds of formula D may be prepared from compounds of formula C according to process step (c) bromo-alkoxylation, which may be effected using a brominating agent such as N-bromosuccinimide. in the presence of an alcohol. The reaction typically proceeds under ambient conditions.

Compounds of formula E may be prepared from compounds of formula D according to process step (d), an elimination reaction which is carried out using a nonnucleophilic base such as potassium tert-butoxide under ambient conditions in an inert solvent such as tetrahydrofuran. Compounds of formula F may be prepared from compounds of formula E according to process step (e), a deprotection/hydrolysis with a suitable acid such as hydrochloric acid in a mixed aqueous/organic solvent such as dioxane.

Compounds of formula G may be prepared from compounds of formula F according to process step (f), an acylation with a heteroaryl carboxylic acid under suitable basic conditions. Preferred conditions comprise N-ethyl-N-(propan-2-yl)propan-2-amine (DIPEA) in the presence of 1-[bis(dimethylamino)methylene]-1H-1,2,3-triazolo[4,5-b]pyridinium 3-oxide hexafluorophosphate (HATU). In alternative conditions, reagents may include propanephosphonic acid anhydride in the presence of triethylamine in a dipolar solvent such as DMF at 25° C. Other effective conditions include a water-soluble carbodiimide such as 1-ethyl-3-(3-dimethylaminopropyl)carbodiimide (EDCl) in the presence of hydroxybenzotriazole (HOBt) and triethylamine in DMF at 25° C.

Scheme 2

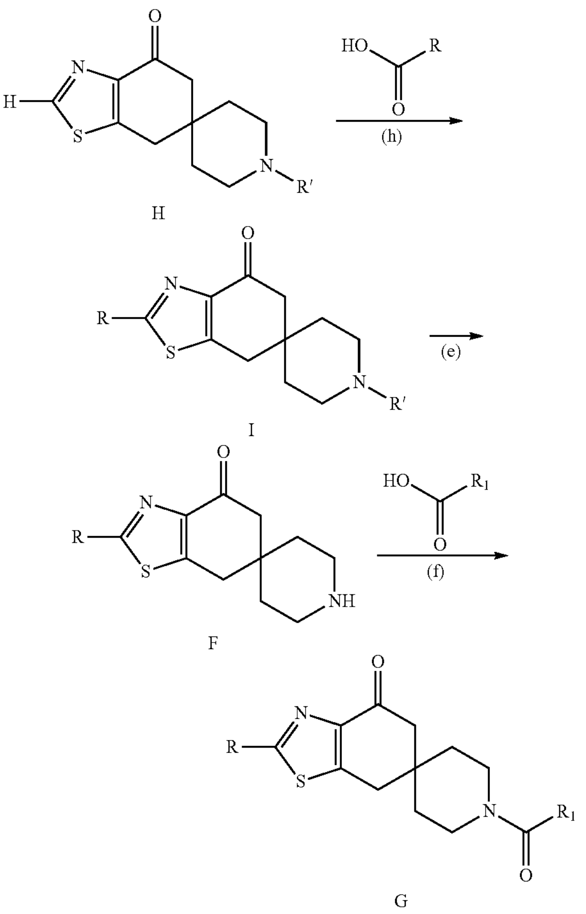

Compounds Prepared Via Scheme 2

Compounds of formula I may be prepared from compounds of formula H via Minisci coupling with a carboxylic acid using 9-mesityl-10-methyl acridinium perchlorate and irradiation Steps (e) and (f) follow the same processes as the ones described in Scheme 1

Accordingly, the derivatives of the formula I can be prepared by the procedures described in the general methods presented below or by routine modifications thereof. The present invention also encompasses any one or more of these processes for preparing the derivatives of formula I, in addition to any novel intermediates used therein. The person skilled in the art will appreciate that the following reactions may be heated thermally or under microwave irradiation.

In the non-limiting Examples and Preparation set out below that illustrate the invention, and in the aforementioned Scheme, the following the abbreviations, definitions and analytical procedures may be referred to:

AcOH: acetic acid
atm: atmosphere
aq: aqueous
$BOC_2O$: BOC anhydride, di-tert-butyl dicarbonate
br: broad
° C.: degrees Celsius
CBZ: carboxybenzyl; benzyloxycarbonyl
conc. or c.: concentrated
b: chemical shift
d: doublet
dd: doublet of doublets
ddd: doublet of doublet of doublets
dt: doublet of triplets
DCM: dichloromethane
DHP: dihydropyran
DMAC: N,N-dimethylacetamide
DMAP: 4-dimethylaminopyridine
DMF: dimethylformamide
DMSO: dimethyl sulfoxide
EDCl: 1-Ethyl-3-(3-dimethylaminopropyl)carbodiimide hydrochloride
ESI-MS: electrospray ionization mass spectrometry
EtOAc: ethyl acetate
$Et_3N$: triethylamine
equiv.: equivalent
g: gram
h: hour(s)
HATU: (1-[Bis(dimethylamino)methylene]-1H-1,2,3-triazolo[4,5-b]pyridinium 3-oxide
hexafluorophosphate
HOPO: 2-hydroxypyridine 1-oxide
HPLC: high pressure liquid chromatography
$iPr_2NEt$: N,N-diisopropylethylamine amine, Hunig's base
iPrOH: isopropanol, 2-propanol
Kg: Kilogram
KOtBu: potassium tert-butoxide
L: liter
LAH: Lithium aluminum hydride, $LiAlH_4$
LCMS: liquid chromatography mass spectrometry
LDA: Lithium diisopropylamide
LiHMDS: Lithium bis(trimethylsilyl)amide
M: multiplet
M: molar
MeCN: acetonitrile
MHz: mega Hertz
min: minutes
mL: milliliter
mm: millimeter
mmol: millimole
μmol: micromole
mol: mole
MS m/z: mass spectrum peak
MTBE: methyl tert-butyl ether
N: normal
n-BuLi: n-butyl lithium
NBS: N-bromosuccinimide
NCS: N-chlorosuccinimide
$NH_4OH$: 33 aq. ammonia
NMP: N-methyl pyrrolidine
NMR: nuclear magnetic resonance
$Pd_2(dba)_3$: Tris(dibenzylideneacetone)dipalladium(0)
Pd/C: palladium on carbon
PE: petroleum ether
Prep: preparatory
pTSA-$H_2O$: p-toluenesulfonic acid monohydrate
q: quartet
quint: quintet
RT: room temperature
s: singlet
sat.: saturated
SFC: supercritical fluid chromatography
t: triplet
t-BuOH: tert-butanol
TFA: trifluoroacetic acid
THF: tetrahydrofuran
TMSOTf: trimethylsilyl trifluoromethanesulfonate
TTBP $HBF_4$: tri-tert-butylphosphonium tetrafluoroborate
T3P: propylphosphonic anhydride
X-Phos: 2-dicyclohexylphosphino-2',4',6'-triisopropylbiphenyl
μm: micrometer
μL: microliter

GENERAL EXPERIMENTAL SECTION

Unless otherwise stated all reactions are run under a nitrogen atmosphere. The abbreviation RT refers to "room temperature" and is generally taken to mean approximately 22° C. (±5° C.). Unless otherwise stated, the term "concentrated" refers to the process of removal of volatile compounds such as solvents by use of a rotary evaporator under reduced pressure. The term "chromatography" refers to silica gel chromatography with mobile phase consisting of mixtures or gradients of either EtOAc/heptane or methanol/DCM or some combination thereof.

$^1H$ NMR spectra were in all cases consistent with the proposed structures. Characteristic δ for $^1H$ NMR are reported relative to residual solvent signals (for $CDCl_3$, δH=7.27 ppm; for DMSO-$d_6$, δH=2.50 ppm, for CD30D, δH=3.30 ppm) using conventional abbreviations for designation of major peaks. The skilled person will appreciate that tautomers may be recorded within the NMR data and some exchangeable protons may not be visible. Likewise, the skilled person will appreciate that a mixture of rotamers may be recorded within the NMR data.

Mass spectra were recorded using either ESI-MS. Where relevant and unless otherwise stated the m/z data provided are for isotopes $^{19}F$, 35Cl, $^{79}Br$ and/or $^{81}Br$.

Where silica gel chromatography, preparative HPLC or SFC chromatography have been used, the skilled person will appreciate that any suitable solvent or solvent combination may be employed to purify the desired compound.

Nomenclature for the compounds of the Preparations and Examples that follow was generated using ChemDraw Professional 19.0, Perkin Elmer, in accordance with the IUPAC (International Union of Pure and Applied Chemistry).

Amidation Methods

A) To a mixture of carboxylic acid (1.0 equiv.) was added DIPEA (4.0 equiv.) in DMF (c=0.14 M), followed by HATU (1.5 equiv.). The resulting mixture was stirred at about 15° C. for about 10 min, then amine (1.0 equiv.) was added to the mixture. The reaction was stirred for about 16 h at about 15° C. The reaction was filtered, and the filtrate was purified by prep HPLC.

B) To the carboxylic acid (1.0 equiv.) was added TPTU stock solution (1.5 equiv., 0.30 M in DMF), followed by amine (1.0 equiv., 0.20 M stock solution in DMF) with 2 equiv. DIPEA (2.20 mmol, 383 μl). The mixture was stirred at about 65° C. for about 14 h. The solvent was evaporated under a stream of $N_2$ gas. The resulting residue was dissolved in DMSO, filtered, and purified by prep HPLC.

C) A mixture of amine (1.0 equiv.), acid (1.0 equiv.), and EDCl (1.5 equiv.) in pyridine (final concentration=65 mM) were heated to about 110° C. using a microwave reactor for about 30 min. The solvent was evaporated, and it was further purified by prep HPLC.

D) To a mixture of carboxylic acid (1.0 equiv.) under $N_2$, a solution of amine (1.0 equiv.) in DMF (c=0.25 M) and triethylamine (6.0 equiv.) were added. The resulting mixture was stirred at about 23° C. for about 5 min, then cooled in an ice/water bath for another 5 min. T3P (50% in DMF) was slowly added (2.0 equiv.) dropwise to the reaction mixture over 10 min. The reaction was slowly warmed to about 15° C. over about 1.5 h, after which time $H_2O$ (3× volume of the reaction mixture) was added. The workup mixture was filtered, and the precipitate was collected, which was dried and purified by prep HPLC.

Preparation 1: 2-(tert-butyl)-5H-spiro[benzo[d]thiazole-6,4'-piperidin]-4(7H)-one hydrochloride salt (P1)

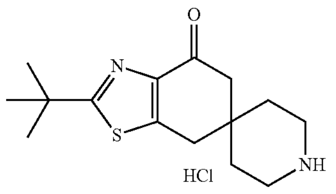 [SMILES: CC(C)(C)c1nc2c(s1)CC1(CCNCC1)CC2=O ; Cl]

Step 1: Synthesis of tert-butyl 2-(tert-butyl)-7H-spiro[benzo[d]thiazole-6,4'-piperidine]-1'-carboxylate (C1)

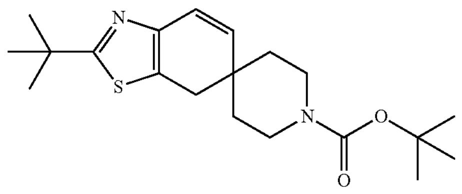 [SMILES: CC(C)(C)OC(=O)N1CCC2(C=Cc3nc(C(C)(C)C)sc3C2)CC1]

To a solution of tert-butyl 9-oxo-3-azaspiro[5.5]undec-7-ene-3-carboxylate (CAS: 873924-07-3; 160 g, 603 mmol) in DCM (2.4 L) was added $Et_3N$ (251 mL, 1.81 mol). The solution was cooled to about −78° C. and a solution of TMSOTf (164 mL, 904 mmol) in DCM (800 mL) was added dropwise. The solution was stirred at about −78° C. for about 30 min, then warmed to about 0° C. and stirred for about 2 h at about 0° C. The solution was cooled to about −78° C. and a suspension of NBS (118 g, 663 mmol) in DCM (800 mL) was added. The mixture was stirred at about −78° C. for about 2 h, then warmed to about 0° C. $Boc_2O$ (52.6 g, 241 mmol) was added, and the mixture was stirred at about 0° C. for about 2 h. Saturated $NaHCO_3$ (aq) (1.6 L) was added, and the organic phase was separated and concentrated under reduced pressure. To the residue was added 2,2-dimethylpropanethioamide (84.8 g, 723 mmol), pyridine (436 mL, 542 mmol), and EtOH (2.1 L). The solution was heated to about 80° C. for about 16 h and then cooled to about 23° C. The mixture was washed with saturated $NaHCO_3$ (aq) (2.0 L) and the organic phase was concentrated under reduced pressure. The residue was purified by column chromatography (silica, petroleum ether:EtOAc=1:0 to 3:1) to provide the title compound (149 g, 68%). $^1H$ NMR (400 MHz, $CDCl_3$) δ=6.65 (d, 1H), 5.87 (d, 1H), 3.57-3.51 (m, 2H), 3.40-3.33 (m, 2H), 2.82 (s, 2H), 1.71-1.67 (m, 2H), 1.53-1.48 (m, 2H), 1.46 (s, 9H), 1.43 (s, 9H); LC/MS m/z $(M+H)^+$=363.1.

Step 2: Synthesis of 2-(tert-butyl)-5H-spiro[benzo[d]thiazole-6,4'-piperidin]-4(7H)-one hydrochloride (P1)

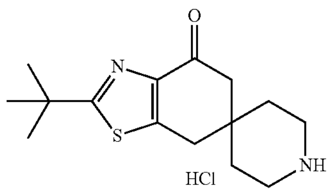 [SMILES: CC(C)(C)c1nc2c(s1)CC1(CCNCC1)CC2=O ; Cl]

To compound C1 (188 g, 519 mmol) was added MeOH (1.88 L). The solution was cooled to about 15° C. and NBS (96.9 g, 545 mmol) was added in batches. The resulting mixture was stirred at about 15° C. for about 2 h and concentrated under reduced pressure. To the residue was added THF (2.5 L) and the resulting solution was cooled to about 15° C. KOtBu (1 M in THF, 2.1 L) was added and the solution was stirred at about 15° C. for 16 h. Water (4.9 L) was added and the mixture was extracted with isopropyl acetate (3×2.8 L). The combined organic phases were concentrated under reduced pressure to provide crude tert-butyl 2-(tert-butyl)-4-methoxy-7H-spiro[benzo[d]thiazole-6,4'-piperidine]-1'-carboxylate (intermediate C1b). To the resulting residue was added additional intermediate C1b (21.6 g, 55 mmol) from a prior batch and dioxane (970 mL), followed by dropwise addition of HCl (4 M in dioxane, 2.26 L). The solution was stirred at about 25° C. for about 16 h and then concentrated under reduced pressure. MeOH (3.5 L) was added and the solution was heated to about 60° C. and cooled to about 25° C. The solution was concentrated under reduced pressure to remove 2.8 L of MeOH. The resulting mixture was stirred at about 25° C. for about 16 h. EtOAc (2.0 L) was added, and the resulting mixture was stirred at about 25° C. for about 16 h. The resulting slurry was filtered, and the cake was dried under reduced pressure at about 40° C. to afford the title compound (157 g, 87%). $^1$H NMR (400 MHz, DMSO-d6) δ=9.01 (br s, 1H), 8.93 (br s, 1H), 3.22 (s, 2H), 3.06 (br s, 4H), 2.62 (s, 2H), 1.76-1.65 (m, 4H), 1.37 (s, 9H); LC/MS m/z $(M+H)^+$=279.2.

Preparation 2: 5-methyl-2-(methylamino)quinoline-7-carboxylic acid (P2)

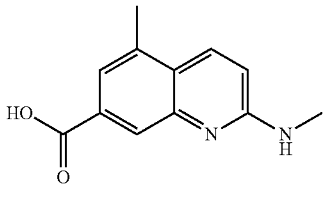 [SMILES: CNc1ccc2c(C)cc(C(=O)O)cc2n1]

Step 1: 7-bromo-N,5-dimethylquinolin-2-amine (C2)

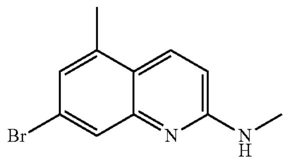

To a solution of 7-bromo-2-chloro-5-methylquinoline (8.96 g, 34.9 mmol, prepared by the method of Aciro, C. et al. PCT Int. Appl. (2013), WO 2013185103) in methylamine (175 mL of 2 M solution in THF, 349 mmol) at about 25° C. was added cesium fluoride (10.6 g, 69.9 mmol). The mixture was heated to about 100° C. for about 48 h. The mixture was diluted with saturated $NH_4Cl$ (30 mL) and extracted with EtOAc. The combined organic phases were washed with brine (30 mL), dried over $MgSO_4$, filtered, and concentrated under reduced pressure. The residue was purified by SFC (Column: Chiral Tech OX-H, 30×250 mm, 5 μm; Mobile Phase A: carbon dioxide; Mobile phase B: MeOH/1% $NH_3$; 95%-70% B gradient, 3.5 min; flow rate 80 mL/min) to provide the title compound (2.81 g, 32%). LC/MS m/z $(M+H)^+$=252.1.

Step 2: methyl 5-methyl-2-(methylamino)quinoline-7-carboxylate (C3)

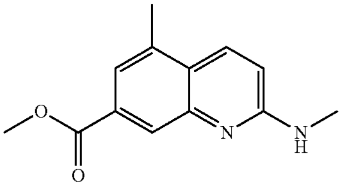

To a solution of compound C2 (1.15 g, 4.59 mmol) in MeOH (50 mL) was added triethylamine (2.0 mL, 14 mmol) and $Pd(dppf)Cl_2CH_2Cl_2$ (613 mg, 0.751 mmol). The solution was added to a Parr reactor and flushed with nitrogen three times. The reactor was flushed with CO three times, then sealed at about 75 PSI CO. The reactor was heated to about 80° C. for about 24 h. The solution was cooled to about 25° C. and diluted with EtOAc. The solution was washed with water and brine. The organic phase was dried over $Na_2SO_4$ and concentrated under reduced pressure. The residue was purified by column chromatography to provide the title compound (853 mg, 81%). LC/MS m/z $(M+H)^+$=231.3.

Step 3: 5-methyl-2-(methylamino)quinoline-7-carboxylic acid (P2)

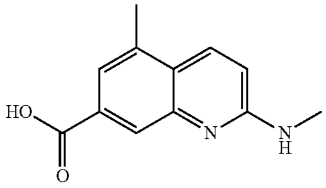 [SMILES: CNc1ccc2c(C)cc(C(=O)O)cc2n1]

To a solution of compound C3 (840 mg, 3.65 mmol) in THF (18 mL) was added 1 M sodium hydroxide (22 mL, 22 mmol). The solution was stirred at about 25° C. for about 16 h. HCl (1 M) was added dropwise until a precipitate formed (pH ~5). The precipitate was filtered to provide the title compound (789 mg, 88%). $^1$H NMR (400 MHz, DMSO-d6) δ 8.01 (d, 1H), 7.94 (s, 1H), 7.49 (s, 1H), 7.11 (d, 1H), 6.86 (d, 1H), 2.91 (d, 3H), 2.55 (s, 3H); LC/MS m/z $(M+H)^+$=217.2.

Preparation 3: 2-(tert-butyl)-5H-spiro[benzo[d]thiazole-6,4'-piperidin]-4(7H)-one hydrochloride salt (P3)

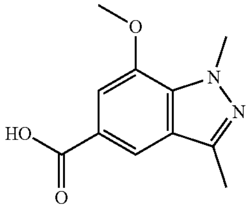 [SMILES: COc1cc(C(=O)O)cc2c(C)nn(C)c12]

Step 1: Synthesis of 4-(1,3-dimethyl-1H-pyrazol-4-yl)-3-(ethoxycarbonyl)but-3-enoic acid

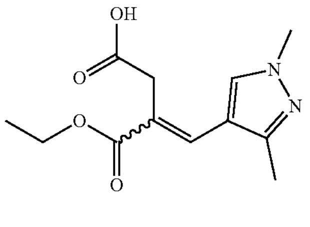 [SMILES: CCOC(=O)C(=Cc1cn(C)nc1C)CC(=O)O]

To a solution of solid KOtBu (36.2 g, 322 mmol) in ethanol (200 mL) at about 25° C. was added 1,3-dimethyl- 1H-pyrazole-4-carbaldehyde (CAS: 25016-21-0; 20 g, 160 mmol) and diethyl succinate (42.1 g, 40 mL, 242 mmol). The reaction was heated at about 80° C. for about 18 h, then cooled to RT and quenched using AcOH (23 mL, 403 mmol). The reaction mixture was concentrated to about (40 mL) and heptane (2×100 mL) was added, and reaction mixture concentrated. The reaction was cooled to about 0-10° C., charged with water (200 mL) and the pH of the aqueous layer adjusted to 4-5 with aqueous HCl. The resulting suspension was filtered and rinsed with water (60 mL). The solids were dried to provide the title compound (33.4 g, 82.1%). $^1$H NMR (400 MHz, Methanol-d4) δ 7.81 (s, 1H), 7.63 (s, 1H), 4.25 (q, 2H), 3.85 (s, 3H), 3.53 (s, 2H), 2.28 (s, 3H), 1.32 (t, 2H); LC/MS m/z $(M+H)^+$=253.1.

Step 2: Synthesis of ethyl 7-acetoxy-1,3-dimethyl-1H-indazole-5-carboxylate (C5)

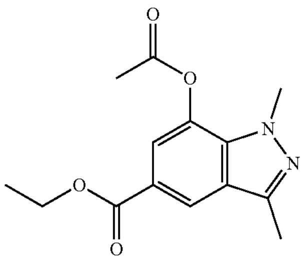 [SMILES: CCOC(=O)c1cc(OC(C)=O)c2c(c1)c(C)nn2C]

To a solution of compound C4 (32.0 g, 126.9 mmol) in DMAC (128 mL) was added sodium acetate (26.0 g, 317 mmol) and acetic anhydride (32 mL, 2.67 mmol). The reaction was heated at about 95-105° C. for about 18 h, then cooled to about 0-10° C., and water (512 mL) was added dropwise. The resulting suspension was filtered and rinsed with water (100 mL). The precipitate was recrystallized using water and dried to provide the title compound (28.8 g, 82.9%). $^1$H NMR (400 MHz, Methanol-d4) δ 8.33 (s, 1H), 7.76 (s, 1H), 4.42 (q, 2H), 4.11 (s, 3H), 2.59 (s, 3H), 2.47 (s, 3H), 1.44 (t, 3H); %); LC/MS m/z $(M+H)^+$=277.1.

Step 3: Synthesis of ethyl 7-hydroxy-1,3-dimethyl-1H-indazole-5-carboxylate (C6)

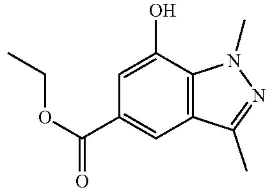 [SMILES: CCOC(=O)c1cc(O)c2c(c1)c(C)nn2C]

To a solution of compound C5 (1.11 g, 4.0 mmol) in ethanol (16 mL) was added potassium carbonate (2.76 g, 5.0 mmol). The reaction was heated at reflux for about 1.5 h and then concentrated. The residue was diluted with EtOAc (25 mL) and water (25 mL) and pH of the aqueous layer was adjusted to 4-5 with aqueous citric acid. The organic layer was separated, washed with brine (25 mL), dried over $MgSO_4$, filtered, and concentrated, residue was diluted with hexanes (25 mL) and the resulting mixture concentrated under reduced pressure, dried using high vacuum around 50° C. to provide the title compound (0.89 g, 95% yield) as a light pink solid. $^1$H NMR (400 MHz, DMSO-d6) δ 10.47 (s, 1H), 7.81 (d, 1H), 7.26 (s, 1H), 4.29 (q, 2H), 4.15 (s, 3H), 2.45 (s, 3H), 1.33 (t, 3H); LC/MS m/z $(M+H)^+$=235.1.

Step 4: Synthesis of ethyl 7-methoxy-1,3-dimethyl-1H-indazole-5-carboxylate (C7)

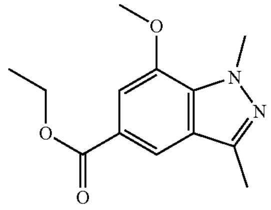 [SMILES: CCOC(=O)c1cc(OC)c2c(c1)c(C)nn2C]

To a solution of compound C6 (0.7 g, 3.0 mmol) in acetone (20 mL) was added potassium carbonate (0.83 g, 6.0 mmol) and methyl iodide (0.64 g, 0.28 mL, 4.5 mmol). The reaction was heated at reflux for about 24 h and then concentrated. The residue was diluted with water (25 mL) and extracted with EtOAc (2×25 mL). The combined EtOAc extracts were washed with brine (25 mL), dried over $MgSO_4$, filtered, and concentrated. The residue was purified by chromatography (silica, 0-25% EtOAc in hexanes) to provide the title compound (0.71 g, 95.3% yield) as a white solid. $^1$H NMR (400 MHz, Chloroform-d) δ 8.04 (s, 1H), 7.37 (s, 1H), 4.44 (q, 2H), 4.27 (s, 3H), 4.03 (s, 3H), 2.59 (s, 3H), 1.46 (t, 3H); LC/MS m/z $(M+H)^+$=249.1.

Step 5: Synthesis of 7-methoxy-1,3-dimethyl-1H-indazole-5-carboxylic acid (P3)

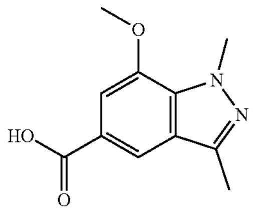 [SMILES: COc1cc(C(=O)O)cc2c(C)nn(C)c12]

To compound C7 (0.3 g, 1.21 mmol) in EtOH (4.8 mL), THF (4.3 mL), was added 1N NaOH (4.83 mL, 4.83 mmol). The mixture was heated to about 45° C. for about 2 h, then cooled to about 25° C. and concentrated. The residue was diluted with water (2 mL), the pH of aqueous layer adjusted to 4-5 using 1.5 M citric acid. The resulting suspension was filtered and rinsed with water (5 mL). The precipitate was dried at 50° C. to provide the title compound (0.23 g, 86.4%). $^1$H NMR (400 MHz, Methanol-d4) δ 7.99 (d, J=1.2 Hz, 1H, 4), 7.38 (d, J=1.2 Hz, 1H, 2), 4.19 (s, 3H, 16), 4.00 (s, 3H, 10), 2.51 (s, 3H, 11); LC/MS m/z $(M+H)^+$=221.1.

EXAMPLES

Example 1: 1'-(3,7-dimethyl-2H-indazole-5-carbonyl)-2-(1-methylcyclopropyl)-5H-spiro[benzo[d]thiazole-6,4'-piperidin]-4(7H)-one

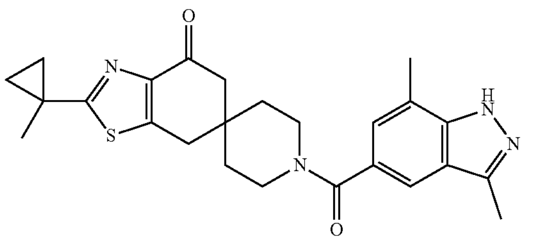 [SMILES: Cc1n[nH]c2c(C)cc(C(=O)N3CCC4(CC3)CC(=O)c3nc(C5(C)CC5)sc3C4)cc12]

A solution of 2-(1-methylcyclopropyl)-5H-spiro[benzo[d]thiazole-6,4'-piperidin]-4(7H)-one, prepared like compound P1, (0.06 g, 0.22 mmol), 3,7-dimethyl-1H-indazole-5-carboxylic acid (0.05 g, 0.26 mmol), EDCl HCl (0.08 g, 0.43 mmol), and pyridine (2 mL) was microwaved at about 110° C. for about 30 min. The resulting mixture was filtered, and the residue was purified by prep-HPLC (Column: YMC Actus Triart C18, 150×30 mm, 5 μm); Mobile Phase A: water (0.225% v/v formic acid); Mobile Phase B: MeCN; 30-50% B gradient, 11 min, hold at 100% B for 2 min; flow rate 35 mL/min to provide the title compound (15 mg, 16%). $^{1}H$ NMR (400 MHz, Methanol-d4) b 7.64 (d, 1H), 7.20 (t, 1H), 3.79 (m, 2H), 3.55 (m, 2H), 3.21 (s, 2H), 2.70 (s, 2H), 2.56 (s, 3H), 2.55 (s, 3H), 1.64 (s, 4H), 1.55 (s, 3H), 1.29 (q, 2H), 1.04-0.95 (m, 2H); LC/MS m/z $(M+H)^+$=449.4.

Example 2: 1'-(3,7-dimethyl-1H-indazole-5-carbonyl)-2-(1-methylcyclobutyl)-5H-spiro[benzo[d]thiazole-6,4'-piperidin]-4(7H)-one

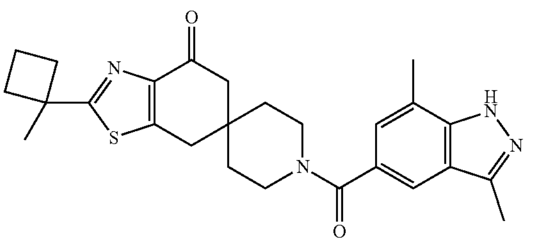 [SMILES: Cc1n[nH]c2c(C)cc(C(=O)N3CCC4(CC3)CC(=O)c3nc(C5(C)CCC5)sc3C4)cc12]

A solution of 2-(1-methylcyclobutyl)-5H-spiro[benzo[d]thiazole-6,4'-piperidin]-4(7H)-one, prepared like compound P1, (0.022 g, 0.077 mmol), 3,7-dimethyl-1H-indazole-5-carboxylic acid (0.017 g, 0.092 mmol), EDCl HCl (0.029 g, 0.154 mmol), and pyridine (1 mL) was microwaved at about 110° C. for about 30 min. The resulting mixture was filtered, and the residue was purified by prep-HPLC using water/acetonitrile (Column: Sunfire C18, 19×100 mm, 5 μm) to provide the title compound (6.9 mg, 19%). LC/MS m/z $(M+H)^+$=463.3.

Example 3: 1'-(3,7-dimethyl-1H-indazole-5-carbonyl)-2-(2,3-dimethylbutan-2-yl)-5H-spiro[benzo[d]thiazole-6,4'-piperidin]-4(7H)-one

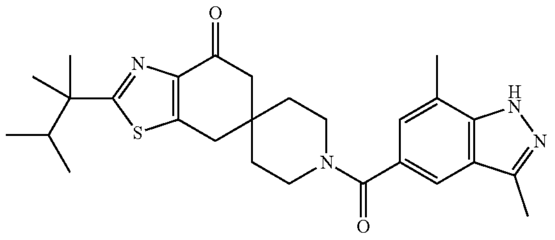 [SMILES: Cc1n[nH]c2c(C)cc(C(=O)N3CCC4(CC3)CC(=O)c3nc(C(C)(C)C(C)C)sc3C4)cc12]

Step 1: Synthesis of tert-butyl 2-(2,3-dimethylbutan-2-yl)-4-oxo-4,7-dihydro-5H-spiro[benzo[d]thiazole-6,4'-piperidine]-1'-carboxylate (C8)

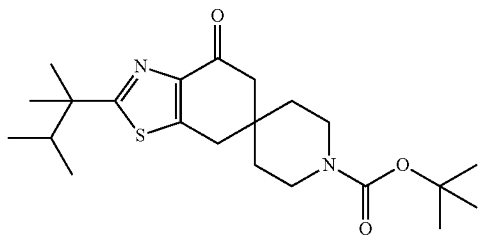 [SMILES: CC(C)C(C)(C)c1nc2c(s1)CC1(CCN(C(=O)OC(C)(C)C)CC1)CC2=O]

To a solution of tert-butyl 4-oxo-4,7-dihydro-5H-spiro[benzo[d]thiazole-6,4'-piperidine]-1'-carboxylate, prepared like compound P1, (0.1 g, 0.31 mmol) in acetonitrile (1.5 mL) and water (1.5 mL) was added 2,2,3-trimethylbutanoic acid (0.121 g, 0.93 mmol), $Na_2HPO_4$ (0.132 g, 0.93 mmol) and 9-mesityl-10-methyl acridinium perchlorate (3.83 g, 0.0093 mmol). The reaction mixture was irradiated with a 72 W blue LED strip for about 60 h. The resulting mixture was filtered, and the residue was purified by prep-HPLC (Column: Phenomenex Gemini-NX C18, 50×250 mm, 10 μm); Mobile Phase A: water (0.05% v/v conc. $NH_4OH$); Mobile Phase B: MeCN; 63-83% B gradient, 9 min, hold at 100% B for 2 min; flow rate 25 mL/min to provide the title compound (30 mg, 23.8%). $^{1}H$ NMR (400 MHz, Methanol-d4) δ 3.52-3.44 (m, 4H), 3.20 (s, 2H), 2.68 (s, 2H), 2.12 (h, 1H), 1.60 (m, 4H), 1.47 (s, 9H), 1.38 (s, 6H), 0.88 (s, 3H), 0.87 (s, 3H); LC/MS m/z $(M+H)^+$=407.4.

Step 2: Synthesis of 2-(2,3-dimethylbutan-2-yl)-5H-spiro[benzo[d]thiazole-6,4'-piperidin]-4(7H)-one (C9)

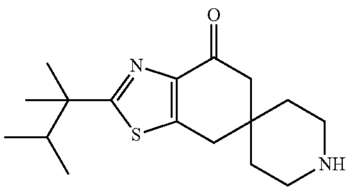 [SMILES: CC(C)C(C)(C)c1nc2c(s1)CC1(CCNCC1)CC2=O]

To a solution of compound C8 (0.03 g, 0.074 mmol) in MeOH (2 mL) was added 4 N HCl in dioxane (1 mL) and stirred at about 20° C. for about 2 h. The reaction mixture was concentrated to give yellow oil, acetonitrile (2×5 mL) was added, and reaction was concentrated under reduced pressure, dried in vacuum to provide title compound (25 mg, 99%). LC/MS m/z $(M+H)^+$=307.1.

Step 3: Synthesis of 1'-(3,7-dimethyl-1H-indazole-5-carbonyl)-2-(2,3-dimethylbutan-2-yl)-5H-spiro[benzo[d]thiazole-6,4'-piperidin]-4(7H)-one

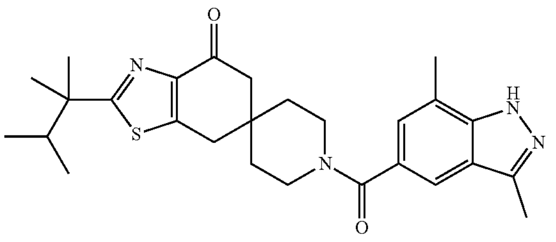 [SMILES: Cc1n[nH]c2c(C)cc(C(=O)N3CCC4(CC3)CC(=O)c3nc(C(C)(C)C(C)C)sc3C4)cc12]

A solution of 2-(2,3-dimethylbutan-2-yl)-5H-spiro[benzo[d]thiazole-6,4'-piperidin]-4(7H)-one, (0.015 g, 0.08 mmol), 3,7-dimethyl-1H-indazole-5-carboxylic acid (0.025 g, 0.07 mmol), EDCl HCl (0.027 g, 0.146 mmol), and pyridine (2 mL) was microwaved at about 110° C. for about 30 min. The resulting mixture was concentrated, and the residue was purified by prep-HPLC (Column: Phenomenex Gemini-NX C18, 40×80 mm, 3 μm); Mobile Phase A: water (0.05% v/v conc. $NH_4OH$); Mobile Phase B: MeCN; 31-71% B gradient, 9 min, hold at 100% B for 2 min; flow rate 25 mL/min to provide the title compound (5.56 mg, 16%). $^1H$ NMR (400 MHz, Methanol-$d_4$) b 7.67 (dd, 1H), 7.23 (t, 1H), 3.82 (m, 2H), 3.58 (m, 2H), 3.27 (s, 2H), 2.76 (s, 2H), 2.55 (s, 3H), 2.54 (s, 3H), 2.12 (h, 1H), 1.53 (m, 4H), 1.37 (s, 6H), 0.88 (s, 3H), 0.87 (s, 3H); LC/MS m/z $(M+H)^+$=479.4.

Example 4: 1'-(3,7-dimethyl-1H-indazole-5-carbonyl)-2-(1-methylcyclopentyl)-5H-spiro[benzo[d]thiazole-6,4'-piperidin]-4(7H)-one

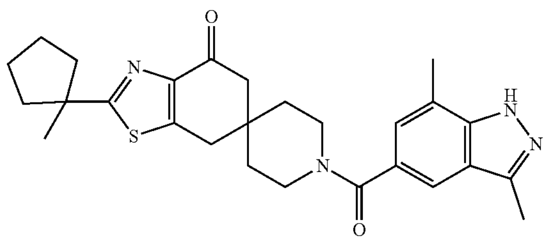 [SMILES: Cc1n[nH]c2c(C)cc(C(=O)N3CCC4(CC3)CC(=O)c3nc(C5(C)CCCC5)sc3C4)cc12]

A solution of 2-(1-methylcyclopentyl)-5H-spiro[benzo[d]thiazole-6,4'-piperidin]-4(7H)-one, prepared like compound C9, (0.024 g, 0.07 mmol), 3,7-dimethyl-1H-indazole-5-carboxylic acid (0.015 g, 0.07 mmol), EDCl HCl (0.027 g, 0.141 mmol), and pyridine (2 mL) was microwaved at about 110° C. for about 30 min. The resulting mixture was filtered, and the residue was purified by prep-HPLC (Column: Phenomenex Gemini-NX C18, 40×80 mm, 3 μm); Mobile Phase A: water (0.05% v/v conc. $NH_4OH$); Mobile Phase B: MeCN; 29-69% B gradient, 9 min, hold at 100% B for 2 min; flow rate 25 mL/min to provide the title compound (7.2 mg, 21%). $^1H$ NMR (400 MHz, Methanol-d4) δ 7.66 (s, 1H), 7.22 (s, 1H), 3.82 (m, 2H), 3.59 (m, 2H), 3.27 (s, 2H), 2.75 (s, 2H), 2.58 (m, 6H), 2.19 (m, 2H), 1.86-1.75 (m, 7H), 1.68 (s, 3H), 1.46 (s, 3H); LC/MS m/z $(M+H)^+$=477.3.

Example 5: 1'-(3,7-dimethyl-1H-indazole-5-carbonyl)-2-(tert-pentyl)-5H-spiro[benzo[d]thiazole-6,4'-piperidin]-4(7H)-one

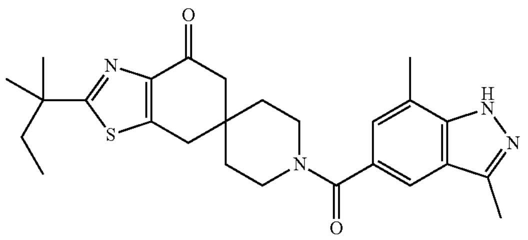 [SMILES: CCC(C)(C)c1nc2c(s1)CC1(CCN(C(=O)c3cc(C)c4[nH]nc(C)c4c3)CC1)CC2=O]

Prepared in the same manner as Example 3, substituting 2,2-dimethylbutanoic acid for 2,2,3-trimethylbutanoic acid in Step 1, to provide the title compound (8.3 mg). LC/MS m/z $(M+H)^+$=465.3.

Example 6: 1'-(3,7-dimethyl-1H-indazole-5-carbonyl)-2-ethyl-5H-spiro[benzo[d]thiazole-6,4'-piperidin]-4(7H)-one

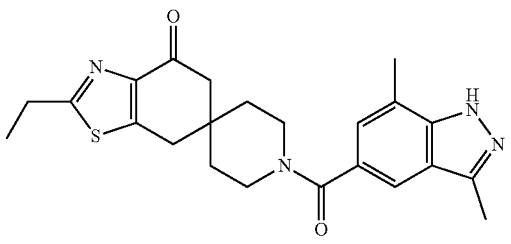 [SMILES: CCc1nc2c(s1)CC1(CCN(C(=O)c3cc(C)c4[nH]nc(C)c4c3)CC1)CC2=O]

According to amidation method A, 2-ethyl-5H-spiro[benzo[d]thiazole-6,4'-piperidin]-4(7H)-one, prepared like compound P1, (0.08 g, 0.28 mmol) was coupled with 3,7-dimethyl-1H-indazole-5-carboxylic acid (0.056 g, 0.28 mmol). The residue was purified by prep-HPLC (Column: Phenomenex Gemini-NX C18, 40×80 mm, 3 μm); Mobile Phase A: water (0.05% v/v conc. $NH_4OH$); Mobile Phase B: MeCN; 9-60% B gradient, 9 min, hold at 100% B for 2 min; flow rate 25 mL/min to provide the title compound (45 mg, 38%). $^1H$ NMR (400 MHz, Methanol-$d_4$) b 7.67 (d, 1H), 7.22 (d, 1H), 3.83 (m, 2H), 3.55 (m, 2H), 3.26 (s, 2H), 3.03 (q, 2H), 2.75 (s, 2H), 2.58 (s, 3H), 2.57 (s, 3H), 1.75 (m, 2H), 1.65 (m, 2H), 1.38 (t, 3H); LC/MS m/z $(M+H)^+$=423.1.

Example 7: 2-(bicyclo[1.1.1]pentan-1-yl)-1'-(3,7-dimethyl-1H-indazole-5-carbonyl)-5H-spiro[benzo[d]thiazole-6,4'-piperidin]-4(7H)-one

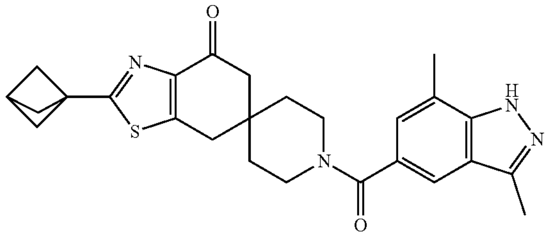 [SMILES: Cc1n[nH]c2c(C)cc(C(=O)N3CCC4(CC3)CC(=O)c3nc(C56CC(C5)C6)sc3C4)cc12]

According to amidation method A, 2-(bicyclo[1.1.1]pentan-1-yl)-5H-spiro[benzo[d]thiazole-6,4'-piperidin]-4(7H)-one, prepared like compound P1, (0.08 g, 0.28 mmol) was coupled with 3,7-dimethyl-1H-indazole-5-carboxylic acid (0.056 g, 0.28 mmol). The residue was purified by prep-HPLC (Column: Phenomenex Gemini-NX C18, 40×80 mm, 3 μm); Mobile Phase A: water (0.225% v/v formic acid); Mobile Phase B: MeCN; 19-59% B gradient, 9 min, hold at 100% B for 2 min; flow rate 25 mL/min to provide the title compound (28.5 mg, 40%). $^1$H NMR (400 MHz, Methanol-$d_4$) δ 7.66 (dd, 1H), 7.22 (t, 1H), 3.81 (s, 2H), 3.57 (s, 2H), 3.26 (s, 2H), 2.75 (s, 2H), 2.57 (s, 3H) 2.56 (s, 3H), 2.27 (s, 7H), 1.74 (s, 2H), 1.65 (s, 2H); LC/MS m/z $(M+H)^+$=461.4.

Example 8: 2-isopropyl-1'-(5-methyl-2-(methylamino)quinoline-7-carbonyl)-5H-spiro[benzo[d]thiazole-6,4'-piperidin]-4(7H)-one

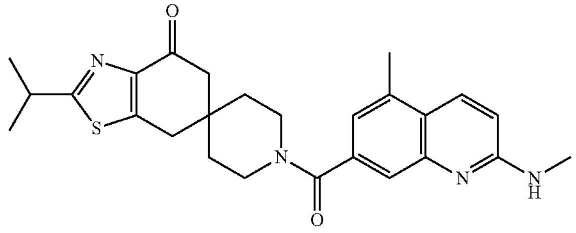 [SMILES: CNc1ccc2c(C)cc(C(=O)N3CCC4(CC3)CC(=O)c3nc(C(C)C)sc3C4)cc2n1]

According to amidation method A, 2-isopropyl-5H-spiro[benzo[d]thiazole-6,4'-piperidin]-4(7H)-one, prepared like compound P1, (0.034 g, 0.116 mmol) was coupled with 5-methyl-2-(methylamino)quinoline-7-carboxylic acid (0.03 g, 0.14 mmol). The residue was purified by prep-HPLC (Column: Phenomenex Gemini-NX C18, 40×80 mm, 3 μm); Mobile Phase A: water (0.225% v/v formic acid); Mobile phase B: MeCN; 20-50% B gradient, 9 min, hold at 100% B for 2 min; flow rate 25 mL/min to provide the title compound (23.2 mg, 36%). $^1$H NMR (400 MHz, Methanol-$d_4$) δ 8.06 (dd, 1H), 7.57-7.50 (m, 1H), 7.05 (dd, 1H), 6.83 (d, 1H), 3.85 (m, 2H), 3.55 (m, 2H), 3.31 (h, 1H), 3.27 (s, 2H), 3.03 (s, 3H), 2.75 (d, 2H), 2.61 (s, 3H), 1.78 (m, 2H), 1.66 (m, 2H), 1.40 (d, 6H); LC/MS m/z $(M+H)^+$=463.4.

Example 9: 1'-(5-methyl-2-(methylamino)quinoline-7-carbonyl)-2-(1-methylcyclopropyl)-5H-spiro[benzo[d]thiazole-6,4'-piperidin]-4(7H)-one

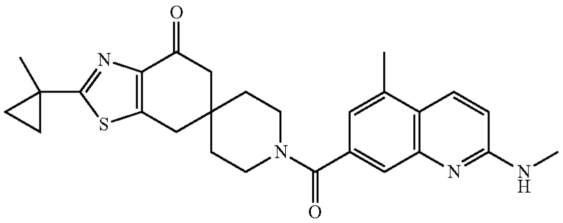 [SMILES: CNc1ccc2c(C)cc(C(=O)N3CCC4(CC3)CC(=O)c3nc(C5(C)CC5)sc3C4)cc2n1]

According to amidation method A, 2-(1-methylcyclopropyl)-5H-spiro[benzo[d]thiazole-6,4'-piperidin]-4(7H)-one, prepared like example P1, (0.036 g, 0.116 mmol) was coupled with 5-methyl-2-(methylamino)quinoline-7-carboxylic acid (0.03 g, 0.14 mmol). The residue was purified by prep-HPLC (Column: Boston Prime C18, 150×30 mm, 5 μm); mobile phase A: water (0.05% v/v conc. $NH_4OH$); mobile phase B: MeCN; 26-56% B gradient, 9 min, hold at 100% B for 2 min; flow rate 25 mL/min to provide the title compound (24.7 mg, 38%). $^1$H NMR (400 MHz, Methanol-$d_4$) δ 8.06 (dd, 1H), 7.57-7.50 (m, 1H), 7.05 (dd, 1H), 6.83 (d, 1H), 3.91-3.78 (m, 2H), 3.57-3.51 (m, 2H), 3.25 (s, 2H), 3.03 (s, 3H), 2.73 (d, 2H), 2.61 (s, 3H), 1.80-1.74 (m, 2H), 1.68-1.62 (m, 2H), 1.58 (s, 3H), 1.36-1.27 (m, 2H), 1.06-0.93 (m, 2H); LC/MS m/z $(M+H)^+$=475.4.

Example 10: 2-isopropyl-1'-(7-methoxy-1,3-dimethyl-1H-indazole-5-carbonyl)-5H-spiro[benzo[d]thiazole-6,4'-piperidin]-4(7H)-one

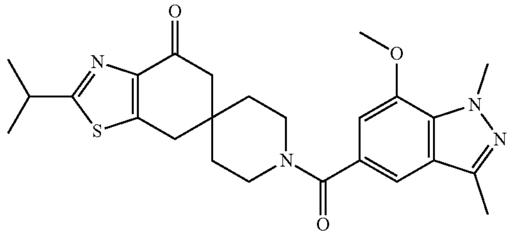 [SMILES: COc1cc(C(=O)N2CCC3(CC2)CC(=O)c2nc(C(C)C)sc2C3)cc2c(C)nn(C)c12]

According to amidation method A, 2-isopropyl-5H-spiro[benzo[d]thiazole-6,4'-piperidin]-4(7H)-one, prepared like example P1, (0.047 g, 0.159 mmol) was coupled with 7-methoxy-1,3-dimethyl-1H-indazole-5-carboxylic acid (0.035 g, 0.16 mmol). The residue was purified by prep-HPLC (Column: Boston Prime C18, 150×30 mm, 5 μm); mobile phase A: water (0.05% v/v formic acid); mobile phase B: MeCN; 14-54% B gradient, 9 min, hold at 100% B for 2 min; flow rate 25 mL/min to provide the title compound (17.7 mg, 24%). $^1$H NMR (400 MHz, Methanol-$d_4$) δ 7.35 (d, 1H), 6.87 (d, 1H), 4.21 (s, 3H), 4.02 (s, 3H), 3.80 (m, 2H), 3.61 (m, 2H), 3.29 (h, 1H), 3.27 (s, 2H), 2.75 (s, 2H), 2.51 (s, 3H), 1.71 (m, 4H), 1.40 (d, 6H); LC/MS m/z $(M+H)^+$=467.3.

Example 11: 1'-(7-methoxy-1,3-dimethyl-1H-indazole-5-carbonyl)-2-(1-methylcyclopropyl)-5H-spiro[benzo[d]thiazole-6,4'-piperidin]-4(7H)-one

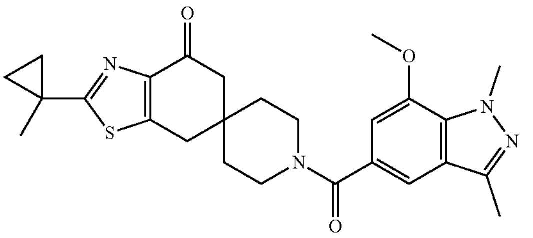 [SMILES: COc1cc(C(=O)N2CCC3(CC2)CC(=O)c2nc(C4(C)CC4)sc2C3)cc2c(C)nn(C)c12]

According to amidation method A, 2-(1-methylcyclopropyl)-5H-spiro[benzo[d]thiazole-6,4'-piperidin]-4(7H)-one, prepared like example P1, (0.05 g, 0.16 mmol) was coupled with 7-methoxy-1,3-dimethyl-1H-indazole-5-carboxylic acid (0.035 g, 0.16 mmol). The residue was purified by prep-HPLC (Column: YMC Triart C18, 150×25 mm, 5 μm); Mobile Phase A: water (0.05% v/v conc. $NH_4OH$); Mobile phase B: MeCN; 26-56% B gradient, 9 min, hold at 100% B for 2 min; flow rate 25 mL/min to provide the title compound (19 mg, 25%). $^1H$ NMR (400 MHz, Methanol-$d_4$) δ 7.35 (d, 1H), 6.86 (d, 1H), 4.21 (s, 3H), 4.02 (s, 3H), 3.83-3.76 (m, 2H), 3.63-3.57 (m, 2H), 3.24 (s, 2H), 2.73 (s, 2H), 2.51 (s, 3H), 1.72-1.66 (m, 4H), 1.58 (s, 3H), 1.36-1.27 (m, 2H), 1.07-0.97 (m, 2H); LC/MS m/z $(M+H)^+$=479.4.

Example 12: 1'-(7-methoxy-1,3-dimethyl-1H-indazole-5-carbonyl)-2-(2-(methyl-d3)propan-2-yl-1,1,1,3,3,3-d6)-5H-spiro[benzo[d]thiazole-6,4'-piperidin]-4(7H)-one

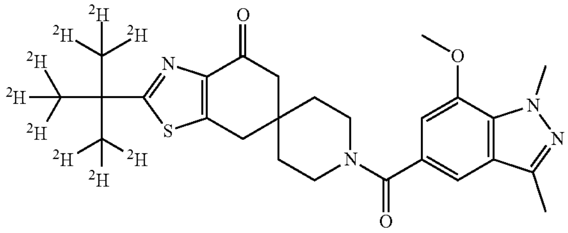 [SMILES: [2H]C([2H])([2H])C(c1nc2c(s1)CC1(CCN(C(=O)c3cc(OC)c4c(c3)c(C)nn4C)CC1)CC2=O)(C([2H])([2H])[2H])C([2H])([2H])[2H]]

To a solution of 2-(2-(methyl-d3)propan-2-yl-1,1,1,3,3,3-d6)-5H-spiro[benzo[d]thiazole-6,4'-piperidin]-4(7H)-one, prepared like preparation P1 (0.105 g, 0.366 mmol), 7-methoxy-1,3-dimethyl-1H-indazole-5-carboxylic acid (0.1 g, 0.454 mmol), EDCl HCl (0.126 g, 1.8 mmol), and HOBt (0.79 g, 0.586 mmol) in DMF (15 mL) at about 25° C. was added $Et_3N$ (0.51 mL, 3.66 mmol). The mixture was stirred at about 25° C. for about 16 h, then diluted with EtOAc (50 mL). The mixture was washed with saturated aqueous $Na_2CO_3$ (2×25 mL), and brine (2×25 mL). The organic phase was dried over $MgSO_4$, filtered, and concentrated. The residue was purified by chromatography (silica, EtOAc: Heptane's, 0-100%) to provide the title compound (0.15 g, 67.5%) as a white solid. $^1H$ NMR (400 MHz, Methanol-d4) δ 7.35 (s, 1H), 6.87 (s, 1H), 4.22 (s, 3H), 4.03 (s, 3H), 3.64 (m, 4H, 11), 3.28 (s, 2H), 2.76 (s, 2H), 2.52 (s, 3H), 1.72 (m, 4H); LC/MS m/z $(M+H)^+$=490.2.

Example 13: 2-(tert-butyl)-1'-(7-methoxy-1,3-dimethyl-1H-indazole-5-carbonyl)-5H-spiro[benzo[d]thiazole-6,4'-piperidin]-4(7H)-one

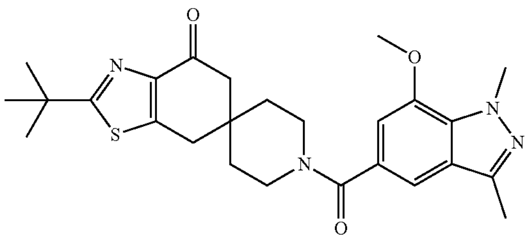 [SMILES: COc1cc(C(=O)N2CCC3(CC2)CC(=O)c2nc(C(C)(C)C)sc2C3)cc2c(C)nn(C)c12]

To a solution of preparation P1 (0.97 g, 3.1 mmol), preparation P3 (0.68 g, 3.1 mmol), EDCl HCl (0.89 g, 4.65 mmol), and HOBt (0.73 g, 4.65 mmol) in DMF (25.8 mL) at about 25° C. was added $^iPr_2NEt$ (2.97 mL, 17.0 mmol). The mixture was stirred at about 25° C. for about 16 h, then diluted with EtOAc (50 mL). The mixture was washed sequentially with 5% aqueous LiCl (25 mL), 0.5 N HCl (25 mL), saturated aqueous $NaHCO_3$ (20 mL), and 1:1 brine-water (30 mL). The organic phase was dried over $MgSO_4$, filtered, concentrated, heptane (2×25 mL) was added and resulting mixture was concentrated under reduced pressure. The residue product was purified by chromatography (silica, EtOAc/Hexanes, 0-100% then MeOH: EtOAc, 0-10%) to provide the title compound (1.05 g, 70.4% yield) as a white solid. $^1H$ NMR (400 MHz, $CDCl_3$) b 7.23 (s, 1H), 6.74 (s, 1H), 4.22 (s, 3H), 3.96 (s, 3H), 3.73 (m, 2H), 3.62 (m, 2H), 3.10 (s, 2H), 2.71 (s, 2H), 2.50 (s, 3H), 1.68 (m, 4H), 1.45 (s, 9H); LC/MS m/z $(M+H)^+$=481.3.

Example 14: 2-(tert-butyl)-1'-(7-ethoxy-1,3-dimethyl-1H-indazole-5-carbonyl)-5H-spiro[benzo[d]thiazole-6,4'-piperidin]-4(7H)-one

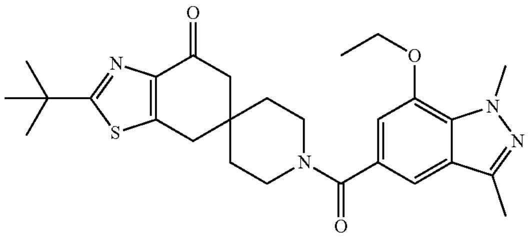 [SMILES: CCOc1cc(C(=O)N2CCC3(CC2)CC(=O)c2nc(C(C)(C)C)sc2C3)cc2c(C)nn(C)c12]

Step 1: Synthesis of ethyl 7-ethoxy-1,3-dimethyl-1H-indazole-5-carboxylate (C10)

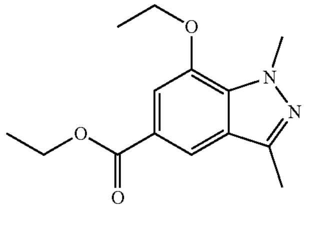 [SMILES: CCOC(=O)c1cc(OCC)c2c(c1)c(C)nn2C]

To a solution of compound C6 (0.328 g, 1.4 mmol) in acetone (9.3 mL) was added potassium carbonate (0.33 g, 1.7 mmol) and ethyl iodide (0.30 g, 0.16 mL, 1.96 mmol). The reaction was heated at reflux for about 24 h and then concentrated. The residue was diluted with water (25 mL) and extracted with EtOAc (2×25 mL). The combined EtOAc extracts, washed with brine (25 mL), dried over $MgSO_4$, filtered, and concentrated. The residue was purified by chromatography (silica, EtOAc/Hexanes, 0-25%) to provide the title compound (0.27 g, 74% yield) as a white solid. $^1H$ NMR (400 MHz, $CDCl_3$) δ 7.99 (s, 1H), 7.32 (s, 1H), 4.40 (q, 2H), 4.23 (s, 3H), 4.22 (q, 2H), 2.56 (s, 3H), 1.52 (t, 3H), 1.42 (t, 3H); LC/MS m/z $(M+H)^+$=263.1.

Step 2: Synthesis of 7-ethoxy-1,3-dimethyl-1H-indazole-5-carboxylic acid (C11)

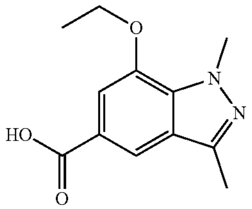 [SMILES: CCOc1cc(C(=O)O)cc2c(C)nn(C)c12]

To compound C10 (268 mg, 1.02 mmol) in EtOH (5.1 mL) and THF (5.1 mL) was added 1 M aqueous NaOH (5.1 mL, 5.1 mmol). The mixture was stirred at about 25° C. for about 17 h, then concentrated under reduced pressure. To the mixture was added 1.5 M aqueous citric acid (2.5 mL) and water (2 mL). After stirring for about 3 minutes, the precipitate was isolated via filtration to provide the title compound (230 mg, 96.3%). $^1H$ NMR (400 MHz, DMSO-d6) δ 12.78 (s, 1H), 7.91 (d, 1H), 7.27 (s, 1H), 4.22 (q, 2H), 4.16 (s, 3H), 2.46 (s, 3H), 1.45 (t, 3H).

Step 3: 2-(tert-butyl)-1'-(7-ethoxy-1,3-dimethyl-1H-indazole-5-carbonyl)-5H-spiro[benzo[d]thiazole-6,4'-piperidin]-4(7H)-one (Example 14)

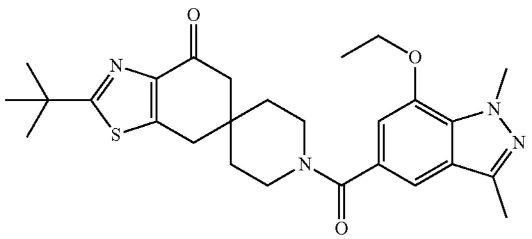

To a flask containing compound C11 (1.23 g, 5.0 mmol), EDCl·HCl (1.2 g, 6.25 mmol) and HOPO (0.694 mg, 6.25 mmol) was added acetonitrile (25.0 mL) followed by $^iPr_2NEt$ (2.18 mL, 2.5 mmol). The mixture was heated to about 50° C. for about 2 h and then cooled to room temperature. Preparation P1 (2.23 g, 5.5 mmol), $^iPr_2NEt$ (3.48 mL, 4.00 mmol) and water (5.0 mL) was added, and mixture heated again to about 50° C. for about 2 h, followed by stirring at room temperature for about 16 h. The reaction mixture was diluted with EtOAc (150 mL) and washed with water (2×100 mL). The aqueous layer was back extracted using EtOAc (50 mL). The combined EtOAc extracts were then washed with 0.25 N HCl (2×50 mL) and the aqueous layer back extracted using EtOAc (50 mL). The combined EtOAc extracts were then washed with saturated aqueous $NaHCO_3$ (2×50 mL) and aqueous layer back extracted using EtOAc (50 mL). The combined EtOAc extracts were washed with brine (50 mL), dried over $MgSO_4$, filtered over celite and concentrated to give light yellow solid (2.47 g, 99%). The solid was dissolved in EtOAc (20 ml) and heated to about 50° C. for about 10 min followed by addition of heptanes (200 mL) and further heating to about 70° C. for about 2 h. After cooling to room temperature, the mixture was stirred for about 72 h. The solid was filtered, washed with chilled premixed 25% EtOAc-Heptanes (100 mL), dried on high vacuum to provide the title compound (2.1 g, 84.9%). $^1H$ NMR (400 MHz, $CD_3OD$) δ 7.31 (s, 1H), 6.82 (s, 1H), 4.23 (q, 2H), 4.21 (s, 3H), 3.80-3.60 (m, 4H), 3.25 (s, 2H), 2.73 (s, 2H), 2.49 (s, 3H), 1.68 (m, 4H), 1.52 (t, 3H), 1.43 (s, 9H); LC/MS m/z $(M+H)^+$=495.1

Example 15: 2-(tert-butyl)-1'-(8-methyl-3-(methylamino)quinoline-6-carbonyl)-5H-spiro[benzo[d]thiazole-6,4'-piperidin]-4(7H)-one

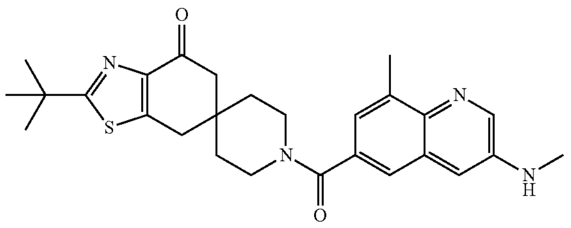 [SMILES: CNc1cnc2c(C)cc(C(=O)N3CCC4(CC3)CC(=O)c3nc(C(C)(C)C)sc3C4)cc2c1]

Step 1: Synthesis of ethyl 8-methylquinoline-6-carboxylate (C12)

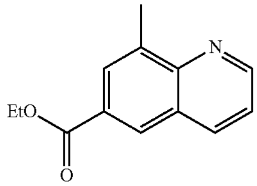 [SMILES: CCOC(=O)c1cc(C)c2ncccc2c1]

To a solution of 6-bromo-8-methylquinoline (900 mg, 4.05 mmol) in EtOH (25 mL) was added $Pd(OAc)_2$ (91 mg, 0.405 mmol), DBU (0.91 mL, 6.08 mmol), $Mo(CO)_6$ (588 mg, 2.23 mmol), and TTBP $HBF_4$ (118 mg, 0.405 mmol). The mixture was sparged with $N_2$ for about 1 min, sealed in a microwave tube, and irradiated in the microwave (Biotage Smith Synthesizer) at about 120° C. for about 70 min. The mixture was concentrated under reduced pressure to provide the crude residue. Purification by chromatography (0 to 25% EtOAc in petroleum ether) provided the title compound (800 mg, 92%). LC/MS m/z $(M+H)^+$=215.9.

Step 2: Synthesis of ethyl 3-bromo-8-methylquinoline-6-carboxylate (C13)

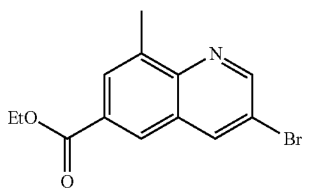 [SMILES: CCOC(=O)c1cc(C)c2ncc(Br)cc2c1]

The following reaction was carried out in 2 batches in parallel. To a solution of compound C12 (350 mg, 1.63 mmol) in $CCl_4$ (15 mL) was added pyridine (0.26 mL, 3.25 mmol) and $Br_2$ (0.10 mL, 1.95 mmol). The resulting solution was stirred at about 70° C. for about 4 h. The mixture was cooled to about 25° C. and poured into $H_2O$ (20 mL). The mixture was extracted with EtOAc (2×15 mL), washed with sat. aq. $NaHCO_3$ solution, dried over $Na_2SO_4$, filtered, and concentrated under reduced pressure. The 2 batches were combined, and the residue was purified by chromatography (0% to 20% EtOAc in petroleum ether) to provide the title compound (500 mg, 26% per reaction). $^1H$ NMR (400 MHz, DMSO-d6) δ=9.08 (d, 1H), 8.91 (d, 1H), 8.49 (s, 1H), 8.10 (s, 1H), 4.39 (q, 2H), 2.74 (s, 3H), 1.38 (t, 3H); LC/MS m/z $(M+H)^+$=295.8.

Step 3: ethyl 3-((tert-butoxycarbonyl)(methyl) amino)-8-methylquinoline-6-carboxylate (C14)

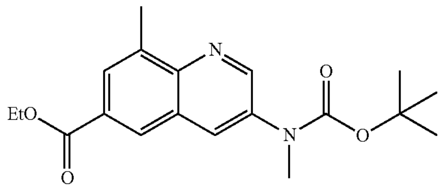 [SMILES: CCOC(=O)c1cc(C)c2ncc(N(C)C(=O)OC(C)(C)C)cc2c1]

To compound C13 (500 mg, 1.70 mmol) was added tert-butyl methylcarbamate (334 mg, 2.55 mmol), $Pd_2(dba)_3$ (78 mg, 0.085 mmol), X-Phos (81 mg, 0.17 mmol), $Cs_2CO_3$ (1.66 g, 5.1 mmol) and toluene (17 mL). The mixture was sparged with $N_2$. The mixture was stirred at about 120° C. for about 16 h. The mixture was cooled to about 25° C. and filtered. The filtrate was concentrated under reduced pressure and diluted with EtOAc (20 mL). The mixture was washed with $H_2O$ (3×5 mL), dried over $Na_2SO_4$, filtered, and concentrated under reduced pressure. The residue was purified by chromatography (0% to 30% EtOAc in petroleum ether) to provide the title compound (450 mg, 77%). LC/MS m/z $(M+H)^+$=345.2.

Step 4: 3-((tert-butoxycarbonyl)(methyl)amino)-8-methylquinoline-6-carboxylic acid (C15)

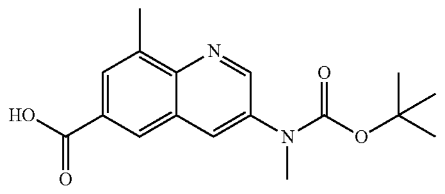 [SMILES: Cc1cc(C(=O)O)cc2cc(N(C)C(=O)OC(C)(C)C)cnc12]

To compound C14 (450 mg, 1.31 mmol) in MeOH (12 mL) and $H_2O$ (4.0 mL) was added $LiOH{\cdot}H_2O$ (164 mg, 3.92 mmol). The mixture was stirred at about 25° C. for about 4 h. The reaction mixture was concentrated under reduced pressure then diluted with $H_2O$ (10 mL). 1 N HCl was added until the pH was 3-4 and the mixture was extracted with EtOAc (2×20 mL). The combined organic phases were dried over $Na_2SO_4$, filtered, and concentrated under reduced pressure to provide the title compound (400 mg, 97%). $^1H$ NMR (400 MHz, DMSO-d6) δ=9.01 (d, 1H), 8.46 (s, 1H), 8.39 (d, 1H), 8.03 (s, 1H), 3.33 (s, 3H), 2.74 (s, 3H), 1.43 (s, 9H); LC/MS m/z $(M+H)^+$=317.3.

Step 5: 8-methyl-3-(methylamino)quinoline-6-carboxylic acid hydrochloride salt (C16)

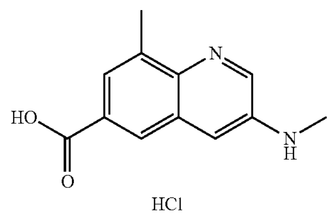 [SMILES: CNc1cnc2c(C)cc(C(=O)O)cc2c1 ; Cl]

To compound C15 (500 mg, 1.58 mmol) in dioxane (6.0 mL) was added 4 N HCl in dioxane (6.0 mL). The solution was stirred at about 25° C. for about 1.5 h, then concentrated under reduced pressure to provide the title compound (399 mg, 100%). LC/MS m/z $(M+H)^+$=217.0.

Step 6: Synthesis of 2-(tert-butyl)-1'-(8-methyl-3-(methylamino)quinoline-6-carbonyl)-5H-spiro[benzo[d]thiazole-6,4'-piperidin]-4(7H)-one (Example 15)

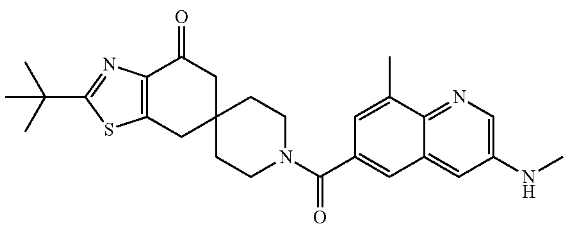 [SMILES: CNc1cnc2c(C)cc(C(=O)N3CCC4(CC3)CC(=O)c3nc(C(C)(C)C)sc3C4)cc2c1]

To a solution of compound C16 (200 mg, 0.79 mmol) in DMF (4.0 mL) was added HATU (301 mg, 0.79 mmol) and $iPr_2NEt$ (0.40 mL, 2.31 mmol). The mixture was stirred at about 25° C. for about 10 min. Then was added Preparation P1 (208 mg, 0.66 mmol). The mixture was stirred at about 25° C. for about 1 h. The residue was concentrated and purified by prep-HPLC (Column: Boston Prime C18, 30×150 mm, 5 μm; Mobile Phase A: water (0.05% v/v conc. $NH_4OH$); Mobile phase B: MeCN; 28-58% B gradient, 9 min, hold at 100% B for 2 min; flow rate 25 mL/min) to provide the title compound (229 mg, 61%). $^1H$ NMR (400 MHz, $CD_3OD$) δ=8.45 (d, 1H), 7.58 (d, 1H), 7.21 (dd, 1H), 7.10 (d, 1H), 3.83 (m, 2H), 3.52 (s, 2H), 3.25 (s, 2H), 2.89 (s, 3H), 2.73 (d, 2H), 2.69 (s, 3H), 1.70 (m, 4H), 1.43 (s, 9H). LC/MS m/z $(M+H)^+$=477.3.

Example 16: 2-(tert-butyl)-1'-(4-methyl-2-naphthoyl)-5H-spiro[benzo[d]thiazole-6,4'-piperidin]-4(7H)-one

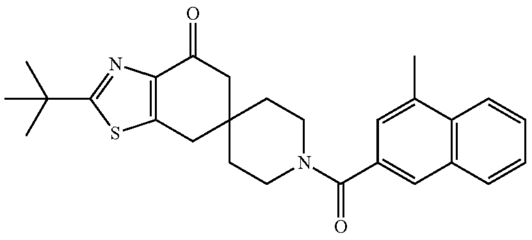 [SMILES: Cc1cc(C(=O)N2CCC3(CC2)CC(=O)c2nc(C(C)(C)C)sc2C3)cc2ccccc12]

Step 1: Synthesis of methyl 4-hydroxy-2-naphthoate (C17)

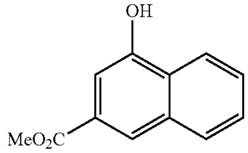 [SMILES: COC(=O)c1cc(O)c2ccccc2c1]

To a solution of 4-hydroxy-2-naphthoic acid (18.8 g, 100 mmol) in MeOH (500 mL) was added conc. $H_2SO_4$ (8.33 mL, 150 mmol) slowly than the reaction was refluxed for about 48 h. The solvent was concentrated under reduced pressure and the residue was diluted with EtOAc (250 mL), washed sequentially with water (150 mL), and brine (150 mL), dried over $MgSO_4$, filtered, and concentrated to provide dark brown solid (19.6 g, 96.9%) used directly in the next step without further purification; $^1$H NMR (400 MHz, Chloroform-d) δ 8.28 (d, 1H), 8.23 (s, 1H), 7.94 (d, 1H), 7.67-7.54 (m, 4H), 4.02 (s, 3H); LC/MS m/z $(M-H)^+$=201.1.

Step 2: Synthesis of methyl 4-(((trifluoromethyl) sulfonyl)oxy)-2-naphthoate (C18)

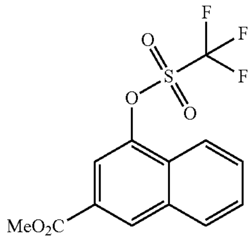 [SMILES: COC(=O)c1cc(OS(=O)(=O)C(F)(F)F)c2ccccc2c1]

To a solution of methyl 4-hydroxy-2-naphthoate C17 (19.4 g, 96 mmol) in $CH_2Cl_2$ (480 mL) at about 0° C. was added $iPr_2NEt$ (83.6 mL, 480 mmol) followed by slow addition of N-Phenyl-bis(trifluoromethanesulfonamide) (45.3 g, 127 mmol) portion-wise over about 10 min. The mixture was allowed to stir at about 25° C. for about 16 h. The reaction was quenched using 1 N HCl (350 mL), then the organic phase was separated. The aqueous phase was extracted with additional $CH_2Cl_2$. The combined organic phases were washed sequentially with saturated aqueous $Na_2CO_3$ (200 mL) and brine (100 mL), dried over $MgSO_4$, filtered, and concentrated. The residue was purified by chromatography (silica, EtOAc/Hexanes, 0-10%) to provide the title compound (30 g, 93% yield) as a white solid; $^1$H NMR (400 MHz, Chloroform-d) δ 8.65 (s, 1H), 8.12 (d, 1H), 8.08-8.01 (m, 2H), 7.78 (t, 1H), 7.69 (t, 1H), 7.56 (dt, 1H), 7.41 (d, 1H), 4.01 (s, 3H); LC/MS m/z $(M+H)^+$=335.1.

Step 3: Synthesis of methyl 4-methyl-2-naphthoate (C19)

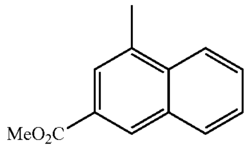

To a solution of methyl 4-(((trifluoromethyl)sulfonyl)oxy)-2-naphthoate C18 (22.4 g, 67 mmol) in dioxane (134 mL) was added potassium carbonate (30.6 g, 221 mmol), trimethylboroxine (25.2 g, 28.1 mL, 210 mmol), and water (3.36 mL, 2.78 mmol). The mixture was degassed and purged with $N_2$/vacuum cycle (3 times) then Pd(dppf)$Cl_2$ (1.37 g, 1.68 mmol) was added. The reaction was heated to about 60° C. for about 2 h. The mixture was cooled to about 25° C. and diluted with EtOAc (250 mL). The EtOAc layer washed with water (100 mL), brine (100 ml), dried over $MgSO_4$, filtered, and concentrated. The residue was purified by chromatography (silica, EtOAc/Hexanes, 0-5%) to provide the title compound (10.2 g, 75% yield) as a white solid; $^1$H NMR (400 MHz, Chloroform-d) δ 8.38 (s, 1H), 7.93 (d, 1H), 7.87 (d, 1H), 7.83 (d, 1H), 7.59-7.39 (m, 2H), 3.92-3.87 (m, 3H), 2.64 (s, 3H); LC/MS m/z $(M+H)^+$=201.1.

Step 4: Synthesis of 4-methyl-2-naphthoic acid (C20)

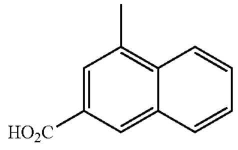

To a solution of methyl 4-methyl-2-naphthoate C19 (13.8 g, 68.9 mmol) in THF (230 mL) and methanol (230 mL) was added a premixed solution of LiOH (6.6 g, 276 mmol) in water (138 mL). After about 96 h, the mixture was concentrated, and the residue diluted with 1 N NaOH (50 mL). The aqueous residue was extracted with EtOAc (2×50 mL), and the organic layer was discarded. The pH of the aqueous layer was adjusted to 4-5 with conc. HCl. The resulting suspension was filtered. The solids were dried to provide the title compound (9.6 g, 74.8%). $^1$H NMR (400 MHz, Methanol-d4) δ 8.48 (s, 1H), 8.10 (d, 1H), 8.01 (d, 1H), 7.91 (s, 1H), 7.72-7.64 (m, 1H), 7.59 (t, 1H), 2.75 (s, 3H); LC/MS m/z $(M-H)^+$=185.2.

Step 5: Synthesis of 2-(tert-butyl)-1'-(4-methyl-2-naphthoyl)-5H-spiro[benzo[d]thiazole-6,4'-piperidin]-4(7H)-one (Example 16)

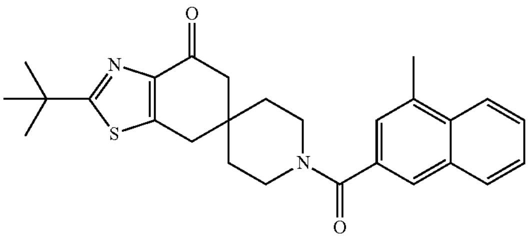 [SMILES: Cc1cc(C(=O)N2CCC3(CC2)CC(=O)c2nc(C(C)(C)C)sc2C3)cc2ccccc12]

To a solution of preparation P1 (15.7 g, 50 mmol), 4-methyl-2-naphthoic acid C20 (9.31 g, 50 mmol), EDCl HCl (14.4 g, 75 mmol), and HOBt (11.9 g, 75 mmol) in DMF (333 mL) at about 25° C. was added $^{i}Pr_2NEt$ (61 mL, 350 mmol). The mixture was stirred at about 25° C. for about 16 h, then diluted with EtOAc (300 mL). The mixture was washed sequentially with 1 N HCl (300 mL), saturated aqueous $NaHCO_3$ (200 mL), and brine (200 mL). The organic phase was dried over $MgSO_4$, filtered, and concentrated. The residue was redissolved in DCM (300 mL) and washed with 5% aqueous LiCl (100 mL). The DCM layer was separated and dried over $MgSO_4$ to provide the solid. The residue was purified by chromatography (silica, EtOAc/Hexanes, 10-86%) to provide the title compound (16.9 g, 76% yield) as a white solid; $^1H$ NMR (400 MHz, Methanol-d4) δ 8.08 (d, 1H), 7.95 (d, 1H), 7.80 (s, 1H), 7.60 (m, 2H), 7.37 (s, 1H), 3.87 (m, 2H), 3.55 (m, 2H), 3.27 (s, 2H), 2.75 (s, 2H), 2.74 (s, 3H), 1.79 (m, 2H), 1.65 (m, 2H), 1.45 (s, 9H); LC/MS m/z $(M+H)^+$=447.2.

Example 17: 2-(tert-butyl)-1'-(7-methyl-1H-indole-5-carbonyl)-5H-spiro[benzo[d]thiazole-6,4'-piperidin]-4(7H)-one

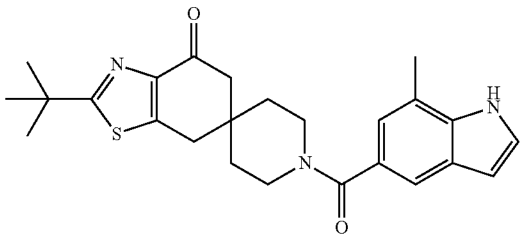 [SMILES: Cc1cc(C(=O)N2CCC3(CC2)CC(=O)c2nc(C(C)(C)C)sc2C3)cc2cc[nH]c12]

To a solution of preparation P1 (6.3 g, 20 mmol), 7-methyl-1H-indole-5-carboxylic acid (4.2 g, 24 mmol, commercial vendor PharmaBlock), EDCl HCl (4.79 g, 25 mmol), and HOBt (3.97 g, 25 mmol) in DMF (100 mL) at about 25° C. was added $iPr_2NEt$ (20.9 mL, 120 mmol). The mixture was stirred at about 25° C. for about 16 h, then diluted with EtOAc (200 mL). The resulting mixture was washed sequentially with 5% aqueous LiCl (100 mL), saturated aqueous $NaHCO_3$ (50 mL), and brine (50 mL). The organic phase was dried over $MgSO_4$, filtered, and concentrated. The residue was purified by chromatography (silica, EtOAc/Hexanes 5-100% then MeOH-EtOAc, 0-10%) to provide the title compound (8.0 g, 84% yield) as a white solid; $^1H$ NMR (400 MHz, Methanol-d4) δ 7.52 (s, 1H), 7.32 (d, 1H), 7.00 (s, 1H), 6.53 (d, 1H), 3.65 (m, 4H), 3.23 (s, 2H), 2.72 (s, 2H), 2.54 (s, 3H), 1.67 (m, 4H), 1.45 (s, 9H); LC/MS m/z $(M+H)^+$=436.1.

Example 18: 2-(tert-butyl)-1'-(3-(ethylamino)-8-methylquinoline-6-carbonyl)-5H-spiro[benzo[d]thiazole-6,4'-piperidin]-4(7H)-one

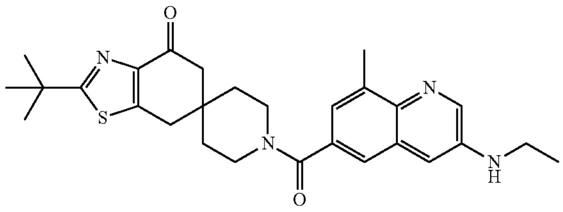 [SMILES: CCNc1cnc2c(C)cc(C(=O)N3CCC4(CC3)CC(=O)c3nc(C(C)(C)C)sc3C4)cc2c1]

Prepared in the same manner as Example 15, substituting tert-butyl ethylcarbamate for tert-butyl methylcarbamate in Step 3, to provide the title compound (353 mg). $^1H$ NMR (400 MHz, $CD_3OD$) δ 8.46 (s, 1H), 7.56 (s, 1H), 7.20 (s, 1H), 7.11 (s, 1H), 3.86-3.79 (m, 4H), 3.52 (m, 2H), 3.25-3.20 (m, 2H), 2.72 (s, 2H), 2.69 (s, 3H), 1.76-1.63 (m, 4H), 1.43 (s, 9H), 1.32 (t, 3H); LC/MS m/z $(M+H)^+$=491.2.

Example 19: 2-(tert-butyl)-1'-(3-methoxy-8-methylquinoline-6-carbonyl)-5H-spiro[benzo[d]thiazole-6,4'-piperidin]-4(7H)-one

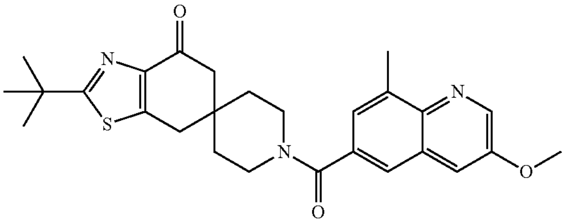

Prepared in the same manner as Example 15, substituting methanol for tert-butyl methylcarbamate in Step 3, to provide the title compound (56 mg). $^1H$ NMR (400 MHz, $CD_3OD$) δ 8.63 (s, 1H), 7.75 (s, 1H), 7.72 (s, 1H), 7.43 (s, 1H), 3.98 (s, 3H), 3.88-3.82 (m, 2H), 3.51 (m, 2H), 3.26 (s, 2H), 2.76 (s, 3H), 2.73 (s, 2H), 1.77-1.64 (m, 4H), 1.43 (s, 9H); LC/MS m/z $(M+H)^+$=478.3.

Example 20: 2-(tert-butyl)-1'-(3-ethoxy-8-methylquinoline-6-carbonyl)-5H-spiro[benzo[d]thiazole-6,4'-piperidin]-4(7H)-one

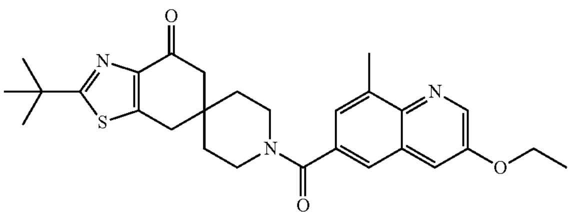 [SMILES: CCOc1cnc2c(C)cc(C(=O)N3CCC4(CC3)CC(=O)c3nc(C(C)(C)C)sc3C4)cc2c1]

Prepared in the same manner as Example 15, substituting ethanol for tert-butyl methylcarbamate in Step 3, to provide the title compound (2.5 mg). $^1H$ NMR (400 MHz, $CD_3OD$) δ 8.64 (s, 1H), 7.75 (s, 1H), 7.71 (s, 1H), 7.44 (s, 1H), 4.24 (q, 2H), 3.80-3.60 (m, 2H), 3.53 (m, 2H), 3.28 (s, 2H), 2.77 (s, 3H), 2.76 (s, 2H), 1.79-1.63 (m, 4H), 1.52 (t, 3H), 1.45 (s, 9H); LC/MS m/z $(M+H)^+$=492.3.

Example 21: 2-(tert-butyl)-1'-(8-methyl-3-(methylthio)quinoline-6-carbonyl)-5H-spiro[benzo[d]thiazole-6,4'-piperidin]-4(7H)-one

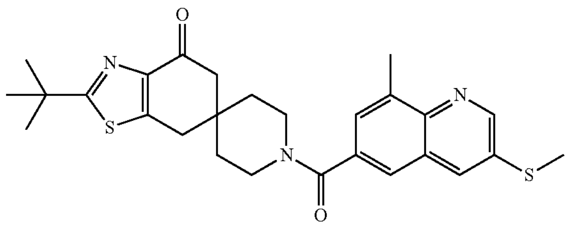 [SMILES: CSc1cnc2c(C)cc(C(=O)N3CCC4(CC3)CC(=O)c3nc(C(C)(C)C)sc3C4)cc2c1]

Prepared in the same manner as Example 15, substituting 2-methyl-2-thiopseudourea hemisulfate for tert-butyl methylcarbamate and $PdCl_2$dppf in Step 3, to provide the title compound (28 mg). $^1H$ NMR (400 MHz, $CD_3OD$) δ 8.78 (d, 1H), 8.13 (d, 1H), 7.77 (s, 1H), 7.54 (s, 1H), 3.90-3.84 (m, 2H), 3.53 (m, 2H), 3.28 (s, 2H), 2.78 (s, 3H), 2.76 (s, 2H), 2.66 (s, 3H), 1.79-1.60 (m, 4H), 1.45 (s, 9H); LC/MS m/z $(M+H)^+$=494.3.

Example 22: 4-(4-(2-(tert-butyl)-4-oxo-4,7-dihydro-5H-spiro[benzo[d]thiazole-6,4'-piperidine]-1'-carbonyl)-6-(dimethylamino)pyridin-2-yl)benzamide

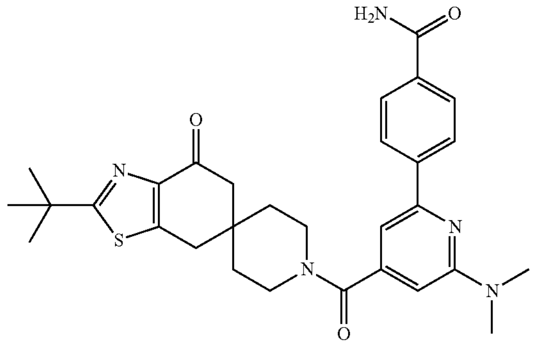 [SMILES: CN(C)c1cc(C(=O)N2CCC3(CC2)CC(=O)c2nc(C(C)(C)C)sc2C3)cc(-c2ccc(C(N)=O)cc2)n1]

Step 1: Synthesis of 2-(4-carbamoylphenyl)-6-(dimethylamino)isonicotinic acid (C21)

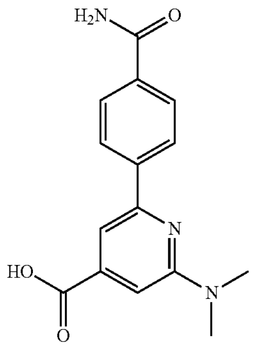 [SMILES: CN(C)c1cc(C(=O)O)cc(-c2ccc(C(N)=O)cc2)n1]

To methyl 2-chloro-6-(dimethylamino)isonicotinate (104 mg, 0.486 mmol) in dioxane (3.0 mL) and water (1.0 mL) in a microwave vial was added $Na_2CO_3$ (64 mg, 0.61 mmol), $Pd(PPh_3)_4$ (14 mg, 0.012 mmol), and 4-(4,4,5,5-tetramethyl-1,3,2-dioxaborolan-2-yl)benzamide (100 mg, 0.41 mmol). The mixture was sparged with nitrogen, placed in the microwave, and irradiated at about 100° C. for about 45 min. The mixture was cooled to about 25° C. and concentrated under reduced pressure. The aqueous residue was acidified to approximately pH 5 with 2 N HCl and the resulting precipitate was filtered to provide the title compound (78 mg, 68% yield). $^1H$ NMR (400 MHz, $CD_3OD$) δ 8.20 (d, 1H), 7.99 (d, 1H), 7.65 (s, 1H), 7.19 (s, 1H), 3.24 (s, 6H); LC/MS m/z $(M+H)^+$=285.9.

Step 2: 4-(4-(2-(tert-butyl)-4-oxo-4,7-dihydro-5H-spiro[benzo[d]thiazole-6,4'-piperidine]-1'-carbonyl)-6-(dimethylamino)pyridin-2-yl)benzamide (Example 22)

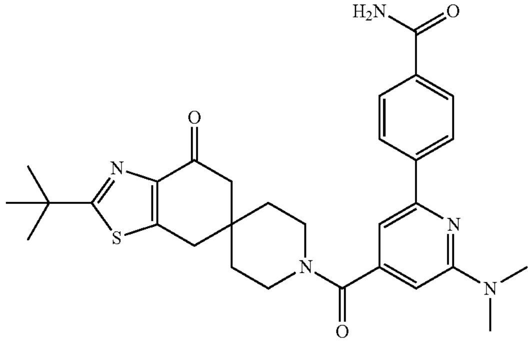 [SMILES: CN(C)c1cc(C(=O)N2CCC3(CC2)CC(=O)c2nc(C(C)(C)C)sc2C3)cc(-c2ccc(C(N)=O)cc2)n1]

To a solution of preparation P1 (50 mg, 0.16 mmol), compound C21 (68 mg, 0.24 mmol), and EDCl (61 mg, 0.32 mmol) in a microwave vial was added pyridine (3.0 mL). The mixture was irradiated in the microwave at about 110° C. for about 30 min. The mixture was concentrated under reduced pressure and purified by prep-HPLC (Column: C18-1, 30×150 mm, 5 μm); Mobile Phase A: water (0.05% v/v conc. $NH_4OH$); Mobile phase B: MeCN; 30-70% B gradient, 9 min, hold at 100% B for 2 min; flow rate 30 mL/min) to provide the title compound (21 mg, 24%). $^1H$ NMR (400 MHz, $CD_3OD$) δ 8.16 (d, 2H), 7.96 (d, 2H), 7.13 (s, 1H), 6.58 (s, 1H), 3.90-3.75 (m, 2H), 3.54 (m, 2H), 3.26 (s, 2H), 3.21 (s, 6H), 2.76 (s, 2H), 1.80-1.62 (m, 4H), 1.43 (s, 9H); LC/MS m/z $(M+H)^+$=546.4.

Example 23: 4-(4-(2-(tert-butyl)-4-oxo-4,7-dihydro-5H-spiro[benzo[d]thiazole-6,4'-piperidine]-1'-carbonyl)-6-methoxypyridin-2-yl)benzamide

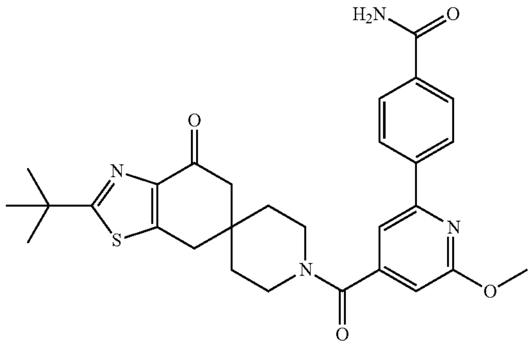

Prepared in the same manner as Example 22, substituting 2-chloro-6-methoxyisonicotinic acid for methyl 2-chloro-6-(dimethylamino)isonicotinate in Step 1, to provide the title compound (18 mg). $^1$H NMR (400 MHz, $CD_3OD$) δ 8.23 (d, 2H), 8.01 (d, 2H), 7.54 (s, 1H), 6.77 (s, 1H), 4.06 (s, 3H), 3.49 (m, 2H), 3.30-3.25 (m, 4H), 2.73 (s, 2H), 1.80-1.63 (m, 4H), 1.43 (s, 9H); LC/MS m/z $(M+H)^+$=533.4.

Example 24: 2-(tert-butyl)-1'-(5-methyl-1-(methylamino)isoquinoline-7-carbonyl)-5H-spiro[benzo[d]thiazole-6,4'-piperidin]-4(7H)-one

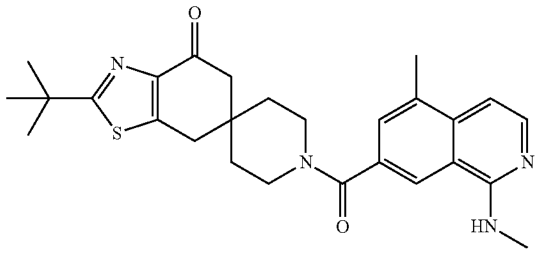 [SMILES: CNc1nccc2c(C)cc(C(=O)N3CCC4(CC3)CC(=O)c3nc(C(C)(C)C)sc3C4)cc12]

Step 1: 3-bromo-N-(2,2-dimethoxyethyl)-5-methylbenzamide (C22)

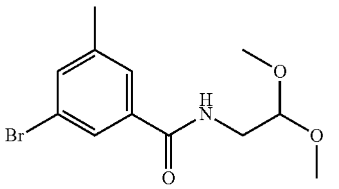 [SMILES: COC(CNC(=O)c1cc(C)cc(Br)c1)OC]

To a solution of 2,2-dimethoxyethan-1-amine (1.34 g, 12.8 mmol) in DCM (50 mL) was added triethylamine (1.76 g, 17.4 mmol). The reaction was cooled to about 0° C., then 3-bromo-5-methylbenzoyl chloride (2.71 g, 11.6 mmol) in DCM (10 mL) was added dropwise. The reaction was allowed to warm to about 30° C. over about 16 h. Water (10 mL) was added and the mixture was extracted with DCM (2×20 mL). The combined organic phases were dried over $Na_2SO_4$, filtered, and concentrated under reduced pressure. The residue was purified by column chromatography to provide the title compound (3.0 g, 85%).

Step 2: 7-bromo-5-methylisoquinolin-1(2H)-one (C23)

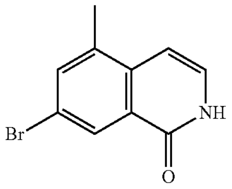

To compound C22 (3.50 g, 12.3 mmol) at about 0° C. was added concentrated $H_2SO_4$ (30 mL). The mixture was stirred at about 25° C. for about 16 h, then heated to about 50° C. for about 5 h. The mixture was slowly poured into ice water (200 mL), then extracted with EtOAc (3×300 mL). The combined organic phases were dried over $Na_2SO_4$, filtered, and concentrated under reduced pressure. The residue was suspended in petroleum ether/EtOAc (50 mL/20 mL) and stirred at about 25° C. for about 10 min. The solids were collected by filtration to provide a mixture of the title compound and regioisomer, 5-bromo-7-methylisoquinolin-1(2H)-one (1.8 g, 76%). LC/MS m/z $(M+H)^+$=238.0.

Step 3: methyl 5-methyl-1-oxo-1,2-dihydroisoquinoline-7-carboxylate (C24)

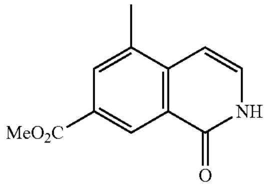 [SMILES: COC(=O)c1cc(C)c2cc[nH]c(=O)c2c1]

To compound C23 (mix of regioisomers, 1.00 g, 4.2 mmol) in MeOH (50 mL) was added $Pd(dppf)Cl_2$ (461 mg, 0.63 mmol) and triethylamine (1.28 g, 12.6 mmol). The mixture was heated to about 80° C. under CO atmosphere (50 psi) for about 48 h. The mixture was cooled to about 25° C., filtered, and the filtrate was concentrated under reduced pressure. The residue was purified by chromatography (0% to 30% EtOAc in petroleum ether) to provide the title compound and regioisomer, methyl 7-methyl-1-oxo-1,2-dihydroisoquinoline-5-carboxylate (600 mg, 66%). The isomers were separated via prep-SFC (Column: Daicel Chiralpak AD, 30×250 mm, 10 μm; Mobile Phase A: water (0.1% v/v $NH_4OH$); Mobile phase B: EtOH; 35% B, flow rate 80 mL/min) to provide the title compound (100 mg, 11%). LC/MS m/z $(M+H)^+$=218.0.

Step 4: methyl 1-chloro-5-methylisoquinoline-7-carboxylate (C25)

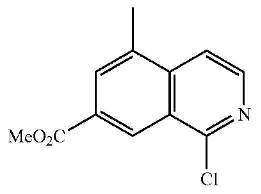 [SMILES: COC(=O)c1cc(C)c2ccnc(Cl)c2c1]

To compound C24 (100 mg, 0.46 mmol) was added $POCl_3$ (1.41 g, 9.2 mmol). The mixture was heated to about 100° C. for about 2 h. The reaction was concentrated under reduced pressure and the pH was adjusted to about 8 with $NaHCO_3$ (aq). The organic phase was dried over $Na_2SO_4$, filtered, and concentrated under reduced pressure. The residue was purified by chromatography (0% to 50% EtOAc in petroleum ether) to provide the title compound (105 mg, 97%). LC/MS m/z $(M+H)^+$=236.0.

Step 5: methyl 5-methyl-1-(methylamino)isoquinoline-7-carboxylate (C26)

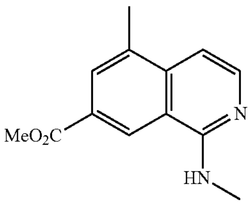 [SMILES: CNc1nccc2c(C)cc(C(=O)OC)cc12]

To compound C25 (105 mg, 0.45 mmol) in NMP (5 mL) was added i-$Pr_2NEt$ (0.39 mL, 2.23 mmol) and methylamine hydrochloride (90 mg, 1.3 mmol). The mixture was stirred at about 110° C. for about 16 h. The solution was cooled to about 30° C. and diluted with water (10 mL). The mixture was extracted with EtOAc (2×10 mL) and the combined organic phases were dried over $Na_2SO_4$, filtered, and concentrated under reduced pressure. The residue was purified by chromatography (0% to 50% EtOAc in petroleum ether) to provide the title compound (50 mg, 49%). LC/MS m/z $(M+H)^+$=231.0.

Step 6: 5-methyl-1-(methylamino)isoquinoline-7-carboxylic acid (C27)

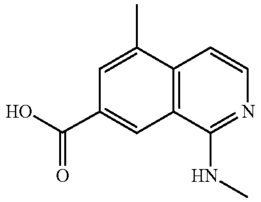 [SMILES: CNc1nccc2c(C)cc(C(=O)O)cc12]

To compound C26 (50 mg, 0.22 mmol) in MeOH (5 mL) and water (2 mL) was added LiOH monohydrate (36 mg, 0.87 mmol). The mixture was stirred at about 30° C. for about 16 h. The mixture was concentrated under reduced pressure and cooled to about 0° C. 1 M HCl (aq) was added to adjust the solution to pH 5. A precipitate formed and was collected by filtration to provide the title compound (28 mg, 60%). LC/MS m/z $(M+H)^+$=217.0.

Step 7: 2-(tert-butyl)-1'-(5-methyl-1-(methylamino) isoquinoline-7-carbonyl)-5H-spiro[benzo[d]thiazole-6,4'-piperidin]-4(7H)-one

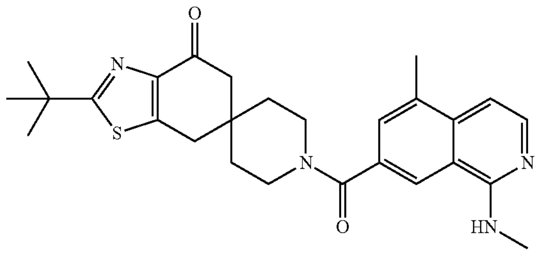 [SMILES: CNc1nccc2c(C)cc(C(=O)N3CCC4(CC3)CC(=O)c3nc(C(C)(C)C)sc3C4)cc12]

According to amidation method A, compound C27 (28 mg, 0.13 mmol) was coupled to preparation P1. The residue was purified by prep-HPLC (Column: Boston Prime C18, 30×150 mm, 5 μm); Mobile Phase A: water (0.05% v/v conc. $NH_4OH$); Mobile phase B: MeCN; 29-69% B gradient, 9 min, hold at 100% B for 2 min; flow rate 25 mL/min) to provide the title compound (40 mg, 64%). $^1H$ NMR (400 MHz, $CD_3OD$) δ 8.02 (s, 1H), 7.93 (d, 1H), 7.51 (s, 1H), 7.04 (d, 1H), 3.88-3.83 (m, 2H), 3.53 (m, 1H), 3.27 (s, 2H), 3.06 (s, 3H), 2.75 (s, 2H), 2.62 (s, 3H), 1.78-1.66 (m, 4H), 1.45 (s, 9H). LC/MS m/z $(M+H)^+$=477.3.

Example 25: 2-(tert-butyl)-1'-(1-cyclopropyl-5-methylisoquinoline-7-carbonyl)-5H-spiro[benzo[d] thiazole-6,4'-piperidin]-4(7H)-one

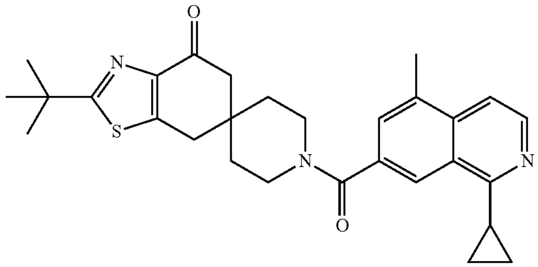 [SMILES: Cc1cc(C(=O)N2CCC3(CC2)CC(=O)c2nc(C(C)(C)C)sc2C3)cc2c(C3CC3)nccc12]

Prepared in the same manner as Example 24, substituting cyclopropylboronic acid for methylamine hydrochloride in Step 5, to provide the title compound (32 mg). $^1H$ NMR (400 MHz, $CD_3OD$) δ 8.37 (s, 1H), 8.27 (d, 1H), 7.65 (d, 1H), 7.53 (s, 1H), 3.81-3.77 (m, 2H), 3.46 (m, 2H), 3.18 (s, 2H), 2.76 (m, 1H), 2.66 (s, 2H), 2.63 (s, 3H), 1.71 (m, 2H), 1.57 (m, 2H), 1.35 (s, 9H), 1.08 (d, 4H); LC/MS m/z $(M+H)^+$=488.4.

Example 26: 2-(tert-butyl)-1'-(4-methyl-1-(methylamino)isoquinoline-7-carbonyl)-5H-spiro[benzo[d] thiazole-6,4'-piperidin]-4(7H)-one

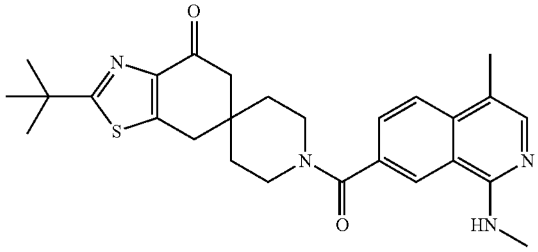 [SMILES: CNc1ncc(C)c2ccc(C(=O)N3CCC4(CC3)CC(=O)c3nc(C(C)(C)C)sc3C4)cc12]

Step 1: methyl 1-((tert-butoxycarbonyl)(methyl) amino)-4-methylisoquinoline-7-carboxylate (C28)

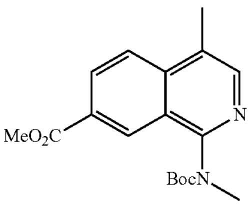 [SMILES: COC(=O)c1ccc2c(C)cnc(N(C)C(=O)OC(C)(C)C)c2c1]

To 1-chloro-4-methylisoquinoline-7-carboxylate (140 mg, 0.594 mmol), tert-butyl-N-methylcarbamate (100 mg, 0.594 mmol), $Pd_2(dba)_3$ (27 mg, 0.030 mmol), $Cs_2CO_3$ (581 mg, 1.78 mmol), and X-Phos (28 mg, 0.059 mmol) was added toluene (5 mL). The mixture was sparged with nitrogen. The mixture was heated to about 110° C. for about 16 h. The solution was concentrated under reduced pressure and the residue was purified by chromatography (0% to 30% EtOAc in petroleum ether) to provide the title compound (15 mg, 8%). LC/MS m/z $(M+H\text{-}Boc)^+$=231.1.

Step 2: methyl 4-methyl-1-(methylamino)isoquinoline-7-carboxylate (C29)

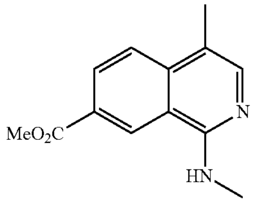 [SMILES: CNc1ncc(C)c2ccc(C(=O)OC)cc12]

To compound C28 (15 mg, 0.045 mmol) in MeOH (1.0 mL) was added HCl (4 M in dioxane, 1.0 mL). The reaction was stirred at about 50° C. for about 2 h. The mixture was concentrated under reduced pressure to provide the title compound (10 mg, 96%). LC/MS m/z $(M+H)^+$=231.0.

Step 3: 4-methyl-1-(methylamino)isoquinoline-7-carboxylic acid (C30)

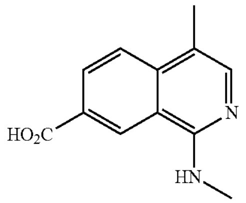 [SMILES: CNc1ncc(C)c2ccc(C(=O)O)cc12]

To compound C29 (10 mg, 0.043 mmol) in EtOH (4.0 mL) was added NaOH (8.7 mg, 0.217 mmol) and water (4.0 mL). The reaction was stirred at about 50° C. for about 1 h. The EtOH was removed under reduced pressure and the mixture was acidified to pH 7 with 2 N HCl. The precipitate was filtered and dried in vacuo to provide the title compound (9.4 mg, 100%). LC/MS m/z $(M+H)^+$=217.0.

Step 3: 2-(tert-butyl)-1'-(4-methyl-1-(methylamino) isoquinoline-7-carbonyl)-5H-spiro[benzo[d]thiazole-6,4'-piperidin]-4(7H)-one

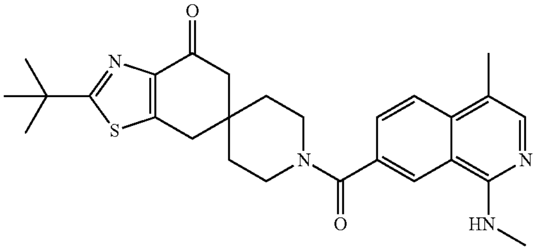 [SMILES: CNc1ncc(C)c2ccc(C(=O)N3CCC4(CC3)CC(=O)c3nc(C(C)(C)C)sc3C4)cc12]

According to amidation method C, compound C30 (9 mg, 0.044 mmol) was coupled to preparation P1. The residue was purified by prep-HPLC (Column: Boston Prime C18, 30×150 mm, 5 μm); Mobile Phase A: water (0.05% v/v conc. $NH_4OH$); Mobile phase B: MeCN; 32-62% B gradient, 9 min, hold at 100% B for 2 min; flow rate 25 mL/min) to provide the title compound (2.9 mg, 14%). $^1H$ NMR (400 MHz, $CD_3OD$) δ 8.17 (s, 1H), 7.89 (d, 1H), 7.72-7.70 (m, 2H), 3.87-3.81 (m, 2H), 3.50 (m, 2H), 3.25 (s, 2H), 3.03 (s, 3H), 2.73 (s, 2H), 2.40 (s, 3H), 1.77-1.58 (m, 4H), 1.42 (s, 9H); LC/MS m/z $(M+H)^+$=477.3.

Example 27: 2-(tert-butyl)-1'-(1,4-dimethylisoquinoline-7-carbonyl)-5H-spiro[benzo[d]thiazole-6,4'-piperidin]-4(7H)-one

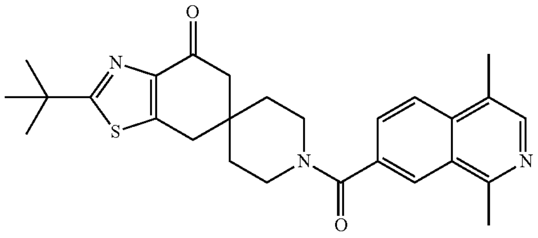 [SMILES: Cc1cnc(C)c2cc(C(=O)N3CCC4(CC3)CC(=O)c3nc(C(C)(C)C)sc3C4)ccc12]

Prepared in the same manner as Example 26, substituting trimethylboroxine for tert-butyl-N-methylcarbamate in Step 1, to provide the title compound (42 mg). $^1H$ NMR (400 MHz, $CD_3OD$) δ 8.31 (s, 1H), 8.20 (s, 1H), 8.15 (d, 1H), 7.84 (d, 1H), 3.91-3.86 (m, 2H), 3.53 (m, 2H), 3.27 (s, 2H), 2.93 (s, 3H), 2.75 (s, 2H), 2.63 (s, 3H), 1.85-1.65 (m, 4H), 1.43 (s, 9H); LC/MS m/z $(M+H)^+$=462.3.

Example 28: 2-(tert-butyl)-1'-(5-methoxy-1-methylisoquinoline-7-carbonyl)-5H-spiro[benzo[d]thiazole-6,4'-piperidin]-4(7H)-one

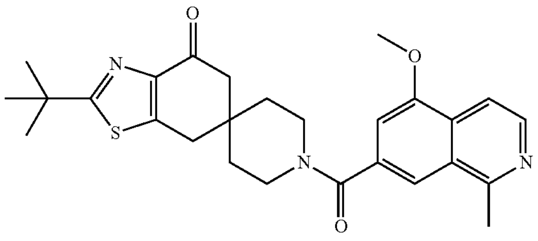 [SMILES: COc1cc(C(=O)N2CCC3(CC2)CC(=O)c2nc(C(C)(C)C)sc2C3)cc2c(C)nccc12]

Step 1: methyl 5-methoxyisoquinoline-7-carboxylate (C31)

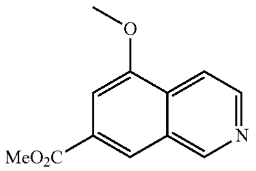

To methyl 5-bromoisoquinoline-7-carboxylate (1.00 g, 3.76 mmol; prepared as described by World patent application WO 2021/028806), RockPhos-Pd-G3 (95 mg, 0.113 mmol), and $Cs_2CO_3$ (1.22 g, 3.76 mmol) was added MeOH (1.2 g, 37.6 mmol) and dioxane (20 mL). The mixture was heated to about 70° C. for about 16 h. The mixture was cooled to about 25° C., filtered, and concentrated under reduced pressure. The residue was purified by chromatography (0% to 40% EtOAc in petroleum ether) to provide the title compound (450 mg, 55%). LC/MS m/z $(M+H)^+$=217.9.

Step 2: 5-methoxy-7-(methoxycarbonyl)isoquinoline 2-oxide (C32)

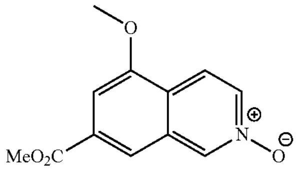

To a solution of compound C31 (450 mg, 2.07 mmol) in DCM (10 mL) at about 0° C. was added m-CPBA (429 mg, 2.49 mmol). The mixture was stirred at about 45° C. for about 16 h. Saturated $Na_2S_2O_3$ (aq) was added, followed by saturated $Na_2CO_3$ (aq) until the pH was >8. The mixture was stirred for about 30 min, then extracted with DCM (2×10 mL) and $H_2O$ (2×10 mL). The DCM extracts were dried over $Na_2SO_4$, filtered, and concentrated under reduced pressure to provide the title compound (450 mg, 93%). LC/MS m/z $(M+H)^+$=234.0.

Step 3: methyl 1-chloro-5-methoxyisoquinoline-7-carboxylate (C33)

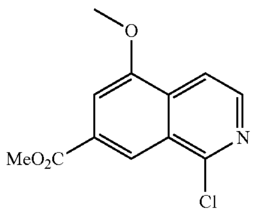 [SMILES: COC(=O)c1cc(OC)c2ccnc(Cl)c2c1]

To a solution of compound C32 (450 mg, 1.93 mmol) in DCM (10 mL) was added $POCl_3$ (0.90 mL, 9.65 mmol). The mixture was stirred at about 50° C. for about 2 h, then cooled to about 25° C. The mixture was concentrated under reduced pressure and $NaHCO_3$ (aq) was added until the pH was about 8. The organic phase was separated, dried over $Na_2SO_4$, filtered, and concentrated under reduced pressure. The residue was purified by chromatography (0% to 40% EtOAc in petroleum ether) to provide the title compound (200 mg, 41%). LC/MS m/z $(M+H)^+$=252.0.

Step 4: methyl 5-methoxy-1-methylisoquinoline-7-carboxylate (C34)

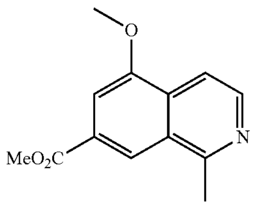 [SMILES: COC(=O)c1cc(OC)c2ccnc(C)c2c1]

To a solution of compound C33 (60 mg, 0.24 mmol) and trimethylboroxine (60 mg, 0.24 mmol) in THE (2 mL) was added $Pd(dtbpf)Cl_2$ (7.8 mg, 0.012 mmol) and $Cs_2CO_3$ (155 mg, 0.477 mmol). The mixture was heated to about 70° C. for about 2 h, then concentrated under reduced pressure. The residue was purified by chromatography (0% to 30% EtOAc in petroleum ether) to provide the title compound (40 mg, 73%). LC/MS m/z $(M+H)^+$=232.0.

Step 5: 5-methoxy-1-methylisoquinoline-7-carboxylic acid (C35)

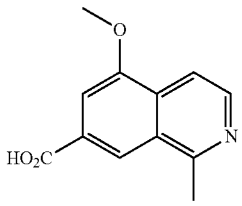 [SMILES: COc1cc(C(=O)O)cc2c(C)nccc12]

To a solution of compound C34 (40 mg, 0.17 mmol) in MeOH (2 mL) and water (1 mL) was added $LiOHH_2O$ (15 mg, 0.35 mmol). The mixture was stirred at about 25° C. for about 2 h, then heated to about 50° C. for about 2 h. The solution was concentrated under reduced pressure and the pH was adjusted to about 5 with 1 M HCl. The resulting precipitate was filtered to provide the title compound (38 mg, 100%). LC/MS m/z $(M+H)^+$=217.9.

Step 6: 2-(tert-butyl)-1'-(5-methoxy-1-methylisoquinoline-7-carbonyl)-5H-spiro[benzo[d]thiazole-6,4'-piperidin]-4(7H)-one (Example 28)

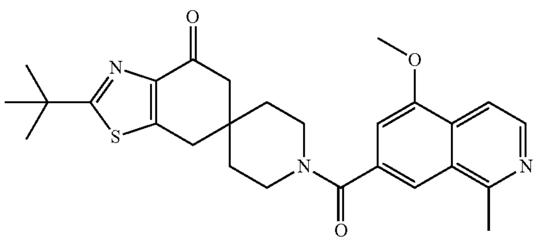 [SMILES: COc1cc(C(=O)N2CCC3(CC2)CC(=O)c2nc(C(C)(C)C)sc2C3)cc2c(C)nccc12]

According to amidation method A, compound C35 (38 mg, 0.17 mmol) was coupled to preparation P1. The residue was purified by prep-HPLC (Column: Boston Prime C18, 30×150 mm, 5 μm); Mobile Phase A: water (0.05% v/v conc. $NH_4OH$); Mobile phase B: MeCN; 29-59% B gradient, 9 min, hold at 100% B for 2 min; flow rate 30 mL/min) to provide the title compound (24 mg, 28%). $^1H$ NMR (400 MHz, $CD_3OD$) δ 8.33 (d, 1H), 7.97 (d, 1H), 7.81 (s, 1H), 7.18 (s, 1H), 4.07 (s, 3H), 3.89-3.84 (m, 2H), 3.54 (m, 2H), 3.26 (s, 2H), 2.93 (s, 3H), 2.75 (s, 2H), 1.79-1.65 (m, 4H), 1.43 (s, 9H); LC/MS m/z $(M+H)^+$=478.4.

Example 29: 2-(tert-butyl)-1'-(1-ethyl-5-methoxy-isoquinoline-7-carbonyl)-5H-spiro[benzo[d]thiazole-6,4'-piperidin]-4(7H)-one

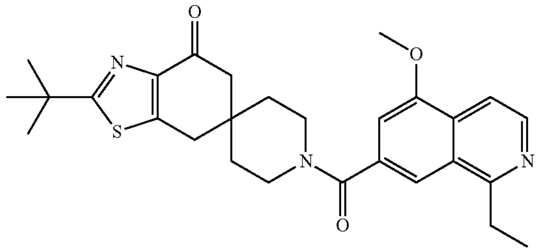 [SMILES: CCc1nccc2c(OC)cc(C(=O)N3CCC4(CC3)CC(=O)c3nc(C(C)(C)C)sc3C4)cc12]

Prepared in the same manner as Example 28, substituting triethylborane for trimethylboroxine in Step 1, to provide the title compound (5.0 mg). $^1H$ NMR (400 MHz, $CD_3OD$) δ 8.37 (d, 1H), 7.98 (d, 1H), 7.85 (s, 1H), 7.18 (s, 1H), 4.07 (s, 3H), 3.91-3.83 (m, 2H), 3.55 (m, 2H), 3.35-3.31 (m, 2H), 3.27 (s, 2H), 2.75 (s, 2H), 1.80-1.65 (m, 4H), 1.43 (s, 9H), 1.37 (t, 3H); LC/MS m/z $(M+H)^+$=492.3.

Example 30: 2-(tert-butyl)-1'-(2-(isopropylamino) quinoline-7-carbonyl)-5H-spiro[benzo[d]thiazole-6, 4'-piperidin]-4(7H)-one

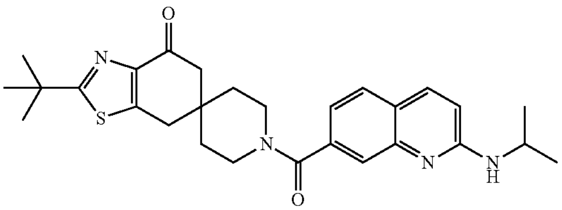 [SMILES: CC(C)Nc1ccc2ccc(C(=O)N3CCC4(CC3)CC(=O)c3nc(C(C)(C)C)sc3C4)cc2n1]

Step 1: methyl 2-(isopropylamino)quinoline-7-carboxylate (C36)

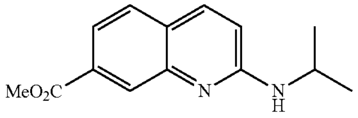 [SMILES: COC(=O)c1ccc2ccc(NC(C)C)nc2c1]

To a solution of 7-(methoxycarbonyl)quinoline 1-oxide (200 mg, 0.98 mmol) in DCM (15 mL) at about −70° C. was added trifluoromethanesulfonic anhydride (304 mg, 1.08 mmol) dropwise. The mixture was stirred for about 5 min at about −70° C., then a 2 M solution of isopropylamine in THF was added (2.94 mL, 5.88 mmol) dropwise. The mixture was stirred for about 5 min at about −70° C., then water (15 mL) was added. The layers were separated, and the aqueous phase was extracted with DCM (20 mL). The combined DCM extracts were washed with brine (2×10 mL), dried over $Na_2SO_4$, filtered, and concentrated under reduced pressure. The residue was purified by chromatography (0% to 40% EtOAc in petroleum ether) to provide the title compound (150 mg, 63%). LC/MS m/z $(M+H)^+$=245.1.

Step 2: 2-(isopropylamino)quinoline-7-carboxylic acid (C37)

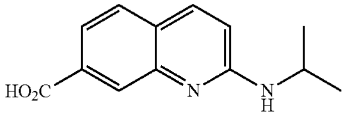 [SMILES: CC(C)Nc1ccc2ccc(C(=O)O)cc2n1]

To a solution of compound C36 (150 mg, 0.614 mmol) in EtOH (4 mL) and water (4 mL) was added NaOH (123 mg, 3.07 mmol). The mixture was heated to about 50° C. for about 16 h. The mixture was concentrated under reduced pressure and treated with 2 M HCl until the pH was about 5. The resulting precipitate was filtered to provide the title compound (135 mg, 96%). LC/MS m/z $(M+H)^+$=231.1.

Step 3: 2-(tert-butyl)-1'-(2-(isopropylamino)quinoline-7-carbonyl)-5H-spiro[benzo[d]thiazole-6,4'-piperidin]-4(7H)-one (Example 30)

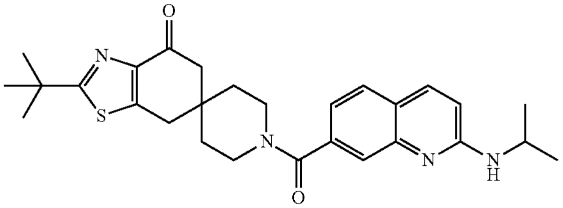 [SMILES: CC(C)Nc1ccc2ccc(C(=O)N3CCC4(CC3)CC(=O)c3nc(C(C)(C)C)sc3C4)cc2n1]

According to amidation method A, compound C37 (50 mg, 0.22 mmol) was coupled to preparation P1. The residue was purified by prep-HPLC (Column: Boston Prime C18, 30×150 mm, 5 μm); Mobile Phase A: water (0.05% v/v conc. $NH_4OH$); Mobile phase B: MeCN; 32-62% B gradient, 9 min, hold at 100% B for 2 min; flow rate 25 mL/min) to provide the title compound (36 mg, 34%). $^1H$ NMR (400 MHz, $CD_3OD$) δ 7.83 (d, 1H), 7.68-7.63 (m, 2H), 7.19 (dd, 1H), 6.78 (d, 1H), 4.30 (sept, 1H), 3.88-3.83 (m, 2H), 3.55 (m, 2H), 3.27 (s, 2H), 2.75 (d, 2H), 1.78-1.66 (m, 4H), 1.45 (s, 9H), 1.28 (d, 6H); LC/MS m/z $(M+H)^+$=491.4.

Example 31: 2-(tert-butyl)-1'-(2-(cyclobutylamino) quinoline-7-carbonyl)-5H-spiro[benzo[d]thiazole-6, 4'-piperidin]-4(7H)-one

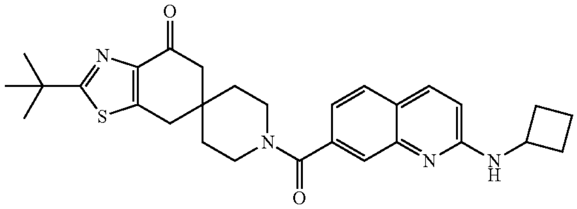 [SMILES: CC(C)(C)c1nc2c(s1)CC1(CCN(C(=O)c3ccc4ccc(NC5CCC5)nc4c3)CC1)CC2=O]

Prepared in the same manner as Example 30, substituting cyclobutylamine for isopropylamine in Step 1, to provide the title compound (46 mg). $^1$H NMR (400 MHz, $CD_3OD$) b 7.83 (d, 1H), 7.65 (d, 1H), 7.60 (s, 1H), 7.17 (d, 1H), 6.76 (d, 1H), 4.54 (m, 1H), 3.87-3.79 (m, 2H), 3.52 (m, 1H), 3.26 (s, 2H), 2.73 (s, 2H), 2.46 (m, 2H), 2.04 (m, 2H), 1.82-1.64 (m, 6H), 1.43 (s, 9H); LC/MS m/z $(M+H)^+$=503.4.

Example 32: 2-(tert-butyl)-1'-(2-(ethylamino)quinoline-7-carbonyl)-5H-spiro[benzo[d]thiazole-6,4'-piperidin]-4(7H)-one

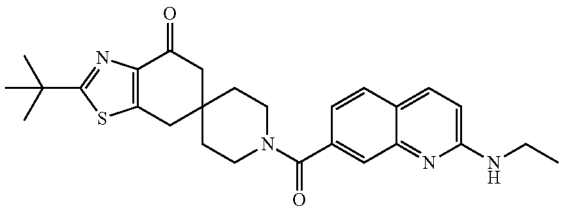 [SMILES: CCNc1ccc2ccc(C(=O)N3CCC4(CC3)CC(=O)c3nc(C(C)(C)C)sc3C4)cc2n1]

Prepared in the same manner as Example 30, substituting ethylamine for isopropylamine in Step 1, to provide the title compound (27 mg). $^1$H NMR (400 MHz, $CD_3OD$) δ 7.82 (d, 1H), 7.66 (d, 1H), 7.63 (s, 1H), 7.17 (d, 1H), 6.78 (d, 1H), 3.87-3.81 (m, 2H), 3.52-3.46 (m, 4H), 3.26 (s, 2H), 2.73 (s, 2H), 1.76-1.64 (m, 4H), 1.43 (s, 9H), 1.28 (t, 3H); LC/MS m/z $(M+H)^+$=477.4.

Example 33: 2-(tert-butyl)-1'-(5-methoxy-4-methyl-1H-indazole-7-carbonyl)-5H-spiro[benzo[d]thiazole-6,4'-piperidin]-4(7H)-one

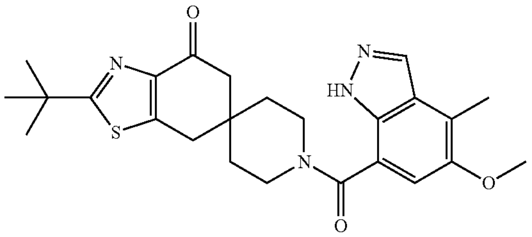

Step 1: Synthesis of 6-bromo-4-methoxy-2,3-dimethylaniline (C38)

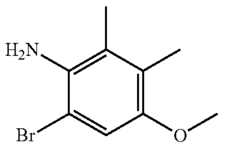

To 4-methoxy-2,3-dimethylaniline (500 mg, 3.31 mmol) in MeCN (10 mL) was added NBS (706 mg, 3.97 mmol). The mixture was stirred at about 25° C. for about 2 h. The reaction mixture was concentrated under reduced pressure. The resulting residue was purified by chromatography (17% EtOAc in petroleum ether, then 20% MeOH in EtOAc) to provide the title compound (600 mg, 79%). $^1$H NMR (400 MHz, $CDCl_3$) δ=6.88 (s, 1H), 3.77 (s, 3H), 2.18 (s, 3H), 2.15 (s, 3H); LC/MS m/z $(M+H)^+$=231.9.

Step 2: Synthesis of 7-bromo-5-methoxy-4-methyl-1H-indazole (C39)

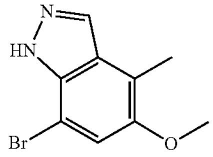

To compound C38 (600 mg, 2.61 mmol) in $H_2O$ (4 mL) was added conc. HCl (4 mL). The mixture was heated to about 60° C. for about 30 min, then cooled to about 0° C. A solution of $NaNO_2$ (198 mg, 2.87 mmol) in $H_2O$ (1 mL) was added dropwise and the mixture was stirred at about 0° C. for about 1 h. To the mixture was added sat. aq. NaOAc until the pH was 4-5. A solution of 2-methylpropane-2-thiol (259 mg, 2.87 mmol) in EtOH (7 mL) was added. The mixture was slowly warmed to about 25° C. and stirred about 16 h. The mixture was diluted with EtOAc (20 mL), washed with water (20 mL), and washed with brine (20 mL). The organic phase was dried over $Na_2SO_4$, filtered, and concentrated under reduced pressure. The resulting residue was dissolved in DMSO (5 mL) and a solution of KOtBu (1.69 g, 15 mmol) in DMSO (10 mL) was added dropwise. The mixture was stirred at about 25° C. for about 2 h. The mixture was diluted with EtOAc (50 mL), washed with water (50 mL), and washed with brine (50 mL). The organic phase was dried over $Na_2SO_4$, filtered, and concentrated under reduced pressure. The residue was purified by chromatography (17% EtOAc in petroleum ether) to provide the title compound (170 mg, 27%). $^1$H NMR (400 MHz, $CDCl_3$) δ=8.12 (s, 1H), 7.29 (s, 1H), 3.90 (s, 3H), 2.45 (s, 3H); LC/MS m/z $(M+H)^+$=242.8.

Step 3: Synthesis of ethyl 5-methoxy-4-methyl-1H-indazole-7-carboxylate (C40)

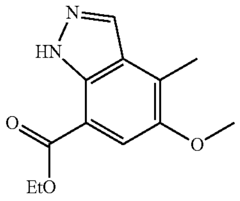 [SMILES: CCOC(=O)c1cc(OC)c(C)c2cn[nH]c12]

To compound C39 in EtOH (5.0 mL) was added $Mo(CO)_6$ (93 mg, 0.353 mmol), TTBP-$HBF_4$ (21 mg, 0.0705 mmol), DBU (0.16 mL, 1.06 mmol), and $Pd(OAc)_2$ (15.8 mg, 0.0705 mmol). The mixture was irradiated at about 100° C. for about 1 h in a microwave reactor, then cooled to about 25° C. The mixture was concentrated under reduced pressure and purified by chromatography (17% EtOAc in petroleum ether) to provide the title compound (70 mg, 42%). $^1$H NMR (400 MHz, $CDCl_3$) δ=8.11 (s, 1H), 7.78 (s, 1H), 4.51 (q, 2H), 3.96 (s, 3H), 2.57 (s, 3H), 1.51 (t, 3H); LC/MS m/z $(M+H)^+$=235.0.

Step 4: Synthesis of 5-methoxy-4-methyl-1H-indazole-7-carboxylic acid (C41)

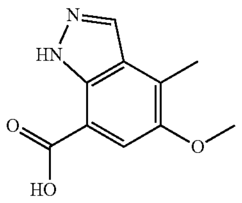

To compound C40 (70 mg, 0.30 mmol) in MeOH (1.0 mL) and THF (2.0 mL) was added a solution of LiOH $H_2O$ (38 mg, 0.90 mmol) in $H_2O$ (1.0 mL). The mixture was stirred at about 25° C. for about 16 h, then $H_2O$ (10 mL) was added. The mixture was washed with EtOAc (10 mL), then the aqueous phase was acidified with sat. aq. citric acid to pH ~6. The resulting suspension was filtered and the filter cake was collected to provide the title compound (62 mg, 100%). LC/MS m/z $(M+H)^+$=207.0.

Step 5: Synthesis of 2-(tert-butyl)-1'-(5-methoxy-4-methyl-1H-indazole-7-carbonyl)-5H-spiro[benzo[d]thiazole-6,4'-piperidin]-4(7H)-one (Example 33)

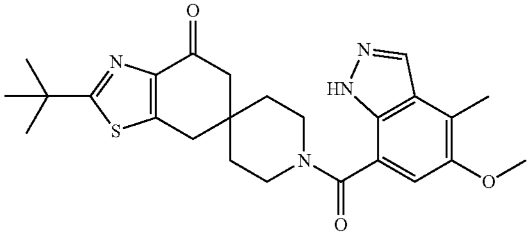 [SMILES: COc1cc(C(=O)N2CCC3(CC2)CC(=O)c2nc(C(C)(C)C)sc2C3)c2[nH]ncc2c1C]

To a solution of compound C41 (62 mg, 0.30 mmol) in DMF (2.0 mL) at about 0° C. was added $Et_3N$ (0.17 mL, 1.2 mmol) and T3P (0.36 mL of a 50% w/w solution in EtOAc, 0.60 mmol). Preparation P1 (95 mg, 0.30 mmol) was added. The resulting solution was stirred at about 25° C. for about 16 h. The mixture was diluted with EtOAc (15 mL), washed with water (15 mL) and brine (15 mL). The organic phase was dried over $Na_2SO_4$, filtered, and concentrated under reduced pressure. The residue was purified by prep-HPLC (Column: Boston Green ODS, 30×150 mm, 5 μm; Mobile Phase A: water (0.2% v/v conc. HCl); Mobile phase B: MeCN; 23-63% B gradient, 9 min, hold at 100% B for 2 min; flow rate 30 mL/min) to provide the title compound (27 mg, 19%). $^1$H NMR (400 MHz, $CD_3OD$) δ=8.19 (d, 1H), 7.29 (t, 1H), 3.90 (s, 3H), 3.65 (m, 4H), 3.24 (s, 2H), 2.73 (s, 2H), 2.48 (s, 3H), 1.69 (m, 4H), 1.43 (s, 9H). LC/MS m/z $(M+Na)^+$=489.1.

Example 34: 2-(tert-butyl)-1'-(4-chloro-5-methyl-1H-indazole-7-carbonyl)-5H-spiro[benzo[d]thiazole-6,4'-piperidin]-4(7H)-one

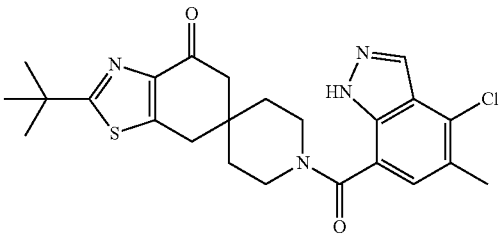 [SMILES: Cc1cc(C(=O)N2CCC3(CC2)CC(=O)c2nc(C(C)(C)C)sc2C3)c2[nH]ncc2c1Cl]

Prepared in the same manner as Example 33, substituting 3-chloro-2,4-dimethylaniline for 4-methoxy-2,3-dimethylaniline in Step 1, to provide the title compound (15 mg). 1H NMR (400 MHz, $CD_3OD$) δ 8.11 (s, 1H), 7.37 (s, 1H), 3.87-3.48 (m, 4H), 3.24 (s, 2H), 2.73 (s, 2H), 2.49 (s, 3H), 1.77-1.58 (m, 4H), 1.43 (s, 9H); LC/MS m/z $(M+H)^+$=471.3.

Example 35: 2-(tert-butyl)-1'-(4,5-dimethyl-1H-indazole-7-carbonyl)-5H-spiro[benzo[d]thiazole-6,4'-piperidin]-4(7H)-one

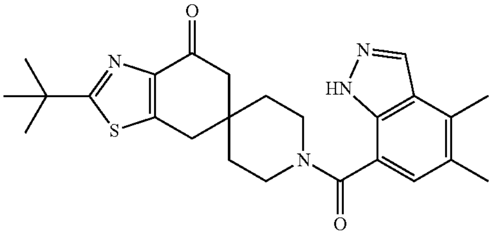 [SMILES: Cc1cc(C(=O)N2CCC3(CC2)CC(=O)c2nc(C(C)(C)C)sc2C3)c2[nH]ncc2c1C]

Prepared in the same manner as Example 33, substituting 2,3,4-trimethylaniline in place of 4-methoxy-2,3-dimethylaniline in Step 1, to provide the title compound (26 mg). $^1$H NMR (400 MHz, $CD_3OD$) δ 8.13 (s, 1H), 7.26 (s, 1H), 3.70-3.59 (m, 4H), 3.23 (s 2H), 2.73 (s, 2H), 2.55 (s, 3H), 2.39 (s, 3H), 1.76-1.67 (m, 4H), 1.43 (s, 9H); LC/MS m/z $(M+H)^+$=451.4.

Example 36: 2-(tert-butyl)-1'-(4-methoxy-5-methyl-1H-indazole-7-carbonyl)-5H-spiro[benzo[d]thiazole-6,4'-piperidin]-4(7H)-one

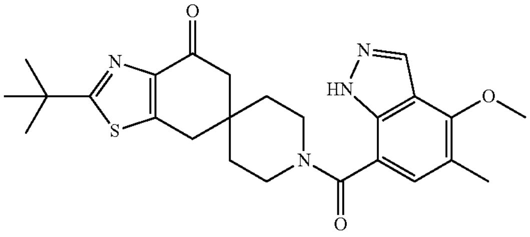 [SMILES: COc1c(C)cc(C(=O)N2CCC3(CC2)CC(=O)c2nc(C(C)(C)C)sc2C3)c2[nH]ncc12]

Step 1: Synthesis of 4-methoxy-5-methyl-1-(tetrahydro-2H-pyran-2-yl)-1H-indazole (C42)

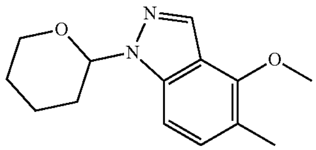 [SMILES: COc1c(C)ccc2c1cnn2C1CCCCO1]

To 5-methyl-1-(tetrahydro-2H-pyran-2-yl)-1H-indazol-4-ol (2.5 g, 10.76 mmol) and $K_2CO_3$ (2.98 g, 21.5 mmol) was added DMF (30 mL). The mixture was cooled to about 0-5° C. and stirred for about 10 min. Iodomethane (1.01 mL, 16.1 mmol) was added dropwise, and the mixture was stirred at about 25° C. for about 20 h. Water (30 mL) was added and the mixture was extracted with EtOAc (3×30 mL). The combined EtOAc extracts were washed with saturated brine, dried over $MgSO_4$, filtered, and concentrated under reduced pressure. The residue was purified by column chromatography (0-20% EtOAc in petroleum ether) to provide the title compound (2.40 g, 91%). LC/MS m/z $(M+H)^+$=247.0.

Step 2: Synthesis of 7-bromo-4-methoxy-5-methyl-1H-indazole (C43)

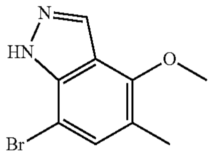

To a solution of compound C42 (2.40 g, 9.74 mmol) in DCM (50 mL) was added pyridinium tribromide (3.43 g, 10.7 mmol). The mixture was stirred at about 25° C. for about 2 h. Water (30 mL) was added, and the mixture was extracted with EtOAc (3×20 mL). The combined EtOAc extracts were washed with saturated brine, dried over $MgSO_4$, filtered, and concentrated under reduced pressure. The residue was purified by column chromatography (0-20% EtOAc in petroleum ether) to provide the title compound (1.90 g, 81%). LC/MS m/z $(M+H)^+$=242.8.

Step 3: Synthesis of ethyl 4-methoxy-5-methyl-1H-indazole-7-carboxylate (C44)

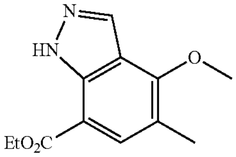 [SMILES: CCOC(=O)c1cc(C)c(OC)c2cn[nH]c12]

To a solution of compound C43 (1.20 g, 3.0 mmol) in EtOH (20 mL) was added $Pd(OAc)_2$ (54 mg, 0.239 mmol), $tBu_3P \cdot BF_4$ (87 mg, 0.30 mmol), DBU (682 mg, 4.48 mmol), and $Mo(CO)_6$ (237 mg, 0.90 mmol). The mixture was irradiated in the microwave at 100° C. for 30 min. The mixture was filtered, and the filtrate was concentrated under reduced pressure. The residue was purified by column chromatography (0-30% EtOAc in petroleum ether) to provide the title compound (450 mg, 64%). LC/MS m/z $(M+H)^+$=235.0.

Step 4: Synthesis of 4-methoxy-5-methyl-1H-indazole-7-carboxylic acid (C45)

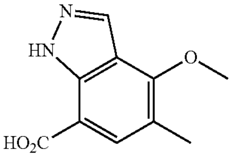

To a solution of compound C44 (700 mg, 2.99 mmol) in EtOH (5 mL) was added NaOH (598 mg, 14.9 mmol) and water (5 mL). The mixture was stirred at about 50° C. for about 16 h. The mixture was concentrated under reduced pressure and the residue was acidified to pH 5 with 2 N HCl. The precipitate was filtered to provide the title compound (580 mg, 94%). LC/MS m/z $(M+H)^+$=206.9.

Step 5: Synthesis of 2-(tert-butyl)-1'-(4-methoxy-5-methyl-1H-indazole-7-carbonyl)-5H-spiro[benzo[d]thiazole-6,4'-piperidin]-4(7H)-one

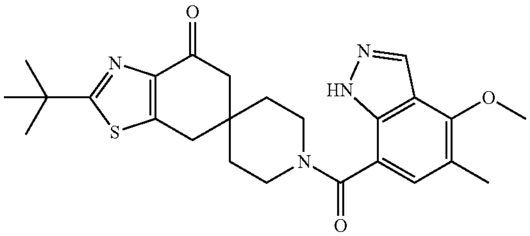 [SMILES: COc1c(C)cc(C(=O)N2CCC3(CC2)CC(=O)c2nc(C(C)(C)C)sc2C3)c2[nH]ncc12]

According to amidation method A, compound C45 (300 mg, 1.45 mmol) was coupled to preparation P1. The residue was purified by prep-HPLC (Column: Boston Prime C18, 30×150 mm, 5 μm); Mobile Phase A: water (0.05% v/v conc. $NH_4OH$); Mobile phase B: MeCN; 30-60% B gradient, 9 min, hold at 100% B for 2 min; flow rate 30 mL/min) to provide the title compound (345 mg, 51%). $^1H$ NMR (400 MHz, $CD_3OD$) δ 8.32 (s, 1H), 7.28 (s, 1H), 4.25 (s, 3H), 3.69 (m, 4H), 3.24 (s, 2H), 2.73 (s, 2H), 2.29 (s, 3H), 1.68 (m, 4H), 1.43 (s, 9H); LC/MS m/z $(M+H)^+$=467.4.

Example 37: 2-(tert-butyl)-1'-(4-chloro-5-methoxy-1H-indole-7-carbonyl)-5H-spiro[benzo[d]thiazole-6,4'-piperidin]-4(7H)-one

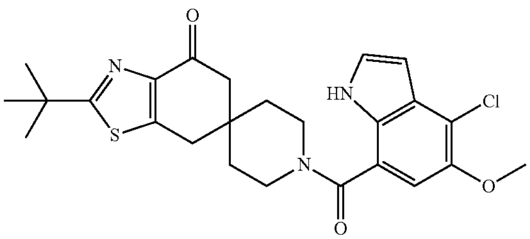 [SMILES: COc1cc(C(=O)N2CCC3(CC2)CC(=O)c2nc(C(C)(C)C)sc2C3)c2[nH]ccc2c1Cl]

Step 1: Synthesis of 1-bromo-4-chloro-5-methoxy-2-nitrobenzene (C46)

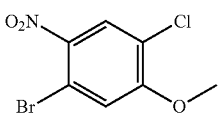

To 4-bromo-1-chloro-2-methoxybenzene (1.00 g, 4.52 mmol) was added $H_2SO_4$ (3 mL) and the mixture was cooled to about 0° C. and stirred for about 10 min. $HNO_3$ (0.43 mL, 11.3 mmol) was added portion-wise. The mixture was allowed to slowly warm to about 20° C. over about 16 h. The mixture was poured onto ice water and adjusted to pH 7-9 with $Na_2CO_3$. The mixture was extracted with EtOAc (3×200 mL) and the combined EtOAc extracts were dried over $Na_2SO_4$, filtered, and concentrated under reduced pressure. The residue was purified by column chromatography (0-2% EtOAc in DCM) to provide the title compound and the dinitrated byproduct, 2-bromo-5-chloro-4-methoxy-1,3-dinitrobenzene (1.10 g, <91% yield). $^1H$ NMR (400 MHz, $CDCl_3$) δ 8.10 (s, 1H), 7.22 (s, 1H), 4.01 (s, 3H).

Step 2: Synthesis of 7-bromo-4-chloro-5-methoxy-1H-indole (C47)

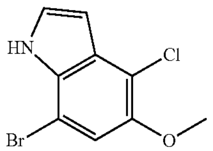

To compound C46 (1.10 g, about 20% purity, 0.83 mmol) in THF (10 mL) at about −50° C. was added vinylmagnesium bromide (1 M, 15 mL, 15 mmol). The mixture was allowed to warm to about −20° C. and stirred for about 16 h. The mixture was warmed to 0° C. and $NH_4Cl$ (30 mL) and EtOAc (50 mL) were added. The phases were separated, and the aqueous phase was extracted with EtOAc (3×20 mL). The combined EtOAc extracts were washed with brine (20 mL), dried over $Na_2SO_4$, filtered, and concentrated under reduced pressure. The residue was purified by column chromatography (5% EtOAc in petroleum ether) to provide the title compound (30 mg, 14% yield). LC/MS m/z $(M+H)^+$ =261.8.

Step 3: Synthesis of ethyl 4-chloro-5-methoxy-1H-indole-7-carboxylate (C48)

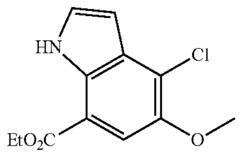 [SMILES: CCOC(=O)c1cc(OC)c(Cl)c2cc[nH]c12]

To a solution of compound C47 (50 mg, 0.19 mmol) in EtOH (10 mL) was added $Pd(OAc)_2$ (3.5 mg, 0.0154 mmol), $tBu_3P{\cdot}BF_4$ (5.6 mg, 0.0192 mmol), DBU (44 mg, 0.288 mmol), and $Mo(CO)_6$ (51 mg, 0.192 mmol). The mixture was irradiated in the microwave at about 100° C. for about 1 h. The mixture was filtered and the filtrate was concentrated under reduced pressure. The residue was purified by column chromatography (0-2% EtOAc in petroleum ether) to provide the title compound (20 mg, 41%). LC/MS m/z $(M+H)^+$=254.0.

Step 4: Synthesis of 4-chloro-5-methoxy-1H-indole-7-carboxylic acid (C49)

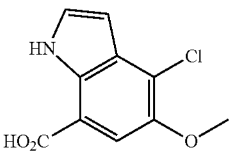

To a solution of compound C48 (20 mg, 0.079 mmol) in water (1 mL) and THF (2 mL) was added LiOH $H_2O$ (6.6 mg, 0.16 mmol) at about 15° C. The mixture was stirred at about 50° C. for about 16 h. The mixture was concentrated under reduced pressure and the residue was acidified to pH 5 with 2 N HCl. The solution was concentrated to provide the title compound (15 mg, 84%). LC/MS m/z $(M+H)^+$=225.9.

Step 5: Synthesis of 2-(tert-butyl)-1'-(4-chloro-5-methoxy-1H-indole-7-carbonyl)-5H-spiro[benzo[d]thiazole-6,4'-piperidin]-4(7H)-one

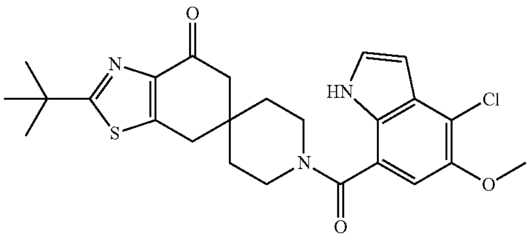 [SMILES: COc1cc(C(=O)N2CCC3(CC2)CC(=O)c2nc(C(C)(C)C)sc2C3)c2[nH]ccc2c1Cl]

According to amidation method A, compound C49 (15 mg, 1.45 mmol) was coupled to preparation P1. The residue was purified by prep-HPLC (Column: Boston Prime C18, 30×150 mm, 5 μm); Mobile Phase A: water (0.05% v/v conc. $NH_4OH$); Mobile phase B: MeCN; 40-70% B gradient, 9 min, hold at 100% B for 2 min; flow rate 30 mL/min) to provide the title compound (4.5 mg, 14%). $^1H$ NMR (400 MHz, $CD_3OD$) δ 7.35 (d, 1H), 7.00 (s, 1H), 6.52 (d, 1H), 3.90 (s, 3H), 3.89-3.48 (m, 4H), 3.23 (s, 2H), 2.73 (s, 2H), 1.79-1.64 (m, 4H), 1.43 (s, 9H); LC/MS m/z $(M+H)^+$=486.3.

Example 38: 2-(tert-butyl)-1'-(5-methyl-2-(methylamino)quinoline-7-carbonyl)-5H-spiro[benzo[d]thiazole-6,4'-piperidin]-4(7H)-one

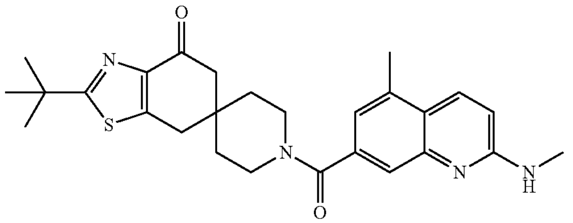 [SMILES: CNc1ccc2c(C)cc(C(=O)N3CCC4(CC3)CC(=O)c3nc(C(C)(C)C)sc3C4)cc2n1]

To a solution of preparation P1 (1.26 g, 4.01 mmol), preparation P2 (581 mg, 2.69 mmol), EDCl (773 mg, 4.04 mmol), and HOBt (582 mg, 4.31 mmol) in DMF (35 mL) at about 25° C. was added $^{i}Pr_2NEt$ (5 mL, 26.9 mmol). The mixture was stirred at about 25° C. for about 16 h, then diluted with EtOAc. The mixture was washed sequentially with 5% aqueous LiCl, saturated aqueous $NaHCO_3$, and 1:1 brine:water (30 mL). The organic phase was dried over MgSO4, filtered, and concentrated. The residue was purified by column chromatography (0 to 20% MeOH in DCM) to provide the title compound (1.28 g, 86%). $^{1}H$ NMR (400 MHz, DMSO-d6) δ 7.99 (d, 1H), 7.31 (s, 1H), 7.07 (s, 1H), 6.96 (s, 1H), 6.81 (d, 1H), 3.75-3.35 (m, 4H), 3.23 (s, 2H), 2.91 (d, 3H), 2.66 (s, 2H), 2.54 (s, 3H), 1.60-1.53 (m, 4H), 1.38 (s, 9H); LC/MS m/z $(M+H)^+$=477.5.

Example 39: 2-(tert-butyl)-1'-(2-(ethylamino)-5-methylquinoline-7-carbonyl)-5H-spiro[benzo[d]thiazole-6,4'-piperidin]-4(7H)-one

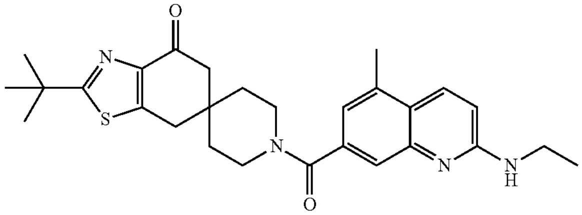 [SMILES: CCNc1ccc2c(C)cc(C(=O)N3CCC4(CC3)CC(=O)c3nc(C(C)(C)C)sc3C4)cc2n1]

Step 1: Synthesis of 7-bromo-N-ethyl-5-methylquinolin-2-amine (C50)

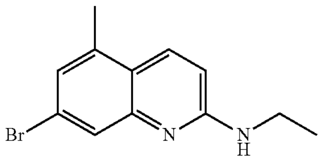

To 7-bromo-2-chloro-5-methylquinoline (prepared as described in patent application WO 2013185103 A1, 50 mg, 0.19 mmol) was added $iPr_2NEt$ (67 μL, 0.39 mmol), ethylamine (70% solution in water, 0.234 mmol), and NMP (0.2 mL). The mixture was heated to about 110° C. for about 18 h, then heated to about 140° C. for about 24 h. The mixture was cooled to about 25° C. and diluted with water. The mixture was extracted with diethyl ether (3×). The combined ether extracts were dried over $MgSO_4$, filtered, and concentrated under reduced pressure. The residue was purified by column chromatography (0% to 60% EtOAc in heptanes) to provide the title compound (14 mg, 27%). LC/MS m/z $(M+H)^+$=265.2.

Step 2: Synthesis of 2-(tert-butyl)-1'-(2-(ethylamino)-5-methylquinoline-7-carbonyl)-5H-spiro[benzo[d]thiazole-6,4'-piperidin]-4(7H)-one

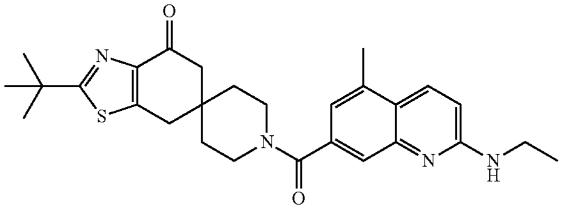 [SMILES: CCNc1ccc2c(C)cc(C(=O)N3CCC4(CC3)CC(=O)c3nc(C(C)(C)C)sc3C4)cc2n1]

To compound C50 (80 mg, 0.30 mmol) was added 2,4,6-trichlorophenyl formate (136 mg, 0.60 mmol) and Xantphos (11 mg, 0.018 mmol). A degassed solution of triethylamine (85 μL, 0.60 mmol) and toluene (0.30 mL) was added. The mixture was heated to about 80° C. for about 18 h. The mixture was diluted with ether and filtered through celite. The mixture was concentrated under reduced pressure, redissolved in DCM, and filtered through silica. The mixture was concentrated under reduced pressure. To the residue was added THF (0.2 mL), triethylamine (21 μL, 0.15 mmol), preparation P1 (25 mg, 0.087 mmol), and DMAP (0.5 mg, 0.004 mmol). The mixture was stirred at about 50° C. for about 16 h. Water was added and the mixture was extracted with EtOAc (2×). The combined EtOAc extracts were dried over $MgSO_4$, filtered, and concentrated under reduced pressure. The residue was purified by prep-HPLC (Column: XBridge C18, 19×100 mm, 5 μm) to provide the title compound (27 mg, 18%). LC/MS m/z $(M+H)^+$=491.5.

Example 40: 2-(tert-butyl)-1'-(5-methoxy-2-(methylamino)quinoline-7-carbonyl)-5H-spiro[benzo[d]thiazole-6,4'-piperidin]-4(7H)-one

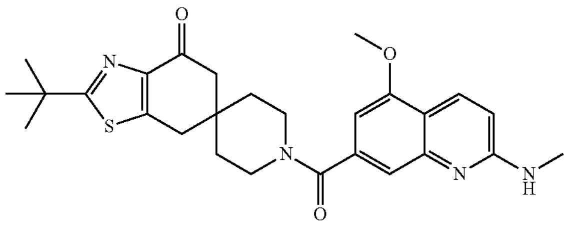 [SMILES: CNc1ccc2c(OC)cc(C(=O)N3CCC4(CC3)CC(=O)c3nc(C(C)(C)C)sc3C4)cc2n1]

Step 1: Synthesis of 5-methoxy-7-(methoxycarbonyl)quinoline 1-oxide (C51)

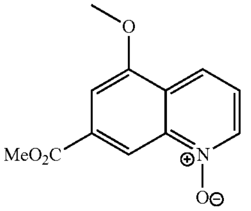 [SMILES: COC(=O)c1cc(OC)c2ccc[n+]([O-])c2c1]

The following reaction was carried out in 2 batches in parallel. To methyl 5-methoxyquinoline-7-carboxylate (1.20 g, 4.70 mmol) in DCM (25 mL) was added m-CPBA (972 mg, 5.63 mmol). The mixture was stirred at about 20° C. for about 16 h. The two batches were combined and saturated aqueous $Na_2S_2O_3$ was added. Saturated aqueous Na2CO3 was added until the pH was >8, then the mixture was stirred for about 30 min. The mixture was filtered and the filtrate was concentrated under reduced pressure. The residue was diluted with DCM (50 mL) and washed with water (3×20 mL). The DCM extract was dried over $Na_2SO_4$, filtered, and concentrated under reduced pressure. The residue was purified via column chromatography (0% to 15% MeOH in EtOAc) to provide the title compound (1.90 g, 95% average yield). LC/MS m/z $(M+H)^+$=233.9.

Step 2: Synthesis of methyl 5-methoxy-2-(methylamino)quinoline-7-carboxylate (C52)

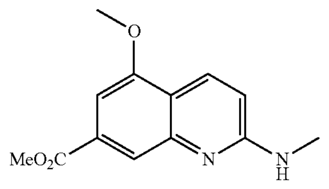 [SMILES: CNc1ccc2c(OC)cc(C(=O)OC)cc2n1]

To compound C51 (1.20 g, 5.15 mmol) in DCM (30 mL) at about −70° C. was added $Tf_2O$ (1.60 g, 5.66 mmol) dropwise. The mixture was stirred for about 15 min at −70° C., then $MeNH_2$ (2 M in THF, 20.6 mL, 41.2 mmol) was added dropwise. The mixture was stirred at about −70° C. for about 15 min, then water (30 mL) was added. The aqueous phase was extracted with DCM (30 mL). The combined DCM extracts were washed with brine (2×10 mL), dried over $Na_2SO_4$, filtered, and concentrated under reduced pressure. The residue was purified via column chromatography (0% to 60% EtOAc in petroleum ether) to provide the title compound (800 mg, 63% yield). LC/MS m/z $(M+H)^+$=247.0.

Step 3: Synthesis of 5-methoxy-2-(methylamino)quinoline-7-carboxylic acid (C53)

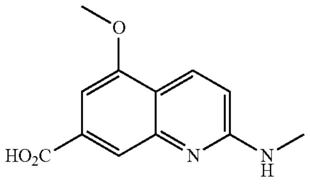 [SMILES: CNc1ccc2c(OC)cc(C(=O)O)cc2n1]

To compound C52 (800 mg, 3.25 mmol) in EtOH (6 mL) was added NaOH (650 mg, 16.2 mmol) and water (6 mL). The reaction was stirred at about 50° C. for about 2 h. Ethanol was removed under reduced pressure and the residue was acidified to pH 5 with 2 N HCl. The precipitate was filtered to provide the title compound (730 mg, 97% yield). LC/MS m/z $(M+H)^+$=232.9.

Step 4: Synthesis of 2-(tert-butyl)-1'-(5-methoxy-2-(methylamino)quinoline-7-carbonyl)-5H-spiro[benzo[d]thiazole-6,4'-piperidin]-4(7H)-one

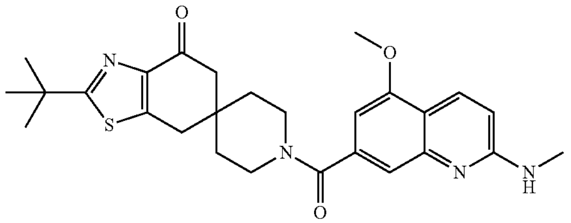 [SMILES: CNc1ccc2c(OC)cc(C(=O)N3CCC4(CC3)CC(=O)c3nc(C(C)(C)C)sc3C4)cc2n1]

Compound C53 (300 mg, 1.29 mmol) was coupled according to general amide coupling procedure A. The residue was purified by prep-HPLC (Column: Boston Prime C18, 30×150 mm, 5 μm); Mobile Phase A: water (0.05% v/v conc. $NH_4OH$); Mobile phase B: MeCN; 28-58% B gradient, 9 min, hold at 100% B for 2 min; flow rate 30 mL/min) to provide the title compound (259 mg, 41%). $^1H$ NMR (400 MHz, $CD_3OD$) δ 8.14 (d, 1H), 7.25 (s, 1H), 6.72 (d, 1H), 6.66 (s, 1H), 3.97 (s, 3H), 3.88-3.79 (m, 2H), 3.55 (m, 2H), 3.26 (s, 2H), 2.99 (s, 3H), 2.74 (s, 2H), 1.77-1.65 (m, 4H), 1.43 (s, 9H); LC/MS m/z $(M+H)^+$=493.4.

Example 41: 2-(tert-butyl)-1'-(4-methoxy-8-methylquinoline-6-carbonyl)-5H-spiro[benzo[d]thiazole-6,4'-piperidin]-4(7H)-one

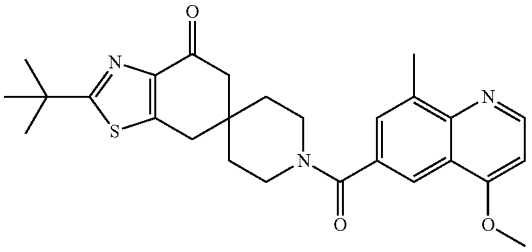 [SMILES: COc1ccnc2c(C)cc(C(=O)N3CCC4(CC3)CC(=O)c3nc(C(C)(C)C)sc3C4)cc12]

Step 1: Synthesis of 6-bromo-4-methoxy-8-methylquinoline (C54)

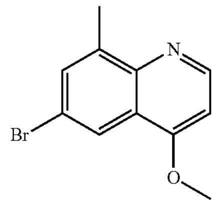

To 6-bromo-4-chloro-8-methylquinoline (2.67 g, 9.9 mmol) in MeOH (30 mL) was added sodium methoxide (2.61 g, 48.3 mmol). The mixture was stirred at about 80° C. for about 48 h. The mixture was cooled to about 25° C. and diluted with EtOAc. The mixture was washed with water (2×) and brine. The combined EtOAc extracts were dried over $Na_2SO_4$, filtered, and concentrated under reduced pressure to provide a 1:1 mixture of 6-bromo-4-chloro-8-methylquinoline the title compound (2.50 g). LC/MS m/z $(M+H)^+$=254.2.

Step 2: Synthesis of methyl 4-methoxy-8-methylquinoline-6-carboxylate (C55)

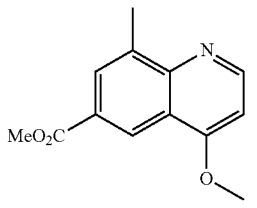 [SMILES: COC(=O)c1cc(C)c2nccc(OC)c2c1]

To a solution of compound C54 (3.06 g, 12.2 mmol) in MeOH (100 mL) was added triethylamine (5.5 mL, 39 mmol) and $Pd(dppf)Cl_2$ (720 mg, 0.882 mmol). The mixture was added to a Parr reactor, flushed with nitrogen (3×), and flushed with CO (3×). The mixture was stirred at about 80° C. and 75 PSI of CO for about 16 h. The mixture was cooled to about 25° C. and filtered through celite. The filtrate was concentrated under reduced pressure, then purified via column chromatography (0% to 100% EtOAc in heptanes) to provide the title compound (1.96 g, 70%). LC/MS m/z $(M+H)^+$=232.5.

Step 3: Synthesis of 4-methoxy-8-methylquinoline-6-carboxylic acid (C56)

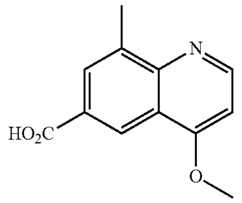 [SMILES: COc1ccnc2c(C)cc(C(=O)O)cc12]

To a solution of compound C55 (1.96 g, 8.48 mmol) in THF (65 mL) was added 2 M NaOH (25 mL, 50 mmol). The mixture was stirred at about 25° C. for about 18 h. The mixture was acidified with conc. HCl to pH 6. The mixture was extracted with EtOAc (2×) and the combined EtOAc extracts were washed with brine, dried over $Na_2SO_4$, filtered, and concentrated under reduced pressure to provide the title compound (1.46 g, 79%). LC/MS m/z $(M+H)^+$=218.0.

Step 4: Synthesis of 2-(tert-butyl)-1'-(4-methoxy-8-methylquinoline-6-carbonyl)-5H-spiro[benzo[d]thiazole-6,4'-piperidin]-4(7H)-one

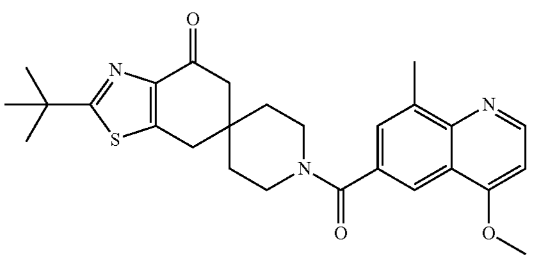 [SMILES: COc1ccnc2c(C)cc(C(=O)N3CCC4(CC3)CC(=O)c3nc(C(C)(C)C)sc3C4)cc12]

To a solution of preparation P1 (325 mg, 1.03 mmol), compound C56 (264 mg, 1.22 mmol), EDCl (243 mg, 1.27 mmol), and HOBt (263 mg, 1.80 mmol) in DMF (5 mL) at about 25° C. was added $^iPr_2NEt$ (1.0 mL, 5.6 mmol). The mixture was stirred at about 25° C. for about 16 h. To the mixture was added additional EDCl (225 mg, 1.17 mmol), HOBt (198 mg, 1.40 mmol), and $Et_3N$ (0.72 mL, 5.2 mmol). The mixture was stirred at about 25° C. for about 2 h, then diluted with EtOAc. The mixture was washed sequentially with 5% aqueous LiCl, saturated aqueous $NaHCO_3$, and 1:1 brine:water. The organic phase was dried over $MgSO_4$, filtered, and concentrated under reduced pressure. The residue was purified by column chromatography (0 to 8% MeOH in DCM) to provide the title compound (435 mg, 88%). $^1H$ NMR (400 MHz, DMSO-d6) δ 8.82 (d, 1H), 7.98 (s, 1H), 7.60 (s, 1H), 7.11 (d, 1H), 4.06 (s, 3H), 3.66-3.41 (m, 4H), 3.23 (s, 2H), 2.72 (s, 3H), 2.66 (s, 2H), 1.62-1.51 (m, 4H), 1.38 (s, 9H); LC/MS m/z $(M+H)^+$=478.5.

Example 42: 2-(tert-butyl)-1'-(3-chloro-7-methyl-1H-indole-5-carbonyl)-5H-spiro[benzo[d]thiazole-6,4'-piperidin]-4(7H)-one

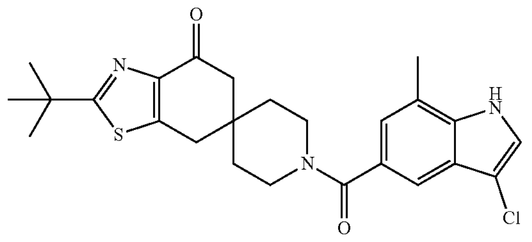 [SMILES: Cc1cc(C(=O)N2CCC3(CC2)CC(=O)c2nc(C(C)(C)C)sc2C3)cc2c(Cl)c[nH]c12]

Step 1: Synthesis of ethyl 3-chloro-7-methyl-1H-indole-5-carboxylate (C61)

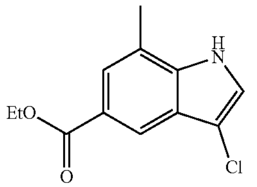 [SMILES: CCOC(=O)c1cc(C)c2[nH]cc(Cl)c2c1]

To a solution of ethyl 7-methyl-1H-indole-5-carboxylate (commercial; 0.45 g, 2.21 mmol) in THF (22 mL) was added NCS (0.5 g, 3.76 mmol). The reaction was stirred at about 25° C. for about 3 h and diluted with EtOAc (20 mL) and water (20 mL). The organic layer was separated, and the aqueous layer was extracted using EtOAc (2×20 mL). The combined EtOAc extracts were dried over $MgSO_4$, filtered, and concentrated under reduced pressure to provide the title compound (380 mg, 72%) as a yellow solid. $^1H$ NMR (400 MHz, Chloroform-d) δ 8.36 (s, 0.5H), 8.31-8.26 (m, 0.5H), 8.24 (s, 0.5H), 8.18 (d, 0.5H), 7.79 (d, 1H), 7.24 (d, 1H), 4.43 (q, 2H), 2.53 (s, 3H), 1.45 (t, 3H).

Step 2: Synthesis of 3-chloro-7-methyl-1H-indole-5-carboxylic acid (C62)

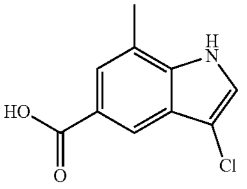

To compound ethyl 3-chloro-7-methyl-1H-indole-5-carboxylate C61 (0.38 g, 1.6 mmol) in MeOH (9 mL), and $H_2O$ (3 mL), was added LiOH $H_2O$ (0.2 g, 4.80 mmol). The mixture was heated to about 25° C. for about 4 h and then concentrated. The mixture was diluted with water (6 mL) and extracted with EtOAc (2×20 mL); the EtOAc extract was discarded. The pH of the aqueous layer was adjusted to 3-4 with 1 N HCl and extracted using EtOAc (2×20 mL). The combined EtOAc extracts were dried over $MgSO_4$, filtered, and concentrated under reduced pressure to provide the title compound (210 mg, 63%) as a yellow solid. $^1$H NMR (400 MHz, DMSO-d6) b 12.60 (s, 1H), 11.77 (s, 1H), 8.04 (s, 1H), 7.74-7.67 (m, 1H), 7.66 (s, 1H), 2.56 (s, 3H, overlap with d-DMSO).

Step 3: Synthesis of 2-(tert-butyl)-1'-(3-chloro-7-methyl-1H-indole-5-carbonyl)-5H-spiro[benzo[d]thiazole-6,4'-piperidin]-4(7H)-one

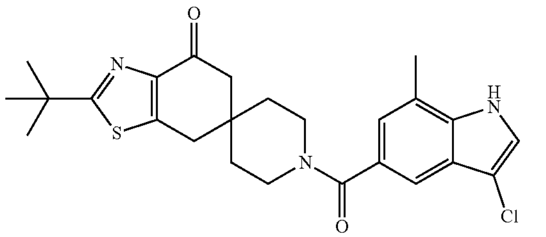 [SMILES: Cc1cc(C(=O)N2CCC3(CC2)CC(=O)c2nc(C(C)(C)C)sc2C3)cc2c(Cl)c[nH]c12]

According to amidation method C, (EDCl, Pyridine, MW) preparation P1, (0.3 g, 0.95 mmol) was coupled with 3-chloro-7-methyl-1H-indole-5-carboxylic acid (0.2 g, 0.95 mmol). The residue was purified by prep-HPLC (Column: Boston Prime C18, 150×30 mm, 3 μm); Mobile Phase A: water (0.05% v/v conc. $NH_4OH$); Mobile phase B: MeCN; 9-60% B gradient, 9 min, hold at 100% B for 2 min; flow rate 25 mL/min to provide the title compound (170 mg, 34.5%). $^1$H NMR (400 MHz, DMSO-d6) δ 11.56 (d, 1H), 7.60 (d, 1H), 7.36-7.30 (m, 1H), 7.03 (d, 1H), 3.52 (m, 4H), 3.22 (s, 2H), 2.64 (s, 2H), 2.48 (s, 3H), 1.54 (m, 4H), 1.37 (s, 9H); LC/MS m/z $(M+H)^+$=470.3.

Example 43: 2-(tert-butyl)-1'-(4,8-dimethoxyisoquinoline-6-carbonyl)-5H-spiro[benzo[d]thiazole-6,4'-piperidin]-4(7H)-one

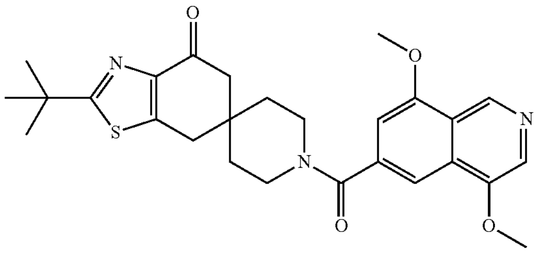 [SMILES: COc1cc(C(=O)N2CCC3(CC2)CC(=O)c2nc(C(C)(C)C)sc2C3)cc2c(OC)cncc12]

Step 1: Synthesis of ethyl 8-bromoisoquinoline-6-carboxylate (C63)

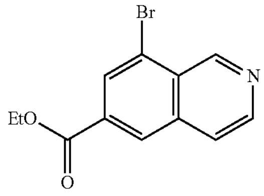 [SMILES: CCOC(=O)c1cc(Br)c2cnccc2c1]

To a solution of ethyl isoquinoline-6-carboxylate (commercial; 22.6 g, 112.3 mmol) in conc. $H_2SO_4$ (200 mL) was added NBS (22 g, 124 mmol) in portions. The reaction was stirred at about 10° C. for about 16 h. Additional NBS (3 g, 16.9 mmol) was added, and reaction was stirred at about 10° C. for an additional 16 h. The reaction was quenched by pouring into ice (500 mL), cooled to 0° C. and the pH was adjusted to ~8 using 3 N NaOH (500 mL). The reaction mixture was extracted using DCM (2×800 mL), washed with brine (100 mL), dried over $Na_2SO_4$, filtered, and concentrated under reduced pressure. The residue was purified by chromatography using silica gel [(Petroleum ether/DCM=1:1): EtOAc=100:0 to 90:10] to provide the title compound (22.2 g, 70.6%) as a white solid. $^1$H NMR (400 MHz, Chloroform-d) δ 9.69 (s, 1H), 8.72 (d, 1H), 8.54 (t, 1H), 8.45 (d, 1H), 7.79-7.73 (m, 1H), 4.49 (q, 2H), 1.48 (t, 3H); LC/MS m/z $(M+H)^+$=279.9.

Step 2: Synthesis of ethyl 8-bromo-4-chloroisoquinoline-6-carboxylate (C64)

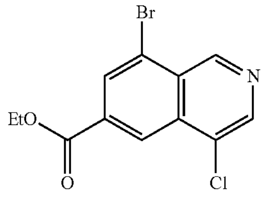 [SMILES: CCOC(=O)c1cc(Br)c2cncc(Cl)c2c1]

To a solution of ethyl 8-bromoisoquinoline-6-carboxylate C63 (0.25 g, 0.89 mmol) in AcOH (5 mL) was added NCS (0.143 g, 1.07 mmol). The reaction mixture was stirred at about 50° C. for about 16 h and then the temperature was increased to about 60° C. for an additional 16 h. The reaction was concentrated, then diluted using EtOAc (50 mL) and sat. aqueous $NaHCO_3$ (20 mL). The layers were separated, and the aqueous layer extracted using EtOAc (3×50 mL). The combined EtOAc layers was washed with brine (2×30 mL), dried over $Na_2SO_4$, filtered, and concentrated under reduced pressure. The residue was purified by chromatography (0% to 20% EtOAc in petroleum ether) to provide the title compound (0.2 g, 71.2%). $^1H$ NMR (400 MHz, Chloroform-d) δ 9.51 (d, 1H), 8.82 (t, 1H), 8.67 (s, 1H), 8.42 (d, 1H), 4.43 (q, 2H), 1.41 (t, 3H); LC/MS m/z $(M+H)^+$=315.9.

Step 3: Synthesis of methyl 4,8-dimethoxyisoquinoline-6-carboxylate (C65)

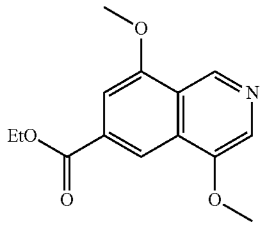 [SMILES: COc1cc(C(=O)O)cc2c(OC)cncc12]

To a solution of ethyl 8-bromo-4-chloroisoquinoline-6-carboxylate (0.2 g, 0.636 mmol) in dioxane (5 mL) was added Rockphos-Pd-G3 (0.053 g, 0.0636 mmol), $Cs_2CO_3$ (0.414 g, 1.27 mmol) and MeOH (0.102 g, 3.18 mmol). The reaction mixture was stirred at about 80° C. for about 16 h, cooled to room temperature, filtered, and concentrated. The residue was purified by chromatography (0% to 40% EtOAc in petroleum ether) to provide the title compound (0.09 g, 57%) as a yellow solid. $^1H$ NMR (400 MHz, Chloroform-d) δ 9.22 (d, 1H), 8.42 (dt, 1H), 8.11 (s, 1H), 7.43 (d, 1H), 4.10-3.99 (m, 6H), 3.93 (s, 3H); LC/MS m/z $(M+H)^+$=248.1.

Step 4: Synthesis of 4,8-dimethoxyisoquinoline-6-carboxylic acid (C66)

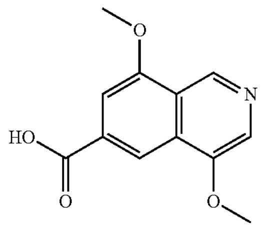

To compound methyl 4,8-dimethoxyisoquinoline-6-carboxylate C65 (0.09 g, 0.36 mmol) in MeOH (3 mL), and $H_2O$ (1 mL), was added $LiOHH_2O$ (0.076 g, 1.82 mmol). The reaction mixture was stirred at about 20° C. for about 16 h. The solvent was concentrated, and pH of residue was adjusted to 3-4 using 1 N HCl. The resulting solid was filtered and dried under vacuum to provide the title compound (40 mg, 47%) as a yellow solid. $^1H$ NMR (400 MHz, DMSO-d6) b 13.45 (s, 1H), 9.16 (s, 1H), 8.32 (s, 2H), 7.51 (s, 1H), 4.08 (d, 6H); LC/MS m/z $(M+H)^+$=233.9.

Step 5: Synthesis of 2-(tert-butyl)-1'-(4,8-dimethoxyisoquinoline-6-carbonyl)-5H-spiro[benzo[d]thiazole-6,4'-piperidin]-4(7H)-one (Example 43)

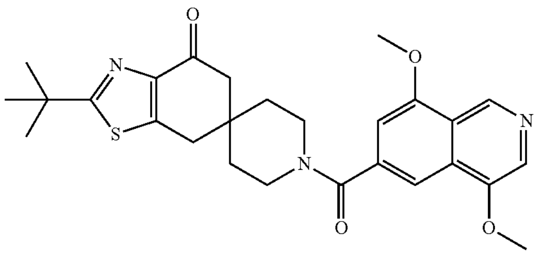 [SMILES: COc1cc(C(=O)N2CCC3(CC2)CC(=O)c2nc(C(C)(C)C)sc2C3)cc2c(OC)cncc12]

According to amidation method A, preparation P1 (0.06 g, 0.17 mmol) was coupled with 4,8-dimethoxyisoquinoline-6-carboxylic acid (0.04 g, 0.17 mmol). The residue was purified by prep-HPLC (Column: Boston Prime C18, 150×30 mm, 5 μm); Mobile Phase A: water (0.05% v/v conc. $NH_4OH$); Mobile Phase B: MeCN; 25-55% B gradient, 9 min, hold at 100% B for 2 min; flow rate 25 mL/min to provide the title compound (57.4 mg, 68%). $^1H$ NMR (400 MHz, Methanol-d4) δ 9.03 (s, 1H), 8.03 (s, 1H), 7.65 (t, 1H), 7.00 (d, 1H), 3.99 (s, 6H), 3.76 (d, 2H), 3.39 (s, 2H), 3.16 (s, 2H), 2.63 (d, 2H), 1.68 (s, 2H), 1.52 (s, 2H), 1.32 (s, 9H); LC/MS m/z $(M+H)^+$=494.4.

The following compounds of the invention were prepared similarly using the amidation methods described above. For those examples characterized by HPLC retention time, the following HPLC conditions were used:

Method 1

Column: ACQUITY UPLC BEH C18 50×2.1 mm, 1.7 μm.

Mobile phase A: 10 mM Ammonium Acetate in Water/acetonitrile-95/5 v/v.

Mobile phase B: 10 mM Ammonium Acetate in acetonitrile/Water-95/5 v/v.

Gradient: 5% D increase to 100% D within 1 min; hold at 100% D for 0.2 min; then back to 0% D at 1.21 min and hold for 0.29 min. Flow: 1.0 mL/min.

Method 2

Column: Atlantis dC18 4.6×50 mm 5 μm.

Mobile phase A: 0.05% TFA in water (v/v).

Mobile phase B: 0.05% TFA in Acetonitrile (v/v).

Gradient: 95% water/5% acetonitrile linear to 5% water/95% acetonitrile in 4.0 min, HOLD at 5% water/95% acetonitrile for 5 min.

Flow: 2 mL/min.

Method 3

Column: Xbridge C18 2.1×50 mm 5 μm

Mobile phase A: 0.0375% TFA in water

Mobile phase B: 0.01875% TFA in acetonitrile

Gradient: Hold 10% B for 0.5 min then linear to 100% B at 4 min, drop to 10% B at 4.30 min until 4.70 min.

Flow: 0.8 mL/min.

Method 4

Column: Xbridge C18 2.1×50 mm 5 μm

Mobile phase A: 0.0375% TFA in water.

Mobile phase B: 0.01875% TFA in acetonitrile.

Gradient: Hold 1% B for 0.6 min then linear to 100% B at 4 min, drop to 1% B at 4.30 min until 4.70 min.

Flow: 0.8 mL/min.

Method 5

Column: Waters Acquity HSS T3, 2.1 mm×50 mm, 1.7 μm.

Mobile phase A: 0.1% formic acid in water (v/v).

Mobile phase B: 0.1% formic acid in acetonitrile (v/v).

Gradient: Initial conditions A-95%:B-5%; hold at initial from 0.0-0.1 min; Linear Ramp to A-5%:B-95% over 0.1-1.0 min; hold at A-5%:B-95% from 1.0-1.1 min; return to initial conditions 1.1-1.5 min.

Flow: 1.25 mL/min.

| Ex. | | Reactant | Source | Amidation | $MH^+$ | Characterization |
|---|---|---|---|---|---|---|
| 44 | 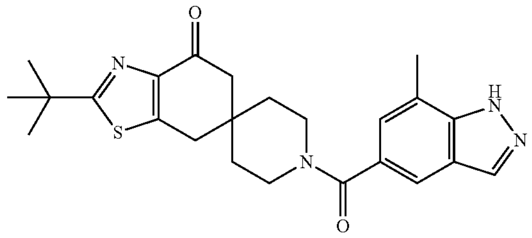 | 1031417-41-0 | Commercial | A | 437.3 (M + 1) | RT = 0.824 min (method1) $^1$H NMR (400 MHz, MeOD) δ 8.10 (s, 1H), 7.70 (s, 1H), 7.21 (t, 1H), 3.78 (m, 2H), 3.53 (m, 2H), 3.23 (s, 2H), 2.71 (s, 2H), 2.58 (s, 3H), 1.65 (m, 4H), 1.41 (s, 9H). |
| 45 | 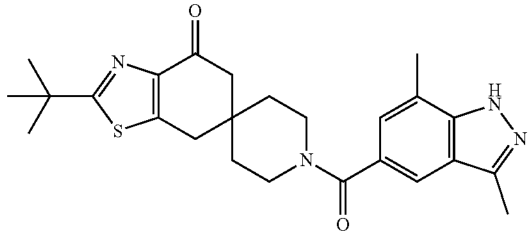 | 1031417-75-0 | Commercial | A | 451.2 (M + 1) | RT = 0.842 min (method1) $^1$H NMR (400 MHz, MeOD) δ 7.67 (s, 1H), 7.22 (s, 1H), 3.82 (m, 2H), 3.58 (m, 2H), 3.27 (s, 2H), 2.75 (s, 2H), 2.58 (d, 6H), 1.65 (m, 4H), 1.44 (s, 9H). |
| 46 | 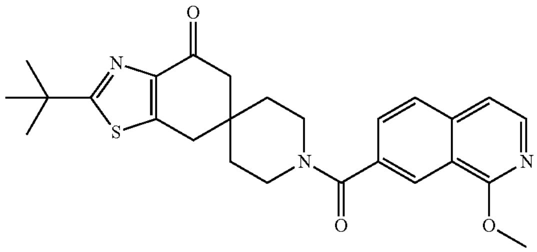 | 1369280-83-0 | Commercial | A | 464.3 (M + 1) | RT = 0.982 min (method1) $^1$H NMR (400 MHz, MeOD) δ 8.29 (t, 1H), 8.02 (d, 1H), 7.91 (d, 1H), 7.74 (dd, 1H), 7.35 (d, 1H), 4.13 (s, 3H), 3.85 (d, 2H), 3.51 (s, 2H), 3.26 (s, 2H), 2.74 (d, 2H), 1.70 (m, 4H), 1.43 (s, 9H). |
| 47 | 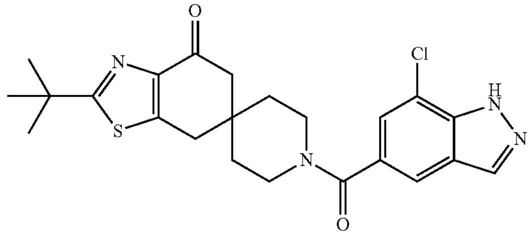 | 1031417-54-5 | Commercial | A | 471.2 (M + 1) | RT = 0.892 min (method1). $^1$H NMR (400 MHz, MeOD) δ 7.79 (d, 1H), 7.48 (d, 1H), 3.80 (s, 2H), 3.57 (s, 2H), 3.26 (s, 2H), 2.74 (s, 2H), 2.59 (s, 3H), 1.70 (s, 4H), 1.43 (s, 9H). |

-continued
| Ex. | | Reactant | Source | Amid-ation | MH+ | Characterization |
|---|---|---|---|---|---|---|
| 48 | 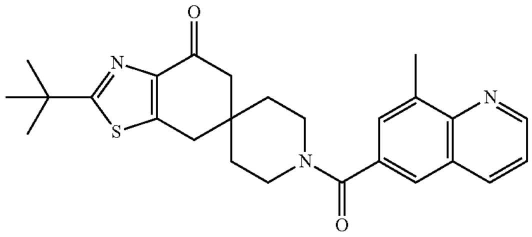 [SMILES: Cc1cc(C(=O)N2CCC3(CC2)CC(=O)c2nc(C(C)(C)C)sc2C3)cc2cccnc12] | 926217-76-7 | Commercial | B | 448.4 (M + 1) | RT = 1.96 min, (method2) |
| 49 | 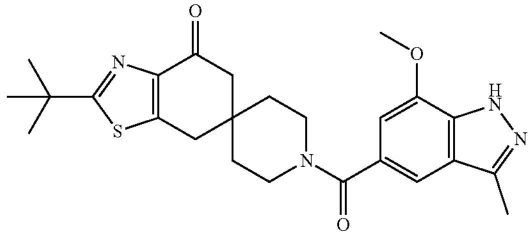 | | Pfizer patent PCT Int. Appl., 2009144554, 03 Dec 2009 | A | 467.4 (M + 1) | RT = 0.858 min (method1) $^{1}$H NMR (400 MHz, MeOD) δ 7.38 (d, 1H), 6.86 (s, 1H), 4.03 (s, 3H), 3.75 (m, 4H), 3.27 (s, 2H), 2.75 (s, 2H), 2.55 (s, 3H), 1.71 (m, 4H), 1.44 (s, 9H). |
| 50 | 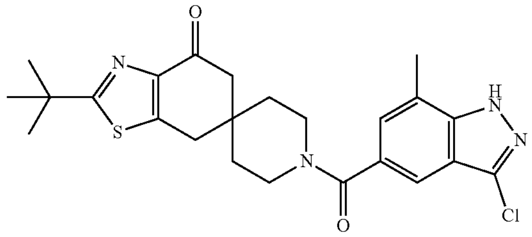 [SMILES: Cc1cc(C(=O)N2CCC3(CC2)CC(=O)c2nc(C(C)(C)C)sc2C3)cc2c(Cl)n[nH]c12] | | | C | 473.3 (M + 1) | RT = 0.957 min (method1) $^{1}$H NMR (400 MHz, MeOD) δ 7.59 (d, 1H), 7.28 (t, 1H), 3.81 (s, 2H), 3.53 (br. s, 2H), 3.25 (br. s, 2H), 2.73 (s, 2H), 2.58 (s, 3H), 1.69 (m, 4H), 1.43 (s, 9H). |
| 51 | 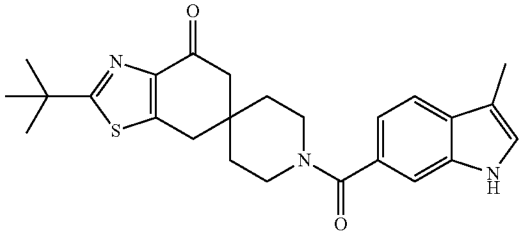 [SMILES: Cc1c[nH]c2cc(C(=O)N3CCC4(CC3)CC(=O)c3nc(C(C)(C)C)sc3C4)ccc12] | 201286-69-3 | Commercial | C | 436.0 (M + 1) | RT = 2.973 min (method 3) |
| 52 | 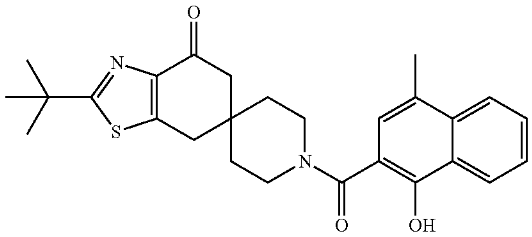 [SMILES: Cc1cc(C(=O)N2CCC3(CC2)CC(=O)c2nc(C(C)(C)C)sc2C3)c(O)c2ccccc12] | 679835-09-7 | Commercial | C | 463 (M + 1) | RT = 3.405 min (method3) |
| 53 | 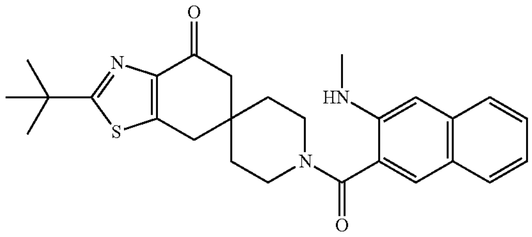 [SMILES: CNc1cc2ccccc2cc1C(=O)N1CCC2(CC1)CC(=O)c1nc(C(C)(C)C)sc1C2] | 71711-41-6 | Commercial | C | 462 (M + 1) | RT = 3.21 min (method 3) |

-continued
| Ex. | | Reactant | Source | Amid-ation | MH+ | Characterization |
|---|---|---|---|---|---|---|
| 54 | 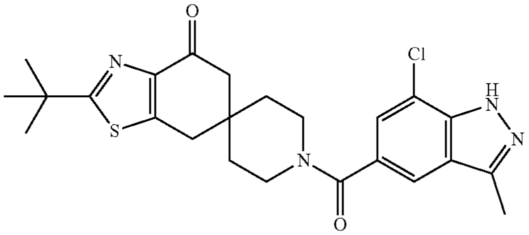 [SMILES: Cc1n[nH]c2c(Cl)cc(C(=O)N3CCC4(CC3)CC(=O)c3nc(C(C)(C)C)sc3C4)cc12] | | Pfizer patent PCT Int. Appl., 2009144554, 03 Dec 2009 | A | 472.4 (M + 1) | RT = 0.892 min (method1) $^{1}$H NMR (400 MHz, MeOD) δ 7.79 (d, 1H), 7.48 (d, 1H), 3.80 (s, 2H), 3.57 (br s, 2H), 3.26 (br s, 2H), 2.74 (s, 2H), 2.59 (s, 3H), 1.70 (m, 4H), 1.43 (s, 9H) |
| 55 | 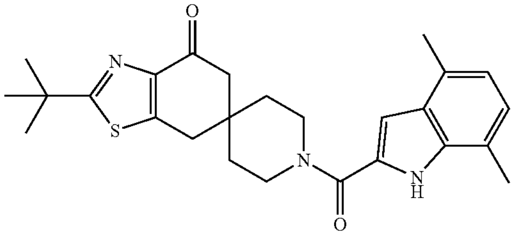 [SMILES: Cc1ccc(C)c2[nH]c(C(=O)N3CCC4(CC3)CC(=O)c3nc(C(C)(C)C)sc3C4)cc12] | 103988-96-1 | Commercial | C | 450.5 (M + 1) | RT = 1.093 min (method1) $^{1}$H NMR (400 MHz, MeOD) δ 6.88 (dd, 1H), 6.78 (s, 1H), 6.77 - 6.72 (m, 1H), 3.81 (s, 4H), 3.12 (s, 2H), 2.64 (s, 2H), 2.46 (d, 6H), 1.69 - 1.57 (m, 4H), 1.43 (s, 9H). |
| 56 | 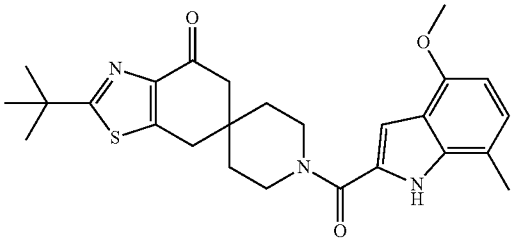 [SMILES: COc1ccc(C)c2[nH]c(C(=O)N3CCC4(CC3)CC(=O)c3nc(C(C)(C)C)sc3C4)cc12] | 383132-77-2 | Commercial | C | 466 (M + 1) | RT = 3.227 min (method3) |
| 57 | 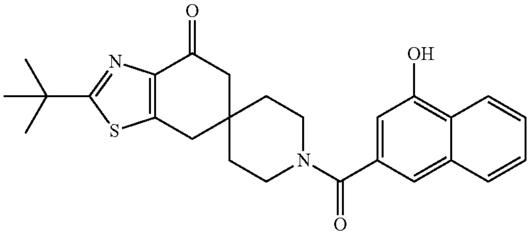 [SMILES: CC(C)(C)c1nc2c(s1)CC1(CCN(C(=O)c3cc(O)c4ccccc4c3)CC1)CC2=O] | 1573-91-7 | Commercial | C | 449 (M + 1) | RT = 2.951 min, (method 3) |
| 58 | 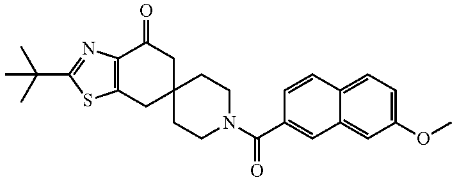 [SMILES: COc1ccc2ccc(C(=O)N3CCC4(CC3)CC(=O)c3nc(C(C)(C)C)sc3C4)cc2c1] | | PCT Int. Appl. (2013), WO 2013079425 A1 Jun 06, 2013 | C | 463 (M + 1) | RT = 3.215 min, (method3) |
| 59 | 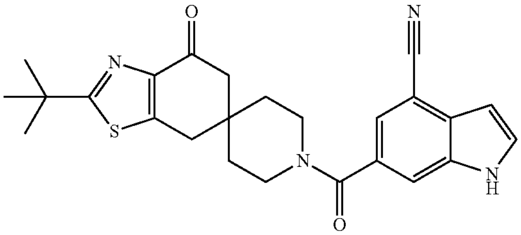 [SMILES: CC(C)(C)c1nc2c(s1)CC1(CCN(C(=O)c3cc(C#N)c4cc[nH]c4c3)CC1)CC2=O] | 1427502-44-0 | Commercial | C | 449 (M + 1) | RT = 2.829 min, (method 3) |

-continued
| Ex. | | Reactant | Source | Amid-ation | MH+ | Characterization |
|---|---|---|---|---|---|---|
| 60 | 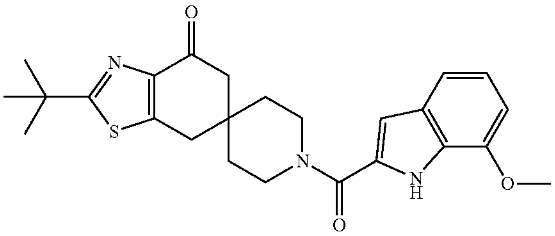 [SMILES: COc1cccc2cc(C(=O)N3CCC4(CC3)CC(=O)c3nc(C(C)(C)C)sc3C4)[nH]c12] | 24610-33-1 | Commercial | C | 452 (M + 1) | RT = 3.15 min, (method 3) |
| 61 | 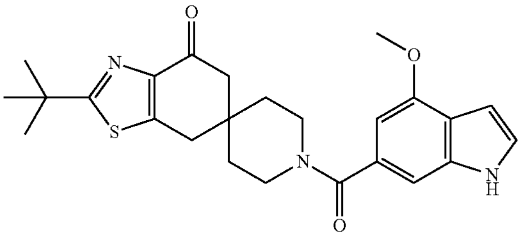 [SMILES: COc1cc(C(=O)N2CCC3(CC2)CC(=O)c2nc(C(C)(C)C)sc2C3)cc2[nH]ccc12] | 40990-53-2 | Commercial | C | 452 (M + 1) | RT = 3.016 min (method4) |
| 62 | 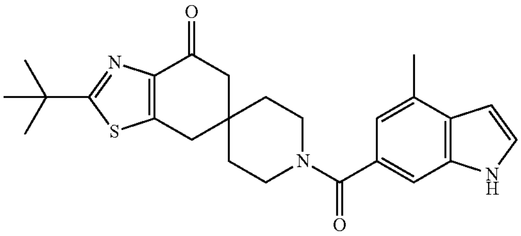 [SMILES: Cc1cc(C(=O)N2CCC3(CC2)CC(=O)c2nc(C(C)(C)C)sc2C3)cc2[nH]ccc12] | 1545472-15-8 | Commercial | C | 436 (M + 1) | RT 2.946 min.(method 3) |
| 63 | 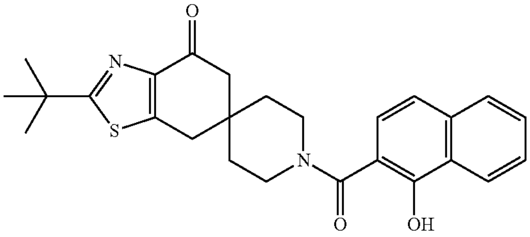 [SMILES: CC(C)(C)c1nc2c(s1)CC1(CCN(C(=O)c3ccc4ccccc4c3O)CC1)CC2=O] | 86-48-6 | Commercial | C | 449 (M + 1) | RT = 3.35 min. (method3) |
| 64 | 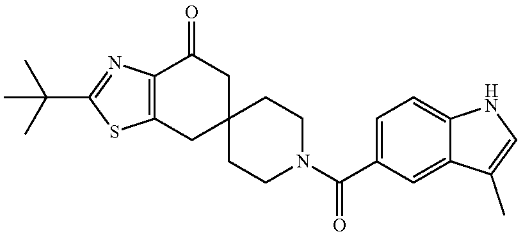 [SMILES: Cc1c[nH]c2ccc(C(=O)N3CCC4(CC3)CC(=O)c3nc(C(C)(C)C)sc3C4)cc12] | 588688-44-2 | Commercial | C | 436 | RT = 2.878 min (method3) |
| 65 | 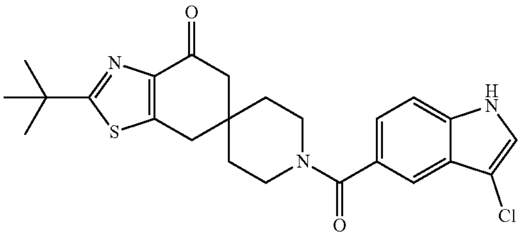 [SMILES: CC(C)(C)c1nc2c(s1)CC1(CCN(C(=O)c3ccc4[nH]cc(Cl)c4c3)CC1)CC2=O] | | Pfizer Patent PCT Int. Appl., 2008065508, 05 Jun 2008 | C | 456 | RT 2.932 min.(method3) |

-continued

| Ex. | | Reactant | Source | Amid-ation | MH⁺ | Characterization |
|---|---|---|---|---|---|---|
| 66 | 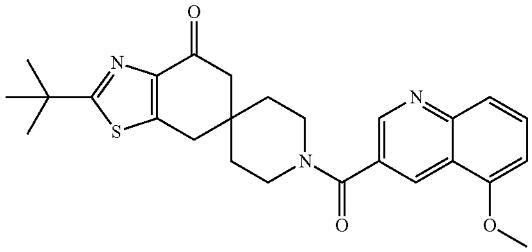 [SMILES: COc1cccc2ncc(C(=O)N3CCC4(CC3)CC(=O)c3nc(C(C)(C)C)sc3C4)cc12] | 1361091-98-6 | Commercial | C | 464 | RT = 2.626 min. (method 3) |
| 67 | 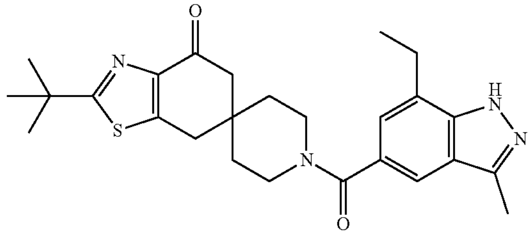 [SMILES: CCc1cc(C(=O)N2CCC3(CC2)CC(=O)c2nc(C(C)(C)C)sc2C3)cc2c(C)n[nH]c12] | | Pfizer patent; PCT Int. Appl., 2009144554, 03 Dec 2009 | A | 465.5 (M + 1) | RT = 0.900 min.(method1) $^1$H NMR (400 MHz, MeOD) δ 7.65 (d, 1H), 7.22 (d, 1H), 3.79 (br s, 2H), 3.56 (br s, 2H), 3.24 (s, 2H), 2.94 (q, 2H), 2.72 (s, 2H), 2.55 (s, 3H), 1.72 (br s, 2H), 1.63 (br s, 2H), 1.42 (s, 9H), 1.34 (t, 3H). |
| 68 | 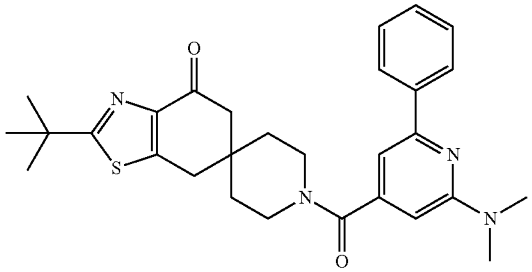 [SMILES: CN(C)c1cc(C(=O)N2CCC3(CC2)CC(=O)c2nc(C(C)(C)C)sc2C3)cc(-c2ccccc2)n1] | 1505806-06-3 | Commercial | D | 503.5 (M + 1) | RT = 2.03 min.(method5) $^1$H NMR (500 MHz, CDCl3) δ 8.05 - 8.00 (m, 2H), 7.43 (dt, 3H), 6.95 (s, 1H), 6.45 (s, 1H), 3.75 (d, 1H), 3.46 (s, 2H), 3.20 (s, 6H), 3.11 (d, 2H), 2.72 (s, 2H), 1.77 (d, 2H), 1.47 (s, 9H), 1.29 (s, 3H). |
| 69 | 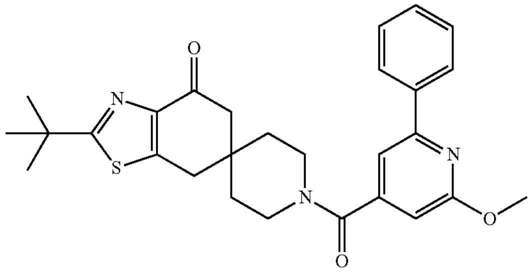 [SMILES: COc1cc(C(=O)N2CCC3(CC2)CC(=O)c2nc(C(C)(C)C)sc2C3)cc(-c2ccccc2)n1] | | Journal of Medicinal Chemistry, 56(12), 5079-5093; 2013 | A | 490.4 (M + 1) | RT = 3.25 min (method 2) |
| 70 | 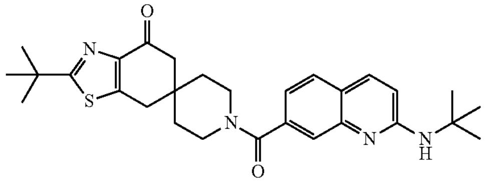 [SMILES: CC(C)(C)Nc1ccc2ccc(C(=O)N3CCC4(CC3)CC(=O)c3nc(C(C)(C)C)sc3C4)cc2n1] | 1403746-69-9 | Commercial | A | 505.4 (M + 1) | RT = 1.091 min (Method1) $^1$H NMR (400 MHz, MeOD) δ 7.75 (d, 1H), 7.62 (d, 1H), 7.58 - 7.54 (m, 1H), 7.13 (dd, 1H), 6.74 (d, 1H), 3.87 (s, 1H), 3.82 (s, 1H), 3.55 (s, 2H), 3.26 (d, 2H), 2.74 (d, 2H), 1.77 (br s, 2H), 1.63 (br s, 2H), 1.53 (s, 9H), 1.44 (s, 9H). |

-continued
| Ex. | | Reactant | Source | Amid-ation | $MH^+$ | Characterization |
|---|---|---|---|---|---|---|
| 71 | 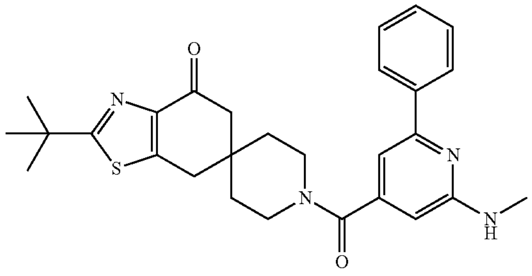 [SMILES: CNc1cc(C(=O)N2CCC3(CC2)CC(=O)c2nc(C(C)(C)C)sc2C3)cc(-c2ccccc2)n1] | 1501037-23-5 | commercial | D | 489.4 (M + 1) | RT = 2.26 min (method 2) |
| 72 | 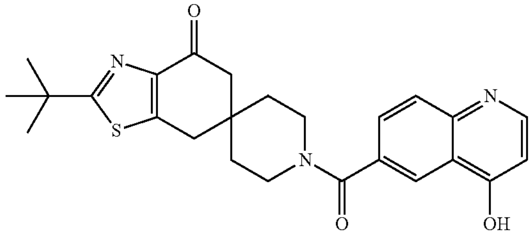 [SMILES: CC(C)(C)c1nc2c(s1)CC1(CCN(C(=O)c3ccc4nccc(O)c4c3)CC1)CC2=O] | 1065092-81-0 | Commercial | B | 450.4 | RT = 1.96 min (method 2) |
| 73 | 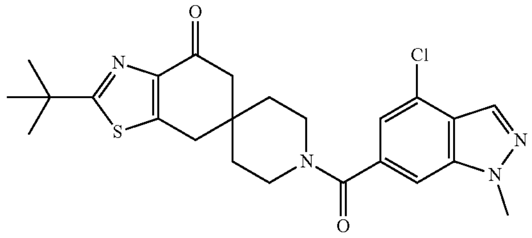 [SMILES: Cn1ncc2c(Cl)cc(C(=O)N3CCC4(CC3)CC(=O)c3nc(C(C)(C)C)sc3C4)cc21] | 1448852-21-8 | Commercial | C | 472.4 (M + 1) | RT = 0.983 (method 1) $^1$H NMR (400 MHZ, MeOD) δ 8.01 (d, 1H), 7.62 (s, 1H), 7.21 (d, 1H), 4.11 (s, 3H), 3.93 (br s, 1H), 3.48 (br s, 2H), 3.25 (s, 2H), 2.73 (s, 2H), 1.77 (br s, 2H), 1.63 (br s, 2H), 1.53 (s, 9H), 1.43 (s, 9H). |
| 74 | 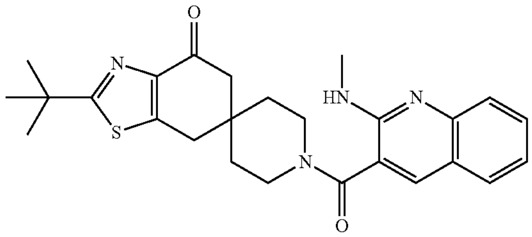 [SMILES: CNc1nc2ccccc2cc1C(=O)N1CCC2(CC1)CC(=O)c1nc(C(C)(C)C)sc1C2] | 1340427-43-1 | commercial | A | 463.4 (M + 1) | RT = 0.974 min (method1) $^1$H NMR (400 MHz, MeOD) δ 7.88 (d, 1H), 7.69 (ddd, 2H), 7.57 (ddd, 1H), 7.25 (ddd, 1H), 3.84 (s, 2H), 3.49 (s, 2H), 3.25 (s, 2H), 3.07 (s, 3H), 2.74 (s, 2H), 1.69 (s, 4H), 1.44 (s, 9H). |
| 75 | 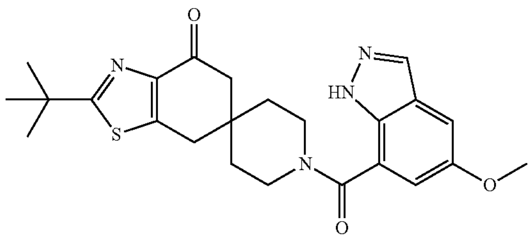 [SMILES: COc1cc(C(=O)N2CCC3(CC2)CC(=O)c2nc(C(C)(C)C)sc2C3)c2[nH]ncc2c1] | 1638764-70-1 | commercial | A | 453.3 (M + 1) | RT 0.898 (method1) $^1$H NMR (400 MHz, MeOD) δ 8.02 (s, 1H), 7.32 (d, 1H), 7.10 (d, 1H), 3.87 (s, 5H), 3.48 (s, 2H), 3.24 (s, 2H), 2.73 (s, 2H), 1.88 - 1.53 (m, 4H), 1.43 (s, 9H). |

-continued

| Ex. | | Reactant | Source | Amid- ation | MH+ | Characterization |
|---|---|---|---|---|---|---|
| 76 | 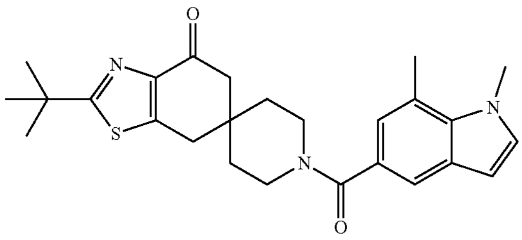 [SMILES: Cc1cc(C(=O)N2CCC3(CC2)CC(=O)c2nc(C(C)(C)C)sc2C3)cc2ccn(C)c12] | 1545200-58-5 | commercial | A | 450.3 (M + 1) | RT = 1.002 min (method1) $^1$H NMR (400 MHz, MeOD) δ 7.45 (d, 1H), 7.12 (d, 1H), 6.95 - 6.88 (m, 1H), 6.43 (d, 1H), 4.08 (s, 3H), 3.74 (s, 4H), 3.24 (s, 2H), 2.79 (s, 3H), 2.72 (s, 2H), 1.79 - 1.54 (m, 4H), 1.43 (s, 9H). |
| 77 | 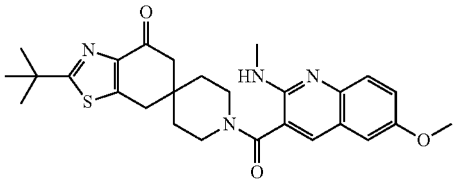 [SMILES: CNc1nc2ccc(OC)cc2cc1C(=O)N1CCC2(CC1)CC(=O)c1nc(C(C)(C)C)sc1C2] | 1785168-34-4 | commercial | A | 493.4 (M + 1) | RT = 0.969 min (method1) $^1$H NMR (400 MHZ, MeOD) δ 7.82 (s, 1H), 7.62 (d, 1H), 7.22 (dd, 1H), 7.11 (d, 1H), 3.86 (s, 5H), 3.46 (s, 2H), 3.24 (s, 2H), 3.02 (s, 3H), 2.72 (s, 2H), 1.88-1.53 (m, 4H), 1.43 (s, 9H). |
| 78 | 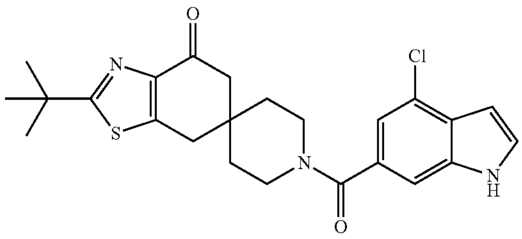 [SMILES: CC(C)(C)c1nc2c(s1)CC1(CCN(C(=O)c3cc(Cl)c4cc[nH]c4c3)CC1)CC2=O] | 885520-25-2 | commercial | A | 456.4 (M + 1) | RT = 2.82 min(method2) |
| 79 | 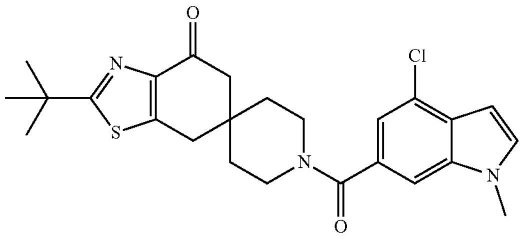 [SMILES: Cn1ccc2c(Cl)cc(C(=O)N3CCC4(CC3)CC(=O)c3nc(C(C)(C)C)sc3C4)cc21] | 1508693-16-0 | commercial | C | 472.0 (M + 1) | RT = 0.91 min (method 5), $^1$H NMR (400 MHZ, MeOD) δ 7.49 (d, 1H), 7.40 (d, 1H), 7.17 (d, 1H), 6.59 (d, 1H), 5.53 (s, 1H), 3.93-3.71 (m, 5H), 3.71 - 3.48 (m, 2H), 3.27 (s, 2H), 2.75 (s, 2H), 1.87 - 1.56 (m, 4H), 1.47 (s, 9H). |
| 80 | 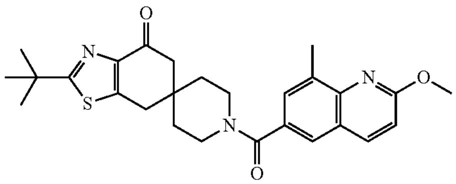 [SMILES: COc1ccc2cc(C(=O)N3CCC4(CC3)CC(=O)c3nc(C(C)(C)C)sc3C4)cc(C)c2n1] | 99471-72-4 | commercial | A | 478.4 (M + 1) | RT = 1.108 min (method1) $^1$H NMR (400 MHz, MeOD) δ 8.13 (d, 1H), 7.70 (d, 1H), 7.53 (dd, 1H), 6.98 (d, 1H), 4.07 (s, 3H), 3.92 - 3.72 (m, 2H), 3.54 (s, 2H), 3.25 (s, 2H), 2.76 - 2.72 (m, 2H), 2.70 (d, 3H), 1.76 (br s, 2H), 1.61 (br s, 2H), 1.43 (s, 9H). |

-continued
| Ex. | | Reactant | Source | Amid-ation | MH+ | Characterization |
|---|---|---|---|---|---|---|
| 81 | 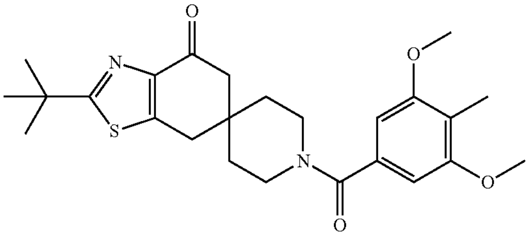 [SMILES: COc1cc(C(=O)N2CCC3(CC2)CC(=O)c2nc(C(C)(C)C)sc2C3)cc(OC)c1C] | 61040-81-1 | commercial | A | 457.4 (M + 1) | RT = 1.034 min (method 1) $^1$H NMR (400 MHz, MeOD) δ 6.62 (s, 2H), 3.87 - 3.70 (m, 8H), 3.51 (s, 2H), 3.24 (s, 2H), 2.72 (s, 2H), 2.05 (s, 3H), 1.73 (s, 2H), 1.62 (s, 2H), 1.43 (s, 9H) |
| 82 | 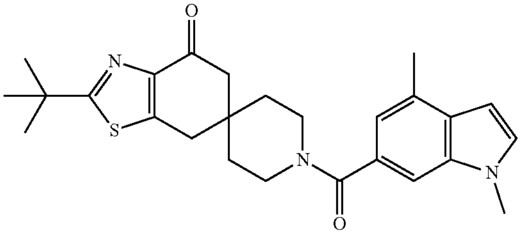 [SMILES: Cc1cc(C(=O)N2CCC3(CC2)CC(=O)c2nc(C(C)(C)C)sc2C3)cc2c1ccn2C] | 1780839-70-4 | commercial | C | 450.4 (M + 1) | RT = 2.82 min (method 2) |
| 83 | 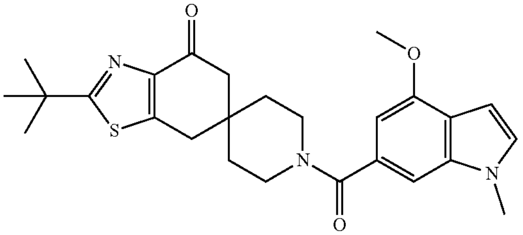 [SMILES: COc1cc(C(=O)N2CCC3(CC2)CC(=O)c2nc(C(C)(C)C)sc2C3)cc2c1ccn2C] | 40990-58-7 | commercial | C | 466.5 (M + 1) | RT = 2.95 min (method2) |
| 84 | 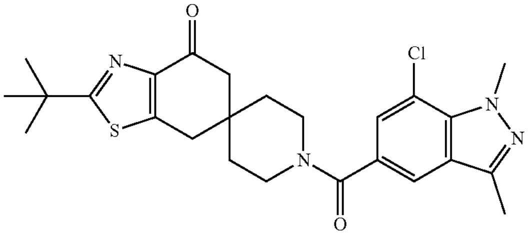 [SMILES: Cc1nn(C)c2c(Cl)cc(C(=O)N3CCC4(CC3)CC(=O)c3nc(C(C)(C)C)sc3C4)cc12] | 1784123-05-2 | commercial | C | 486.4 (M + 1) | RT = 1.008 min (method1) $^1$H NMR (400 MHz, MeOD) δ 7.74 (d, 1H), 7.46 (d, 1H), 4.30 (s, 3H), 3.93- 3.41 (m, 4H), 3.24 (s, 2H), 2.73 (s, 2H), 2.53 (s, 3H), 1.85 - 1.5463 (m, 4H), 1.43 (s, 9H). |
| 85 | 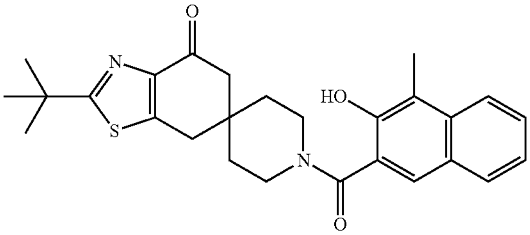 [SMILES: Cc1c(O)c(C(=O)N2CCC3(CC2)CC(=O)c2nc(C(C)(C)C)sc2C3)cc2ccccc12] | 68902-24-9 | commercial | B | 463.6 (M + 1) | RT = 3.11 min (method 2) |
| 86 | 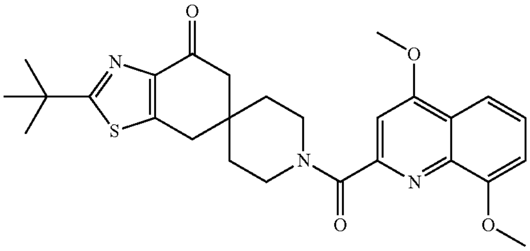 [SMILES: COc1cc(C(=O)N2CCC3(CC2)CC(=O)c2nc(C(C)(C)C)sc2C3)nc2c(OC)cccc12] | 28027-15-8 | commercial | B | 494.6 (M + 1) | RT = 2.33 min (method 2) |

-continued
| Ex. | | Reactant | Source | Amidation | MH+ | Characterization |
|---|---|---|---|---|---|---|
| 87 | 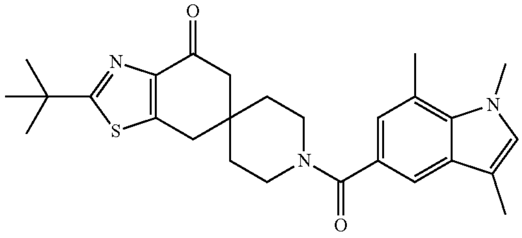 [SMILES: Cc1cn(C)c2c(C)cc(C(=O)N3CCC4(CC3)CC(=O)c3nc(C(C)(C)C)sc3C4)cc12] | 1558111-81-1 | commercial | A | 464.4 (M + 1) | RT = 1.058 min (method1) $^1$H NMR (400 MHz, MeOD) δ 7.40 (d, 1H), 6.93 - 6.86 (m, 2H), 4.01 (s, 3H), 3.88 - 3.46 (m, 4H), 3.24 (s, 2H), 2.76 (s, 3H), 2.72 (s, 2H), 2.25 (d, 3H), 1.84 - 1.52 (m, 4H), 1.43 (s, 9H). |
| 88 | 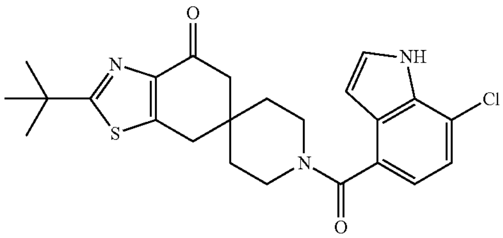 [SMILES: CC(C)(C)c1nc2c(s1)CC1(CCN(C(=O)c3ccc(Cl)c4[nH]ccc34)CC1)CC2=O] | 588688-45-3 | commercial | C | 456 (M + 1) | RT = 2.839 (method 3) |
| 89 | 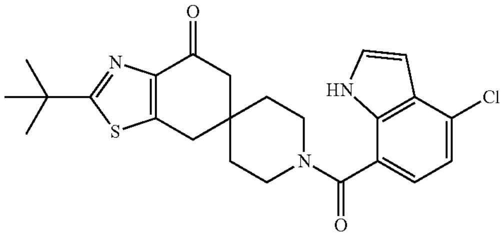 [SMILES: CC(C)(C)c1nc2c(s1)CC1(CCN(C(=O)c3ccc(Cl)c4cc[nH]c34)CC1)CC2=O] | 875305-77-4 | commercial | C | 456 (M + 1) | RT = 3.147 (method 3) |
| 90 | 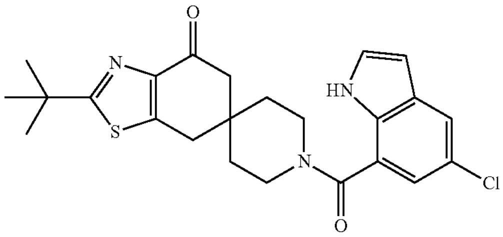 [SMILES: CC(C)(C)c1nc2c(s1)CC1(CCN(C(=O)c3cc(Cl)cc4cc[nH]c34)CC1)CC2=O] | 875305-81-0 | commercial | C | 456 (M + 1) | RT = 3.175 min (method3) |
| 91 | 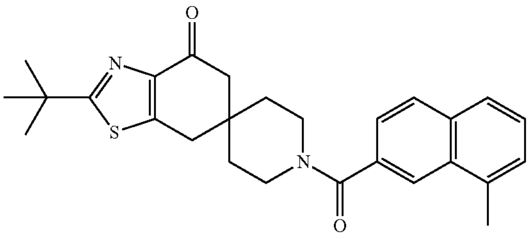 [SMILES: Cc1cccc2ccc(C(=O)N3CCC4(CC3)CC(=O)c3nc(C(C)(C)C)sc3C4)cc12] | 5043-23-2 | commercial | A | 447.3 (M + 1) | RT = 1.088 min (method1) $^1$H NMR (400 MHz, MeOD) δ 8.10 (d, 1H), 7.94 (d, 1H), 7.76 (d, 1H), 7.50 (dd, 1H), 7.43 (dt, 2H), 3.96 - 3.79 (m, 2H), 3.62- 3.51 (m, 2H), 3.27 (s, 2H), 2.74 (d, 2H), 2.71 (s, 3H), 1.85 - 1.71 (s, 2H), 1.69 - 1.60 (s, 2H), 1.43 (s, 9H). |

-continued
| Ex. | | Reactant | Source | Amid-ation | MH+ | Characterization |
|---|---|---|---|---|---|---|
| 92 | 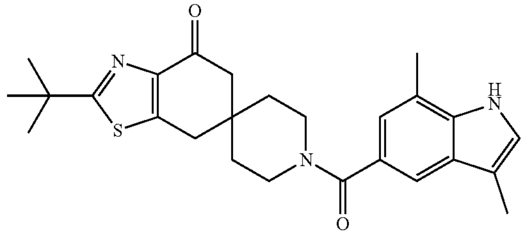 [SMILES: Cc1c[nH]c2c(C)cc(C(=O)N3CCC4(CC3)CC(=O)c3nc(C(C)(C)C)sc3C4)cc12] | 5043-23-2 | commercial | A | 450.3 (M + 1) | RT = 0.969 min (method1) $^1$H NMR (400 MHz, MeOD) δ 7.46 - 7.43 (m, 1H), 7.09 - 7.05 (m, 1H), 7.00 - 6.95 (m, 1H), 3.99 - 3.52 (m, 4H), 3.24 (s, 2H), 2.73 (s, 2H), 2.50 (s, 3H), 2.31 (d, 3H), 1.88 - 1.55 (m, 4H), 1.43 (s, 9H). |
| 93 | 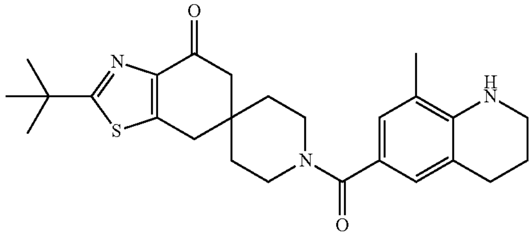 [SMILES: Cc1cc(C(=O)N2CCC3(CC2)CC(=O)c2nc(C(C)(C)C)sc2C3)cc2c1NCCC2] | 2126161-46-2 | commercial | B | 452.4 (M + 1) | RT = 2.75 min (method 2) |
| 94 | 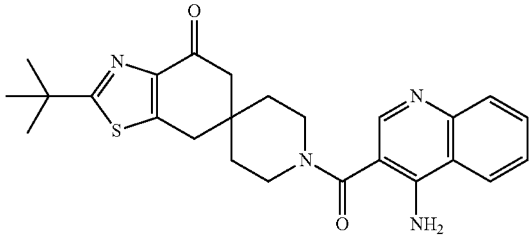 | 68313-46-2 | Commercial | B | 468.4 (M + 1) | RT = 2.41 min (method 2) |
| 95 | 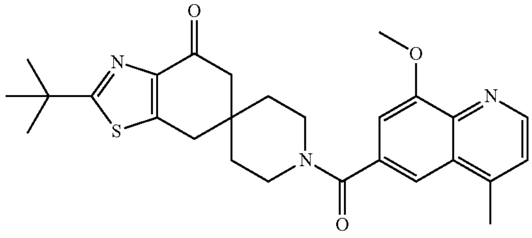 [SMILES: COc1cc(C(=O)N2CCC3(CC2)CC(=O)c2nc(C(C)(C)C)sc2C3)cc2c(C)ccnc12] | | PCT Int. Appl., 2015026792, 26 Feb 2015 | A | 478.4 (M + 1) | RT = 0.868 (method1) $^1$H NMR (400 MHz, MeOD) δ 8.70 (d, 1H), 7.71 (d, 1H), 7.48 (dd, 1H), 7.21 (d, 1H), 4.09 (s, 3H), 3.99-3.74 (m, 2H), 3.55 (s, 2H), 3.27 (s, 2H), 2.79 - 2.70 (m, 5H), 1.90 - 1.56 (m, 4H), 1.43 (s, 9H). |
| 96 | 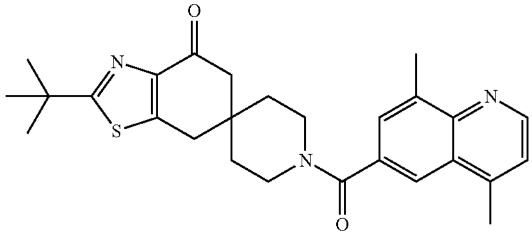 [SMILES: Cc1ccnc2c(C)cc(C(=O)N3CCC4(CC3)CC(=O)c3nc(C(C)(C)C)sc3C4)cc12] | 1522376-81-3 | commercial | A | 462.3 (M + 1) | RT = 0.958 min (method1) $^1$H NMR (400 MHz, MeOD) δ 8.77 (d, 1H), 8.03 (d, 1H), 7.63 (dd, 1H), 7.44 (dd, 1H), 1.03 - 3.74 (m, 2H), 3.53 (s, 2H), 3.26 (s, 2H), 2.79 (s, 3H), 2.75 (dd, 5H), 1.90 - 1.57 (m, 4H), 1.43 (s, 9H). |

-continued

| Ex. | | Reactant | Source | Amid-ation | MH+ | Characterization |
|---|---|---|---|---|---|---|
| 97 | 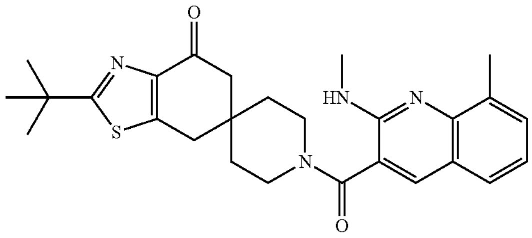 [SMILES: CNc1nc2c(C)cccc2cc1C(=O)N1CCC2(CC1)CC(=O)c1nc(C(C)(C)C)sc1C2] | 1783937-94-9 | commercial | A | 477.3 (M + 1) | RT = 1.118 min (method1), $^{1}$H NMR (400 MHz, MeOD) δ 7.80 (s, 1H), 7.48 (d, 1H), 7.41 (dt, 1H), 7.10 (t, 1H), 3.83 (br s, 2H), 3.47 (br s, 2H), 3.23 (s, 2H), 3.06 (s, 3H), 2.72 (s, 2H), 2.61 (s, 3H), 1.85 - 1.54 (m, 4H), 1.43 (s, 9H). |
| 98 | 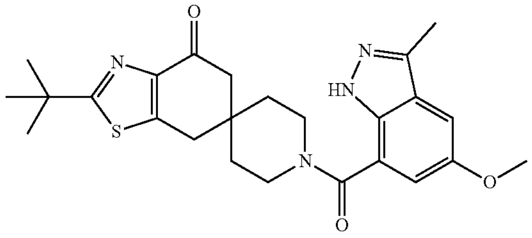 [SMILES: COc1cc(C(=O)N2CCC3(CC2)CC(=O)c2nc(C(C)(C)C)sc2C3)c2[nH]nc(C)c2c1] | 1893122-57-0 | commercial | A | 467.3 (M + 1) | RT = 0.921 min (method1) $^{1}$H NMR (400 MHZ, MeOD) δ 7.22 (s, 1H), 7.08 (d, 1H), 3.87 (s, 5H), 3.45 (br s, 2H), 3.23 (s, 2H), 2.72 (s, 2H), 2.54 (s, 3H), 1.88 - 1.52 (m, 4H), 1.43 (s, 9H). |
| 99 | 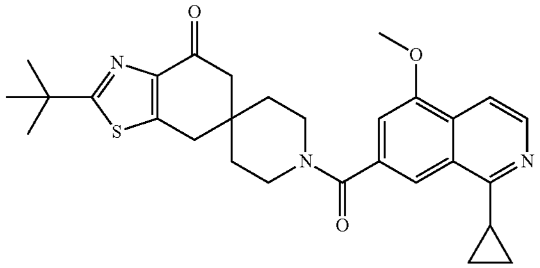 [SMILES: COc1cc(C(=O)N2CCC3(CC2)CC(=O)c2nc(C(C)(C)C)sc2C3)cc2c(C3CC3)nccc12] | | PCT Int. Appl., 2007011809, 25 Jan 2007 | A | 504.3 (M + 1) | RT = 1.039 min (method1) $^{1}$H NMR (400 MHz, MeOD) δ 8.31 (d, 1H), 8.11 (d, 1H), 7.88 (dd, 1H), 7.16 (d, 1H), 4.07 (s, 3H), 3.97 - 3.74 (m, 2H), 3.57 (s, 2H), 3.27 (s, 2H), 2.81 (p, 1H), 2.75 (d, , 2H), 1.91 - 1.55 (m, 4H), 1.43 (s, 9H), 1.20 - 1.11 (m, 4H). |
| 100 | 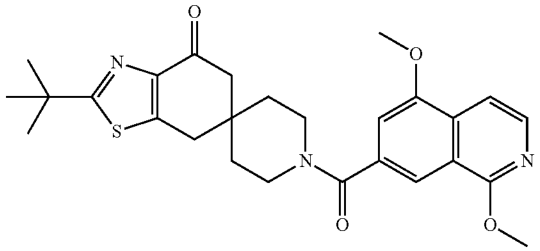 [SMILES: COc1cc(C(=O)N2CCC3(CC2)CC(=O)c2nc(C(C)(C)C)sc2C3)cc2c(OC)nccc12] | 921761-13-9 | commercial | A | 494.4 (M + 1) | RT = 1.031 min (method1), $^{1}$H NMR (400 MHz, MeOD) δ 8.02 (d, 1H), 7.82 (t, 1H), 7.60 (dd, 1H), 7.16 (d, 1H), 4.12 (s, 3H), 4.05 (s, 3H), 3.86 (s, 2H), 3.54 (s, 2H), 3.27 (s, 2H), 2.79 - 2.70 (m, 2H), 1.88 - 1.57 (m, 4H), 1.44 (s, 9H). |
| 101 | 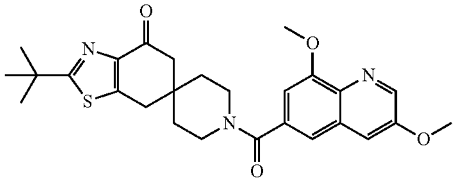 [SMILES: COc1cnc2c(OC)cc(C(=O)N3CCC4(CC3)CC(=O)c3nc(C(C)(C)C)sc3C4)cc2c1] | 2721376-45-8 | commercial | A | 494.3 (M + 1) | RT = 0.875 min (method1) $^{1}$H NMR (400 MHz, MeOD) δ 8.56 (d, 1H), 7.75 (d, 1H), 7.48 (d, 1H), 7.04 (d, 1H), 4.07 (s, 3H), 3.99 (s, 3H), 3.94 - 3.72 (m, 2H), 3.54 (s, 2H), 3.27 (s, 2H), 2.78 - 2.70 (m, 2H), 1.85 - 1.59 (m, 4H), 1.43 (s, 9H). |

-continued

| Ex. | | Reactant | Source | Amid-ation | MH+ | Characterization |
|---|---|---|---|---|---|---|
| 102 | 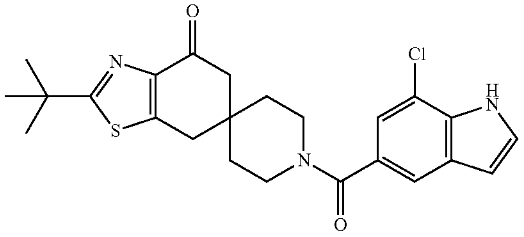 | | PCT Int. Appl., 2014129796, 28 Aug 2014 | C | 450 (M + 1) | RT = 2.592 min (method4) |
| 103 | 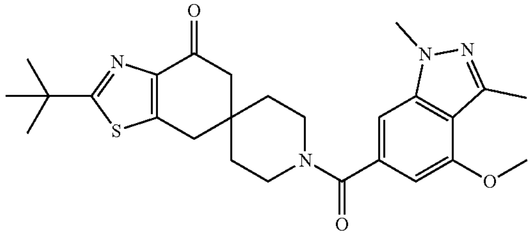 [SMILES: COc1cc(C(=O)N2CCC3(CC2)CC(=O)c2nc(C(C)(C)C)sc2C3)cc2c1c(C)nn2C] | 1893031-47-4 | commercial | A | 481.4 (M + 1) | RT = 0.934 min (method1), $^{1}$H NMR (400 MHz, MeOD) δ 7.10 (d, 1H), 6.52 (d, 1H), 4.00 (s, 3H), 3.97 (s, 3H), 3.91 - 3.75 (m, 2H), 3.53 (br s, 2H), 3.28 (s, 2H), 2.76 (s, 2H), 2.63 (s, 3H), 1.93 - 1.58 (m, 4H), 1.46 (s, 9H). |
| 104 | 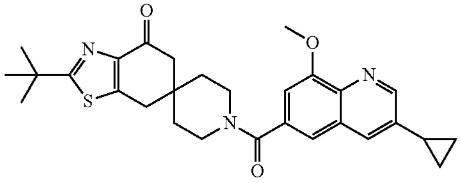 [SMILES: COc1cc(C(=O)N2CCC3(CC2)CC(=O)c2nc(C(C)(C)C)sc2C3)cc2cc(C3CC3)cnc12] | | PCT Int. Appl., 2021066922, 08 Apr 2021 | A | 504.3 (M + 1) | RT = 0.945 min (method1) $^{1}$H NMR (400 MHz, MeOD) δ 8.67 (d, 1H), 7.94 (d, 1H), 7.44 (d, 1H), 7.08 (d, 1H), 4.05 (s, 3H), 3.91 - 3.66 (m, 2H), 3.51 (s, 2H), 3.24 (s, 2H), 2.72 (s, 2H), 2.13 (td, 1H), 1.86 - 1.58 (m, 4H), 1.41 (d, 9H), 1.18 - 1.09 (m, 2H), 0.89 (dt, 2H). |
| 105 | 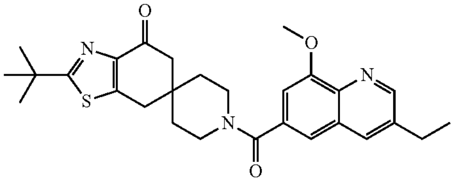 [SMILES: CCc1cnc2c(OC)cc(C(=O)N3CCC4(CC3)CC(=O)c3nc(C(C)(C)C)sc3C4)cc2c1] | | PCT Int. Appl., 2021066922, 08 Apr 2021 | A | 492.3 (M + 1) | RT = 0.938 min (method1), $^{1}$H NMR (400 MHz, MeOD) δ 8.72 (d, 1H), 8.16 (d, 1H), 7.48 (d, 1H), 7.11 (d, 1H), 4.06 (s, 3H), 3.91 - 3.72 (m, 2H), 3.52 (br s, 2H), 3.24 (s, 2H), 2.87 (q, 2H), 2.72 (d, 2H), 1.90 - 1.52 (m, 4H), 1.41 (s, 9H), 1.34 (t, 3H). |
| 106 | 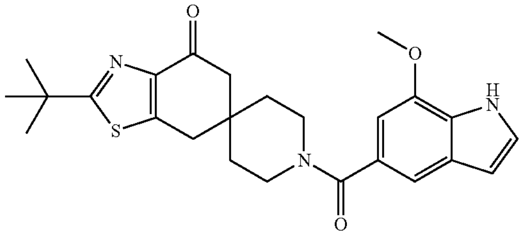 [SMILES: COc1cc(C(=O)N2CCC3(CC2)CC(=O)c2nc(C(C)(C)C)sc2C3)cc2cc[nH]c12] | 180623-99-8 | commercial | A | 452.4 (M + 1) | RT = 0.91 min (method 1) $^{1}$H NMR (400 MHz, MeOD) δ 7.29 (s, 1H), 7.27 (d, 1H), 6.70 (s, 1H), 6.50 (d, 1H), 4.00 (s, 3H), 3.66 (m, 4H), 3.27 (s, 2H), 2.75 (s, 2H), 1.70 (m, 4H), 1.45 (s, 9H). |

-continued

| Ex. | | Reactant | Source | Amidation | MH+ | Characterization |
|---|---|---|---|---|---|---|
| 107 | 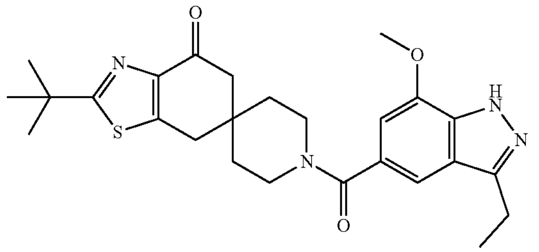 | | WO 2009144554 A1 Dec 03, 2009 | A | 481.4 (M + 1) | $^1$H NMR (400 MHz, MeOD) δ 7.40 (d, 1H), 6.84 (d, 1H), 4.01 (s, 3H), 3.92 - 3.68 (m, 2H), 3.67-3.49 (m, 2H), 3.24 (s, 2H), 2.97 (q, 2H), 2.72 (s, 2H), 1.81-1.55 (m, 4H), 1.42 (s, 9H), 1.35 (t, 3H). |
| 108 | 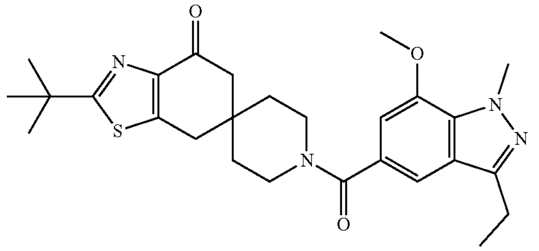 [SMILES: CCc1nn(C)c2c(OC)cc(C(=O)N3CCC4(CC3)CC(=O)c3nc(C(C)(C)C)sc3C4)cc12] | | WO 2009144554 A1 Dec 03, 2009 | A | 495.4 (M + 1) | $^1$H NMR (400 MHz, MeOD) δ 7.34 (d, 1H), 6.82 (d, 1H), 4.18 (s, 3H), 3.98 (s, 3H), 3.88 - 3.66 (m, 2H), 3.62-3.50 (m, 2H), 3.24 (s, 2H), 2.91 (q, 2H), 2.72 (s, 2H), 1.79-1.55 (m, 4H), 1.41 (s, 9H), 1.32 (t, 3H). |

Example 109: rac-(R)-(2-(tert-butyl)-4-hydroxy-4,7-dihydro-5H-spiro[benzo[d]thiazole-6,4'-piperidin]-1'-yl)(7-ethoxy-1,3-dimethyl-1H-indazol-5-yl) methanone

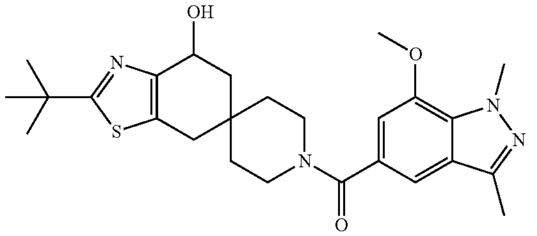 [SMILES: COc1cc(C(=O)N2CCC3(CC2)Cc2sc(C(C)(C)C)nc2C(O)C3)cc2c(C)nn(C)c12]

To a solution of Example 14 (100 mg, 0.2 mmol) in MeOH (3.5 mL) was added $NaBH_4$ (23 mg, 0.6 mmol) and stirred at about 25° C. for about 17 h. The reaction was diluted with 10% MeOH-EtOAc (20 mL) and water (20 mL) and organic layer was separated. The aqueous layer was extracted using EtOAc (2×20 mL). The combined EtOAc extracts were dried over $MgSO_4$, filtered, and concentrated under reduced pressure. The residue was purified by HPLC (Column: Xbridge C18, 19×100 mm, 5 μm) Mobile phase A: 0.05% TFA in water (v/v); Mobile phase B: 0.05% TFA in acetonitrile (v/v), gradient time of 10 min to provide the title compound (67 mg, 68%); $^{1}$H NMR (600 MHz, DMSO-d6) δ 7.27 (s, 1H), 6.77 (s, 1H), 5.35-5.02 (m, 1H), 4.62 (t, 1H), 4.19 (q, 2H), 4.14 (s, 3H), 3.45-3.39 (m, 4H, overlap with d-DMSO), 2.75 (d, 1H), 2.68 (d, 1H), 2.43 (s, 3H), 1.99 (dd, 1H), 1.72 (dd, 1H), 1.69-1.59 (m, 2H), 1.53 (dd, 2H), 1.44 (t, 3H), 1.35 (s, 9H); LC/MS m/z $(M+H)^+$=497.3.

Deuterated Analogues of the Compound of Example 14

The metabolite profile of compound of Example 14 was evaluated in liver microsomes and hepatocytes (mouse, rat, rabbit, dog, monkey, and human), recombinant human cytochrome P450 enzymes, recombinant human UGT enzymes, and plasma from animals (mouse, rat, and dog). The metabolite profile of Compound XXCAN is comprised of oxidation and glucuronidation.

General methods/reviews of obtaining metabolite profile and identifying metabolites of a compound are described in: King, R., "Biotransformations in Drug Metabolism," Ch. 3, Drug Metabolism Handbook Introduction, https://doi.org/10.1002/9781119851042.ch3; Wu, Y., et al, "Metabolite Identification in the Preclinical and Clinical Phase of Drug Development," Current Drug Metabolish, 2021, 22, 11, 838-857, 10.2174/1389200222666211006104502; Godzien, J., et al, "Chapter Fifteen—Metabolite Annotation and Identification," Comprehensive Analytical Chemistry, 2018, 82, 415-445, https://doi.org/10.1016/bs.coac.2018.07.004; Zhang, Z., et al, "Drug metabolism in drug discovery and development," Acta Pharmaceutica Sinica B, 2018, 8(5), 721-732, https://doi.org/10.1016/j.apsb.2018.04.003.

The metabolite profile of a compound can also be obtained from publicly available and commercially available software tools. Examples of such tools include, BioTransofrmer 3.0 (biotransformer.ca/new) which predicts the metabolic biotransformations of small molecules using a database of known metabolic reactions; Lhasa Meteor Nexus (www.lhasalimited.org/products/meteor-nexus.htm) offers prediction of metabolic pathways and metabolite structures using a range of machine learning models, which covers phase I and phase II biotransformations of small molecules.

Prophetic deuterate69d analogs 110-122 set forth hereinbelow may afford certain therapeutic advantages resulting from greater metabolic stability, for example increased in vivo half-life, reduced dosage requirements, reduced CYP450 inhibition (competitive or time dependent), or an improvement in therapeutic index or tolerability.

A person with ordinary skill may make additional deuterated analogs of the compound of Example 14. Such additional deuterated analogs may provide similar therapeutic advantages than may be achieved by nondeuterated analogs.

Example 110

2-tert-butyl-1'-{7-[(1,1-dideuterio)ethyloxy]-1,3-dimethyl-1H-indazole-5-carbonyl}-5H-spiro[[1,3]benzothiazole-6,4'-piperidin]-4(7H)-one

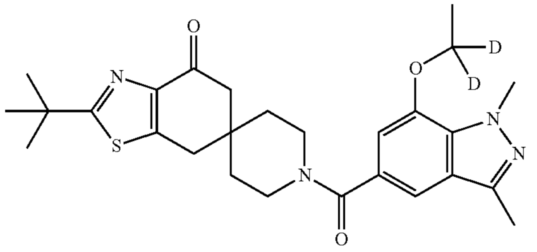 [SMILES: [2H]C([2H])(C)Oc1cc(C(=O)N2CCC3(CC2)CC(=O)c2nc(C(C)(C)C)sc2C3)cc2c(C)nn(C)c12]

Example 111

2-tert-butyl-1'-{7-[(pentadeuterio)ethyloxy]-1,3-dimethyl-1H-indazole-5-carbonyl}-5H-spiro[[1,3]benzothiazole-6,4'-piperidin]-47H)-one

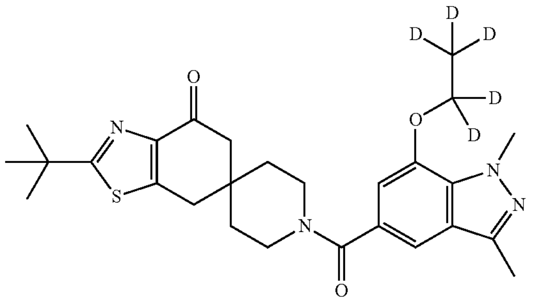 [SMILES: [2H]C([2H])([2H])C([2H])([2H])Oc1cc(C(=O)N2CCC3(CC2)CC(=O)c2nc(C(C)(C)C)sc2C3)cc2c(C)nn(C)c12]

Example 112

1'-{7-[(pentadeuterioethyloxy]-1,3-bis[(trideuterio)methyl](dideuterio)-1H-indazole-5-carbonyl}-2-[2-(trideuterio)methyl(hexadeuterio)propan-2-yl](dodecadeuterio)-5H-spiro[[1,3]benzothiazole-6,4'-piperidin]-4(7H)-one

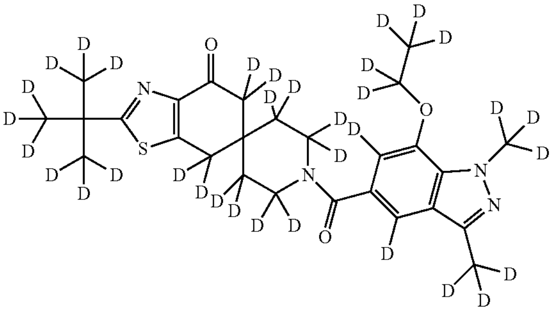 [SMILES: [2H]c1c(C(=O)N2C([2H])([2H])C([2H])([2H])C3(C([2H])([2H])C(=O)c4nc(C(C([2H])([2H])[2H])(C([2H])([2H])[2H])C([2H])([2H])[2H])sc4C3([2H])[2H])C([2H])([2H])C2([2H])[2H])c([2H])c2c(C([2H])([2H])[2H])nn(C([2H])([2H])[2H])c2c1OC([2H])([2H])C([2H])([2H])[2H]]

Example 113

2-tert-butyl-1'-{7-[(pentadeuterio)ethyloxy]-1,3-bis[(trideuterio)methyl](dideuterio)-1H-indazole-5-carbonyl}-5H-spiro[[1,3]benzothiazole-6,4'-piperidin]-4(7H)-one

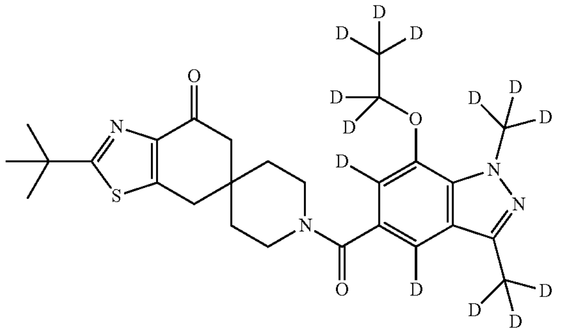 [SMILES: [2H]c1c(C(=O)N2CCC3(CC2)CC(=O)c2nc(C(C)(C)C)sc2C3)c([2H])c2c(C([2H])([2H])[2H])nn(C([2H])([2H])[2H])c2c1OC([2H])([2H])C([2H])([2H])[2H]]

Example 114

2-tert-butyl-1'-{7-[(1,1-dideuterio)ethyloxy]-1,3-bis[(trideuterio)methyl]-1H-indazole-5-carbonyl}-5H-spiro[[1,3]benzothiazole-6,4'-piperidin]-4(7H)-one

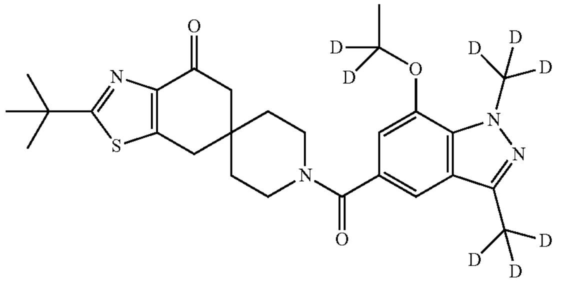 [SMILES: [2H]C([2H])(C)Oc1cc(C(=O)N2CCC3(CC2)CC(=O)c2nc(C(C)(C)C)sc2C3)cc2c(C([2H])([2H])[2H])nn(C([2H])([2H])[2H])c12]

Example 115

2-tert-butyl-1'-{7-ethoxy-1,3-bis[(trideuterio)methyl]-1H-indazole-5-carbonyl}-5H-spiro[[1,3]benzothiazole-6,4'-piperidin]-4(7H)-one

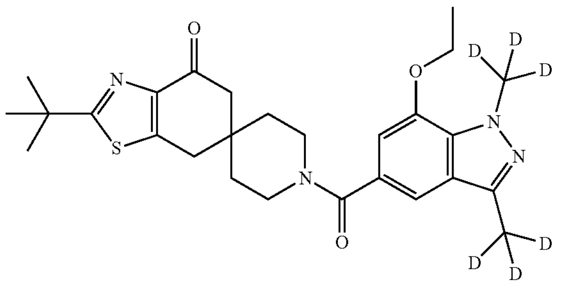 [SMILES: [2H]C([2H])([2H])c1nn(C([2H])([2H])[2H])c2c(OCC)cc(C(=O)N3CCC4(CC3)CC(=O)c3nc(C(C)(C)C)sc3C4)cc12]

Example 116

2-tert-butyl-1'-[7-ethoxy-1-methyl-3-(trideuterio)methyl-1H-indazole-5-carbonyl]-5H-spiro[[1,3]benzothiazole-6,4'-piperidin]-4(7H)-one

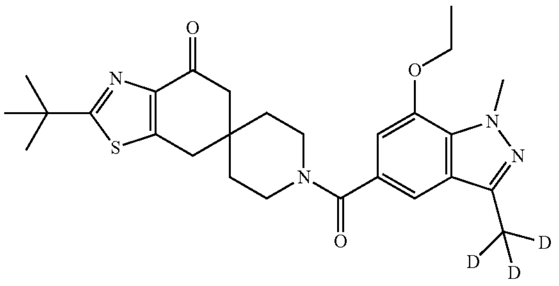 [SMILES: [2H]C([2H])([2H])c1nn(C)c2c(OCC)cc(C(=O)N3CCC4(CC3)CC(=O)c3nc(C(C)(C)C)sc3C4)cc12]

Example 117

2-tert-butyl-1'-[7-ethoxy-3-methyl-1-(trideuterio)methyl-1H-indazole-5-carbonyl]-5H-spiro[[1,3]benzothiazole-6,4'-piperidin]-4(7H)-one

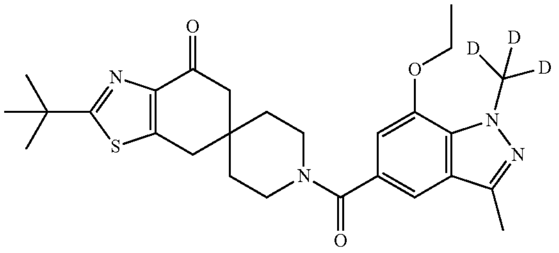 [SMILES: [2H]C([2H])([2H])n1nc(C)c2cc(C(=O)N3CCC4(CC3)CC(=O)c3nc(C(C)(C)C)sc3C4)cc(OCC)c21]

Example 118

2-tert-butyl-1'-{7-[(pentadeuterio)ethyloxy]-1,3-bis[(trideuterio)methyl]-1H-indazole-5-carbonyl}-5H-spiro[[1,3]benzothiazole-6,4'-piperidin]-4(7H)-one

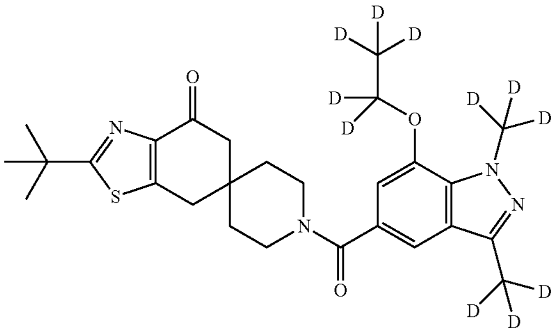 [SMILES: [2H]C([2H])([2H])c1nn(C([2H])([2H])[2H])c2c(OC([2H])([2H])C([2H])([2H])[2H])cc(C(=O)N3CCC4(CC3)CC(=O)c3nc(C(C)(C)C)sc3C4)cc12]

Example 119

1'-{7-[(pentadeuterio)ethyloxy]-1,3-bis[(trideuterio)methyl]-1H-indazole-5-carbonyl}-2-[2-(trideuterio)methyl(hexadeuterio)propan-2-yl]-5H-spiro[[1,3]benzothiazole-6,4'-piperidin]-4(7H)-one

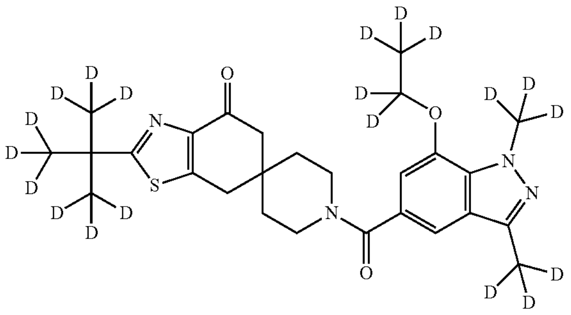 [SMILES: [2H]C([2H])([2H])c1nn(C([2H])([2H])[2H])c2c(OC([2H])([2H])C([2H])([2H])[2H])cc(C(=O)N3CCC4(CC3)CC(=O)c3nc(C(C([2H])([2H])[2H])(C([2H])([2H])[2H])C([2H])([2H])[2H])sc3C4)cc12]

Example 120

1'-{7-[(pentadeuterio)ethyloxy]-1,3-bis[(trideuterio)methyl]-1H-indazole-5-carbonyl}-2-[2-(trideuterio)methyl(hexadeuterio)propan-2-yl](5,5-dideuterio)-5H-spiro[[1,3]benzothiazole-6,4'-piperidin]-4(7H)-one

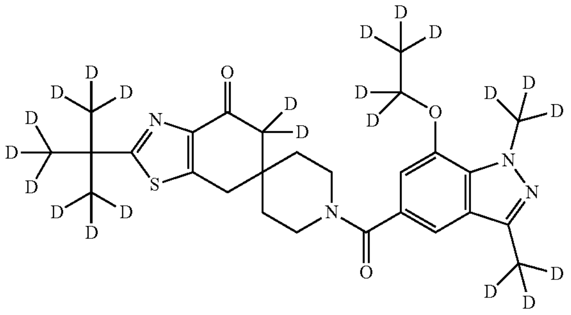 [SMILES: [2H]C([2H])([2H])c1nn(C([2H])([2H])[2H])c2c(OC([2H])([2H])C([2H])([2H])[2H])cc(C(=O)N3CCC4(CC3)Cc3sc(C(C([2H])([2H])[2H])(C([2H])([2H])[2H])C([2H])([2H])[2H])nc3C(=O)C4([2H])[2H])cc12]

Example 121

1'-{7-[(pentadeuterio)ethyloxy]-1,3-bis[(trideuterio)methyl]-1H-indazole-5-carbonyl}-2-[2-(trideuterio)methyl(hexadeuterio)propan-2-yl]-5H-spiro[[1,3]benzothiazole-6,4'-piperidin]-4(7H)-one

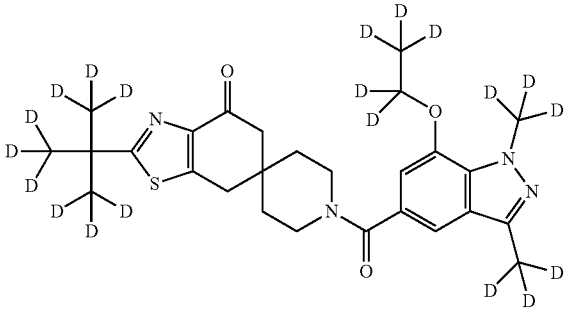 [SMILES: [2H]C([2H])([2H])c1nn(C([2H])([2H])[2H])c2c(OC([2H])([2H])C([2H])([2H])[2H])cc(C(=O)N3CCC4(CC3)CC(=O)c3nc(C(C([2H])([2H])[2H])(C([2H])([2H])[2H])C([2H])([2H])[2H])sc3C4)cc12]

Example 122

2-tert-butyl-1'-(7-ethoxy-1,3-dimethyl-1H-indazole-5-carbonyl)(5,5-dideuterio)-5H-spiro[[1,3]benzothiazole-6,4'-piperidin]-4(7H)-one

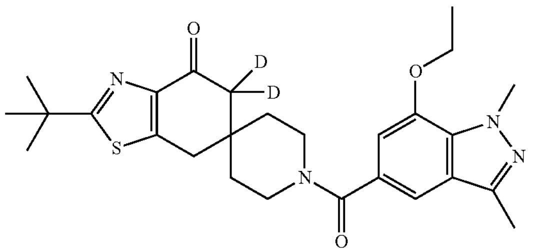 [SMILES: [2H]C1([2H])C(=O)c2nc(C(C)(C)C)sc2CC12CCN(C(=O)c1cc(OCC)c3c(c1)c(C)nn3C)CC2]

Biological Protocols

The utility of the compounds of present invention in the treatment and/or prevention of acne vulgaris in patients may be demonstrated by the activity in the in vitro assays described below. Such assays also provide a means whereby the activities of the compounds of the present invention can be compared with the activities of other known compounds.

Direct Inhibition of the Activity of ACC1

The ACC inhibitory activity of the compounds of the present invention was demonstrated by methods based on standard procedures. The direct inhibition of ACC1 for the compounds of the present invention was determined using preparations of recombinant human ACC1 (rhACC1) (SEQ ID NO. 1)

Preparation of rhACC1

Two liters of SF9 cells, infected with recombinant baculovirus containing full length human ACC1 cDNA, were suspended in ice-cold lysis buffer (25 mM Tris, pH 7.5; 150 mM NaCl; 10% glycerol; 5 mM imidazole (EMD Bioscience; Gibbstown, NJ); 2 mM TCEP (BioVectra; Charlottetown, Canada); Benzonase nuclease (10000 U/100 g cell paste; Novagen; Madison, WI); EDTA-free protease inhibitor cocktail (1 tab/50 ml; Roche Diagnostics; Mannheim, Germany). Cells were lysed by 3 cycles of freeze-thaw and centrifuged at 40,000×g for 40 minutes (4° C.). Supernatant was directly loaded onto a HisTrap FF crude column (GE Healthcare; Piscataway, NJ) and eluted with an imidazole gradient up to 0.5 M over 20 column volumes (CV). ACC1-containing fractions were pooled and diluted 1:5 with 25 mM Tris, pH 7.5, 2 mM TCEP, 10% glycerol and direct loaded onto a CaptoQ (GE Healthcare) column and eluted with an NaCl gradient up to 1 M over 20 CV's. Phosphate groups were removed from purified ACC1 by incubation with lambda phosphatase (100 U/10 μM target protein; New England Biolabs; Beverly, MA) for 14 hours at 4° C.; okadaic acid was added (1 μM final concentration; Roche Diagnostics) to inhibit the phosphatase. Purified ACC1 was exchanged into 25 mM Tris, pH 7.5, 2 mM TCEP, 10% glycerol, 0.5 M NaCl by 6 hour dialysis at 4° C. Aliquots were prepared and frozen at −80° C.

Measurement of rhACC1 Inhibition rhACC1 was assayed in a Corning #3820 (Corning, Tewksbury, MA) 384-well plate using the Transcreener ADP detection FP assay kit (Bellbrook Labs, Madison, Wisconsin) using the manufacturer's recommended conditions for a 50 μM ATP reaction. The final conditions for the assay were 50 mM HEPES, pH 7.2, 10 mM $MgCl_2$, 7.5 mM tripotassium citrate, 2 mM DTT, 0.1 mg/mL BSA, 30 μM acetyl-CoA, 50 μM ATP, and 10 mM KHCO3. Typically, a 10 μM reaction was run for 60 min at room temp, and 10 μl of Transcreener stop and detect buffer was added and the combination incubated at room temp for an overnight (18 hours). The data was acquired on an Envision Fluorescence reader (PerkinElmer) using a 620 excitation Cy5 FP general dual mirror, 620 excitation Cy5 FP filter, 688 emission (S) and a 688 (P) emission filter.

TABLE 1

| Example | Structure | Transcreener assay rhACC1 $IC_{50}$ (nM)* |
|---|---|---|
| 1 | 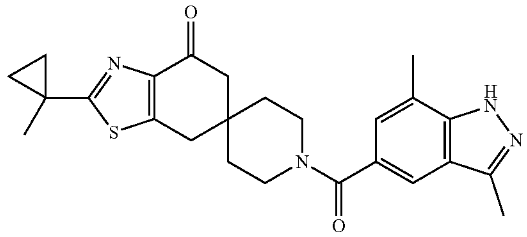 [SMILES: Cc1n[nH]c2c(C)cc(C(=O)N3CCC4(CC3)CC(=O)c3nc(C5(C)CC5)sc3C4)cc12] | 10.6 |
| 2 | 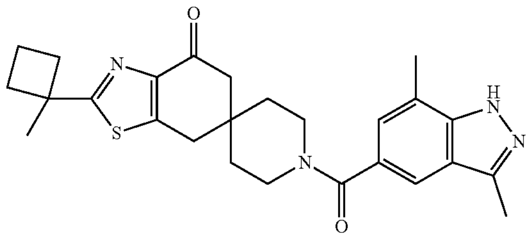 [SMILES: Cc1n[nH]c2c(C)cc(C(=O)N3CCC4(CC3)CC(=O)c3nc(C5(C)CCC5)sc3C4)cc12] | NA |

TABLE 1-continued
| Example | Structure | Transcreener assay rhACC1 $IC_{50}$ (nM)* |
| --- | --- | --- |
| 3 | 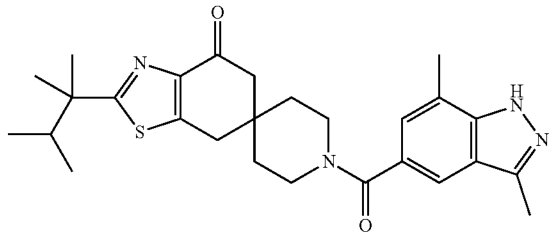 [SMILES: Cc1n[nH]c2c(C)cc(C(=O)N3CCC4(CC3)CC(=O)c3nc(C(C)(C)C(C)C)sc3C4)cc12] | 7.9 |
| 4 | 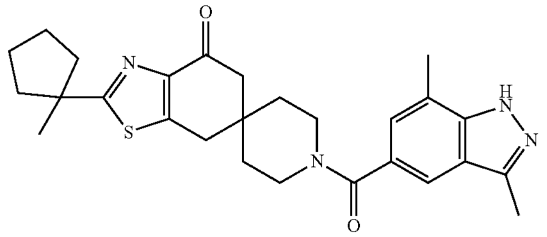 [SMILES: Cc1n[nH]c2c(C)cc(C(=O)N3CCC4(CC3)CC(=O)c3nc(C5(C)CCCC5)sc3C4)cc12] | NA |
| 5 | 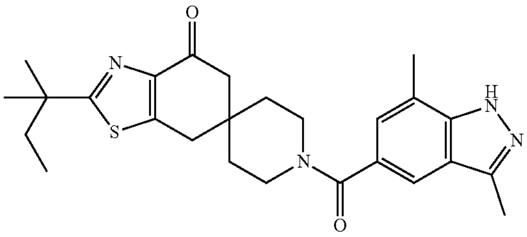 [SMILES: CCC(C)(C)c1nc2c(s1)CC1(CCN(C(=O)c3cc(C)c4[nH]nc(C)c4c3)CC1)CC2=O] | NA |
| 6 | 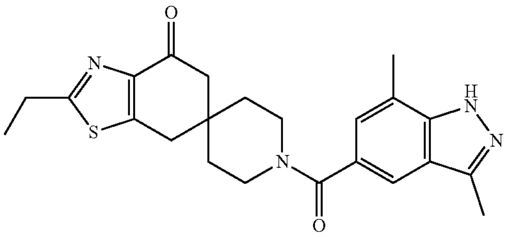 [SMILES: CCc1nc2c(s1)CC1(CCN(C(=O)c3cc(C)c4[nH]nc(C)c4c3)CC1)CC2=O] | 45.5 |
| 7 | 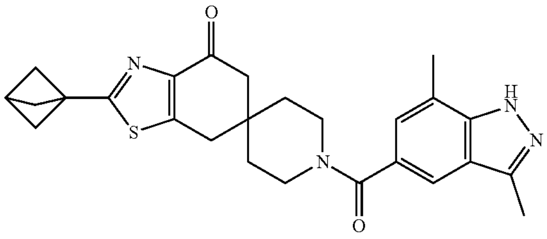 [SMILES: Cc1n[nH]c2c(C)cc(C(=O)N3CCC4(CC3)CC(=O)c3nc(C56CC(C5)C6)sc3C4)cc12] | 11 |
| 8 | 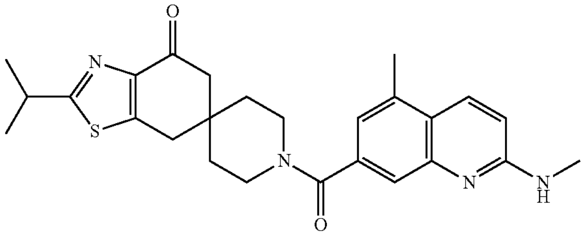 [SMILES: CNc1ccc2c(C)cc(C(=O)N3CCC4(CC3)CC(=O)c3nc(C(C)C)sc3C4)cc2n1] | 5.5 |

TABLE 1-continued
| Example | Structure | Transcreener assay rhACC1 $IC_{50}$ (nM)* |
|---|---|---|
| 9 | 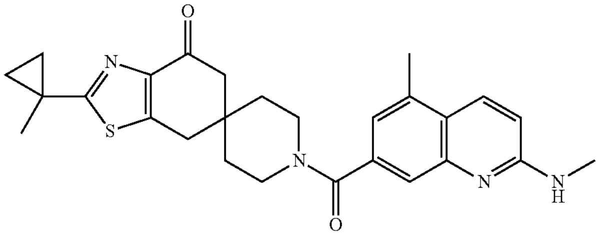 [SMILES: CNc1ccc2c(C)cc(C(=O)N3CCC4(CC3)CC(=O)c3nc(C5(C)CC5)sc3C4)cc2n1] | 13.4 |
| 10 | 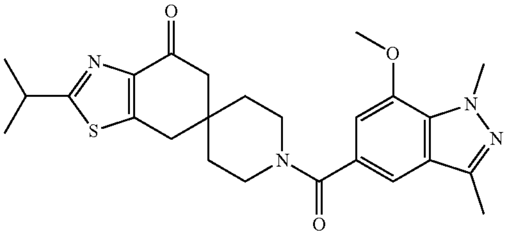 [SMILES: COc1cc(C(=O)N2CCC3(CC2)CC(=O)c2nc(C(C)C)sc2C3)cc2c(C)nn(C)c12] | 10 |
| 11 | 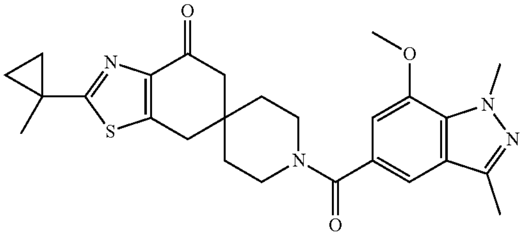 [SMILES: COc1cc(C(=O)N2CCC3(CC2)CC(=O)c2nc(C4(C)CC4)sc2C3)cc2c(C)nn(C)c12] | 4.5 |
| 12 | 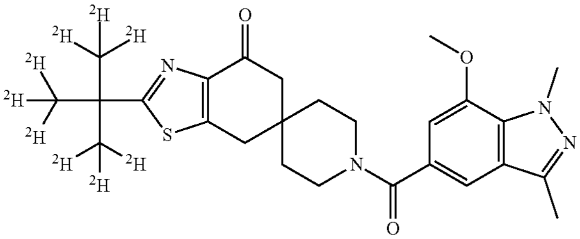 [SMILES: [2H]C([2H])([2H])C(c1nc2c(s1)CC1(CCN(C(=O)c3cc(OC)c4c(c3)c(C)nn4C)CC1)CC2=O)(C([2H])([2H])[2H])C([2H])([2H])[2H]] | 5.2 |
| 13 | 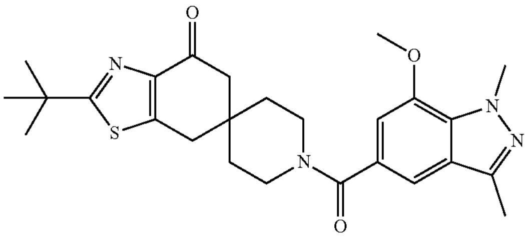 [SMILES: COc1cc(C(=O)N2CCC3(CC2)CC(=O)c2nc(C(C)(C)C)sc2C3)cc2c(C)nn(C)c12] | 5.3 |
| 14 | 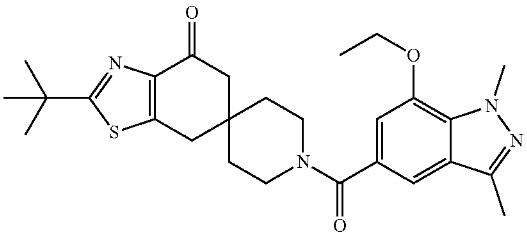 [SMILES: CCOc1cc(C(=O)N2CCC3(CC2)CC(=O)c2nc(C(C)(C)C)sc2C3)cc2c(C)nn(C)c12] | 2.2 |

TABLE 1-continued
| Example | Structure | Transcreener assay rhACC1 $IC_{50}$ (nM)* |
|---|---|---|
| 15 | 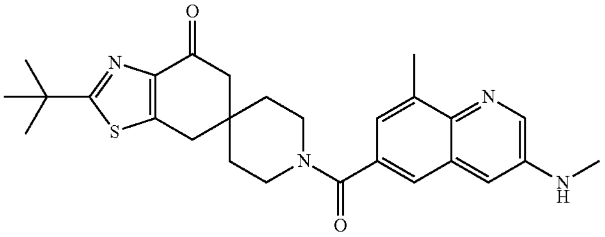 [SMILES: CNc1cnc2c(C)cc(C(=O)N3CCC4(CC3)CC(=O)c3nc(C(C)(C)C)sc3C4)cc2c1] | 3.4 |
| 16 | 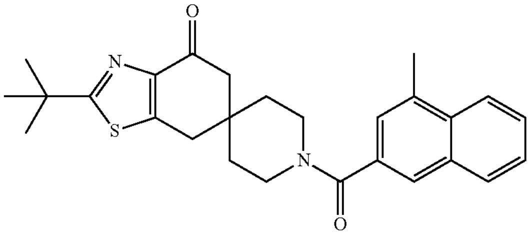 [SMILES: Cc1cc(C(=O)N2CCC3(CC2)CC(=O)c2nc(C(C)(C)C)sc2C3)cc2ccccc12] | 7.3 |
| 17 | 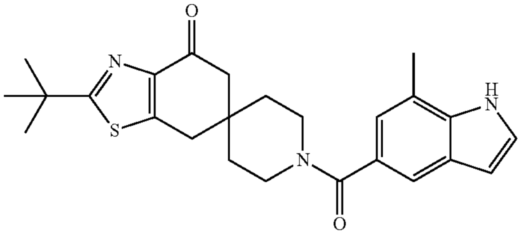 [SMILES: Cc1cc(C(=O)N2CCC3(CC2)CC(=O)c2nc(C(C)(C)C)sc2C3)cc2cc[nH]c12] | 9.6 |
| 18 | 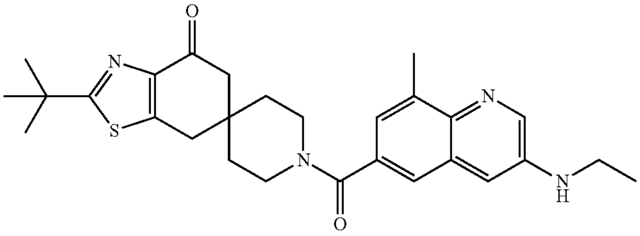 [SMILES: CCNc1cnc2c(C)cc(C(=O)N3CCC4(CC3)CC(=O)c3nc(C(C)(C)C)sc3C4)cc2c1] | 3.2 |
| 19 | 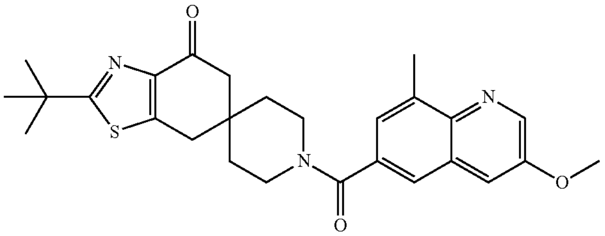 | 9.9 |
| 20 | 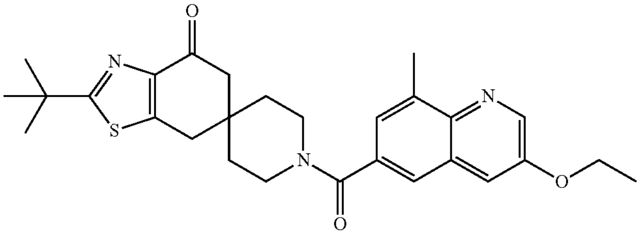 [SMILES: CCOc1cnc2c(C)cc(C(=O)N3CCC4(CC3)CC(=O)c3nc(C(C)(C)C)sc3C4)cc2c1] | 30.1 |

TABLE 1-continued
| Example | Structure | Transcreener assay rhACC1 $IC_{50}$ (nM)* |
|---|---|---|
| 21 | 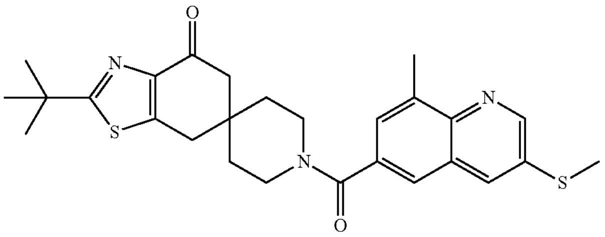 | 3.6* |
| 22 | 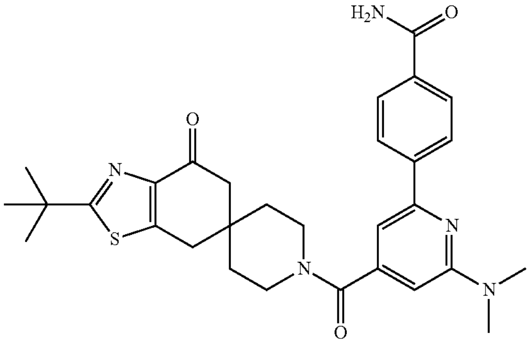 [SMILES: CN(C)c1cc(C(=O)N2CCC3(CC2)CC(=O)c2nc(C(C)(C)C)sc2C3)cc(-c2ccc(C(N)=O)cc2)n1] | 0.9 |
| 23 | 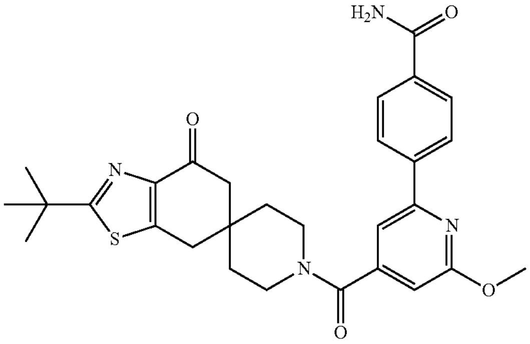 [SMILES: COc1cc(C(=O)N2CCC3(CC2)CC(=O)c2nc(C(C)(C)C)sc2C3)cc(-c2ccc(C(N)=O)cc2)n1] | 7.2 |
| 24 | 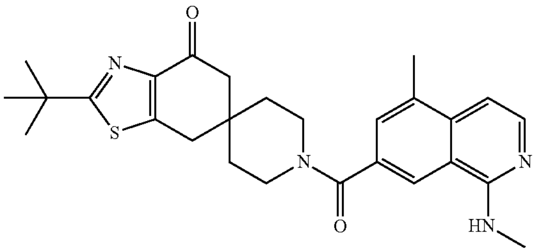 [SMILES: CNc1nccc2c(C)cc(C(=O)N3CCC4(CC3)CC(=O)c3nc(C(C)(C)C)sc3C4)cc12] | 3.1 |
| 25 | 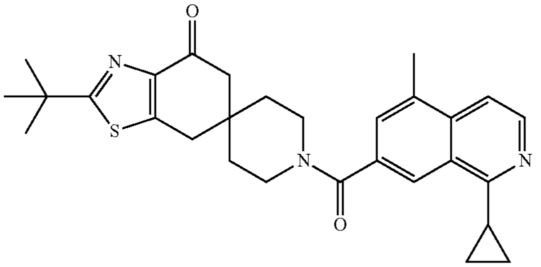 [SMILES: Cc1cc(C(=O)N2CCC3(CC2)CC(=O)c2nc(C(C)(C)C)sc2C3)cc2c(C3CC3)nccc12] | 6.6 |

TABLE 1-continued
| Example | Structure | Transcreener assay rhACC1 $IC_{50}$ (nM)* |
| --- | --- | --- |
| 26 | 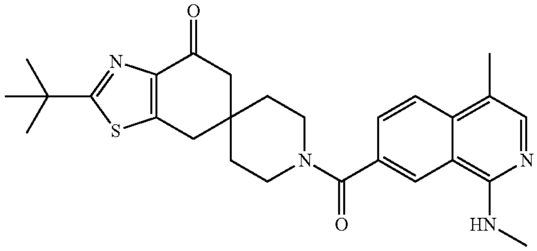 [SMILES: CNc1ncc(C)c2ccc(C(=O)N3CCC4(CC3)CC(=O)c3nc(C(C)(C)C)sc3C4)cc12] | NA |
| 27 | 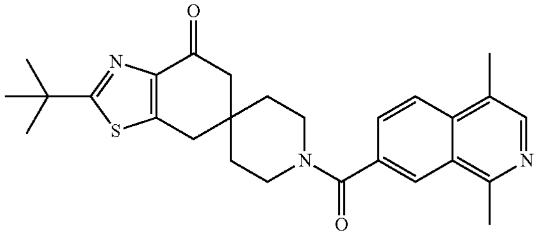 [SMILES: Cc1cnc(C)c2cc(C(=O)N3CCC4(CC3)CC(=O)c3nc(C(C)(C)C)sc3C4)ccc12] | 29.5 |
| 28 | 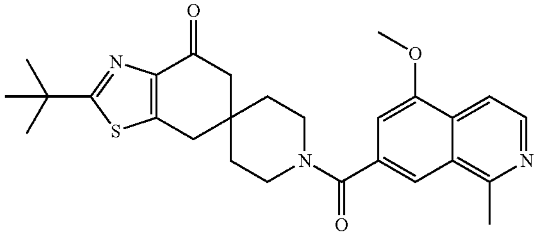 [SMILES: COc1cc(C(=O)N2CCC3(CC2)CC(=O)c2nc(C(C)(C)C)sc2C3)cc2c(C)nccc12] | 6.2 |
| 29 | 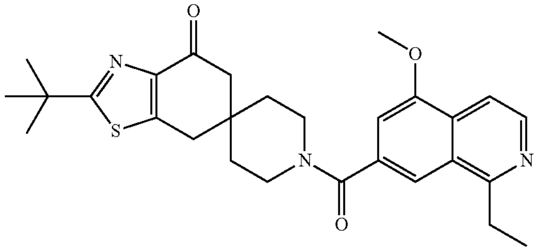 [SMILES: CCc1nccc2c(OC)cc(C(=O)N3CCC4(CC3)CC(=O)c3nc(C(C)(C)C)sc3C4)cc12] | 11.1 |
| 30 | 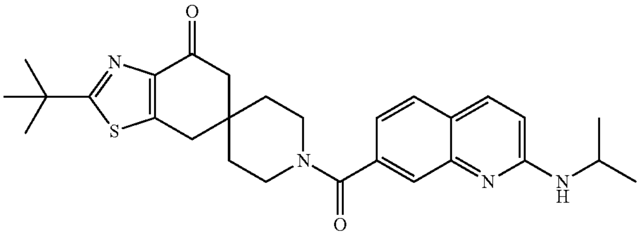 | 4.6 |
| 31 | 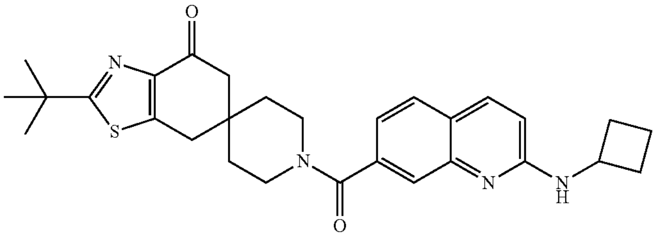 [SMILES: CC(C)(C)c1nc2c(s1)CC1(CCN(C(=O)c3ccc4ccc(NC5CCC5)nc4c3)CC1)CC2=O] | 4 |

TABLE 1-continued
| Example | Structure | Transcreener assay rhACC1 $IC_{50}$ (nM)* |
| --- | --- | --- |
| 32 | 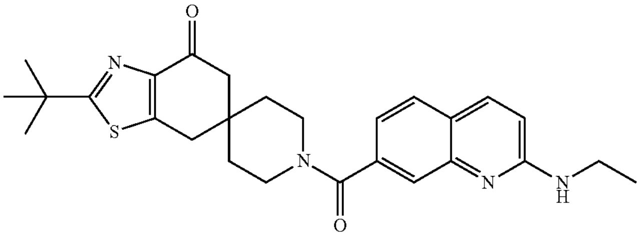 [SMILES: CCNc1ccc2ccc(C(=O)N3CCC4(CC3)CC(=O)c3nc(C(C)(C)C)sc3C4)cc2n1] | 3.5 |
| 33 | 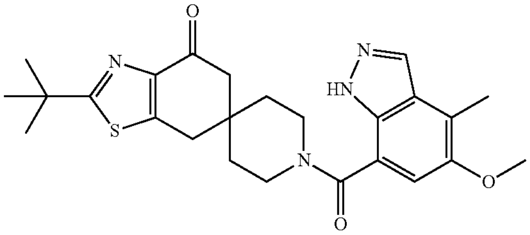 [SMILES: COc1cc(C(=O)N2CCC3(CC2)CC(=O)c2nc(C(C)(C)C)sc2C3)c2[nH]ncc2c1C] | 5.1 |
| 34 | 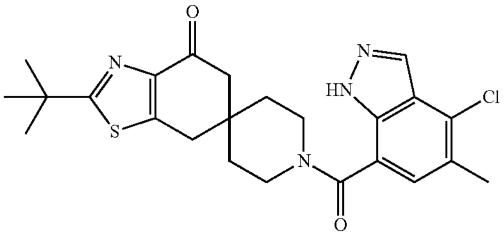 [SMILES: Cc1cc(C(=O)N2CCC3(CC2)CC(=O)c2nc(C(C)(C)C)sc2C3)c2[nH]ncc2c1Cl] | 1.3 |
| 35 | 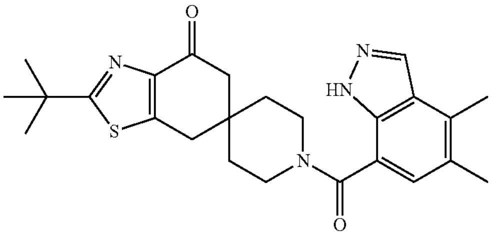 [SMILES: Cc1cc(C(=O)N2CCC3(CC2)CC(=O)c2nc(C(C)(C)C)sc2C3)c2[nH]ncc2c1C] | 2.6 |
| 36 | 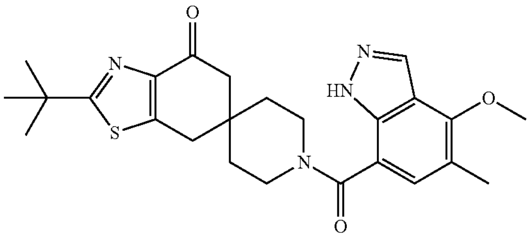 [SMILES: COc1c(C)cc(C(=O)N2CCC3(CC2)CC(=O)c2nc(C(C)(C)C)sc2C3)c2[nH]ncc12] | 23.2 |
| 37 | 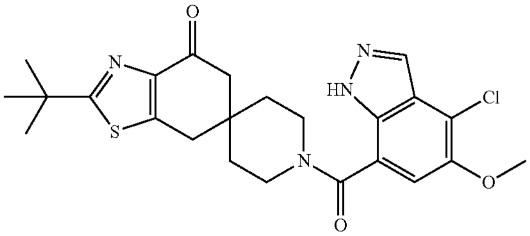 | 1.3 |

TABLE 1-continued
| Example | Structure | Transcreener assay rhACC1 $IC_{50}$ (nM)* |
|---|---|---|
| 38 | 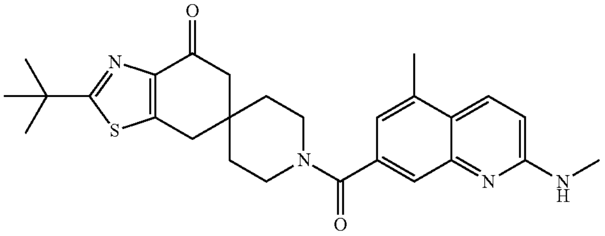 [SMILES: CNc1ccc2c(C)cc(C(=O)N3CCC4(CC3)CC(=O)c3nc(C(C)(C)C)sc3C4)cc2n1] | 4.9 |
| 39 | 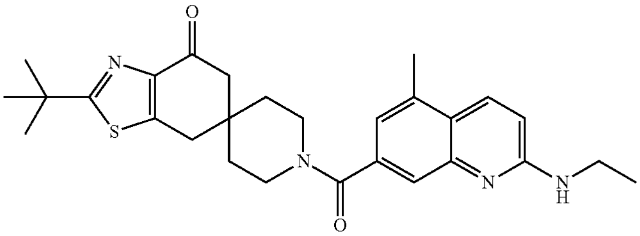 [SMILES: CCNc1ccc2c(C)cc(C(=O)N3CCC4(CC3)CC(=O)c3nc(C(C)(C)C)sc3C4)cc2n1] | 6.4 |
| 40 | 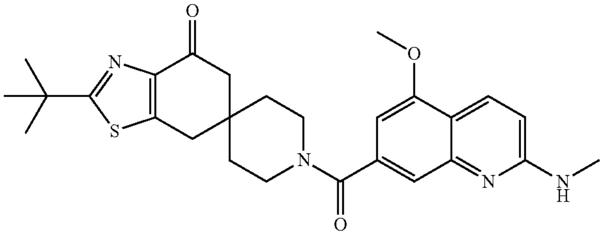 [SMILES: CNc1ccc2c(OC)cc(C(=O)N3CCC4(CC3)CC(=O)c3nc(C(C)(C)C)sc3C4)cc2n1] | 1.5 |
| 41 | 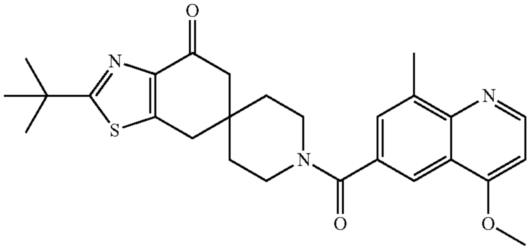 [SMILES: COc1ccnc2c(C)cc(C(=O)N3CCC4(CC3)CC(=O)c3nc(C(C)(C)C)sc3C4)cc12] | 15.3 |
| 42 | 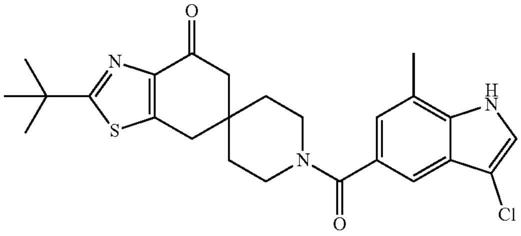 | 3.1 |
| 43 | 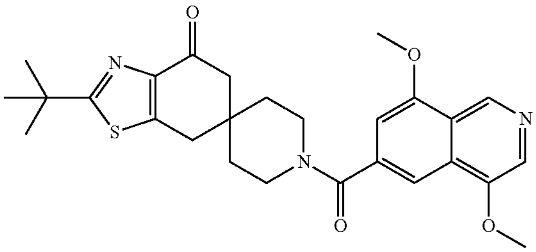 | 5.2 |

TABLE 1-continued
| Example | Structure | Transcreener assay rhACC1 $IC_{50}$ (nM)* |
|---|---|---|
| 44 | 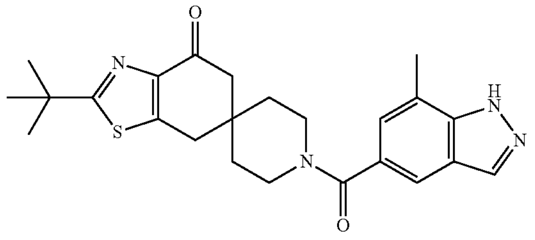 [SMILES: Cc1cc(C(=O)N2CCC3(CC2)CC(=O)c2nc(C(C)(C)C)sc2C3)cc2cn[nH]c12] | NA |
| 45 | 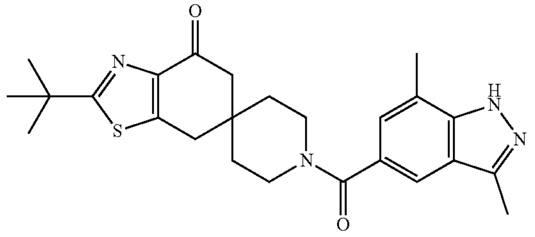 [SMILES: Cc1n[nH]c2c(C)cc(C(=O)N3CCC4(CC3)CC(=O)c3nc(C(C)(C)C)sc3C4)cc12] | 7.6 |
| 46 | 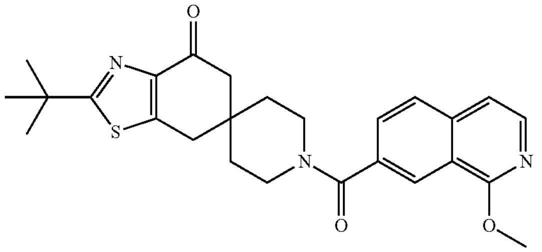 [SMILES: COc1nccc2ccc(C(=O)N3CCC4(CC3)CC(=O)c3nc(C(C)(C)C)sc3C4)cc12] | 85.9* |
| 47 | 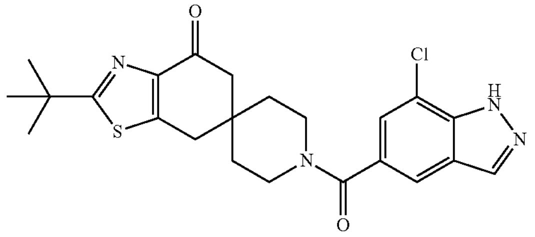 [SMILES: CC(C)(C)c1nc2c(s1)CC1(CCN(C(=O)c3cc(Cl)c4[nH]ncc4c3)CC1)CC2=O] | 23.3* |
| 48 | 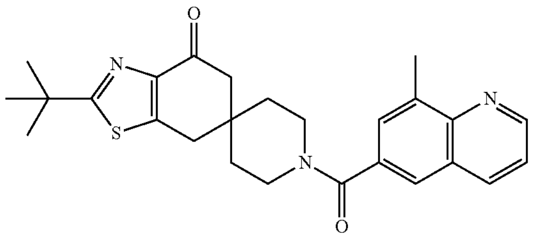 [SMILES: Cc1cc(C(=O)N2CCC3(CC2)CC(=O)c2nc(C(C)(C)C)sc2C3)cc2cccnc12] | 10000* |
| 49 | 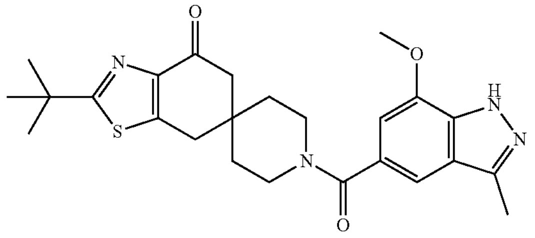 [SMILES: COc1cc(C(=O)N2CCC3(CC2)CC(=O)c2nc(C(C)(C)C)sc2C3)cc2c(C)n[nH]c12] | 6.4 |

TABLE 1-continued
| Example | Structure | Transcreener assay rhACC1 $IC_{50}$ (nM)* |
|---|---|---|
| 50 | 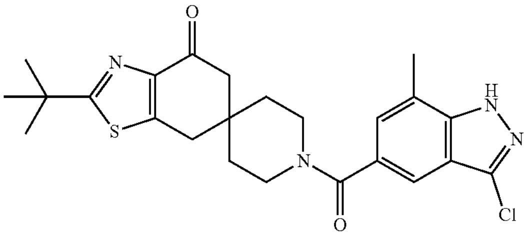 | 5.4 |
| 51 | 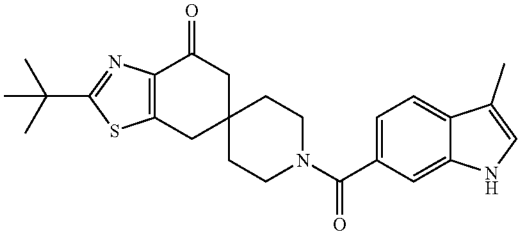 [SMILES: Cc1c[nH]c2cc(C(=O)N3CCC4(CC3)CC(=O)c3nc(C(C)(C)C)sc3C4)ccc12] | 22.4 |
| 52 | 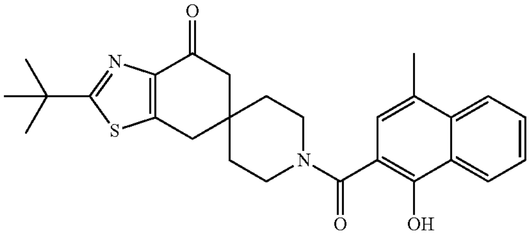 [SMILES: Cc1cc(C(=O)N2CCC3(CC2)CC(=O)c2nc(C(C)(C)C)sc2C3)c(O)c2ccccc12] | 2.4 |
| 53 | 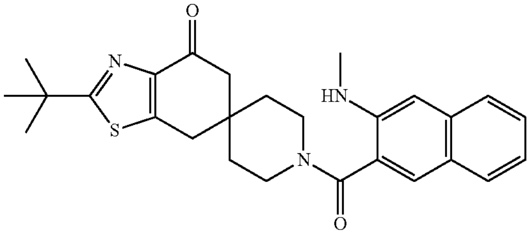 [SMILES: CNc1cc2ccccc2cc1C(=O)N1CCC2(CC1)CC(=O)c1nc(C(C)(C)C)sc1C2] | 18.1 |
| 54 | 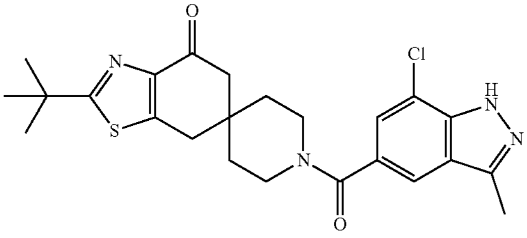 | NA |
| 55 | 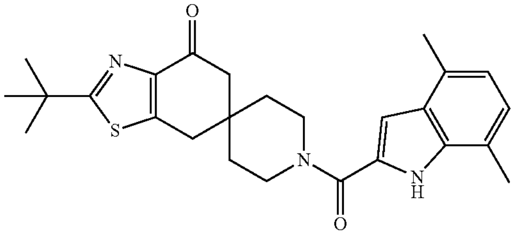 [SMILES: Cc1ccc(C)c2[nH]c(C(=O)N3CCC4(CC3)CC(=O)c3nc(C(C)(C)C)sc3C4)cc12] | 3.5 |

TABLE 1-continued
| Example | Structure | Transcreener assay rhACC1 $IC_{50}$ (nM)* |
|---|---|---|
| 56 | 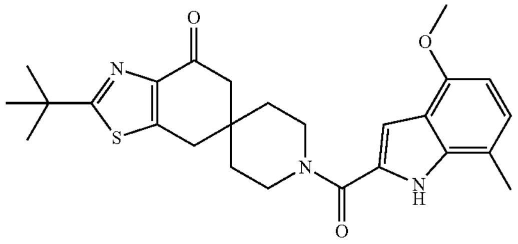 [SMILES: COc1ccc(C)c2[nH]c(C(=O)N3CCC4(CC3)CC(=O)c3nc(C(C)(C)C)sc3C4)cc12] | 5.8 |
| 57 | 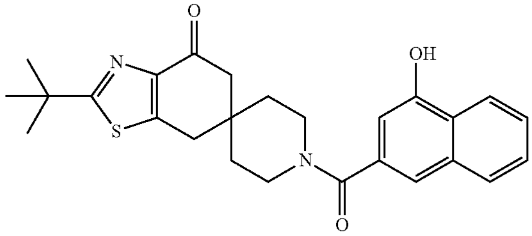 [SMILES: CC(C)(C)c1nc2c(s1)CC1(CCN(C(=O)c3cc(O)c4ccccc4c3)CC1)CC2=O] | 19.7 |
| 58 | 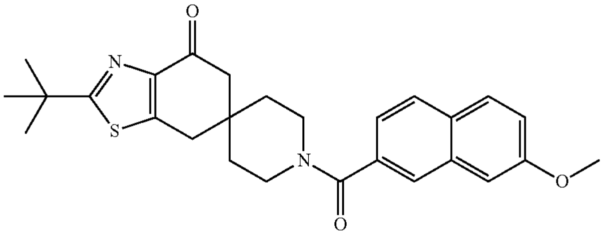 [SMILES: COc1ccc2ccc(C(=O)N3CCC4(CC3)CC(=O)c3nc(C(C)(C)C)sc3C4)cc2c1] | 7.1 |
| 59 | 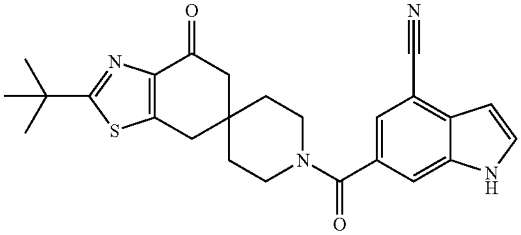 [SMILES: CC(C)(C)c1nc2c(s1)CC1(CCN(C(=O)c3cc(C#N)c4cc[nH]c4c3)CC1)CC2=O] | 8 |
| 60 | 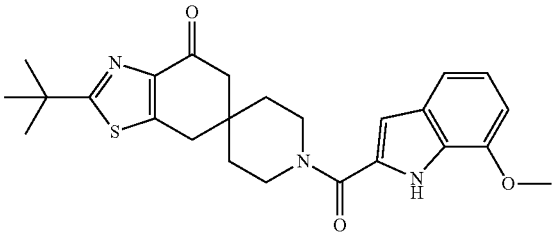 [SMILES: COc1cccc2cc(C(=O)N3CCC4(CC3)CC(=O)c3nc(C(C)(C)C)sc3C4)[nH]c12] | 27.3 |
| 61 | 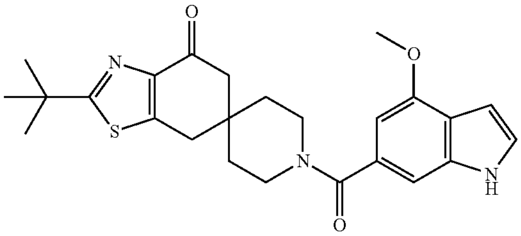 | 4.4 |

TABLE 1-continued
| Example | Structure | Transcreener assay rhACC1 $IC_{50}$ (nM)* |
|---|---|---|
| 62 | 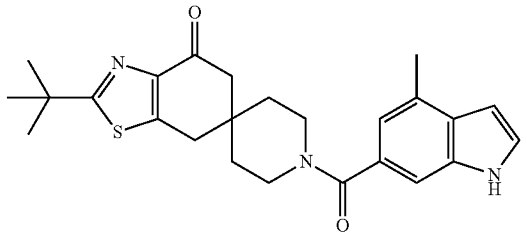 | 3.6 |
| 63 | 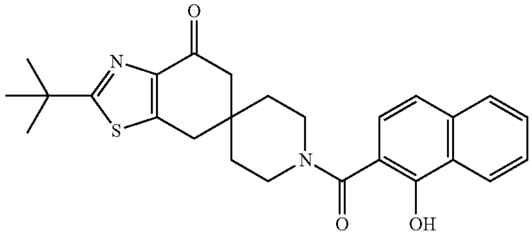 [SMILES: CC(C)(C)c1nc2c(s1)CC1(CCN(C(=O)c3ccc4ccccc4c3O)CC1)CC2=O] | 19.7* |
| 64 | 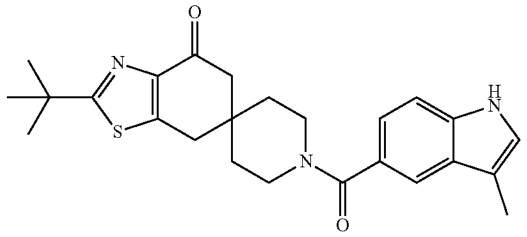 [SMILES: Cc1c[nH]c2ccc(C(=O)N3CCC4(CC3)CC(=O)c3nc(C(C)(C)C)sc3C4)cc12] | 11.8 |
| 65 | 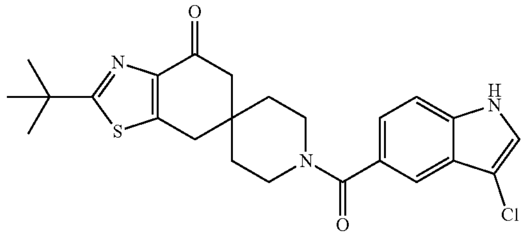 | 13 |
| 66 | 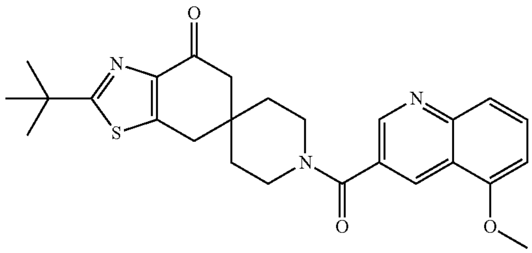 [SMILES: COc1cccc2ncc(C(=O)N3CCC4(CC3)CC(=O)c3nc(C(C)(C)C)sc3C4)cc12] | 115.1 |
| 67 | 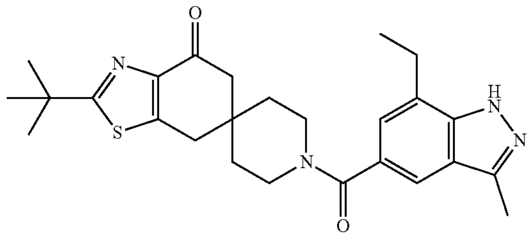 [SMILES: CCc1cc(C(=O)N2CCC3(CC2)CC(=O)c2nc(C(C)(C)C)sc2C3)cc2c(C)n[nH]c12] | NA |

TABLE 1-continued
| Example | Structure | Transcreener assay rhACC1 $IC_{50}$ (nM)* |
| --- | --- | --- |
| 68 | 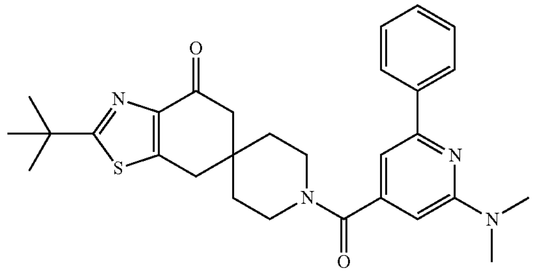 [SMILES: CN(C)c1cc(C(=O)N2CCC3(CC2)CC(=O)c2nc(C(C)(C)C)sc2C3)cc(-c2ccccc2)n1] | 3.9 |
| 69 | 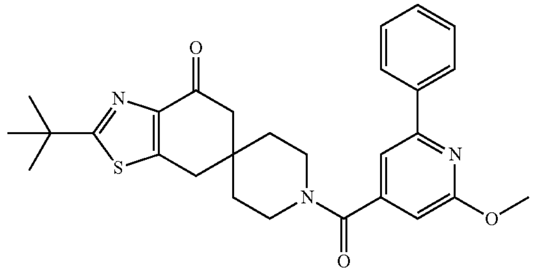 [SMILES: COc1cc(C(=O)N2CCC3(CC2)CC(=O)c2nc(C(C)(C)C)sc2C3)cc(-c2ccccc2)n1] | 16.1 |
| 70 | 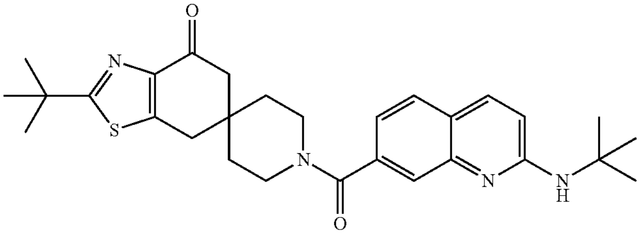 [SMILES: CC(C)(C)Nc1ccc2ccc(C(=O)N3CCC4(CC3)CC(=O)c3nc(C(C)(C)C)sc3C4)cc2n1] | 4.6 |
| 71 | 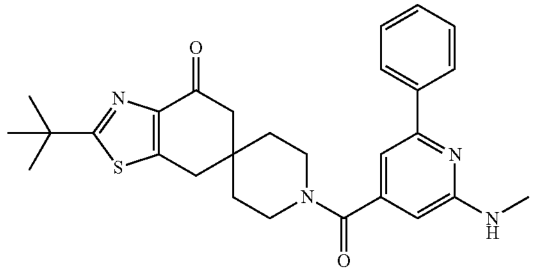 [SMILES: CNc1cc(C(=O)N2CCC3(CC2)CC(=O)c2nc(C(C)(C)C)sc2C3)cc(-c2ccccc2)n1] | 13.6 |
| 72 | 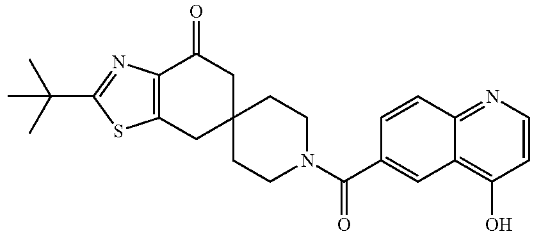 [SMILES: CC(C)(C)c1nc2c(s1)CC1(CCN(C(=O)c3ccc4nccc(O)c4c3)CC1)CC2=O] | 10000* |
| 73 | 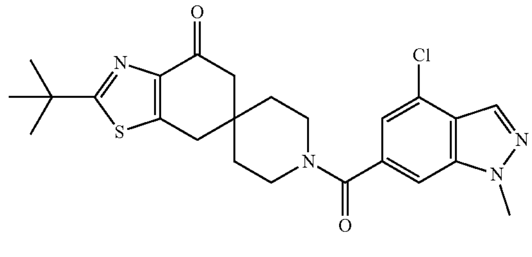 [SMILES: Cn1ncc2c(Cl)cc(C(=O)N3CCC4(CC3)CC(=O)c3nc(C(C)(C)C)sc3C4)cc21] | 22.9 |

TABLE 1-continued
| Example | Structure | Transcreener assay rhACC1 $IC_{50}$ (nM)* |
|---|---|---|
| 74 | 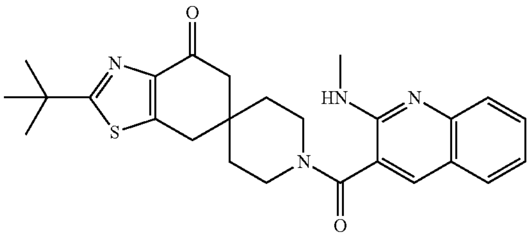 | 189 |
| 75 | 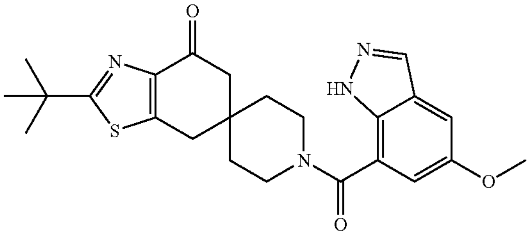 | 17.6 |
| 76 | 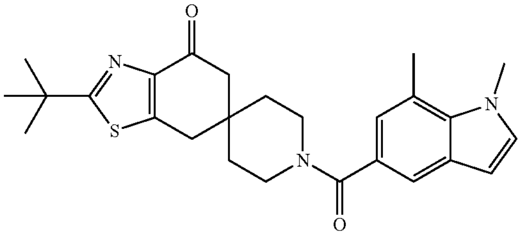 [SMILES: Cc1cc(C(=O)N2CCC3(CC2)CC(=O)c2nc(C(C)(C)C)sc2C3)cc2ccn(C)c12] | 65.4 |
| 77 | 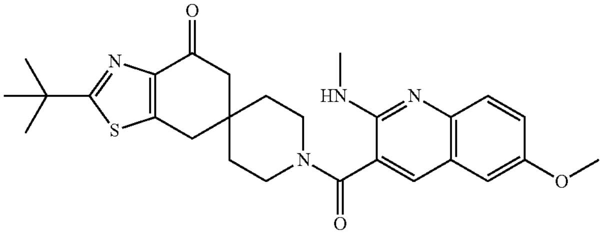 [SMILES: CNc1nc2ccc(OC)cc2cc1C(=O)N1CCC2(CC1)CC(=O)c1nc(C(C)(C)C)sc1C2] | 9.4 |
| 78 | 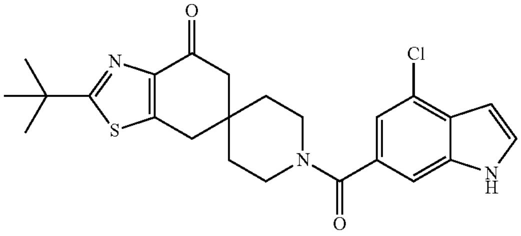 [SMILES: CC(C)(C)c1nc2c(s1)CC1(CCN(C(=O)c3cc(Cl)c4cc[nH]c4c3)CC1)CC2=O] | 7.6 |
| 79 | 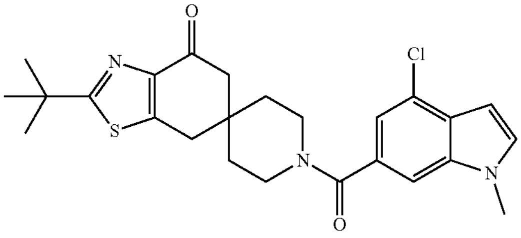 [SMILES: Cn1ccc2c(Cl)cc(C(=O)N3CCC4(CC3)CC(=O)c3nc(C(C)(C)C)sc3C4)cc21] | 4.1 |

TABLE 1-continued
| Example | Structure | Transcreener assay rhACC1 $IC_{50}$ (nM)* |
|---|---|---|
| 80 | 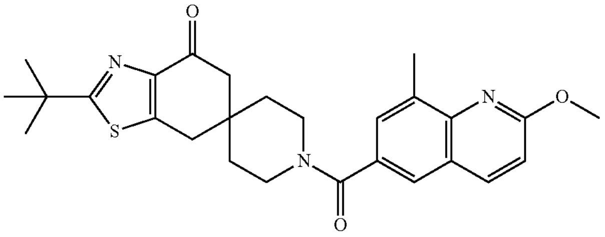 [SMILES: COc1ccc2cc(C(=O)N3CCC4(CC3)CC(=O)c3nc(C(C)(C)C)sc3C4)cc(C)c2n1] | 109.4* |
| 81 | 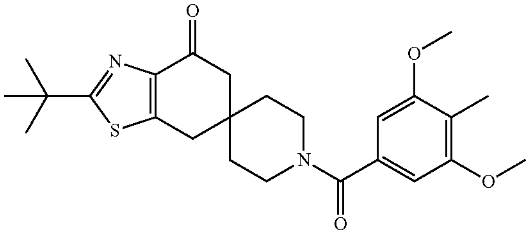 [SMILES: COc1cc(C(=O)N2CCC3(CC2)CC(=O)c2nc(C(C)(C)C)sc2C3)cc(OC)c1C] | 11.7 |
| 82 | 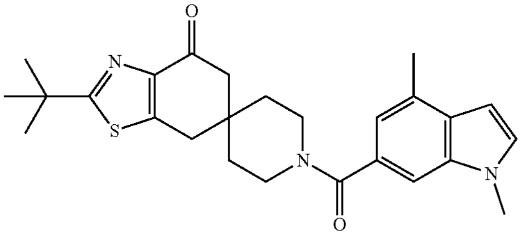 [SMILES: Cc1cc(C(=O)N2CCC3(CC2)CC(=O)c2nc(C(C)(C)C)sc2C3)cc2c1ccn2C] | 6.1 |
| 83 | 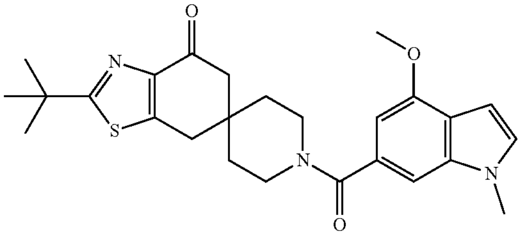 [SMILES: COc1cc(C(=O)N2CCC3(CC2)CC(=O)c2nc(C(C)(C)C)sc2C3)cc2c1ccn2C] | 11.1 |
| 84 | 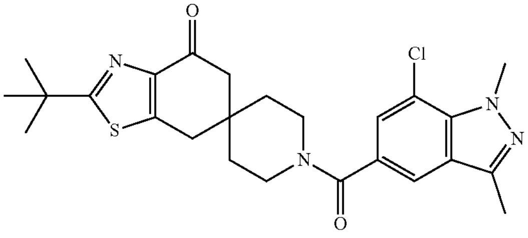 [SMILES: Cc1nn(C)c2c(Cl)cc(C(=O)N3CCC4(CC3)CC(=O)c3nc(C(C)(C)C)sc3C4)cc12] | 92.6 |
| 85 | 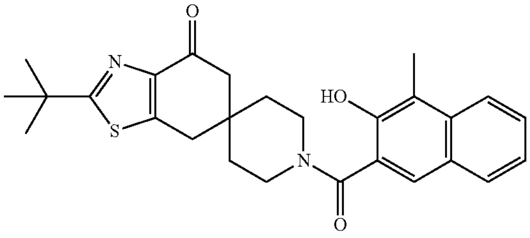 [SMILES: Cc1c(O)c(C(=O)N2CCC3(CC2)CC(=O)c2nc(C(C)(C)C)sc2C3)cc2ccccc12] | 7 |

TABLE 1-continued
| Example | Structure | Transcreener assay rhACC1 $IC_{50}$ (nM)* |
|---|---|---|
| 86 | 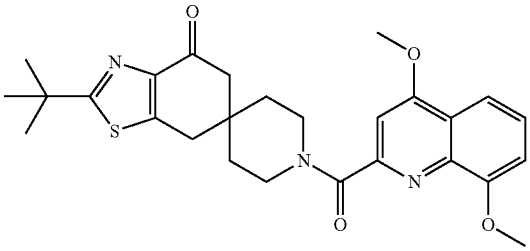 [SMILES: COc1cc(C(=O)N2CCC3(CC2)CC(=O)c2nc(C(C)(C)C)sc2C3)nc2c(OC)cccc12] | 14.3 |
| 87 | 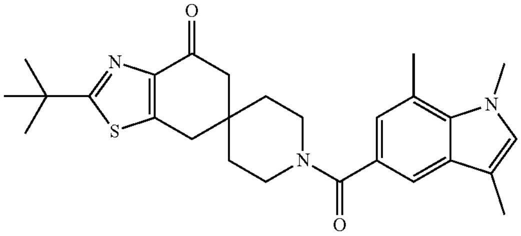 [SMILES: Cc1cn(C)c2c(C)cc(C(=O)N3CCC4(CC3)CC(=O)c3nc(C(C)(C)C)sc3C4)cc12] | 6.2 |
| 88 | 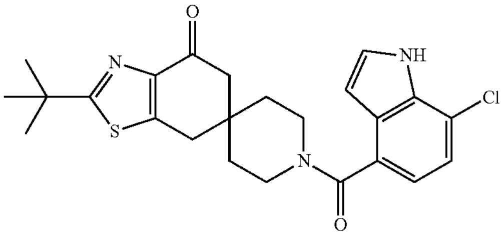 [SMILES: CC(C)(C)c1nc2c(s1)CC1(CCN(C(=O)c3ccc(Cl)c4[nH]ccc34)CC1)CC2=O] | 15 |
| 89 | 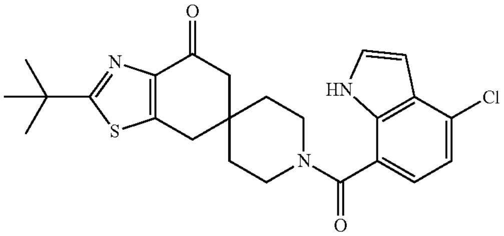 [SMILES: CC(C)(C)c1nc2c(s1)CC1(CCN(C(=O)c3ccc(Cl)c4cc[nH]c34)CC1)CC2=O] | 6.3 |
| 90 | 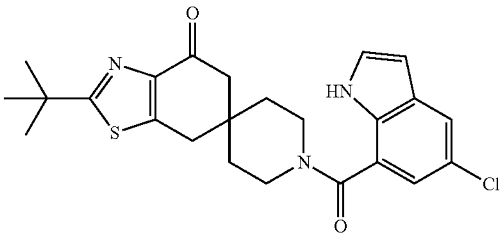 [SMILES: CC(C)(C)c1nc2c(s1)CC1(CCN(C(=O)c3cc(Cl)cc4cc[nH]c34)CC1)CC2=O] | 9.6 |
| 91 | 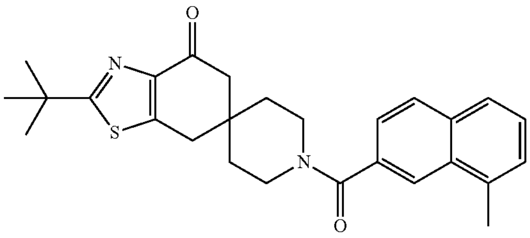 [SMILES: Cc1cccc2ccc(C(=O)N3CCC4(CC3)CC(=O)c3nc(C(C)(C)C)sc3C4)cc12] | 14* |

TABLE 1-continued
| Example | Structure | Transcreener assay rhACC1 $IC_{50}$ (nM)* |
|---|---|---|
| 92 | 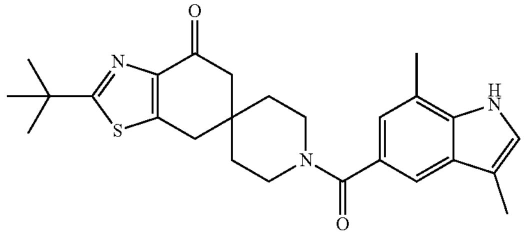 | 2.4 |
| 93 | 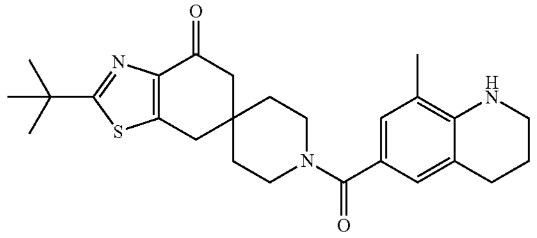 [SMILES: Cc1cc(C(=O)N2CCC3(CC2)CC(=O)c2nc(C(C)(C)C)sc2C3)cc2c1NCCC2] | 19.5 |
| 94 | 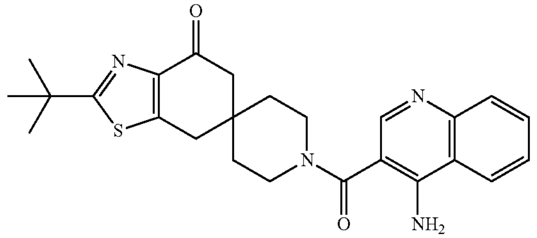 [SMILES: CC(C)(C)c1nc2c(s1)CC1(CCN(C(=O)c3cnc4ccccc4c3N)CC1)CC2=O] | 17.9 |
| 95 | 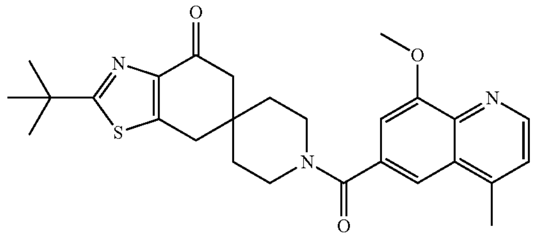 [SMILES: COc1cc(C(=O)N2CCC3(CC2)CC(=O)c2nc(C(C)(C)C)sc2C3)cc2c(C)ccnc12] | 46.5 |
| 96 | 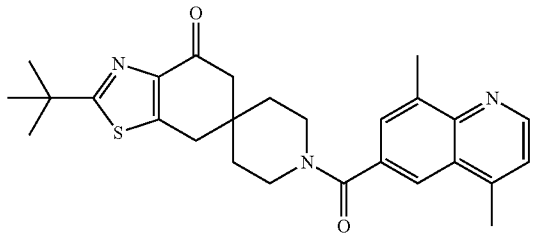 [SMILES: Cc1ccnc2c(C)cc(C(=O)N3CCC4(CC3)CC(=O)c3nc(C(C)(C)C)sc3C4)cc12] | 26.1 |
| 97 | 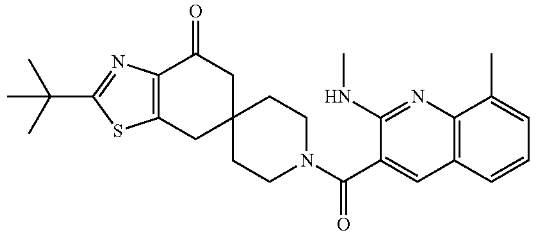 [SMILES: CNc1nc2c(C)cccc2cc1C(=O)N1CCC2(CC1)CC(=O)c1nc(C(C)(C)C)sc1C2] | 1.8 |

TABLE 1-continued
| Example | Structure | Transcreener assay rhACC1 $IC_{50}$ (nM)* |
|---|---|---|
| 98 | 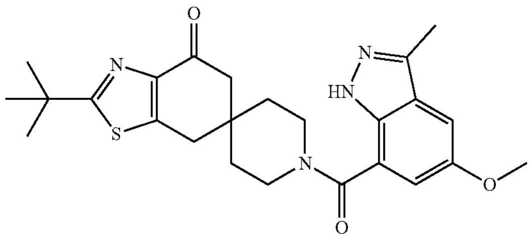 [SMILES: COc1cc(C(=O)N2CCC3(CC2)CC(=O)c2nc(C(C)(C)C)sc2C3)c2[nH]nc(C)c2c1] | 8.6 |
| 99 | 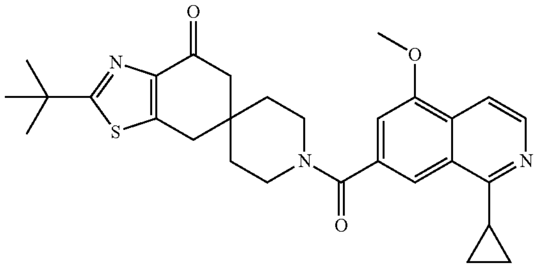 [SMILES: COc1cc(C(=O)N2CCC3(CC2)CC(=O)c2nc(C(C)(C)C)sc2C3)cc2c(C3CC3)nccc12] | 3.9 |
| 100 | 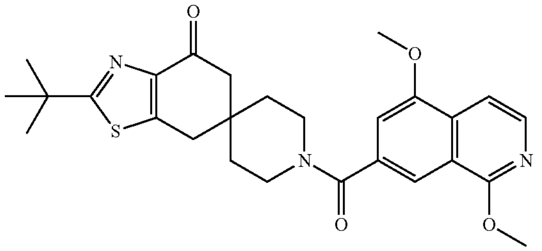 [SMILES: COc1cc(C(=O)N2CCC3(CC2)CC(=O)c2nc(C(C)(C)C)sc2C3)cc2c(OC)nccc12] | 3.1 |
| 101 | 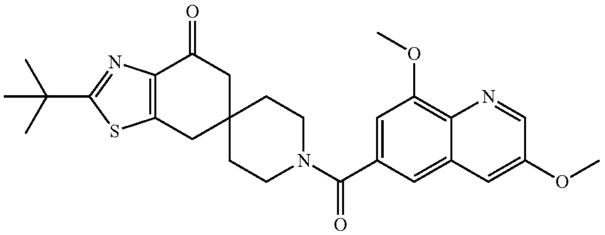 | 10.1 |
| 102 | 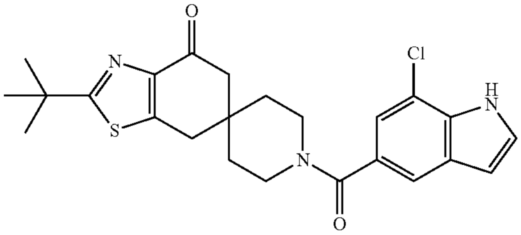 [SMILES: CC(C)(C)c1nc2c(s1)CC1(CCN(C(=O)c3cc(Cl)c4[nH]ccc4c3)CC1)CC2=O] | 7.2* |
| 103 | 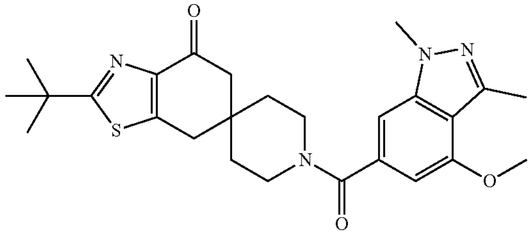 [SMILES: COc1cc(C(=O)N2CCC3(CC2)CC(=O)c2nc(C(C)(C)C)sc2C3)cc2c1c(C)nn2C] | 5.4 |

TABLE 1-continued
| Example | Structure | Transcreener assay rhACC1 $IC_{50}$ (nM)* |
|---|---|---|
| 104 | 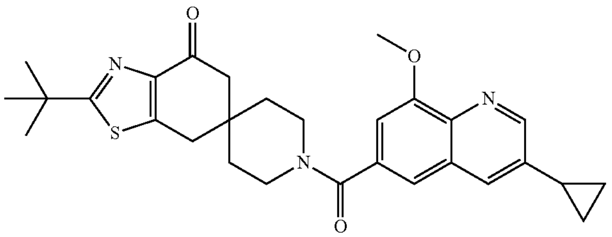 [SMILES: COc1cc(C(=O)N2CCC3(CC2)CC(=O)c2nc(C(C)(C)C)sc2C3)cc2cc(C3CC3)cnc12] | 6.7 |
| 105 | 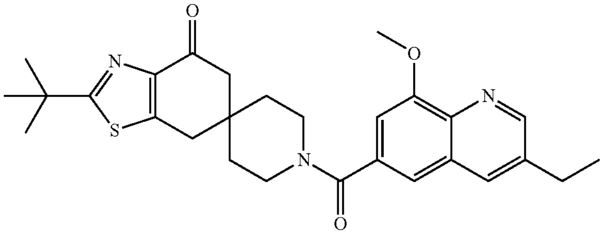 [SMILES: CCc1cnc2c(OC)cc(C(=O)N3CCC4(CC3)CC(=O)c3nc(C(C)(C)C)sc3C4)cc2c1] | 33.6 |
| 106 | 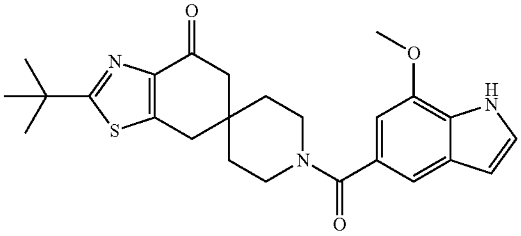 [SMILES: COc1cc(C(=O)N2CCC3(CC2)CC(=O)c2nc(C(C)(C)C)sc2C3)cc2cc[nH]c12] | 12.9 |
| 107 | 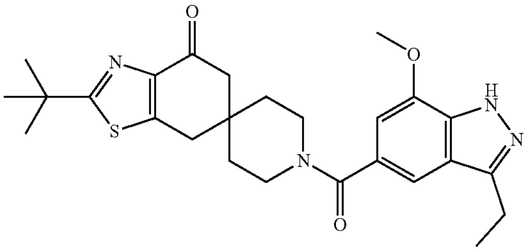 [SMILES: CCc1n[nH]c2c(OC)cc(C(=O)N3CCC4(CC3)CC(=O)c3nc(C(C)(C)C)sc3C4)cc12] | 12.3 |
| 108 | 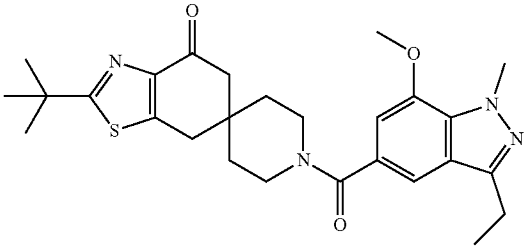 [SMILES: CCc1nn(C)c2c(OC)cc(C(=O)N3CCC4(CC3)CC(=O)c3nc(C(C)(C)C)sc3C4)cc12] | 5.6 |
| 109 | 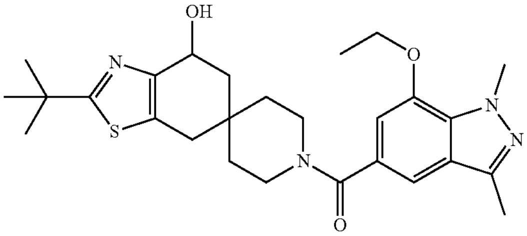 | 23.2 |
Geomean $IC_{50}$ given, number of repeats n ≥ 2 unless symbol "*" then n = 1;
NA = not available High Content Imaging Assay to Quantify Lipid Droplets in a Human Sebocyte Cell Line One week prior to cell dosing, SZ95 human sebocytes were thawed and grown in a T175 tissue culture flask containing 50 mL media. Media was prepared as follows: Sebomed basal medium with stable glutamine and without phenol red (Sigma; Catalog No. F8205), 10% heat inactivated fetal bovine serum (Invitrogen; Cat. No. 10082), 5 ng/mL recombinant human epidermal growth factor (Gibco; Catalog No. PHG0311), 1 mM calcium chloride (Fisher Scientific; Catalog No. BP9742), and 1× penicillin/streptomycin (Thermo Fisher; Catalog No. 15140-122). Cells were cultured at 37° C. and the media was replaced every 48-72 hours until start of assay. Compounds were delivered as a 75 nL spot by the Echo 550 (Labcyte) into 384-well assay plates (PerkinElmer; Catalog No. 6057308) with final compound concentrations of 10, 3.162, 1.000, 0.316, 0.100, 0.032, 0.010, 0.003, 0.001, 0.0003, and 0.0001 μM. The final DMSO concentration was 0.1%. SZ-95 cells were washed with Dulbecco's phosphate buffered saline (DPBS, Lonza; Catalog No. 17-512Q) and then detached with 0.25% Trypsin-EDTA (Gibco; Catalog No. 25200056). Growth media (25 mL) was added to the flask and the cells were further diluted to 1.33x10≡cells/mL. SZ-95 cells were plated at a density of 10,000 cells/well in 75 μL and incubated for 48 hours at 37° C. Using the Biomek FX (Beckman), 25 μL of media was removed and the cells were fixed by adding 18.7 μL of 16% paraformaldehyde (Electron Microscopy Sciences; Cat. No. 50980488). After a 30 minute incubation at room temperature, the plates were washed twice with 75 μl DPBS. Following the second wash, all remaining DPBS was removed. Staining solution was prepared with 2 μM Bodipy (Invitrogen; Cat. No D3922, diluted 1:1000) and Hoechst (Life Technologies; Cat. No. H3570, diluted 1:2000) in DPBS. Using the Biomek FX, 30 μL of the staining solution was added to each well. The cells were incubated for 20 minutes at room temperature, then washed once with 75 μL DPBS. Finally, 30 μL of DPBS was added to each well and the plates were sealed with light blocking film. The plates were read on an Opera Phenix (PerkinElmer) for high content imaging. Nuclei were detected by Hoechst staining and lipid droplets by Bodipy, which stains neutral lipids. Active compounds caused a reduction in the number and area of lipid droplets. The percent (%) effect at each concentration of compound is calculated by Genedata Screener analysis program using a four-parameter logistic dose response equation and is based on and relative to the amount of lipid droplets in the positive and negative control wells contained within each assay plate to determine the 50% inhibition concentration (IC50).

TABLE 2

| Example | Structure | Human SZ95 sebocyte lipid imaging assay/ Percent Inhibition of |
|---|---|---|
| 1 | 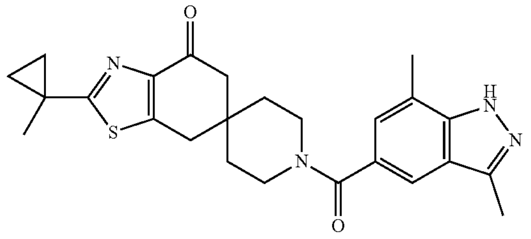 [SMILES: Cc1n[nH]c2c(C)cc(C(=O)N3CCC4(CC3)CC(=O)c3nc(C5(C)CC5)sc3C4)cc12] | 8.7 |
| 2 | 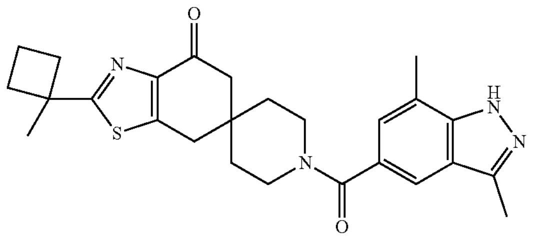 [SMILES: Cc1n[nH]c2c(C)cc(C(=O)N3CCC4(CC3)CC(=O)c3nc(C5(C)CCC5)sc3C4)cc12] | 10.3 |
| 3 | 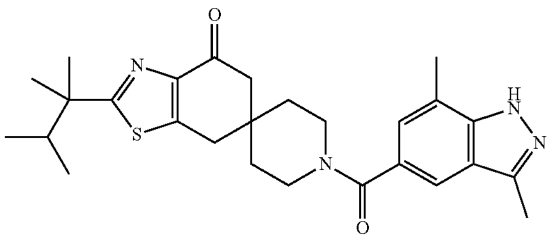 [SMILES: Cc1n[nH]c2c(C)cc(C(=O)N3CCC4(CC3)CC(=O)c3nc(C(C)(C)C(C)C)sc3C4)cc12] | 15 |

TABLE 2-continued
| Example | Structure | Human SZ95 sebocyte lipid imaging assay/ Percent Inhibition of |
|---|---|---|
| 4 | 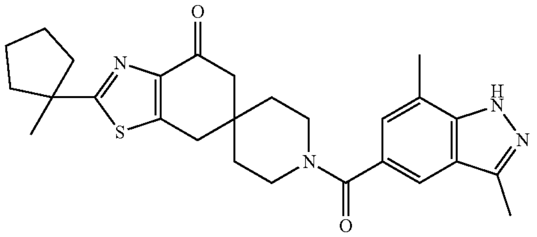 [SMILES: Cc1n[nH]c2c(C)cc(C(=O)N3CCC4(CC3)CC(=O)c3nc(C5(C)CCCC5)sc3C4)cc12] | 9.6 |
| 5 | 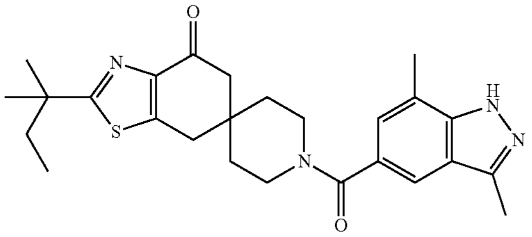 | 17.6 |
| 6 | 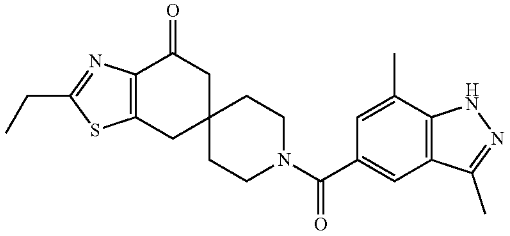 [SMILES: CCc1nc2c(s1)CC1(CCN(C(=O)c3cc(C)c4[nH]nc(C)c4c3)CC1)CC2=O] | 19 |
| 7 | 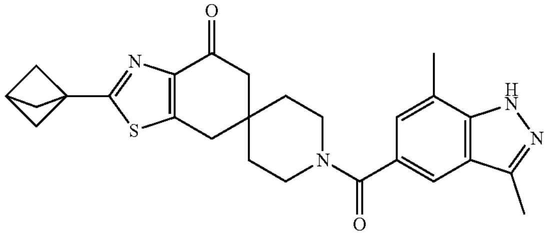 [SMILES: Cc1n[nH]c2c(C)cc(C(=O)N3CCC4(CC3)CC(=O)c3nc(C56CC(C5)C6)sc3C4)cc12] | 19.5 |
| 8 | 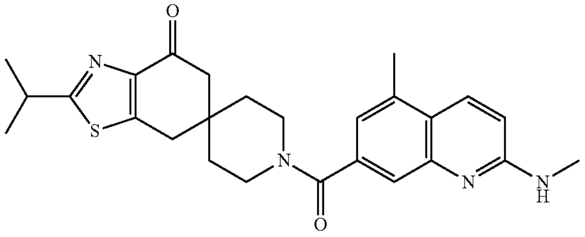 [SMILES: CNc1ccc2c(C)cc(C(=O)N3CCC4(CC3)CC(=O)c3nc(C(C)C)sc3C4)cc2n1] | 8.7 |
| 9 | 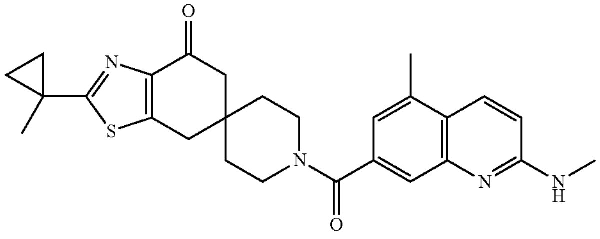 [SMILES: CNc1ccc2c(C)cc(C(=O)N3CCC4(CC3)CC(=O)c3nc(C5(C)CC5)sc3C4)cc2n1] | 4.5 |

TABLE 2-continued
| Example | Structure | Human SZ95 sebocyte lipid imaging assay/ Percent Inhibition of |
|---|---|---|
| 10 | 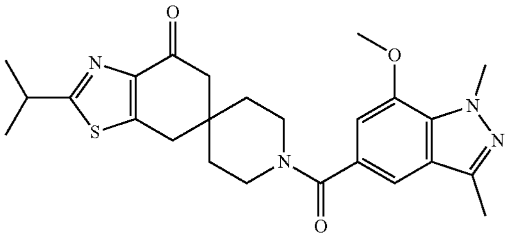 [SMILES: COc1cc(C(=O)N2CCC3(CC2)CC(=O)c2nc(C(C)C)sc2C3)cc2c(C)nn(C)c12] | 16.3 |
| 11 | 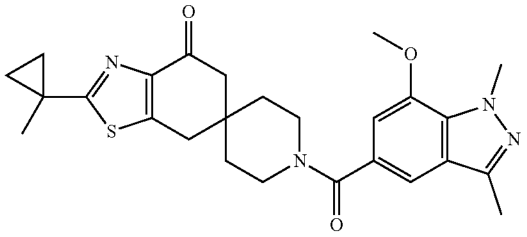 [SMILES: COc1cc(C(=O)N2CCC3(CC2)CC(=O)c2nc(C4(C)CC4)sc2C3)cc2c(C)nn(C)c12] | 10.6 |
| 12 | 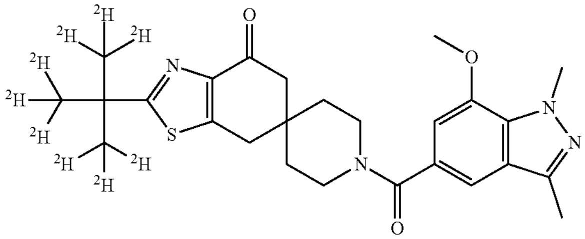 [SMILES: [2H]C([2H])([2H])C(c1nc2c(s1)CC1(CCN(C(=O)c3cc(OC)c4c(c3)c(C)nn4C)CC1)CC2=O)(C([2H])([2H])[2H])C([2H])([2H])[2H]] | 8.4 |
| 13 | 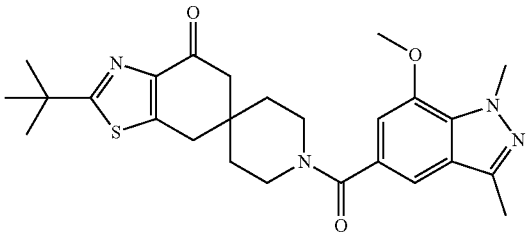 [SMILES: COc1cc(C(=O)N2CCC3(CC2)CC(=O)c2nc(C(C)(C)C)sc2C3)cc2c(C)nn(C)c12] | 5 |
| 14 | 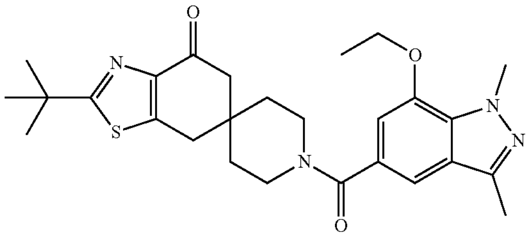 [SMILES: CCOc1cc(C(=O)N2CCC3(CC2)CC(=O)c2nc(C(C)(C)C)sc2C3)cc2c(C)nn(C)c12] | 7.7 |
| 15 | 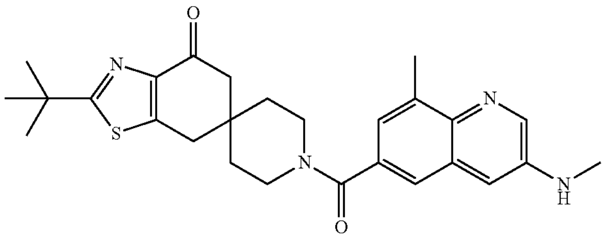 [SMILES: CNc1cnc2c(C)cc(C(=O)N3CCC4(CC3)CC(=O)c3nc(C(C)(C)C)sc3C4)cc2c1] | 6.3 |

TABLE 2-continued
| Example | Structure | Human SZ95 sebocyte lipid imaging assay/ Percent Inhibition of |
|---|---|---|
| 16 | 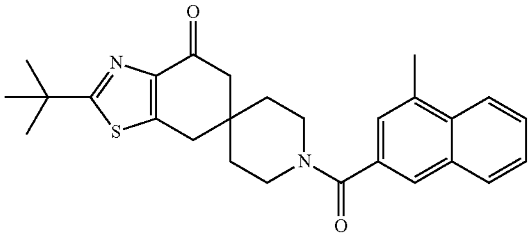 [SMILES: Cc1cc(C(=O)N2CCC3(CC2)CC(=O)c2nc(C(C)(C)C)sc2C3)cc2ccccc12] | 5.8 |
| 17 | 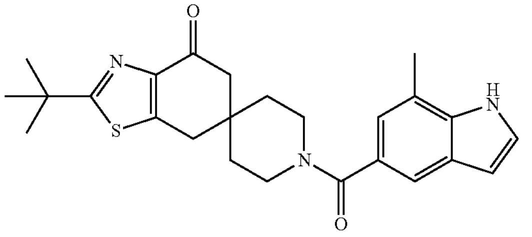 [SMILES: Cc1cc(C(=O)N2CCC3(CC2)CC(=O)c2nc(C(C)(C)C)sc2C3)cc2cc[nH]c12] | 11.3 |
| 18 | 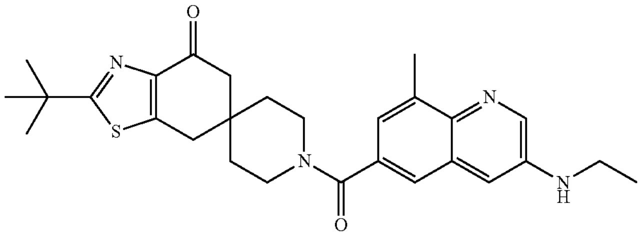 | 10.2 |
| 19 | 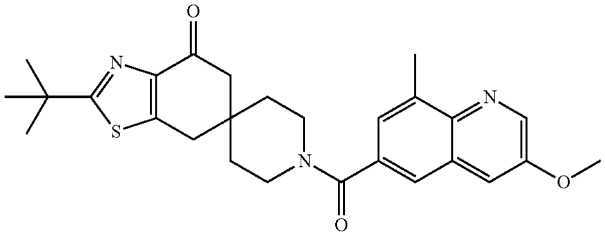 [SMILES: COc1cnc2c(C)cc(C(=O)N3CCC4(CC3)CC(=O)c3nc(C(C)(C)C)sc3C4)cc2c1] | 11.1 |
| 20 | 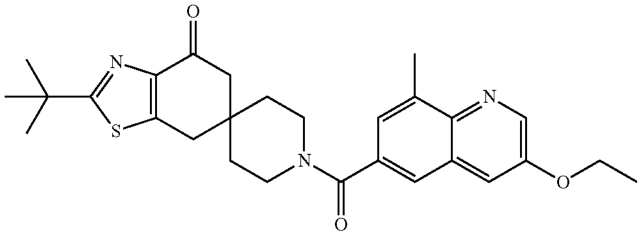 [SMILES: CCOc1cnc2c(C)cc(C(=O)N3CCC4(CC3)CC(=O)c3nc(C(C)(C)C)sc3C4)cc2c1] | 13.9 |
| 21 | 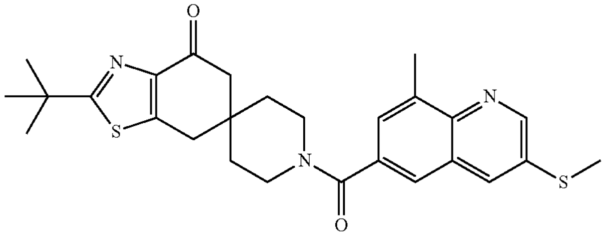 [SMILES: CSc1cnc2c(C)cc(C(=O)N3CCC4(CC3)CC(=O)c3nc(C(C)(C)C)sc3C4)cc2c1] | 8 |

TABLE 2-continued
| Example | Structure | Human SZ95 sebocyte lipid imaging assay/ Percent Inhibition of |
|---|---|---|
| 22 | 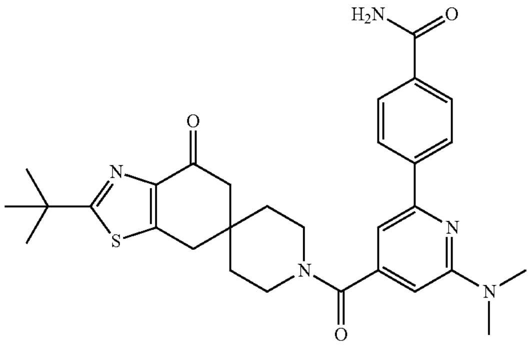 [SMILES: CN(C)c1cc(C(=O)N2CCC3(CC2)CC(=O)c2nc(C(C)(C)C)sc2C3)cc(-c2ccc(C(N)=O)cc2)n1] | 0.9 |
| 23 | 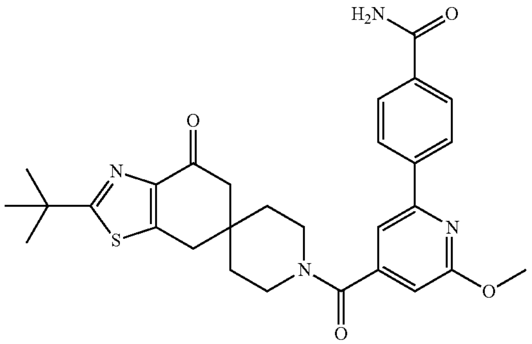 | 6.3 |
| 24 | 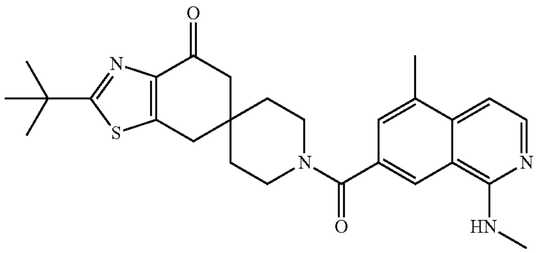 | 4 |
| 25 | 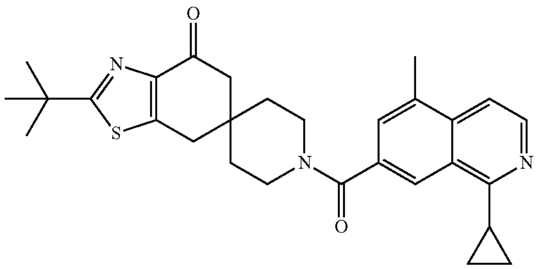 [SMILES: Cc1cc(C(=O)N2CCC3(CC2)CC(=O)c2nc(C(C)(C)C)sc2C3)cc2c(C3CC3)nccc12] | 17.9 |
| 26 | 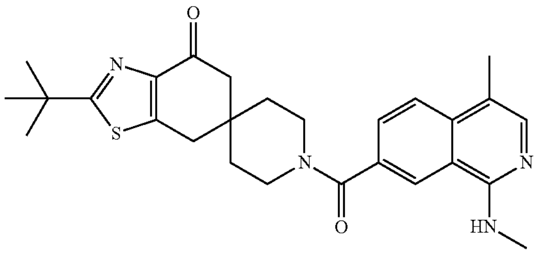 [SMILES: CNc1ncc(C)c2ccc(C(=O)N3CCC4(CC3)CC(=O)c3nc(C(C)(C)C)sc3C4)cc12] | 4.6* |

TABLE 2-continued
| Example | Structure | Human SZ95 sebocyte lipid imaging assay/ Percent Inhibition of |
|---|---|---|
| 27 | 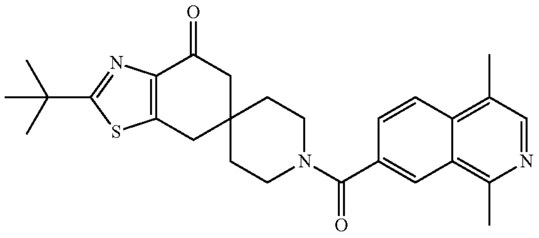 [SMILES: Cc1cnc(C)c2cc(C(=O)N3CCC4(CC3)CC(=O)c3nc(C(C)(C)C)sc3C4)ccc12] | 27.5 |
| 28 | 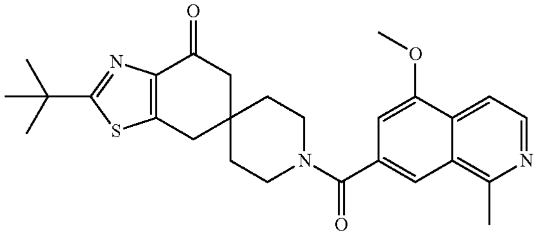 [SMILES: COc1cc(C(=O)N2CCC3(CC2)CC(=O)c2nc(C(C)(C)C)sc2C3)cc2c(C)nccc12] | 10.1 |
| 29 | 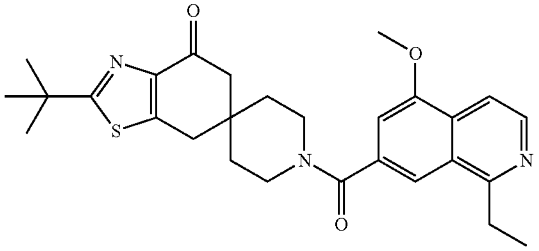 [SMILES: CCc1nccc2c(OC)cc(C(=O)N3CCC4(CC3)CC(=O)c3nc(C(C)(C)C)sc3C4)cc12] | 19.7 |
| 30 | 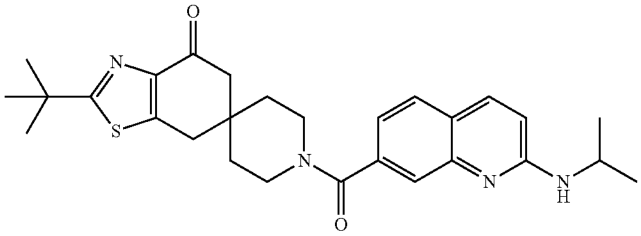 [SMILES: CC(C)Nc1ccc2ccc(C(=O)N3CCC4(CC3)CC(=O)c3nc(C(C)(C)C)sc3C4)cc2n1] | 8.6 |
| 31 | 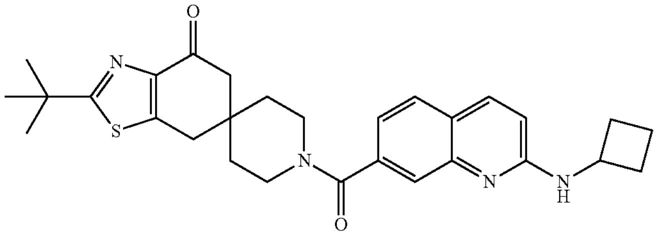 [SMILES: CC(C)(C)c1nc2c(s1)CC1(CCN(C(=O)c3ccc4ccc(NC5CCC5)nc4c3)CC1)CC2=O] | 11 |
| 32 | 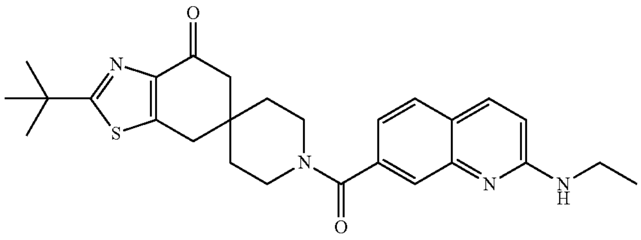 [SMILES: CCNc1ccc2ccc(C(=O)N3CCC4(CC3)CC(=O)c3nc(C(C)(C)C)sc3C4)cc2n1] | 10.2 |

TABLE 2-continued
| Example | Structure | Human SZ95 sebocyte lipid imaging assay/ Percent Inhibition of |
|---|---|---|
| 33 | 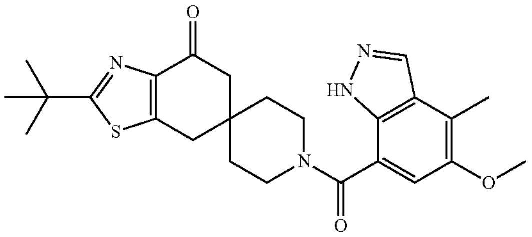 [SMILES: COc1cc(C(=O)N2CCC3(CC2)CC(=O)c2nc(C(C)(C)C)sc2C3)c2[nH]ncc2c1C] | 4.2 |
| 34 | 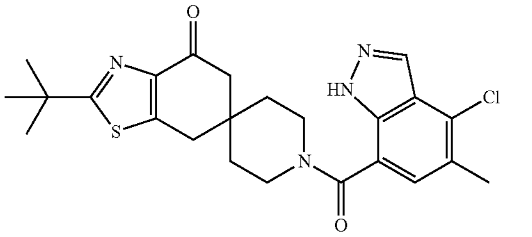 [SMILES: Cc1cc(C(=O)N2CCC3(CC2)CC(=O)c2nc(C(C)(C)C)sc2C3)c2[nH]ncc2c1Cl] | 1.4 |
| 35 | 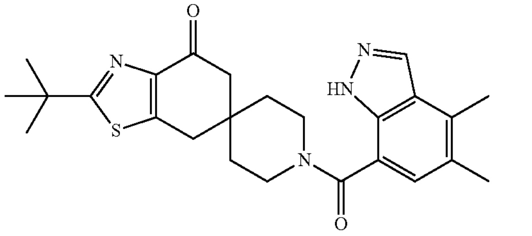 [SMILES: Cc1cc(C(=O)N2CCC3(CC2)CC(=O)c2nc(C(C)(C)C)sc2C3)c2[nH]ncc2c1C] | 14.4 |
| 36 | 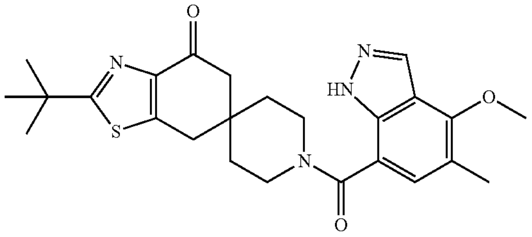 [SMILES: COc1c(C)cc(C(=O)N2CCC3(CC2)CC(=O)c2nc(C(C)(C)C)sc2C3)c2[nH]ncc12] | 9.3 |
| 37 | 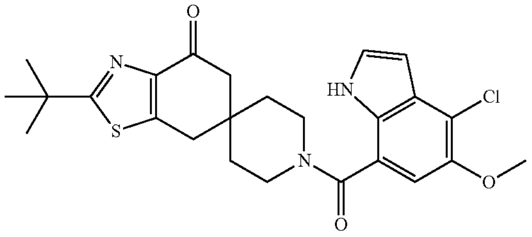 | 2.1 |
| 38 | 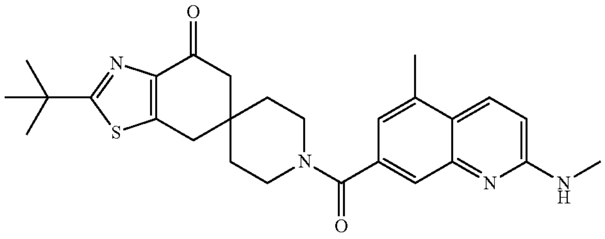 [SMILES: CNc1ccc2c(C)cc(C(=O)N3CCC4(CC3)CC(=O)c3nc(C(C)(C)C)sc3C4)cc2n1] | 8.3 |

TABLE 2-continued
| Example | Structure | Human SZ95 sebocyte lipid imaging assay/ Percent Inhibition of |
|---|---|---|
| 39 | 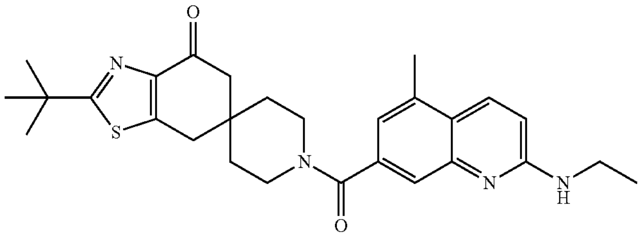 [SMILES: CCNc1ccc2c(C)cc(C(=O)N3CCC4(CC3)CC(=O)c3nc(C(C)(C)C)sc3C4)cc2n1] | 5.2 |
| 40 | 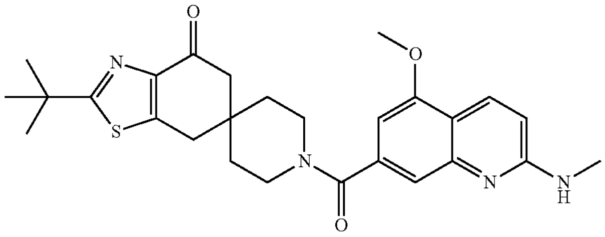 [SMILES: CNc1ccc2c(OC)cc(C(=O)N3CCC4(CC3)CC(=O)c3nc(C(C)(C)C)sc3C4)cc2n1] | 4.7 |
| 41 | 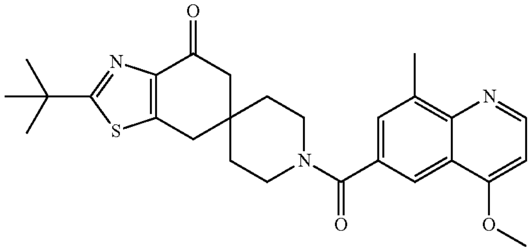 [SMILES: COc1ccnc2c(C)cc(C(=O)N3CCC4(CC3)CC(=O)c3nc(C(C)(C)C)sc3C4)cc12] | 7.7 |
| 42 | 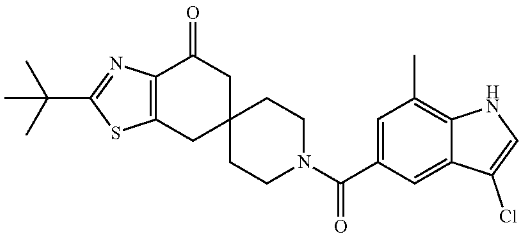 | 3.7 |
| 43 | 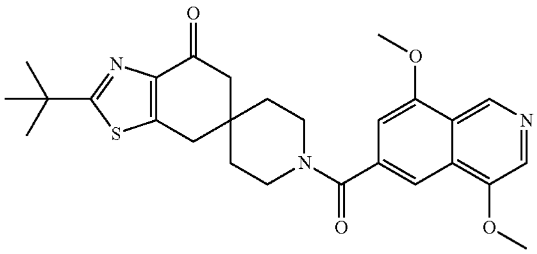 [SMILES: COc1cc(C(=O)N2CCC3(CC2)CC(=O)c2nc(C(C)(C)C)sc2C3)cc2c(OC)cncc12] | 7.6 |
| 44 | 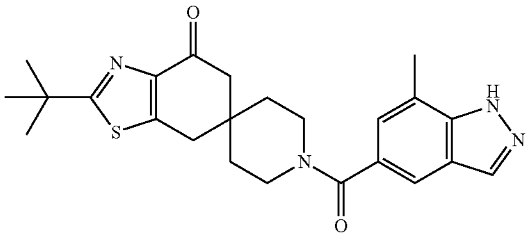 [SMILES: Cc1cc(C(=O)N2CCC3(CC2)CC(=O)c2nc(C(C)(C)C)sc2C3)cc2cn[nH]c12] | 12 |

TABLE 2-continued
| Example | Structure | Human SZ95 sebocyte lipid imaging assay/ Percent Inhibition of |
|---|---|---|
| 45 | 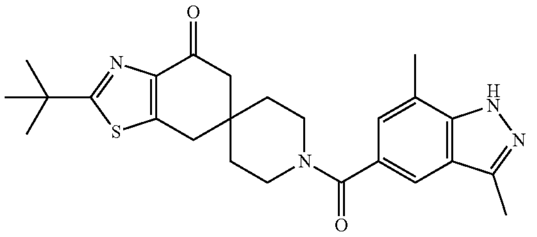 [SMILES: Cc1n[nH]c2c(C)cc(C(=O)N3CCC4(CC3)CC(=O)c3nc(C(C)(C)C)sc3C4)cc12] | 16.6 |
| 46 | 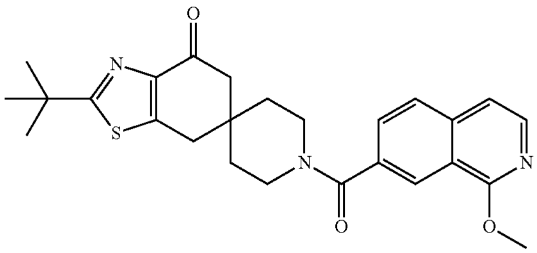 [SMILES: COc1nccc2ccc(C(=O)N3CCC4(CC3)CC(=O)c3nc(C(C)(C)C)sc3C4)cc12] | 21 |
| 47 | 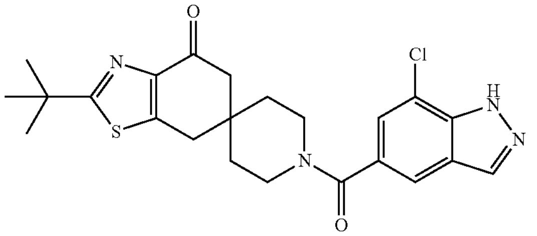 [SMILES: CC(C)(C)c1nc2c(s1)CC1(CCN(C(=O)c3cc(Cl)c4[nH]ncc4c3)CC1)CC2=O] | 20 |
| 48 | 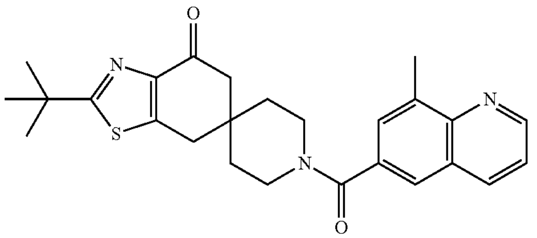 [SMILES: Cc1cc(C(=O)N2CCC3(CC2)CC(=O)c2nc(C(C)(C)C)sc2C3)cc2cccnc12] | 14.7 |
| 49 | 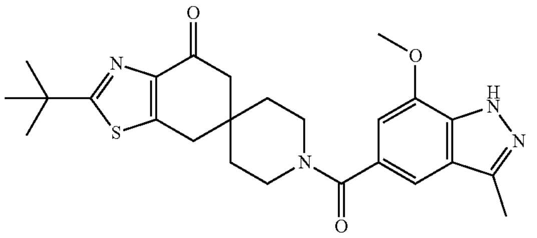 [SMILES: COc1cc(C(=O)N2CCC3(CC2)CC(=O)c2nc(C(C)(C)C)sc2C3)cc2c(C)n[nH]c12] | 12 |
| 50 | 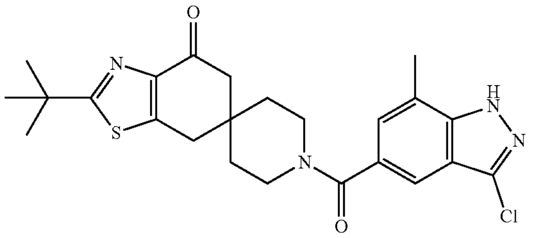 [SMILES: Cc1cc(C(=O)N2CCC3(CC2)CC(=O)c2nc(C(C)(C)C)sc2C3)cc2c(Cl)n[nH]c12] | 5.2 |

TABLE 2-continued
| Example | Structure | Human SZ95 sebocyte lipid imaging assay/ Percent Inhibition of |
|---|---|---|
| 51 | 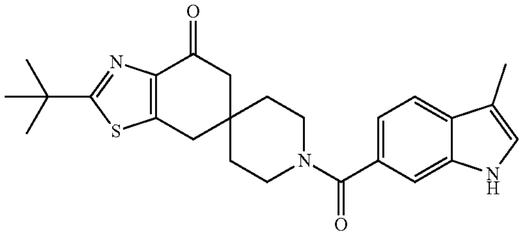 [SMILES: Cc1c[nH]c2cc(C(=O)N3CCC4(CC3)CC(=O)c3nc(C(C)(C)C)sc3C4)ccc12] | 29.1 |
| 52 | 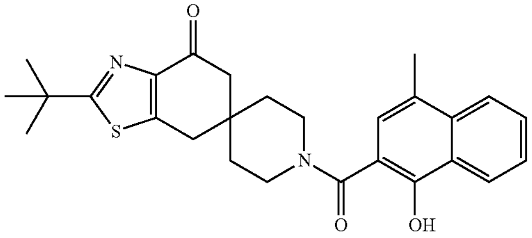 [SMILES: Cc1cc(C(=O)N2CCC3(CC2)CC(=O)c2nc(C(C)(C)C)sc2C3)c(O)c2ccccc12] | 5.2 |
| 53 | 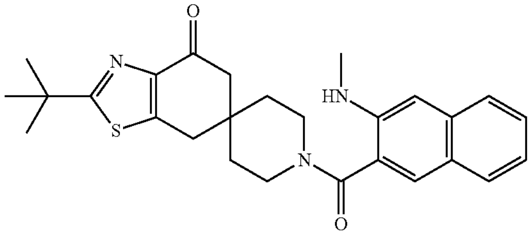 [SMILES: CNc1cc2ccccc2cc1C(=O)N1CCC2(CC1)CC(=O)c1nc(C(C)(C)C)sc1C2] | 8.2 |
| 54 | 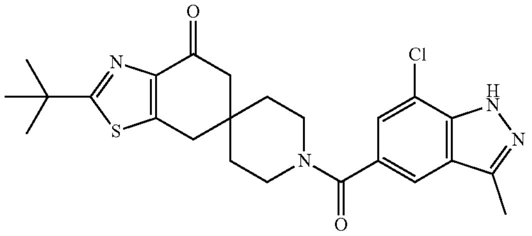 | 7.7 |
| 55 | 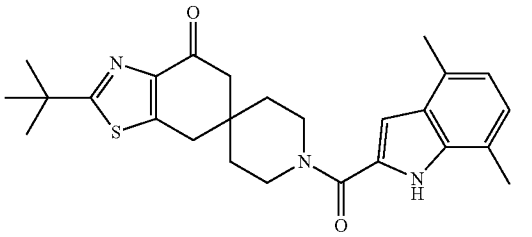 [SMILES: Cc1ccc(C)c2[nH]c(C(=O)N3CCC4(CC3)CC(=O)c3nc(C(C)(C)C)sc3C4)cc12] | 10 |
| 56 | 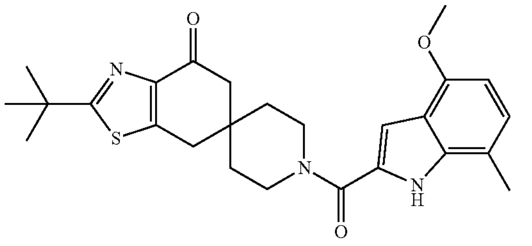 [SMILES: COc1ccc(C)c2[nH]c(C(=O)N3CCC4(CC3)CC(=O)c3nc(C(C)(C)C)sc3C4)cc12] | 5.2 |

TABLE 2-continued
| Example | Structure | Human SZ95 sebocyte lipid imaging assay/ Percent Inhibition of |
|---|---|---|
| 57 | 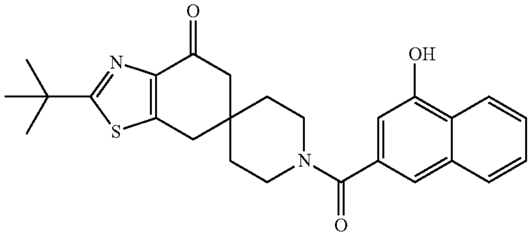 [SMILES: CC(C)(C)c1nc2c(s1)CC1(CCN(C(=O)c3cc(O)c4ccccc4c3)CC1)CC2=O] | 7 |
| 58 | 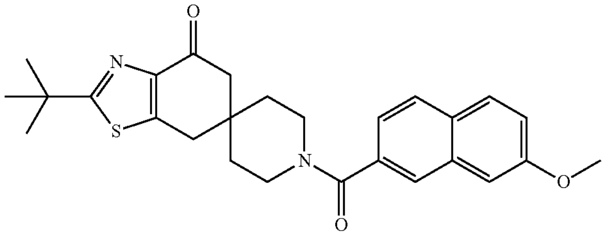 [SMILES: COc1ccc2ccc(C(=O)N3CCC4(CC3)CC(=O)c3nc(C(C)(C)C)sc3C4)cc2c1] | 17.6 |
| 59 | 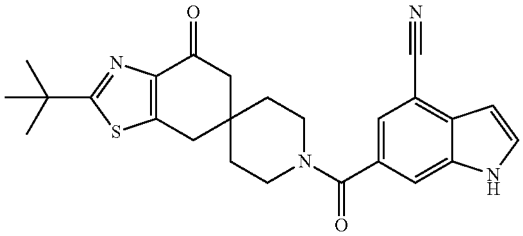 [SMILES: CC(C)(C)c1nc2c(s1)CC1(CCN(C(=O)c3cc(C#N)c4cc[nH]c4c3)CC1)CC2=O] | 22.2 |
| 60 | 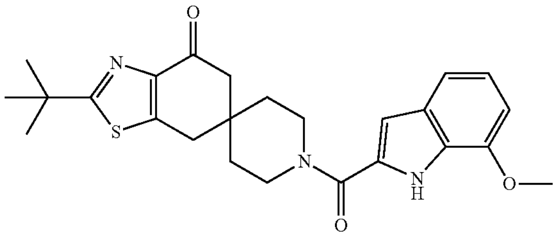 [SMILES: COc1cccc2cc(C(=O)N3CCC4(CC3)CC(=O)c3nc(C(C)(C)C)sc3C4)[nH]c12] | 18.8 |
| 61 | 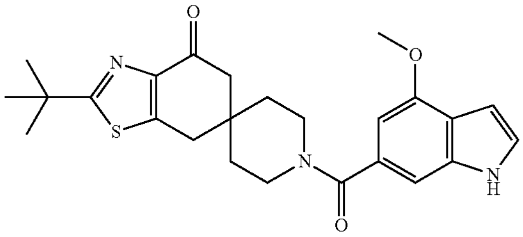 [SMILES: COc1cc(C(=O)N2CCC3(CC2)CC(=O)c2nc(C(C)(C)C)sc2C3)cc2[nH]ccc12] | 8.4 |
| 62 | 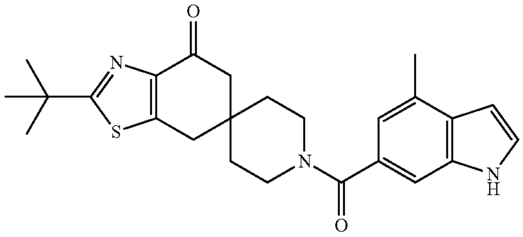 | 10.1 |

TABLE 2-continued
| Example | Structure | Human SZ95 sebocyte lipid imaging assay/ Percent Inhibition of |
|---|---|---|
| 63 | 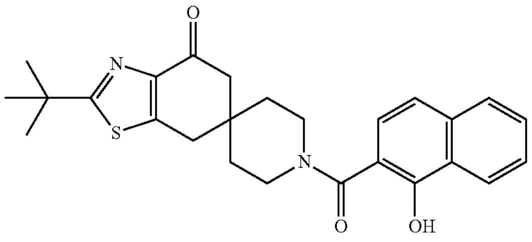 [SMILES: CC(C)(C)c1nc2c(s1)CC1(CCN(C(=O)c3ccc4ccccc4c3O)CC1)CC2=O] | 20 |
| 64 | 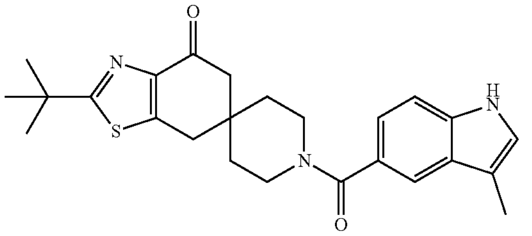 [SMILES: Cc1c[nH]c2ccc(C(=O)N3CCC4(CC3)CC(=O)c3nc(C(C)(C)C)sc3C4)cc12] | 14.7 |
| 65 | 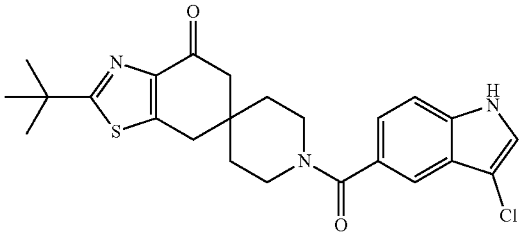 | 13.1 |
| 66 | 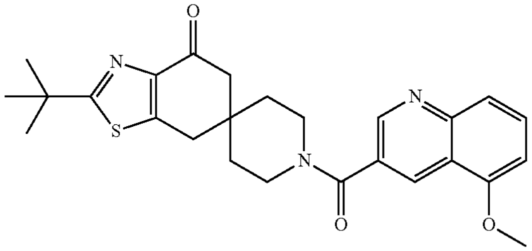 [SMILES: COc1cccc2ncc(C(=O)N3CCC4(CC3)CC(=O)c3nc(C(C)(C)C)sc3C4)cc12] | 19.9 |
| 67 | 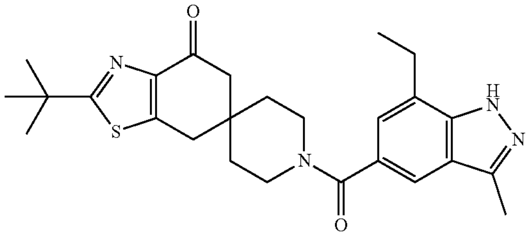 [SMILES: CCc1cc(C(=O)N2CCC3(CC2)CC(=O)c2nc(C(C)(C)C)sc2C3)cc2c(C)n[nH]c12] | 7.1 |
| 68 | 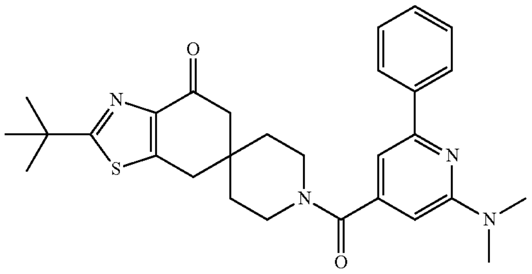 | 5 |

TABLE 2-continued
| Example | Structure | Human SZ95 sebocyte lipid imaging assay/ Percent Inhibition of |
|---|---|---|
| 69 | 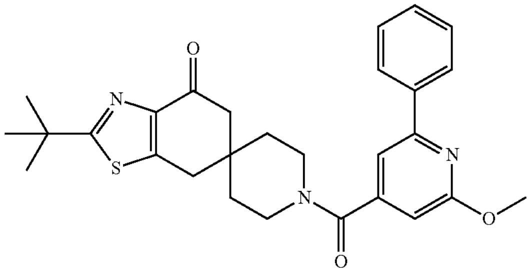 | 23.4 |
| 70 | 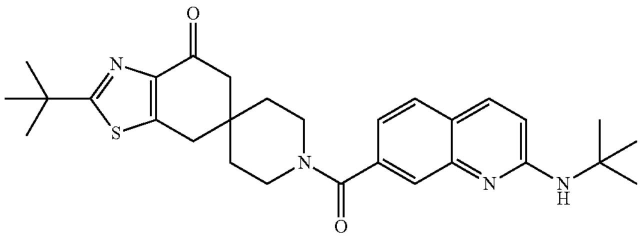 [SMILES: CC(C)(C)Nc1ccc2ccc(C(=O)N3CCC4(CC3)CC(=O)c3nc(C(C)(C)C)sc3C4)cc2n1] | 5.1 |
| 71 | 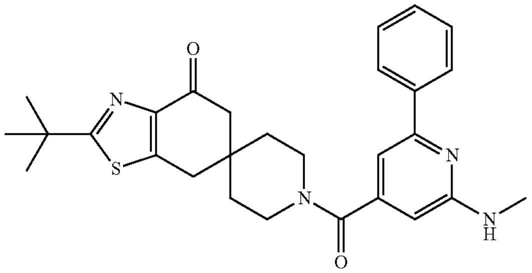 [SMILES: CNc1cc(C(=O)N2CCC3(CC2)CC(=O)c2nc(C(C)(C)C)sc2C3)cc(-c2ccccc2)n1] | 11.4 |
| 72 | 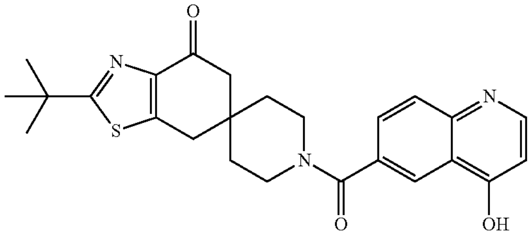 [SMILES: CC(C)(C)c1nc2c(s1)CC1(CCN(C(=O)c3ccc4nccc(O)c4c3)CC1)CC2=O] | 17.6* |
| 73 | 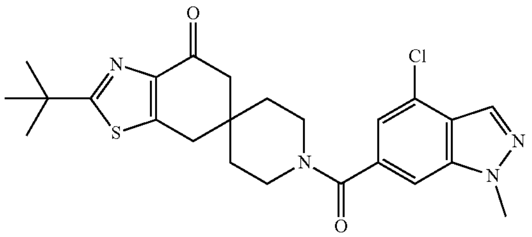 [SMILES: Cn1ncc2c(Cl)cc(C(=O)N3CCC4(CC3)CC(=O)c3nc(C(C)(C)C)sc3C4)cc21] | 9.8 |

TABLE 2-continued
| Example | Structure | Human SZ95 sebocyte lipid imaging assay/ Percent Inhibition of |
|---|---|---|
| 74 | 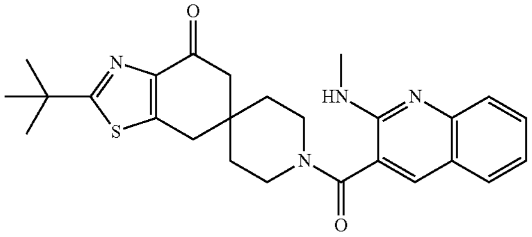 | 11.2 |
| 75 | 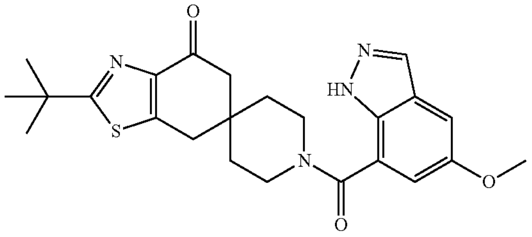 [SMILES: COc1cc(C(=O)N2CCC3(CC2)CC(=O)c2nc(C(C)(C)C)sc2C3)c2[nH]ncc2c1] | 19.5 |
| 76 | 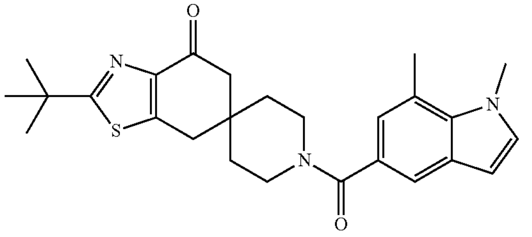 [SMILES: Cc1cc(C(=O)N2CCC3(CC2)CC(=O)c2nc(C(C)(C)C)sc2C3)cc2ccn(C)c12] | 27.9 |
| 77 | 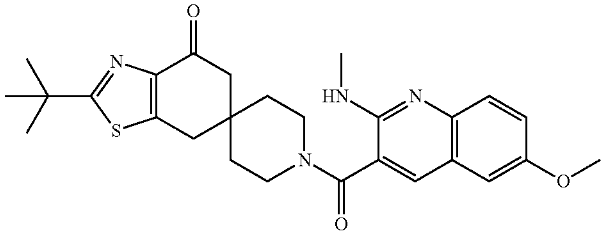 [SMILES: CNc1nc2ccc(OC)cc2cc1C(=O)N1CCC2(CC1)CC(=O)c1nc(C(C)(C)C)sc1C2] | 3.3 |
| 78 | 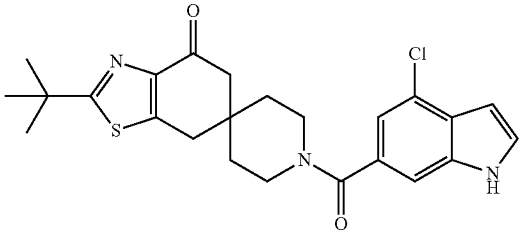 [SMILES: CC(C)(C)c1nc2c(s1)CC1(CCN(C(=O)c3cc(Cl)c4cc[nH]c4c3)CC1)CC2=O] | 22.4 |
| 79 | 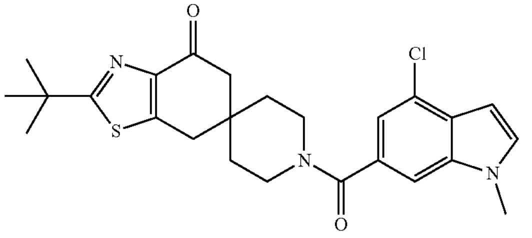 [SMILES: Cn1ccc2c(Cl)cc(C(=O)N3CCC4(CC3)CC(=O)c3nc(C(C)(C)C)sc3C4)cc21] | 7.6 |

TABLE 2-continued
| Example | Structure | Human SZ95 sebocyte lipid imaging assay/ Percent Inhibition of |
|---|---|---|
| 80 | 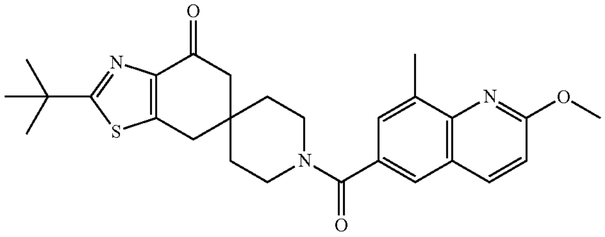 [SMILES: COc1ccc2cc(C(=O)N3CCC4(CC3)CC(=O)c3nc(C(C)(C)C)sc3C4)cc(C)c2n1] | 37 |
| 81 | 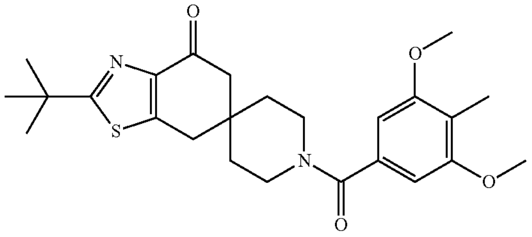 [SMILES: COc1cc(C(=O)N2CCC3(CC2)CC(=O)c2nc(C(C)(C)C)sc2C3)cc(OC)c1C] | 12.2 |
| 82 | 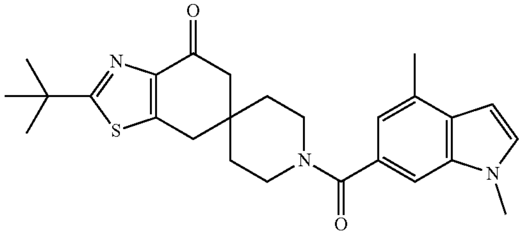 [SMILES: Cc1cc(C(=O)N2CCC3(CC2)CC(=O)c2nc(C(C)(C)C)sc2C3)cc2c1ccn2C] | 13 |
| 83 | 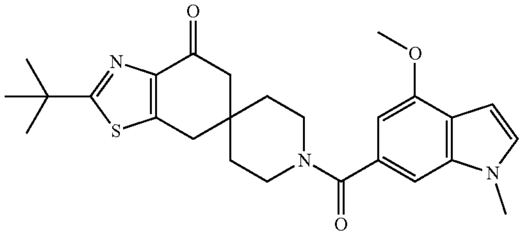 [SMILES: COc1cc(C(=O)N2CCC3(CC2)CC(=O)c2nc(C(C)(C)C)sc2C3)cc2c1ccn2C] | 9.5 |
| 84 | 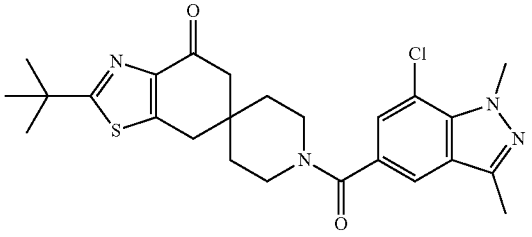 [SMILES: Cc1nn(C)c2c(Cl)cc(C(=O)N3CCC4(CC3)CC(=O)c3nc(C(C)(C)C)sc3C4)cc12] | 15.1 |
| 85 | 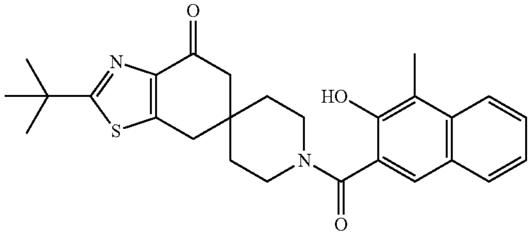 [SMILES: Cc1c(O)c(C(=O)N2CCC3(CC2)CC(=O)c2nc(C(C)(C)C)sc2C3)cc2ccccc12] | 10.1 |

TABLE 2-continued
| Example | Structure | Human SZ95 sebocyte lipid imaging assay/ Percent Inhibition of |
|---|---|---|
| 86 | 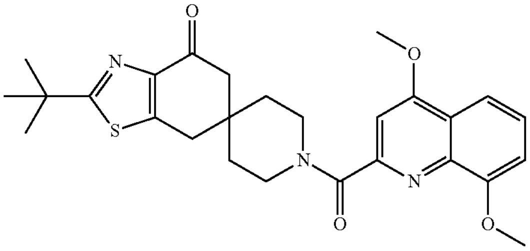 [SMILES: COc1cc(C(=O)N2CCC3(CC2)CC(=O)c2nc(C(C)(C)C)sc2C3)nc2c(OC)cccc12] | 13.3 |
| 87 | 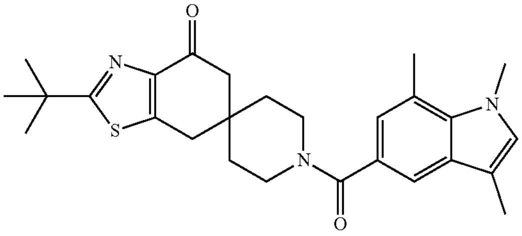 [SMILES: Cc1cn(C)c2c(C)cc(C(=O)N3CCC4(CC3)CC(=O)c3nc(C(C)(C)C)sc3C4)cc12] | 3.9 |
| 88 | 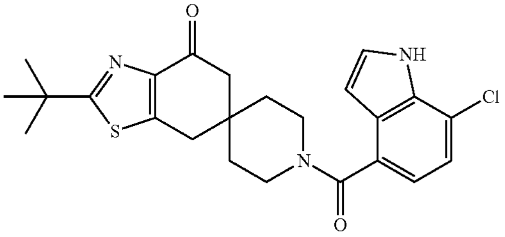 [SMILES: CC(C)(C)c1nc2c(s1)CC1(CCN(C(=O)c3ccc(Cl)c4[nH]ccc34)CC1)CC2=O] | 11.3 |
| 89 | 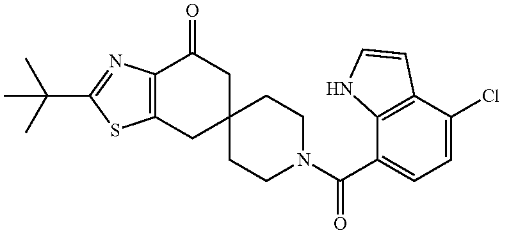 [SMILES: CC(C)(C)c1nc2c(s1)CC1(CCN(C(=O)c3ccc(Cl)c4cc[nH]c34)CC1)CC2=O] | 7.3 |
| 90 | 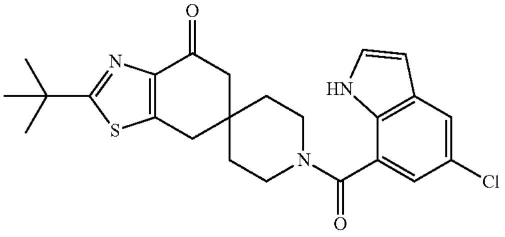 [SMILES: CC(C)(C)c1nc2c(s1)CC1(CCN(C(=O)c3cc(Cl)cc4cc[nH]c34)CC1)CC2=O] | 17.8 |
| 91 | 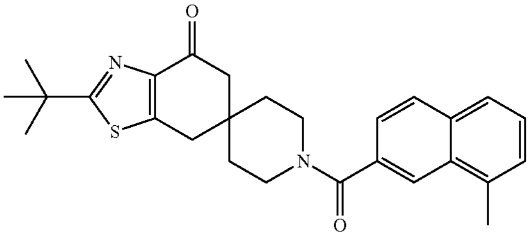 [SMILES: Cc1cccc2ccc(C(=O)N3CCC4(CC3)CC(=O)c3nc(C(C)(C)C)sc3C4)cc12] | 19.1 |

TABLE 2-continued
| Example | Structure | Human SZ95 sebocyte lipid imaging assay/ Percent Inhibition of |
|---|---|---|
| 92 | 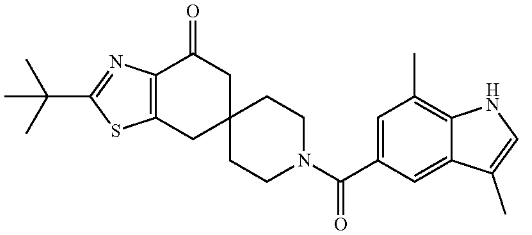 | 4.4 |
| 93 | 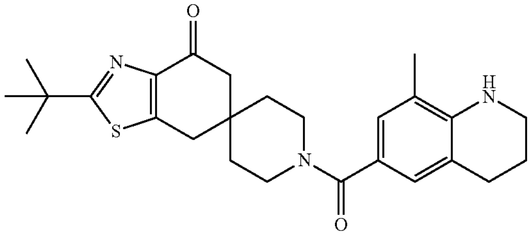 [SMILES: Cc1cc(C(=O)N2CCC3(CC2)CC(=O)c2nc(C(C)(C)C)sc2C3)cc2c1NCCC2] | 14.5 |
| 94 | 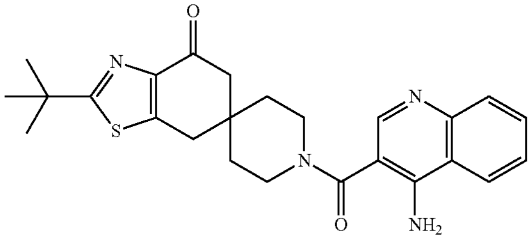 [SMILES: CC(C)(C)c1nc2c(s1)CC1(CCN(C(=O)c3cnc4ccccc4c3N)CC1)CC2=O] | 15.6 |
| 95 | 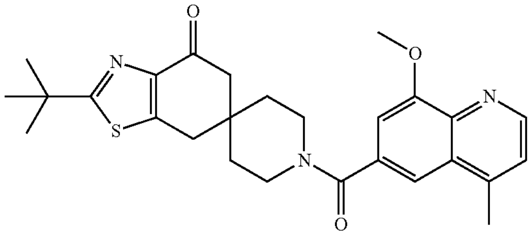 [SMILES: COc1cc(C(=O)N2CCC3(CC2)CC(=O)c2nc(C(C)(C)C)sc2C3)cc2c(C)ccnc12] | 19.9 |
| 96 | 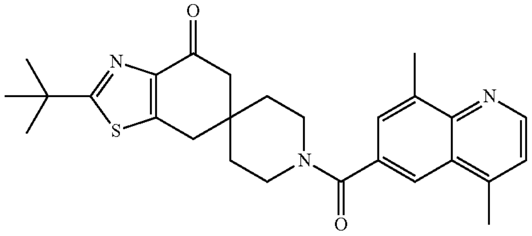 [SMILES: Cc1ccnc2c(C)cc(C(=O)N3CCC4(CC3)CC(=O)c3nc(C(C)(C)C)sc3C4)cc12] | 17.6 |
| 97 | 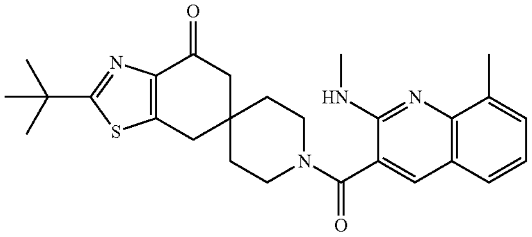 | 5.6 |

TABLE 2-continued
| Example | Structure | Human SZ95 sebocyte lipid imaging assay/ Percent Inhibition of |
|---|---|---|
| 98 | 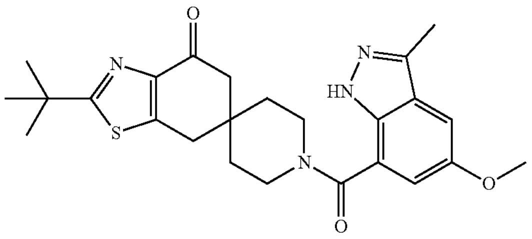 [SMILES: COc1cc(C(=O)N2CCC3(CC2)CC(=O)c2nc(C(C)(C)C)sc2C3)c2[nH]nc(C)c2c1] | 13.4 |
| 99 | 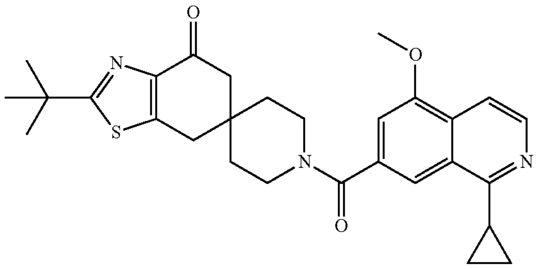 [SMILES: COc1cc(C(=O)N2CCC3(CC2)CC(=O)c2nc(C(C)(C)C)sc2C3)cc2c(C3CC3)nccc12] | 6.1 |
| 100 | 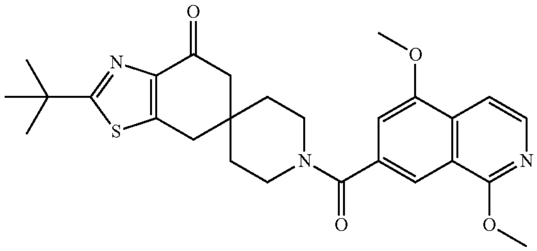 [SMILES: COc1cc(C(=O)N2CCC3(CC2)CC(=O)c2nc(C(C)(C)C)sc2C3)cc2c(OC)nccc12] | 6.1 |
| 101 | 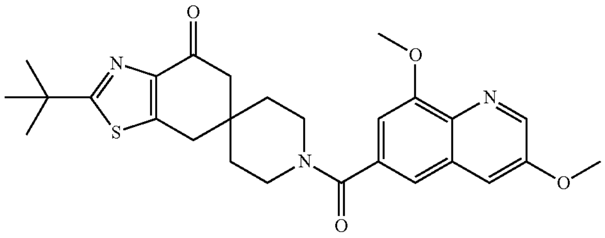 [SMILES: COc1cnc2c(OC)cc(C(=O)N3CCC4(CC3)CC(=O)c3nc(C(C)(C)C)sc3C4)cc2c1] | 15.6 |
| 102 | 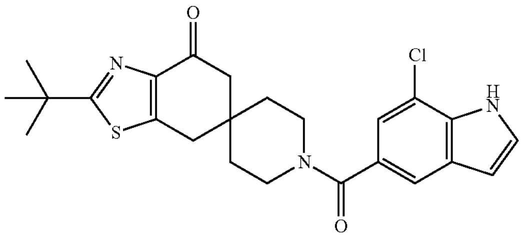 [SMILES: CC(C)(C)c1nc2c(s1)CC1(CCN(C(=O)c3cc(Cl)c4[nH]ccc4c3)CC1)CC2=O] | 14.9 |
| 103 | 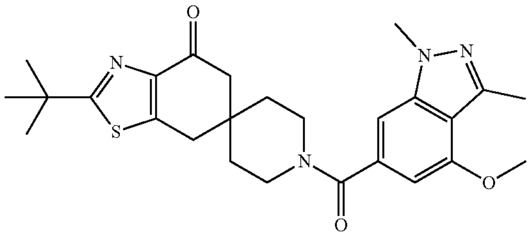 [SMILES: COc1cc(C(=O)N2CCC3(CC2)CC(=O)c2nc(C(C)(C)C)sc2C3)cc2c1c(C)nn2C] | 11.1 |

TABLE 2-continued
| Example | Structure | Human SZ95 sebocyte lipid imaging assay/ Percent Inhibition of |
|---|---|---|
| 104 | 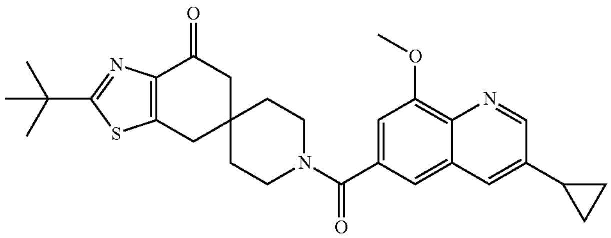 [SMILES: COc1cc(C(=O)N2CCC3(CC2)CC(=O)c2nc(C(C)(C)C)sc2C3)cc2cc(C3CC3)cnc12] | 15.5 |
| 105 | 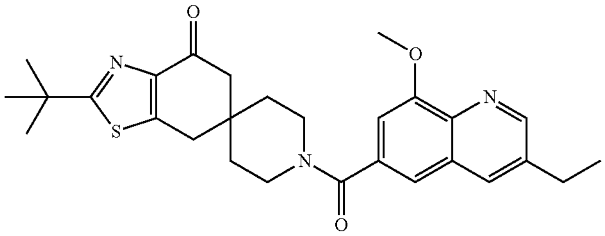 [SMILES: CCc1cnc2c(OC)cc(C(=O)N3CCC4(CC3)CC(=O)c3nc(C(C)(C)C)sc3C4)cc2c1] | 28.8 |
| 106 | 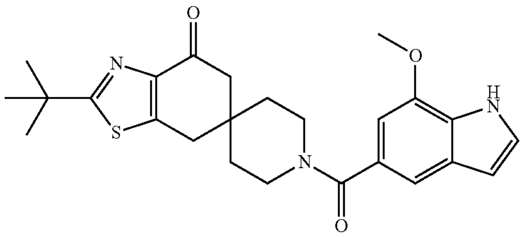 [SMILES: COc1cc(C(=O)N2CCC3(CC2)CC(=O)c2nc(C(C)(C)C)sc2C3)cc2cc[nH]c12] | 14.5 |
| 107 | 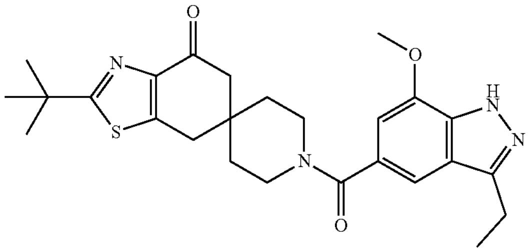 [SMILES: CCc1n[nH]c2c(OC)cc(C(=O)N3CCC4(CC3)CC(=O)c3nc(C(C)(C)C)sc3C4)cc12] | 13.3 |
| 108 | 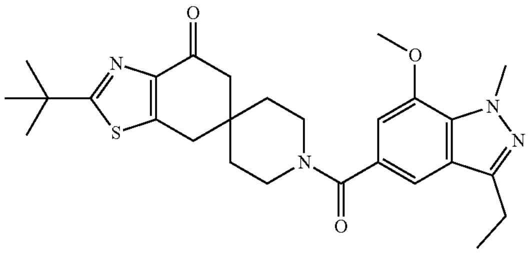 [SMILES: CCc1nn(C)c2c(OC)cc(C(=O)N3CCC4(CC3)CC(=O)c3nc(C(C)(C)C)sc3C4)cc12] | 7.5 |

TABLE 2-continued

| Example | Structure | Human SZ95 sebocyte lipid imaging assay/ Percent Inhibition of |
|---|---|---|
| 109 | 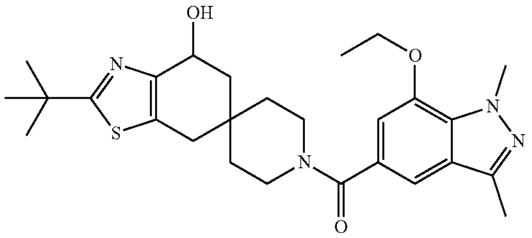 [SMILES: CCOc1cc(C(=O)N2CCC3(CC2)Cc2sc(C(C)(C)C)nc2C(O)C3)cc2c(C)nn(C)c12] | 22.8 |

Geomean $IC_{50}$ given, number of repeats n ≥ 2 unless symbol "*" then n = 1; NA = not available Radiometric Measurement of De Novo Lipogenesis in Cultured Human Sebocytes SZ95 sebocytes were grown in Human Sebocyte Growth Medium (HSGM) containing Sebomed® basal medium (Sigma-Aldrich, F8205) supplemented with 10% heat-inactivated fetal bovine serum (Gibco, 10100-147), 1% penicillin/streptomycin (Gibco, 15070-063), 1 mM calcium chloride (Fisher, BP9742-10X5) and 5 ng/mL recombinant human epidermal growth factor (Gibco, PHG0311). At 90% confluence, cells were washed with PBS and then detached with 0.05% Trypsin-EDTA (Gibco, 25300054). Prior to starting the assay, cells were centrifuged and resuspended in HSGM containing 5% charcoal-stripped serum (Life Technologies, 12676-029) instead of 10% heat-inactivated fetal bovine serum. Cells were added to 24-well plates at a density of $0.25\times10^6$ cells/well and incubated overnight at 37° C. to allow the cells to adhere to the culture plate. Cells were then treated with a dose response of compound (30, 1, 0.03, 0.006, 0.0009, 0.0002, and 0.00003 μM) with each concentration tested in duplicate. Briefly, compounds were dissolved in DMSO stocks and diluted 1:1000 into HSGM with charcoal-stripped media. The vehicle control wells were treated with 0.1% DMSO. After a 1-hour preincubation with compound or vehicle at 37° C., 0.25 μCi $^{14}C$ sodium acetate (American Radiolabeled Chemicals: ARC, 0173A) was added to each well. Plates were incubated for an additional two hours at 37° C. At the end of the incubation period, cells were removed from incubator, placed on ice, and then washed twice with ice-cold PBS to remove free $^{14}C$-sodium acetate. Plates were sealed and stored at −20° C. until analysis. To induce lysis, 125 μL of mammalian protein extraction reagent (MPER; Fisher, 78501) was added to each well. Plates were shaken for 1 hour at room temperature and lysates transferred to individual 2 mL polypropylene tubes. Wells were then washed with 175 μL PBS, which was added to lysates. A chloroform:methanol solution (1:1 v/v, 450 μL) was added to each tube. All tubes were vortexed for 10 seconds and centrifuged at 14,000×g for 5 minutes at room temperature to separate the aqueous and organic phases. A 25 μL aliquot was removed from the bottom organic layer of each sample and added to 6 mL Optiphase Supermix scintillation fluid (PerkinElmer, 1200-439). Counts of $^{14}C$ were assessed by scintillation counting. DNL (counts of $^{14}C$ incorporated into lipids) was expressed as a percentage for compound treated cells relative to the vehicle control. $IC_{50}$ values were determined using a non-linear regression (four parameter with variable slope) in GraphPad Prism.

TABLE 3

| Example | Structure | Human SZ95 sebocytes radiometric assay IC50 (nM)* |
|---|---|---|
| 13 | 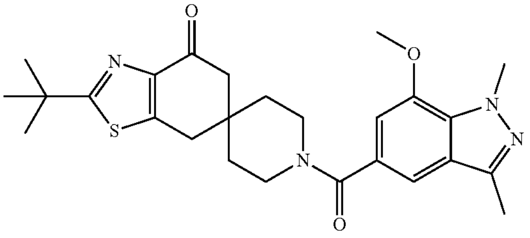 [SMILES: COc1cc(C(=O)N2CCC3(CC2)CC(=O)c2nc(C(C)(C)C)sc2C3)cc2c(C)nn(C)c12] | 13.5 |

TABLE 3-continued
| Example | Structure | Human SZ95 sebocytes radiometric assay IC50 (nM)* |
|---|---|---|
| 14 | 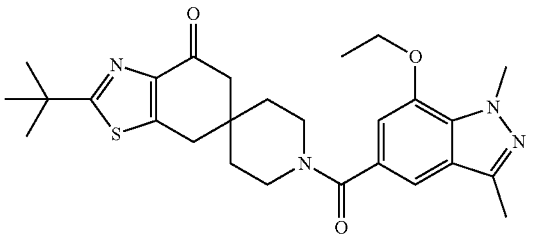 | 5.9 |
| 15 | 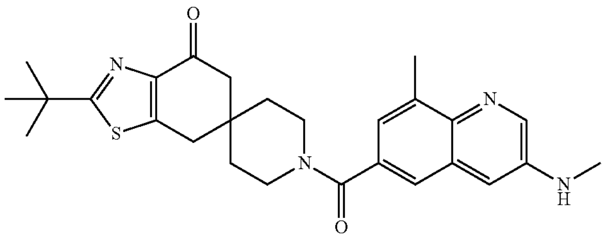 | 12.9 |
| 16 | 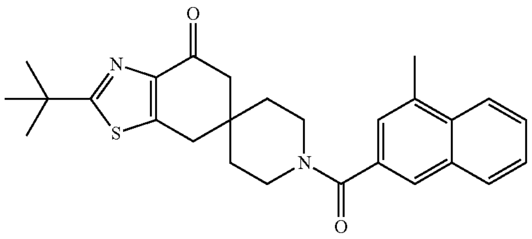 [SMILES: Cc1cc(C(=O)N2CCC3(CC2)CC(=O)c2nc(C(C)(C)C)sc2C3)cc2ccccc12] | 18.1 |
| 17 | 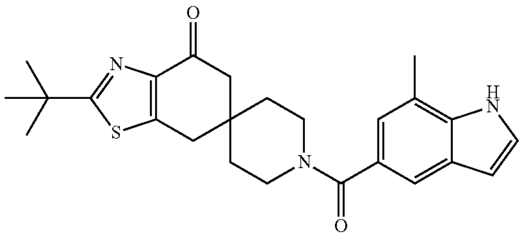 [SMILES: Cc1cc(C(=O)N2CCC3(CC2)CC(=O)c2nc(C(C)(C)C)sc2C3)cc2cc[nH]c12] | 15.6 |
| 19 | 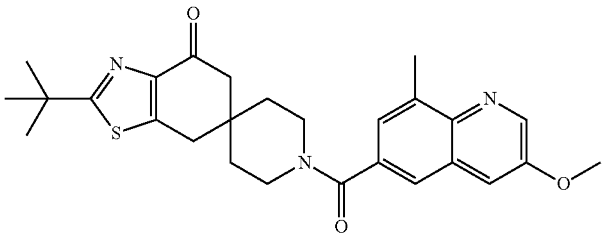 | 21.1* |
| 33 | 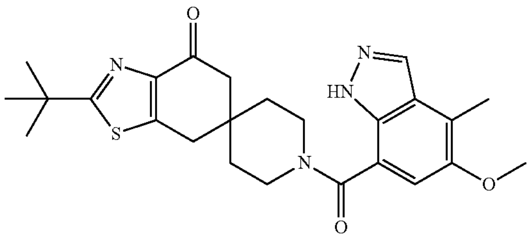 [SMILES: COc1cc(C(=O)N2CCC3(CC2)CC(=O)c2nc(C(C)(C)C)sc2C3)c2[nH]ncc2c1C] | 38.1* |

TABLE 3-continued
| Example | Structure | Human SZ95 sebocytes radiometric assay IC50 (nM)* |
| --- | --- | --- |
| 38 | 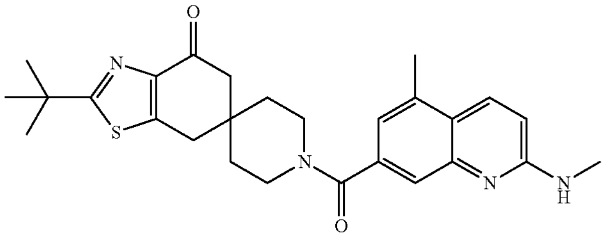 [SMILES: CNc1ccc2c(C)cc(C(=O)N3CCC4(CC3)CC(=O)c3nc(C(C)(C)C)sc3C4)cc2n1] | 14.2 |
| 42 | 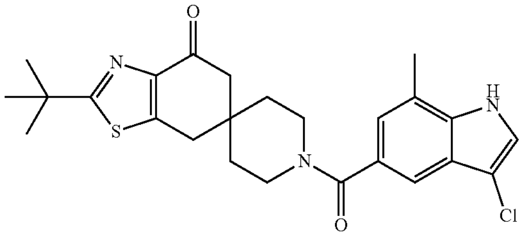 | 15.9 |
| 61 | 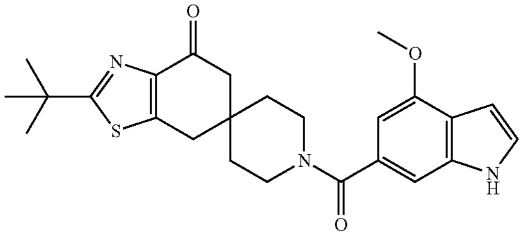 [SMILES: COc1cc(C(=O)N2CCC3(CC2)CC(=O)c2nc(C(C)(C)C)sc2C3)cc2[nH]ccc12] | 30.8* |
| 79 | 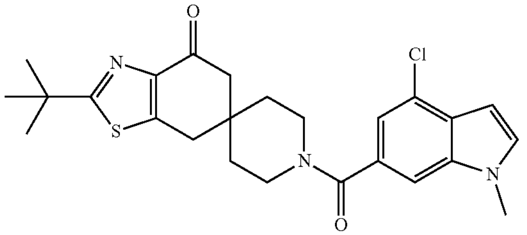 [SMILES: Cn1ccc2c(Cl)cc(C(=O)N3CCC4(CC3)CC(=O)c3nc(C(C)(C)C)sc3C4)cc21] | 16.7* |
| 81 | 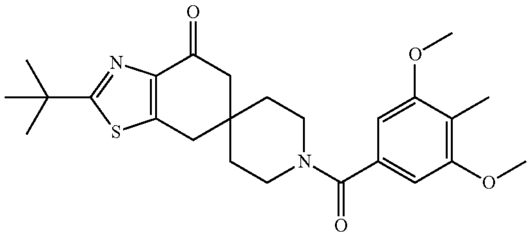 [SMILES: COc1cc(C(=O)N2CCC3(CC2)CC(=O)c2nc(C(C)(C)C)sc2C3)cc(OC)c1C] | 47.2* |
| 97 | 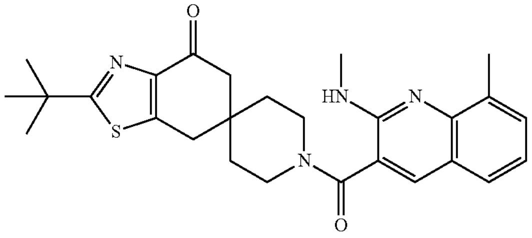 | 16.2* |

TABLE 3-continued

| Example | Structure | Human SZ95 sebocytes radiometric assay IC50 (nM)* |
|---|---|---|
| 99 | 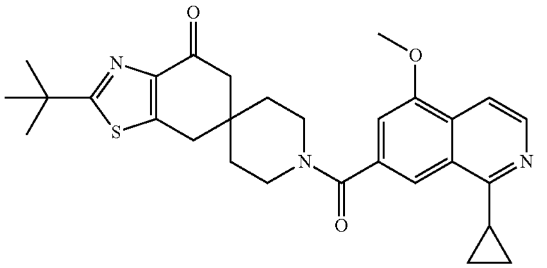 [SMILES: COc1cc(C(=O)N2CCC3(CC2)CC(=O)c2nc(C(C)(C)C)sc2C3)cc2c(C3CC3)nccc12] | 10.0* |

Geomean $IC_{50}$ given, number of repeats n>2 unless symbol "*" then n=1

The invention claimed is:

1. A compound of formula (I) having the structure:

(I)

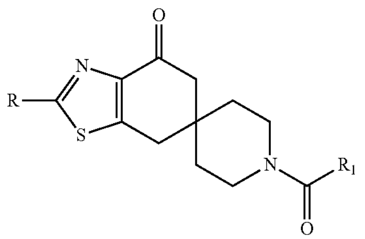

or

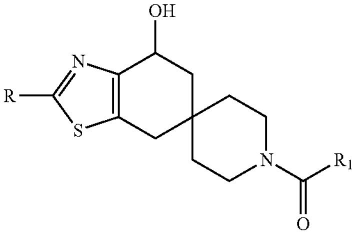

or a pharmaceutically acceptable salt thereof, or a pharmaceutically acceptable solvate of said compound or pharmaceutically acceptable salt, wherein:

R is selected from the group consisting of H, $C_1$-$C_6$ alkoxy, $C_1$-$C_6$ alkyl and —$(CH_2)_m$-W, where Wis $C_3$-$C_8$ cycloalkyl, bicyclo alkyl, bridged bicycloalkyl, phenyl, 5- or 6-membered heteroaryl or heterocyclic containing one, two or three heteroatoms selected from the group consisting of N, S and O atoms; wherein each of said alkyl, cycloalkyl, heterocyclic, phenyl, naphthyl or heteroaryl may be unsubstituted or substituted by phenyl, halo, cyano, deuterium, hydroxy, $C_1$-$C_6$ alkyl, $C_1$-$C_6$ alkoxy, —$SO_2$—R', —CONR'R", NR'COR", —NR'CONR'R", —NR'$CO_2$R", —$(CH_2)_n$—$SO_2$—R', —$NHSO_2$—R', —NR"$SO_2$—R', —$SO_2$NR'R", NR'R" or SR' where R' and R" are independently H, $C_1$-$C_6$ alkyl or $C_3$-$C_8$ cycloalkyl;

$R_1$ is selected from the group consisting of phenyl, naphthyl, 5- or 6-membered heteroaryl or heterocyclic containing one, two, three or four heteroatoms selected from the group consisting of N, S and O atoms; and, a 9- or 10-membered bicyclic aryl, heteroaryl or heterocyclic containing one, two or three heteroatoms selected from the group consisting of N, S and O atoms; wherein each of said phenyl, naphthyl, aryl, heterocyclic, or heteroaryl may be unsubstituted or substituted by halo, cyano, deuterium, hydroxy, $C_1$-$C_6$ alkyl, $C_1$-$C_6$ alkoxy, phenyl, —$SO_2$—R', —CONR'R", NR'COR", —NR'CONR'R", —NR'$CO_2$R", —$(CH_2)_n$—$SO_2$—R', —$NHSO_2$—R', —NR"$SO_2$—R', —$SO_2$NR'R", NR'R", —P(O)R'R",

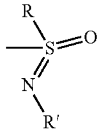

or SR' where R' and R" are independently H, $C_1$-$C_6$ alkyl or $C_3$-$C_8$ cycloalkyl; and, m and n are independently 0, 1, 2 or 3.

2. The compound of claim 1 wherein R is selected from the group consisting of H, $C_1$-$C_6$ alkyl and —$(CH_2)_m$-W, where W is $C_3$-$C_8$ cycloalkyl, wherein each of said alkyl, and cycloalkyl may be unsubstituted or substituted by halo, cyano, deuterium, hydroxy, $C_1$-$C_6$ alkyl and $C_1$-$C_6$ alkoxy; and, m and n are independently 0, 1, 2 or 3.

3. The compound of claim 1 wherein R is t-butyl.

4. A compound according to claim 1 wherein $R_1$ is phenyl, pyridyl, indolyl, indazolyl, pyrrolopyridinyl, quinolinyl, isoquinolinyl or naphthyl; wherein each of said phenyl, pyridyl, indolyl, indazolyl, pyrrolopyridinyl, quinolinyl, isoquinolinyl or naphthyl may be unsubstituted or substituted by halo, cyano, hydroxy, $C_1$-$C_6$ alkyl, $C_1$-$C_6$ alkoxy, phenyl, —CONR'R", NR'R" or SR' where R' and R" are independently H, $C_1$-$C_6$ alkyl or $C_3$-$C_8$ cycloalkyl; and, m and n are independently 0, 1, 2 or 3.

5. The compound of claim 1 selected from the group consisting of:

2-(tert-butyl)-1'-(7-methoxy-1,3-dimethyl-1H-indazole-5-carbonyl)-5H-spiro[benzo[d]thiazole-6,4'-piperidin]-4(7H)-one;

2-(tert-butyl)-1'-(7-methyl-1H-indole-5-carbonyl)-5H-spiro[benzo[d]thiazole-6,4'-piperidin]-4 (7H)-one;

2-(tert-butyl)-1'-(8-methyl-3-(methylamino) quinoline-6-carbonyl)-5H-spiro[benzo[d]thiazole-6,4'-piperidin]-4 (7H)-one;

2-(tert-butyl)-1'-(7-ethoxy-1,3-dimethyl-1H-indazole-5-carbonyl)-5H-spiro[benzo[d]thiazole-6,4'-piperidin]-4 (7H)-one; and, 2-(tert-butyl)-1'-(4-methyl-2-naphthoyl)-5H-spiro[benzo[d]thiazole-6,4'-piperidin]-4(7H)-one;

or, a pharmaceutically acceptable salt thereof, or a pharmaceutically acceptable solvate of said compound or pharmaceutically acceptable salt.

6. The compound of claim 1 wherein the compound is 2-(tert-butyl)-1'-(7-methoxy-1,3-dimethyl-1H-indazole-5-carbonyl)-5H-spiro[benzo[d]thiazole-6,4'-piperidin]-4(7H)-one; or, a pharmaceutically acceptable salt thereof, or a pharmaceutically acceptable solvate of said compound or pharmaceutically acceptable salt.

7. The compound of claim 1 wherein the compound is 2-(tert-butyl)-1'-(7-methyl-1H-indole-5-carbonyl)-5H-spiro[benzo[d]thiazole-6,4'-piperidin]-4(7H)-one; or, a pharmaceutically acceptable salt thereof, or a pharmaceutically acceptable solvate of said compound or pharmaceutically acceptable salt.

8. The compound of claim 1 wherein the compound is 2-(tert-butyl)-1'-(8-methyl-3-(methylamino) quinoline-6-carbonyl)-5H-spiro[benzo[d]thiazole-6,4'-piperidin]-4(7H)-one; or, a pharmaceutically acceptable salt thereof, or a pharmaceutically acceptable solvate of said compound or pharmaceutically acceptable salt.

9. The compound of claim 1 wherein the compound is 2-(tert-butyl)-1'-(7-ethoxy-1,3-dimethyl-1H-indazole-5-carbonyl)-5H-spiro[benzo[d]thiazole-6,4'-piperidin]-4(7H)-one; or, a pharmaceutically acceptable salt thereof, or a pharmaceutically acceptable solvate of said compound or pharmaceutically acceptable salt.

10. The compound of claim 1 wherein the compound is 2-(tert-butyl)-1'-(4-methyl-2-naphthoyl)-5H-spiro[benzo[d]thiazole-6,4'-piperidin]-4(7H)-one; or, a pharmaceutically acceptable salt thereof, or a pharmaceutically acceptable solvate of said compound or pharmaceutically acceptable salt.

11. A pharmaceutical composition comprising a compound according to claim 1, or a pharmaceutically acceptable salt thereof, or a pharmaceutically acceptable solvate of said compound or pharmaceutically acceptable salt, and a pharmaceutically acceptable excipient.

12. A method of treating acne, comprising administering to the subject a therapeutically effective amount of a compound of claim 1 or a pharmaceutically acceptable salt thereof, or a pharmaceutically acceptable solvate of said compound or pharmaceutically acceptable salt.

13. The method of claim 12 wherein the compound is administered topically.

14. The method of claim 12, wherein the compound is administered as a cream, ointment, lotion, gel, solution, suspension, foam, aerosol, spray, shampoo, patch or tape.

* * * * *